(12) United States Patent
Kostrewa et al.

(10) Patent No.: US 7,078,183 B2
(45) Date of Patent: Jul. 18, 2006

(54) MODIFIED PHYTASES

(75) Inventors: Dirk Kostrewa, Freiburg (DE); Luis Pasamontes, Trimbach (CH); Andrea Tomschy, Grenzach-Wyhlen (DE); Adolphus van Loon, Rheinfelden (CH); Kurt Vogel, Basel (CH); Markus Wyss, Liestal (CH)

(73) Assignee: DSM IP Assets B.V., Te Heerlen (NL)

( * ) Notice: Subject to any disclaimer, the term of this patent is extended or adjusted under 35 U.S.C. 154(b) by 163 days.

(21) Appl. No.: 10/776,104

(22) Filed: Feb. 11, 2004

(65) Prior Publication Data

US 2004/0142424 A1    Jul. 22, 2004

Related U.S. Application Data

(62) Division of application No. 10/062,848, filed on Feb. 1, 2002, now Pat. No. 6,734,004, which is a division of application No. 09/044,718, filed on Mar. 19, 1998, now Pat. No. 6,391,605.

(30)    Foreign Application Priority Data

Mar. 25, 1997    (EP)    ................... 97810175

(51) Int. Cl.
    *C12Q 1/34*    (2006.01)
    *C12Q 1/42*    (2006.01)
    *C12N 1/20*    (2006.01)
    *C12N 15/00*    (2006.01)
    *C07H 21/04*    (2006.01)

(52) U.S. Cl. .................. 435/18; 435/252.3; 435/320.1; 435/916; 435/917; 435/196; 435/21; 536/23.2

(58) Field of Classification Search ................. 435/18, 435/21, 195, 196, 252.5, 320.1, 252.3, 916, 435/917; 536/23.2
See application file for complete search history.

(56)    References Cited

OTHER PUBLICATIONS

SEQ ID No. 1 [Aspergillus niger] alighnment with phytase/Accession No. P24031] from yeast [pp. 1, 3-5].*
Mosimann et al. [Proteins : Structure, Function & Genetics, 23 :301-317 (1995)].*

* cited by examiner

*Primary Examiner*—Tekchand Saidha
(74) *Attorney, Agent, or Firm*—Bryan Cave LLP

(57)    ABSTRACT

A process for the production of a modified phytase with a desired property improved over the property of the corresponding unmodified phytase is disclosed, as well as modified phytases, polynucleotides encoding modified phytases, and animal feed including modified phytases.

9 Claims, 95 Drawing Sheets

FIG. 1

```
  1  TCTGTAACCGATAGCGGACCGACTAGGCATCGTTGATCCACAATATCTCA   50
 51  GACAATGCAACTCAGTCGAATATGAAGGGCTACAGCCAGCATTTAAATAC  100
101  GGCCGTCTAGGTCGGGCTCCGGGGATGAGGAGGAGCAGGCTCGTGTTCAT  150
151  TTCGGTCATGGCTTTTTTCACGGTCGCTCTTTCGCTTTATTACTTGCTAT  200
            M  A  F  F  T  V  A  L  S  L  Y  Y  L  L  S    15
201  CGAGgtgagatctctacaatatctgtctgcttagttgaattggtacttat  250
      R                                                   16

251  ctgtacagAGTCTCTGCTCAGGCCCCAGTGGTCCAGAATCATTCATGCAA  300
              V  S  A  Q  A  P  V  V  Q  N  H  S  C  N    30
                                              +
301  TACGGCGGACGGTGGATATCAATGCTTCCCCAATGTCTCTCATGTTTGGG  350
      T  A  D  G  G  Y  Q  C  F  P  N  V  S  H  V  W  G   47
                                +
351  GTCAGTACTCGCCGTACTTCTCCATCGAGCAGGAGTCAGCTATCTCTGAG  400
      Q  Y  S  P  Y  F  S  I  E  Q  E  S  A  I  S  E     63

401  GACGTGCCTCATGGCTGTGAGGTTACCTTTGTGCAGGTGCTCTCGCGGCA  450
      D  V  P  H  G  C  E  V  T  F  V  Q  V  L  S  R  H   80

451  TGGGGCTAGGTATCCGACAGAGTCGAAGAGTAAGGCGTACTCGGGGTTGA  500
      G  A  R  Y  P  T  E  S  K  S  K  A  Y  S  G  L  I   97

501  TTGAAGCAATCCAGAAGAATGCTACCTCTTTTTGGGGACAGTATGCTTTT  550
       E  A  I  Q  K  N  A  T  S  F  W  G  Q  Y  A  F    113
                  +
551  CTGGAGAGTTATAACTATACCCTCGGCGCGGATGACTTGACTATCTTCGG  600
      L  E  S  Y  N  Y  T  L  G  A  D  D  L  T  I  F  G   130
            +
601  CGAGAACCAGATGGTTGATTCGGGTGCCAAGTTCTACCGACGGTATAAGA  650
      E  N  Q  M  V  D  S  G  A  K  F  Y  R  R  Y  K  N   147

651  ATCTCGCCAGGAAAAATACTCCTTTTATCCGTGCATCAGGGTCTGACCGT  700
      L  A  R  K  N  T  P  F  I  R  A  S  G  S  D  R     163
```

FIG. 4-1

```
701  GTCGTTGCGTCTGCGGAGAAGTTCATTAATGGATTTCGCAAGGCTCAGCT  750
      V  V  A  S  A  E  K  F  I  N  G  F  R  K  A  Q  L   180

751  CCACGACCATGGCTCCAAACGTGCTACGCCAGTTGTCAATGTGATTATCC  800
      H  D  H  G  S  K  R  A  T  P  V  V  N  V  I  I  P   197

801  CTGAAATCGATGGGTTTAACAACACCCTGGACCATAGCACGTGCGTATCT  850
      E  I  D  G  F  N  N  T  L  D  H  S  T  C  V  S      213
                     +

851  TTTGAGAATGATGAGCGGGCGGATGAAATTGAAGCCAATTTCACGGCAAT  900
      F  E  N  D  E  R  A  D  E  I  E  A  N  F  T  A  I   230
                        +

901  TATGGGACCTCCGATCCGCAAACGTCTGGAAAATGACCTCCCTGGCATCA  950
      M  G  P  P  I  R  K  R  L  E  N  D  L  P  G  I  K   247

951  AACTTACAAACGAGAATGTAATATATTTGATGGATATGTGCTCTTTCGAC  1000
      L  T  N  E  N  V  I  Y  L  M  D  M  C  S  F  D      263

1001 ACCATGGCGCGCACCGCCCACGGAACCGAGCTGTCTCCATTTTGTGCCAT  1050
      T  M  A  R  T  A  H  G  T  E  L  S  P  F  C  A  I   280

1051 CTTCACTGAAAAGGAGTGGCTGCAGTACGACTACCTTCAATCTCTATCAA  1100
      F  T  E  K  E  W  L  Q  Y  D  Y  L  Q  S  L  S  K   297

1101 AGTACTACGGCTACGGTGCCGGAAGCCCCCTTGGCCCAGCTCAGGGAATT  1150
      Y  Y  G  Y  G  A  G  S  P  L  G  P  A  Q  G  I      313

1151 GGCTTCACCAACGAGCTGATTGCCCGACTAACGCAATCGCCCGTCCAGGA  1200
      G  F  T  N  E  L  I  A  R  L  T  Q  S  P  V  Q  D   330

1201 CAACACAAGCACCAACCACACTCTAGACTCGAACCCAGCCACATTTCCGC  1250
      N  T  S  T  N  H  T  L  D  S  N  P  A  T  F  P  L   347
          +        +

1251 TCGACAGGAAGCTCTACGCCGACTTCTCCCACGACAATAGCATGATATCG  1300
      D  R  K  L  Y  A  D  F  S  H  D  N  S  M  I  S      363

1301 ATATTCTTCGCCATGGGTCTGTACAACGGCACCCAGCCGCTGTCAATGGA  1350
      I  F  F  A  M  G  L  Y  N  G  T  Q  P  L  S  M  D   380
                        +
```

FIG. 4-2

```
1351  TTCCGTGGAGTCGATCCAGGAGATGGACGGTTACGCGGCGTCTTGGACTG  1400
       S  V  E  S  I  Q  E  M  D  G  Y  A  A  S  W  T  V    397

1401  TTCCGTTTGGTGCGAGGGCTTACTTTGAGCTCATGCAGTGCGAGAAGAAG  1450
       P  F  G  A  R  A  Y  F  E  L  M  Q  C  E  K  K       413

1451  GAGCCGCTTGTGCGGGTATTAGTGAATGATCGCGTTGTTCCTCTTCATGG  1500
       E  P  L  V  R  V  L  V  N  D  R  V  V  P  L  H  G    430

1501  CTGCGCAGTTGACAAGTTTGGACGGTGCACTTTGGACGATTGGGTAGAGG  1550
       C  A  V  D  K  F  G  R  C  T  L  D  D  W  V  E  G    447

1551  GCTTGAATTTTGCAAGGAGCGGCGGGAACTGGAAGACTTGTTTTACCCTA  1600
       L  N  F  A  R  S  G  G  N  W  K  T  C  F  T  L       463

1601  TAAAGGGCGTTTGCTCATTCATAAGTGTTGTGCAGGTATAGGAAGGTTAG  1650
1651  GGAATTAGCTGTTTGGCTTTACTCTTATTAGACCAAGAATGATTTGTTTG  1700
1701  TTCTCAAGGCCTTCTAGCATATCGTCAAGTGGGATAAATCACCTATCCTC  1750
1751  CATGTGTAGGTGAACCCGCTCTTGCATCAACCTCTTGTGTTTCAGAGTAG  1800
1801  TTTCACCAAACATATCCTCGTGTCCTCTCTTCTGCTCTTCGGTCTCATAT  1850
1851  TACACTGTTCTCTATCTATATCGTCAACAAAACTACCACCCAAACACCAA  1900
1901  ATGTCACACTTTCCAGCACGAAATTTCTTCG  1931
```

FIG. 4-3

```
  1  TTCCACGCTGAAAGCCTGACTGCGATTTCCAAGCTGCATGCAGGCTGCTC    50
 51  AACTGCCTGCTTATCTTCATCAGACGCAGATACACAACCTGGTCTGTAGA   100
101  TGCACCCATGACGGACGAACGCACCGCTCTCTTGGCCTCCAGGGACCCGG   150
151  AGGTCGAGGGCGATGAGGTCGCGCCCTCGACGGCCTCCCAGTCCCTGTTG   200
201  CAGTTGAGATCTCGCTGCGAACGTCGACCGCAGATATGGTTGTCTTCGAC   250
251  GTTTTCTCGCCTTCGAGGAAGAATTGCTGCTGTGACGATGAGTCTGTTGT   300
                                            M  S  L  L    5

301  TGCTGGTGCTGTCCGGCGGGTTGGTCGCGTTATAgtatgctccttctctc   350
      L  V  L  S  G  G  L  V  A  L  Y                    16

351  tggtcatattgttttctgctaacgttctcataattgaagTGTCTCAAGAA   400
                                             V  S  R  N   20

401  ATCCGCATGTTGATAGCCACTCTTGCAATACAGTGGAAGGAGGGTATCAG   450
      P  H  V  D  S  H  S  C  N  T  V  E  G  G  Y  Q     36

451  TGTCGTCCAGAAATCTCCCACTCCTGGGGCCAGTATTCTCCATTCTTCTC   500
      C  R  P  E  I  S  H  S  W  G  Q  Y  S  P  F  F  S  53

501  CCTGGCAGACCAGTCGGAGATCTCGCCAGATGTCCCACAGAACTGCAAGA   550
      L  A  D  Q  S  E  I  S  P  D  V  P  Q  N  C  K  I  70

551  TTACGTTTGTCCAGCTGCTTTCTCGTCACGGCGCTAGATACCCTACGTCT   600
      T  F  V  Q  L  L  S  R  H  G  A  R  Y  P  T  S     86

601  TCCAAGACGGAGCTGTATTCGCAGCTGATCAGTCGGATTCAGAAGACGGC   650
      S  K  T  E  L  Y  S  Q  L  I  S  R  I  Q  K  T  A 103

651  GACTGCGTACAAAGGCTACTATGCCTTCTTGAAAGACTACAGATACCAGC   700
      T  A  Y  K  G  Y  Y  A  F  L  K  D  Y  R  Y  Q  L 120

701  TGGGAGCGAACGACCTGACGCCCTTTGGGGAAAACCAGATGATCCAGTTG   750
      G  A  N  D  L  T  P  F  G  E  N  Q  M  I  Q  L    136
```

FIG. 5-1

```
751  GGCATCAAGTTTTATAACCATTACAAGAGTCTCGCCAGGAATGCCGTCCC  800
      G  I  K  F  Y  N  H  Y  K  S  L  A  R  N  A  V  P   153

801  ATTCGTTCGTTGCTCCGGCTCTGATCGGGTCATTGCCTCGGGGAGACTTT  850
      F  V  R  C  S  G  S  D  R  V  I  A  S  G  R  L  F   170

851  TCATCGAAGGTTTCCAGAGCGCCAAAGTGCTGGATCCTCATTCAGACAAG  900
       I  E  G  F  Q  S  A  K  V  L  D  P  H  S  D  K    186

901  CATGACGCTCCTCCCACGATCAACGTGATCATCGAGGAGGGTCCGTCCTA  950
      H  D  A  P  P  T  I  N  V  I  I  E  E  G  P  S  Y   203

951  CAATAACACGCTCGACACCGGCAGCTGTCCAGTCTTTGAGGACAGCAGCG  1000
      N  N  T  L  D  T  G  S  C  P  V  F  E  D  S  S  G   220
      +

1001 GGGGACATGACGCACAGGAAAAGTTCGCAAAGCAATTCGCACCAGCTATC  1050
       G  H  D  A  Q  E  K  F  A  K  Q  F  A  P  A  I    236

1051 CTGGAAAAGATCAAGGACCATCTTCCCGGCGTGGACCTGGCCGTGTCGGA  1100
      L  E  K  I  K  D  H  L  P  G  V  D  L  A  V  S  D   253

1101 TGTACCGTACTTGATGGACTTGTGTCCGTTTGAGACCTTGGCTCGCAACC  1150
      V  P  Y  L  M  D  L  C  P  F  E  T  L  A  R  N  H   270
                                            +

1151 ACACAGACACGCTGTCTCCGTTCTGCGCTCTTTCCACGCAAGAGGAGTGG  1200
      T  D  T  L  S  P  F  C  A  L  S  T  Q  E  E  W     286

1201 CAAGCATATGACTACTACCAAAGTCTGGGGAAATACTATGGCAATGGCGG  1250
      Q  A  Y  D  Y  Y  Q  S  L  G  K  Y  Y  G  N  G  G   303

1251 GGGTAACCCGTTGGGGCCAGCCCAAGGCGTGGGGTTTGTCAACGAGTTGA  1300
      G  N  P  L  G  P  A  Q  G  V  G  F  V  N  E  L  I   320

1301 TTGCTCGCATGACCCATAGCCCTGTCCAGGACTACACCACGGTCAACCAC  1350
      A  R  M  T  H  S  P  V  Q  D  Y  T  T  V  N  H     336
                                                    +

1351 ACTCTTGACTCGAATCCGGCGACATTCCCTTTGAACGCGACGCTGTACGC  1400
      T  L  D  S  N  P  A  T  F  P  L  N  A  T  L  Y  A   353
                              +
```

FIG. 5-2

```
1401 AGATTTCAGCCACGACAACACAATGACGTCAATTTTCGCGGCCTTGGGCC 1450
      D  F  S  H  D  N  T  M  T  S  I  F  A  A  L  G  L  370

1451 TGTACAACGGGACCGCGAAGCTGTCCACGACCGAGATCAAGTCCATTGAA 1500
      Y  N  G  T  A  K  L  S  T  T  E  I  K  S  I  E  386
         +

1501 GAGACGGACGGCTACTCGGCGGCGTGGACCGTTCCGTTCGGGGGGCGAGC 1550
      E  T  D  G  Y  S  A  A  W  T  V  P  F  G  G  R  A  403

1551 CTATATCGAGATGATGCAGTGTGATGATTCGGATGAGCCAGTCGTTCGGG 1600
      Y  I  E  M  M  Q  C  D  D  S  D  E  P  V  V  R  V  420

1601 TGCTGGTCAACGACCGGGTGGTGCCACTGCATGGCTGCGAGGTGGACTCC 1650
      L  V  N  D  R  V  V  P  L  H  G  C  E  V  D  S  436

1651 CTGGGGCGATGCAAACGAGACGACTTTGTCAGGGGACTGAGTTTTGCGCG 1700
      L  G  R  C  K  R  D  D  F  V  R  G  L  S  F  A  R  453

1701 ACAGGGTGGGAACTGGGAGGGGTGTTACGCTGCTTCTGAGTAGGTTTATT 1750
      Q  G  G  N  W  E  G  C  Y  A  A  S  E  *  466

1751 CAGCGAGTTTCGACCTTTCTATCCTTCAAACACTGCACAAAGACACACTG 1800
1801 CATGAAATGGTAACAGGCCTGGAGCGTTTTAGAAGGAAAAAAGTT      1845
```

FIG. 5-3

```
  1  AGATTCAACGACGGAGGAATCGCAACCCTAATTGTCGGTATCATGGTGAC   50
                                                  M V T    3

51  TCTGACTTTCCTGCTTTCGGCGGCGTATCTGCTTTCTGGgtgagtggctt  100
      L  T  F  L  L  S  A  A  Y  L  L  S  G              16

101  ggatctattgctcggatagggctgtggtgctgattctgaaacggagTAGA  150
                                                     R   17

151  GTGTCTGCGGCACCTAGTTCTGCTGGCTCCAAGTCCTGCGATACGGTAGA  200
      V  S  A  A  P  S  S  A  G  S  K  S  C  D  T  V  D  34

201  CCTCGGGTACCAGTGCTCCCCTGCGACTTCTCATCTATGGGGCCAGTACT  250
      L  G  Y  Q  C  S  P  A  T  S  H  L  W  G  Q  Y  S  51

251  CGCCATTCTTTTCGCTCGAGGACGAGCTGTCCGTGTCGAGTAAGCTTCCC  300
      P  F  F  S  L  E  D  E  L  S  V  S  S  K  L  P     67

301  AAGGATTGCCGGATCACCTTGGTACAGGTGCTATCGCGCCATGGAGCGCG  350
      K  D  C  R  I  T  L  V  Q  V  L  S  R  H  G  A  R  84

351  GTACCCAACCAGCTCCAAGAGCAAAAAGTATAAGAAGCTTGTGACGGCGA  400
      Y  P  T  S  S  K  S  K  K  Y  K  K  L  V  T  A  I 101

401  TCCAGGCCAATGCCACCGACTTCAAGGGCAAGTTTGCCTTTTTGAAGACG  450
      Q  A  N  A  T  D  F  K  G  K  F  A  F  L  K  T    117
         +

451  TACAACTATACTCTGGGTGCGGATGACCTCACTCCCTTTGGGGAGCAGCA  500
      Y  N  Y  T  L  G  A  D  D  L  T  P  F  G  E  Q  Q 134
         +

501  GCTGGTGAACTCGGGCATCAAGTTCTACCAGAGGTACAAGGCTCTGGCGC  550
      L  V  N  S  G  I  K  F  Y  Q  R  Y  K  A  L  A  R 151

551  GCAGTGTGGTGCCGTTTATTCGCGCCTCAGGCTCGGACCGGGTTATTGCT  600
      S  V  V  P  F  I  R  A  S  G  S  D  R  V  I  A   167
```

FIG. 6-1

```
601  TCGGGAGAGAAGTTCATCGAGGGGTTCCAGCAGGCGAAGCTGGCTGATCC  650
      S  G  E  K  F  I  E  G  F  Q  Q  A  K  L  A  D  P    184

651  TGGCGCGACGAACCGCGCCGCTCCGGCGATTAGTGTGATTATTCCGGAGA  700
      G  A  T  N  R  A  A  P  A  I  S  V  I  I  P  E  S    201

701  GCGAGACGTTCAACAATACGCTGGACCACGGTGTGTGCACGAAGTTTGAG  750
      E  T  F  N  N  T  L  D  H  G  V  C  T  K  F  E       217
              +

751  GCGAGTCAGCTGGGAGATGAGGTTGCGGCCAATTTCACTGCGCTCTTTGC  800
      A  S  Q  L  G  D  E  V  A  A  N  F  T  A  L  F  A    234
                                    +

801  ACCCGACATCCGAGCTCGCGCCGAGAAGCATCTTCCTGGCGTGACGCTGA  850
      P  D  I  R  A  R  A  E  K  H  L  P  G  V  T  L  T    251

851  CAGACGAGGACGTTGTCAGTCTAATGGACATGTGTTCGTTTGATACGGTA  900
      D  E  D  V  V  S  L  M  D  M  C  S  F  D  T  V       267

901  GCGCGCACCAGCGACGCAAGTCAGCTGTCACCGTTCTGTCAACTCTTCAC  950
      A  R  T  S  D  A  S  Q  L  S  P  F  C  Q  L  F  T    284

951  TCACAATGAGTGGAAGAAGTACAACTACCTTCAGTCCTTGGGCAAGTACT  1000
      H  N  E  W  K  K  Y  N  Y  L  Q  S  L  G  K  Y  Y    301

1001 ACGGCTACGGCGCAGGCAACCCTCTGGGACCGGCTCAGGGGATAGGGTTC  1050
      G  Y  G  A  G  N  P  L  G  P  A  Q  G  I  G  F       317

1051 ACCAACGAGCTGATTGCCCGGTTGACTCGTTCGCCAGTGCAGGACCACAC  1100
      T  N  E  L  I  A  R  L  T  R  S  P  V  Q  D  H  T    334

1101 CAGCACTAACTCGACTCTAGTCTCCAACCCGGCCACCTTCCCGTTGAACG  1150
      S  T  N  S  T  L  V  S  N  P  A  T  F  P  L  N  A    351
         +                                         +

1151 CTACCATGTACGTCGACTTTTCACACGACAACAGCATGGTTTCCATCTTC  1200
      T  M  Y  V  D  F  S  H  D  N  S  M  V  S  I  F       367

1201 TTTGCATTGGGCCTGTACAACGGCACTGAACCCTTGTCCCGGACCTCGGT  1250
      F  A  L  G  L  Y  N  G  T  E  P  L  S  R  T  S  V    384
                        +
```

FIG. 6-2

```
1251  GGAAAGCGCCAAGGAATTGGATGGGTATTCTGCATCCTGGGTGGTGCCTT  1300
       E  S  A  K  E  L  D  G  Y  S  A  S  W  V  V  P  F   401

1301  TCGGCGCGCGAGCCTACTTCGAGACGATGCAATGCAAGTCGGAAAAGGAG  1350
       G  A  R  A  Y  F  E  T  M  Q  C  K  S  E  K  E      417

1351  CCTCTTGTTCGCGCTTTGATTAATGACCGGGTTGTGCCACTGCATGGCTG  1400
       P  L  V  R  A  L  I  N  D  R  V  V  P  L  H  G  C   434

1401  CGATGTGGACAAGCTGGGGCGATGCAAGCTGAATGACTTTGTCAAGGGAT  1450
       D  V  D  K  L  G  R  C  K  L  N  D  F  V  K  G  L   451

1451  TGAGTTGGGCCAGATCTGGGGGCAACTGGGGAGAGTGCTTTAGTTGAGAT  1500
       S  W  A  R  S  G  G  N  W  G  E  C  F  S  *         465

1501  GTCATTGTTATGCTATACTCCAATAGACCGTTGCTTAGCCATTCACTTCA  1550
1551  CTTTGCTCGAACCGCCTGCCG                               1571
```

FIG. 6-3

```
  1 ACGTCCCAGGTCGGGGACTACATCCGCTATGTGGTCCTCTACTTCGTCGG    50
 51 AAGAATATACTGTCTCTTGTGGCTACCATGGGGGTTTTCGTCGTTCTATT   100
                          M  G  V  F  V  V  L  L         8

101 ATCTATCGCGACTCTGTTCGGCAGgtatgtgcaccgctctaggttcaact   150
     S  I  A  T  L  F  G  S                             16

151 cgcctggtaactgacaaacagcacagCACATCGGGCACTGCGCTGGGCCC   200
                              T  S  G  T  A  L  G  P     24

201 CCGTGGAAATCACAGCGACTGCACCTCAGTCGACCGGGGGTATCAATGCT   250
     R  G  N  H  S  D  C  T  S  V  D  R  G  Y  Q  C  F  41
        +

251 TCCCTGAGCTCTCCCATAAATGGGGTCTCTACGCGCCCTATTTCTCCCTC   300
     P  E  L  S  H  K  W  G  L  Y  A  P  Y  F  S  L     57

301 CAGGATGAATCTCCGTTTCCTCTGGACGTCCCGGATGACTGCCACATCAC   350
     Q  D  E  S  P  F  P  L  D  V  P  D  D  C  H  I  T  74

351 CTTTGTGCAGGTGCTGGCCCGACATGGAGCGCGGTCTCCAACCGATAGCA   400
     F  V  Q  V  L  A  R  H  G  A  R  S  P  T  D  S  K  91

401 AGACAAAGGCGTATGCCGCGACTATTGCAGCCATCCAGAAGAATGCCACC   450
     T  K  A  Y  A  A  T  I  A  A  I  Q  K  N  A  T    107
                                            +

451 GCGTTGCCGGGCAAATACGCCTTCCTGAAGTCGTACAATTACTCCATGGG   500
     A  L  P  G  K  Y  A  F  L  K  S  Y  N  Y  S  M  G 124
                                     +

501 CTCCGAGAACCTGAACCCCTTCGGGCGGAACCAACTGCAAGATCTGGGCG   550
     S  E  N  L  N  P  F  G  R  N  Q  L  Q  D  L  G  A 141

551 CCCAGTTCTACCGTCGCTACGACACCCTCACCCGGCACATCAACCCTTTC   600
     Q  F  Y  R  R  Y  D  T  L  T  R  H  I  N  P  F   157

601 GTCCGGGCCGCGGATTCCTCCCGCGTCCACGAATCAGCCGAGAAGTTCGT   650
     V  R  A  A  D  S  S  R  V  H  E  S  A  E  K  F  V 174
```

FIG. 7-1

```
651  CGAGGGCTTCCAAAACGCCCGCCAAGGCGATCCTCACGCCAACCCTCACC  700
      E  G  F  Q  N  A  R  Q  G  D  P  H  A  N  P  H  Q   191

701  AGCCGTCGCCGCGCGTGGATGTAGTCATCCCCGAAGGCACCGCCTACAAC  750
      P  S  P  R  V  D  V  V  I  P  E  G  T  A  Y  N    207
                                                    +

751  AACACGCTCGAGCACAGCATCTGCACCGCCTTCGAGGCCAGCACCGTCGG  800
      N  T  L  E  H  S  I  C  T  A  F  E  A  S  T  V  G  224

801  CGACGCCGCGGCAGACAACTTCACTGCCGTGTTCGCGCCGGCGATCGCCA  850
      D  A  A  A  D  N  F  T  A  V  F  A  P  A  I  A  K  241
                  +

851  AGCGTCTGGAGGCCGATCTGCCCGGCGTGCAGCTGTCCGCCGACGACGTG  900
      R  L  E  A  D  L  P  G  V  Q  L  S  A  D  D  V    257

901  GTCAATCTGATGGCCATGTGTCCGTTCGAGACGGTCAGCCTGACCGACGA  950
      V  N  L  M  A  M  C  P  F  E  T  V  S  L  T  D  D  274

951  CGCGCACACGCTGTCGCCGTTCTGCGACCTCTTCACCGCCGCCGAGTGGA  1000
      A  H  T  L  S  P  F  C  D  L  F  T  A  A  E  W  T  291

1001 CGCAGTACAACTACCTGCTCTCGCTGGACAAGTACTACGGCTACGGCGGC  1050
      Q  Y  N  Y  L  L  S  L  D  K  Y  Y  G  Y  G  G    307

1051 GGCAATCCGCTGGGCCCCGTGCAGGGCGTGGGCTGGGCGAACGAGCTGAT  1100
      G  N  P  L  G  P  V  Q  G  V  G  W  A  N  E  L  I  324

1101 CGCGCGGCTGACGCGCTCCCCCGTCCACGACCACACCTGCGTCAACAACA  1150
      A  R  L  T  R  S  P  V  H  D  H  T  C  V  N  N  T  341
                                                       +

1151 CCCTCGACGCCAACCCGGCCACCTTCCCGCTGAACGCCACCCTCTACGCG  1200
      L  D  A  N  P  A  T  F  P  L  N  A  T  L  Y  A    357
                                           +

1201 GACTTTTCGCACGACAGTAACCTGGTGTCGATCTTCTGGGCGCTGGGTCT  1250
      D  F  S  H  D  S  N  L  V  S  I  F  W  A  L  G  L  374
```

FIG. 7-2

```
1251  GTACAACGGCACCAAGCCCCTGTCGCAGACCACCGTGGAGGATATCACCC  1300
       Y  N  G  T  K  P  L  S  Q  T  T  V  E  D  I  T  R   391
          +

1301  GGACGGACGGGTACGCGGCCGCCTGGACGGTGCCGTTTGCCGCCCGCGCC  1350
       T  D  G  Y  A  A  A  W  T  V  P  F  A  A  R  A     407

1351  TACATCGAGATGATGCAGTGTCGCGCGGAGAAGCAGCCGCTGGTGCGCGT  1400
       Y  I  E  M  M  Q  C  R  A  E  K  Q  P  L  V  R  V  424

1401  GCTGGTCAACGACCGTGTCATGCCGCTGCACGGCTGCGCGGTGGATAATC  1450
       L  V  N  D  R  V  M  P  L  H  G  C  A  V  D  N  L  441

1451  TGGGCAGGTGTAAACGGGACGACTTTGTGGAGGGACTGAGCTTTGCGCGG  1500
        G  R  C  K  R  D  D  F  V  E  G  L  S  F  A  R    457

1501  GCAGGAGGGAACTGGGCCGAGTGTTTCTGATGTACATGCTGTAGTTAGCT  1550
       A  G  G  N  W  A  E  C  F  *                       466

1551  TTGAGTCCTGAGGTACC                                    1567
```

FIG. 7-3

```
HEADER    PHOSOHOMONOESTERASE                                            1DIK   1
COMPND    PHYTASE (E.C.3.1.3.8)                                          1DIK   2
SOURCE    (Aspergillus ficuum)                                           1DIK   3
                                                                         1DIK   4
                                                                         1DIK   5
REMARK   2 RESOLUTION. 2.5 ANGSTROMS.                                    1DIK   6
REMARK   3                                                               1DIK   7
REMARK   3 REFINEMENT.                                                   1DIK   8
REMARK   3   PROGRAM                   X-PLOR                            1DIK   9
REMARK   3   AUTHORS                   BRUENGER, A.T.                    1DIK  10
REMARK   3   R VALUE                   0.155                             1DIK  11
REMARK   3   FREE R VALUE              0.211                             1DIK  12
REMARK   3   RMSD BOND DISTANCES       0.009   ANGSTROMS                 1DIK  13
REMARK   3   RMSD BOND ANGLES          1.5     DEGREES                   1DIK  14
REMARK   3                                                               1DIK  15
REMARK   3   NUMBER OF REFLECTIONS     17206                             1DIK  16
REMARK   3   RESOLUTION RANGE      20.0 -2.5   ANGSTROMS                 1DIK  17
REMARK   3   DATA CUTOFF               0.      SIGMA (F)                 1DIK  18
REMARK   3                                                               1DIK  19
REMARK   3   NUMBER OF PROTEIN ATOMS                      3369           1DIK  20
REMARK   3   NUMBER OF SOLVENT ATOMS                       115           1DIK  21
REMARK   3   NUMBER OF SULFATE ATOMS                         5           1DIK  22
REMARK   3                                                               1DIK  23
REMARK   3 CONVENTIONAL RESTRAINED POSITIONAL AND TEMPERATURE FACTOR     1DIK  24
REMARK   3 REFINEMENT.                                                   1DIK  25
REMARK   3 THE STEREOCHEMICAL PARAMETERS FROM ENGH & HUBER WERE USED.    1DIK  26
REMARK   4                                                               1DIK  27
REMARK   5                                                               1DIK  42
REMARK   5 THE ASYMMETRIC UNIT OF THE CRYSTAL CONTAINS OF ONE            1DIK  43
REMARK   5 DEGLYCOSYLATED PROTEIN MONOMER.                               1DIK  44
REMARK   6                                                               1DIK  45
REMARK   6 THE AMINO ACIDS 249 - 252 ARE COMPLETELY DISORDERED.          1DIK  46
REMARK   6 THE FOLLOWING AMINO ACID SIDE CHAINS ARE DISORDERED:          1DIK  47
REMARK   6 GLU  43, LYS 70, GLU 77, GLN 81, LYS 94, GLN 392, GLN 395,    1DIK  48
REMARK   6 ARG 428                                                       1DIK  49
REMARK   6 THE ELECTRON DENSITY OF THE SULFATE IS NOT WELL DEFINED.      1DIK  50
SEQRES   1    434  SER CYS ASP THR VAL ASP GLN GLY TYR GLN CYS PHE SER   1DIK  51
SEQRES   2    434  GLU THR SER HIS LEU TRP GLY GLN TYR ALA PRO PHE PHE   1DIK  52
SEQRES   3    434  SER LEU ALA ASN GLU SER VAL ILE SER PRO GLU VAL PRO   1DIK  53
SEQRES   4    434  ALA GLY CYS ARG VAL THR PHE ALA GLN VAL LEU SER ARG   1DIK  54
SEQRES   5    434  HIS GLY ALA ARG TYR PRO THR ASP SER LYS GLY LYS LYS   1DIK  55
SEQRES   6    434  TYR SER ALA LEU ILE GLU GLU ILE GLN GLN ASN ALA THR   1DIK  56
SEQRES   7    434  THR PHE ASP GLY LYS TYR ALA PHE LEU LYS THR TYR ASN   1DIK  57
SEQRES   8    434  TYR SER LEU GLY ALA ASP ASP LEU THR PRO PHE GLY GLU   1DIK  58
SEQRES   9    434  GLN GLU LEU VAL ASN SER GLY ILE LYS PHE TYR GLN ARG   1DIK  59
SEQRES  10    434  TYR GLU SER LEU THR ARG ASN ILE VAL PRO PHE ILE ARG   1DIK  60
SEQRES  11    434  SER SER GLY SER SER ARG VAL ILE ALA SER GLY LYS LYS   1DIK  61
SEQRES  12    434  PHE ILE GLU GLY PHE GLN SER THR LYS LEU LYS ASP PRO   1DIK  62
SEQRES  13    434  ARG ALA GLN PRO GLY GLN SER SER PRO LYS ILE ASP VAL   1DIK  63
SEQRES  14    434  VAL ILE SER GLU ALA SER SER SER ASN ASN THR LEU ASP   1DIK  64
SEQRES  15    434  PRO GLY THR CYS THR VAL PHE GLU ASP SER GLU LEU ALA   1DIK  65
SEQRES  16    434  ASP THR VAL GLU ALA ASN PHE THR ALA THR PHE VAL PRO   1DIK  66
SEQRES  17    434  SER ILE ARG GLN ARG LEU GLU ASN ASP LEU SER GLY VAL   1DIK  67
SEQRES  18    434  THR LEU THR ASP THR GLU VAL THR TYR LEU MET ASP MET  1DIK  68
SEQRES  19    434  CYS SER PHE ASP THR ILE SER THR THR LYS LEU SER PRO  1DIK  69
SEQRES  20    434  PHE CYS ASP LEU PHE THR HIS ASP GLU TRP ILE ASN TYR  1DIK  70
SEQRES  21    434  ASP TYR LEU GLN SER LEU LYS LYS TYR TYR GLY HIS GLY  1DIK  71
SEQRES  22    434  ALA GLY ASN PRO LEU GLY PRO THR GLN GLY VAL GLY TYR  1DIK  72
SEQRES  23    434  ALA ASN GLU LEU ILE ALA ARG LEU THR HIS SER PRO VAL  1DIK  73
SEQRES  24    434  HIS ASP ASP THR SER SER ASN HIS THR LEU ASP SER SER  1DIK  74
SEQRES  25    434  PRO ALA THR PHE PRO LEU ASN SER THR LEU TYR ALA ASP  1DIK  75
SEQRES  26    434  PHE SER HIS ASP ASN GLY ILE ILE SER ILE LEU PHE ALA  1DIK  76
SEQRES  27    434  LEU GLY LEU TYR ASN GLY THR LYS PRO LEU SER THR THR  1DIK  77
SEQRES  28    434  THR VAL GLU ASN ILE THR GLN THR ASP GLY PHE SER SER  1DIK  78
SEQRES  29    434  ALA TRP THR VAL PRO PHE ALA SER ARG LEU TYR VAL GLU  1DIK  79
SEQRES  30    434  MET MET GLN CYS GLN ALA GLU GLN GLU PRO LEU VAL ARG  1DIK  80
```

FIG. 8-1

```
SEQRES  31  434  VAL LEU VAL ASN ASP ARG VAL VAL PRO LEU HIS GLY CYS    1DIK  81
SEQRES  32  434  PRO VAL ASP ALA LEU GLY ARG CYS THR ARG ASP SER PHE    1DIK  82
SEQRES  33  434  VAL ARG GLY LEU SER PHE ALA ARG SER GLY GLY ASP TRP    1DIK  83
SEQRES  34  434  ALA GLU CYS PHE ALA                                    1DIK  84
HET    SO4   201       5                                                1DIK  85
FORMUL  2  SO4      O4 S1                                               1DIK  86
FORMUL  3  HOH    *115 (H2 O1)                                          1DIK  87
SSBOND  1 CYS      8    CYS     17                                      1DIK  88
SSBOND  2 CYS     48    CYS    391                                      1DIK  89
SSBOND  3 CYS    192    CYS    442                                      1DIK  90
SSBOND  4 CYS    241    CYS    259                                      1DIK  91
SSBOND  5 CYS    413    CYS    421                                      1DIK  92
CRYST1   92.250   92.250  100.890  90.00  90.00 120.00 P 3 2 1       6  1DIK  93
ATOM      1  N   SER     7     -18.097  39.685   9.811  1.00 62.21      1DIK  94
ATOM      2  CA  SER     7     -17.205  40.761   9.300  1.00 63.47      1DIK  95
ATOM      3  C   SER     7     -16.157  41.230  10.307  1.00 63.25      1DIK  96
ATOM      4  O   SER     7     -15.210  41.924   9.918  1.00 63.40      1DIK  97
ATOM      5  CB  SER     7     -18.027  41.947   8.800  1.00 64.21      1DIK  98
ATOM      6  OG  SER     7     -18.983  41.499   7.850  1.00 69.41      1DIK  99
ATOM      7  N   CYS     8     -16.314  40.885  11.590  1.00 60.09      1DIK 100
ATOM      8  CA  CYS     8     -15.278  41.262  12.561  1.00 57.19      1DIK 101
ATOM     10  C   CYS     8     -14.528  40.052  13.134  1.00 54.36      1DIK 102
ATOM     11  O   CYS     8     -13.593  40.225  13.913  1.00 54.16      1DIK 103
ATOM     12  CB  CYS     8     -15.738  42.278  13.657  1.00 55.87      1DIK 104
ATOM     13  SG  CYS     8     -17.414  42.211  14.391  1.00 47.31      1DIK 105
ATOM     14  N   ASP     9     -14.945  38.838  12.748  1.00 49.46      1DIK 106
ATOM     15  CA  ASP     9     -14.217  37.609  13.109  1.00 44.53      1DIK 107
ATOM     16  C   ASP     9     -13.647  37.121  11.763  1.00 43.95      1DIK 108
ATOM     17  O   ASP     9     -14.380  36.543  10.956  1.00 45.30      1DIK 109
ATOM     18  CB  ASP     9     -15.112  36.512  13.687  1.00 36.86      1DIK 110
ATOM     19  CG  ASP     9     -14.324  35.205  13.981  1.00 43.08      1DIK 111
ATOM     20  OD1 ASP     9     -13.169  35.246  14.466  1.00 36.37      1DIK 112
ATOM     21  OD2 ASP     9     -14.860  34.107  13.725  1.00 53.20      1DIK 113
ATOM     22  N   THR    10     -12.360  37.357  11.515  1.00 39.20      1DIK 114
ATOM     23  CA  THR    10     -11.744  36.961  10.248  1.00 34.97      1DIK 115
ATOM     24  C   THR    10     -10.770  35.792  10.388  1.00 35.15      1DIK 116
ATOM     25  O   THR    10     -10.407  35.410  11.502  1.00 32.93      1DIK 117
ATOM     26  CB  THR    10     -10.988  38.148   9.605  1.00 32.39      1DIK 118
ATOM     27  OG1 THR    10      -9.967  38.612  10.500  1.00 36.02      1DIK 119
ATOM     28  CG2 THR    10     -11.937  39.286   9.319  1.00 24.30      1DIK 120
ATOM     29  N   VAL    11     -10.352  35.228   9.256  1.00 35.93      1DIK 121
ATOM     30  CA  VAL    11      -9.398  34.123   9.261  1.00 35.37      1DIK 122
ATOM     31  C   VAL    11      -8.050  34.591   9.798  1.00 36.90      1DIK 123
ATOM     32  O   VAL    11      -7.442  33.912  10.623  1.00 38.05      1DIK 124
ATOM     33  CB  VAL    11      -9.196  33.528   7.840  1.00 36.34      1DIK 125
ATOM     34  CG1 VAL    11      -7.982  32.584   7.806  1.00 29.66      1DIK 126
ATOM     35  CG2 VAL    11     -10.440  32.772   7.429  1.00 36.52      1DIK 127
ATOM     36  N   ASP    12      -7.585  35.749   9.334  1.00 36.93      1DIK 128
ATOM     37  CA  ASP    12      -6.298  36.277   9.774  1.00 35.36      1DIK 129
ATOM     38  C   ASP    12      -6.298  37.009  11.094  1.00 32.61      1DIK 130
ATOM     39  O   ASP    12      -5.449  36.757  11.930  1.00 31.31      1DIK 131
ATOM     40  CB  ASP    12      -5.698  37.195   8.712  1.00 44.11      1DIK 132
ATOM     41  CG  ASP    12      -4.974  36.428   7.629  1.00 54.17      1DIK 133
ATOM     42  OD1 ASP    12      -3.831  35.998   7.891  1.00 59.05      1DIK 134
ATOM     43  OD2 ASP    12      -5.540  36.252   6.523  1.00 57.68      1DIK 135
ATOM     44  N   GLN    13      -7.241  37.918  11.294  1.00 31.17      1DIK 136
ATOM     45  CA  GLN    13      -7.251  38.684  12.530  1.00 31.70      1DIK 137
ATOM     46  C   GLN    13      -7.944  38.049  13.741  1.00 30.12      1DIK 138
ATOM     47  O   GLN    13      -7.706  38.450  14.879  1.00 26.40      1DIK 139
ATOM     48  CB  GLN    13      -7.804  40.090  12.265  1.00 38.39      1DIK 140
ATOM     49  CG  GLN    13      -6.865  40.982  11.450  1.00 44.04      1DIK 141
ATOM     50  CD  GLN    13      -5.467  41.085  12.071  1.00 53.25      1DIK 142
ATOM     51  OE1 GLN    13      -5.251  41.806  13.055  1.00 56.16      1DIK 143
ATOM     52  NE2 GLN    13      -4.510  40.357  11.497  1.00 59.15      1DIK 144
ATOM     53  N   GLY    14      -8.792  37.057  13.520  1.00 26.13      1DIK 145
ATOM     54  CA  GLY    14      -9.476  36.460  14.648  1.00 23.53      1DIK 146
```

FIG. 8-2

```
ATOM     55   C    GLY    14     -10.684  37.301  15.001  1.00  23.28      1DIK 147
ATOM     56   O    GLY    14     -11.198  38.031  14.162  1.00  21.73      1DIK 148
ATOM     57   N    TYR    15     -11.137  37.211  16.241  1.00  26.17      1DIK 149
ATOM     58   CA   TYR    15     -12.312  37.944  16.682  1.00  27.82      1DIK 150
ATOM     59   C    TYR    15     -12.033  39.383  17.139  1.00  29.70      1DIK 151
ATOM     60   O    TYR    15     -11.437  39.617  18.200  1.00  30.97      1DIK 152
ATOM     61   CB   TYR    15     -12.986  37.154  17.786  1.00  27.03      1DIK 153
ATOM     62   CG   TYR    15     -14.380  37.607  18.120  1.00  31.13      1DIK 154
ATOM     63   CD1  TYR    15     -15.471  37.146  17.386  1.00  30.29      1DIK 155
ATOM     64   CD2  TYR    15     -14.620  38.456  19.203  1.00  29.69      1DIK 156
ATOM     65   CE1  TYR    15     -16.767  37.512  17.721  1.00  33.21      1DIK 157
ATOM     66   CE2  TYR    15     -15.912  38.829  19.549  1.00  30.40      1DIK 158
ATOM     67   CZ   TYR    15     -16.982  38.355  18.808  1.00  34.78      1DIK 159
ATOM     68   OH   TYR    15     -18.266  38.709  19.151  1.00  36.84      1DIK 160
ATOM     69   N    GLN    16     -12.482  40.336  16.327  1.00  28.71      1DIK 161
ATOM     70   CA   GLN    16     -12.293  41.760  16.583  1.00  31.69      1DIK 162
ATOM     71   C    GLN    16     -13.566  42.534  16.957  1.00  30.38      1DIK 163
ATOM     72   O    GLN    16     -13.543  43.754  17.038  1.00  35.26      1DIK 164
ATOM     73   CB   GLN    16     -11.616  42.419  15.367  1.00  32.17      1DIK 165
ATOM     74   CG   GLN    16     -10.250  41.819  14.974  1.00  34.26      1DIK 166
ATOM     75   CD   GLN    16      -9.212  41.894  16.098  1.00  40.25      1DIK 167
ATOM     76   OE1  GLN    16      -9.300  42.740  16.991  1.00  44.10      1DIK 168
ATOM     77   NE2  GLN    16      -8.227  41.003  16.060  1.00  37.91      1DIK 169
ATOM     78   N    CYS    17     -14.673  41.836  17.182  1.00  32.53      1DIK 170
ATOM     79   CA   CYS    17     -15.934  42.483  17.563  1.00  34.82      1DIK 171
ATOM     80   C    CYS    17     -15.880  42.811  19.062  1.00  32.69      1DIK 172
ATOM     81   O    CYS    17     -15.355  42.015  19.843  1.00  34.59      1DIK 173
ATOM     82   CB   CYS    17     -17.131  41.544  17.323  1.00  40.76      1DIK 174
ATOM     83   SG   CYS    17     -17.305  40.688  15.705  1.00  49.21      1DIK 175
ATOM     84   N    PHE    18     -16.413  43.965  19.464  1.00  28.18      1DIK 176
ATOM     85   CA   PHE    18     -16.446  44.383  20.882  1.00  26.43      1DIK 177
ATOM     86   C    PHE    18     -15.108  44.212  21.611  1.00  26.33      1DIK 178
ATOM     87   O    PHE    18     -15.098  43.898  22.798  1.00  30.47      1DIK 179
ATOM     88   CB   PHE    18     -17.499  43.579  21.665  1.00  20.51      1DIK 180
ATOM     89   CG   PHE    18     -18.754  43.278  20.892  1.00  19.05      1DIK 181
ATOM     90   CD1  PHE    18     -19.677  44.275  20.610  1.00  21.82      1DIK 182
ATOM     91   CD2  PHE    18     -19.014  41.988  20.447  1.00  16.40      1DIK 183
ATOM     92   CE1  PHE    18     -20.850  43.991  19.892  1.00  21.59      1DIK 184
ATOM     93   CE2  PHE    18     -20.180  41.691  19.729  1.00  19.40      1DIK 185
ATOM     94   CZ   PHE    18     -21.100  42.695  19.451  1.00  21.61      1DIK 186
ATOM     95   N    SER    19     -13.997  44.422  20.912  1.00  29.30      1DIK 187
ATOM     96   CA   SER    19     -12.648  44.228  21.461  1.00  30.72      1DIK 188
ATOM     97   C    SER    19     -12.361  44.754  22.857  1.00  31.50      1DIK 189
ATOM     98   O    SER    19     -11.619  44.128  23.617  1.00  32.76      1DIK 190
ATOM     99   CB   SER    19     -11.603  44.799  20.500  1.00  28.75      1DIK 191
ATOM    100   OG   SER    19     -11.757  46.201  20.381  1.00  33.48      1DIK 192
ATOM    101   N    GLU    20     -12.939  45.899  23.192  1.00  31.46      1DIK 193
ATOM    102   CA   GLU    20     -12.715  46.498  24.497  1.00  34.60      1DIK 194
ATOM    103   C    GLU    20     -13.323  45.653  25.626  1.00  33.63      1DIK 195
ATOM    104   O    GLU    20     -12.963  45.832  26.786  1.00  35.88      1DIK 196
ATOM    105   CB   GLU    20     -13.214  47.961  24.522  1.00  36.86      1DIK 197
ATOM    106   CG   GLU    20     -14.736  48.175  24.598  1.00  47.02      1DIK 198
ATOM    107   CD   GLU    20     -15.534  47.635  23.389  1.00  56.13      1DIK 199
ATOM    108   OE1  GLU    20     -15.103  47.815  22.218  1.00  56.48      1DIK 200
ATOM    109   OE2  GLU    20     -16.615  47.025  23.618  1.00  58.06      1DIK 201
ATOM    110   N    THR    21     -14.234  44.736  25.288  1.00  30.34      1DIK 202
ATOM    111   CA   THR    21     -14.861  43.832  26.267  1.00  27.14      1DIK 203
ATOM    112   C    THR    21     -14.525  42.355  25.983  1.00  26.26      1DIK 204
ATOM    113   O    THR    21     -14.048  41.641  26.868  1.00  24.39      1DIK 205
ATOM    114   CB   THR    21     -16.405  43.965  26.272  1.00  26.34      1DIK 206
ATOM    115   OG1  THR    21     -16.758  45.337  26.448  1.00  32.63      1DIK 207
ATOM    116   CG2  THR    21     -17.026  43.137  27.395  1.00  15.06      1DIK 208
ATOM    117   N    SER    22     -14.763  41.903  24.750  1.00  24.89      1DIK 209
ATOM    118   CA   SER    22     -14.533  40.506  24.377  1.00  21.13      1DIK 210
ATOM    119   C    SER    22     -13.105  40.015  24.621  1.00  20.85      1DIK 211
ATOM    120   O    SER    22     -12.896  38.837  24.919  1.00  19.87      1DIK 212
```

FIG. 8-3

```
ATOM    121  CB  SER    22     -14.924  40.282  22.918  1.00 16.59     1DIK 213
ATOM    122  OG  SER    22     -14.015  40.939  22.044  1.00 23.72     1DIK 214
ATOM    123  N   HIS    23     -12.126  40.911  24.497  1.00 20.46     1DIK 215
ATOM    124  CA  HIS    23     -10.726  40.555  24.708  1.00 20.05     1DIK 216
ATOM    125  C   HIS    23     -10.329  40.455  26.183  1.00 24.47     1DIK 217
ATOM    126  O   HIS    23      -9.196  40.084  26.496  1.00 25.61     1DIK 218
ATOM    127  CB  HIS    23      -9.800  41.536  23.982  1.00 17.77     1DIK 219
ATOM    128  CG  HIS    23      -9.861  41.426  22.484  1.00 24.57     1DIK 220
ATOM    129  ND1 HIS    23      -8.936  42.020  21.651  1.00 20.40     1DIK 221
ATOM    130  CD2 HIS    23     -10.746  40.795  21.670  1.00 23.97     1DIK 222
ATOM    131  CE1 HIS    23      -9.247  41.764  20.392  1.00 20.67     1DIK 223
ATOM    132  NE2 HIS    23     -10.340  41.022  20.376  1.00 23.06     1DIK 224
ATOM    133  N   LEU    24     -11.263  40.776  27.081  1.00 25.15     1DIK 225
ATOM    134  CA  LEU    24     -11.025  40.716  28.524  1.00 24.99     1DIK 226
ATOM    135  C   LEU    24     -11.739  39.538  29.210  1.00 27.65     1DIK 227
ATOM    136  O   LEU    24     -11.984  39.575  30.421  1.00 25.05     1DIK 228
ATOM    137  CB  LEU    24     -11.455  42.034  29.176  1.00 22.74     1DIK 229
ATOM    138  CG  LEU    24     -10.626  43.258  28.774  1.00 22.62     1DIK 230
ATOM    139  CD1 LEU    24     -11.264  44.509  29.324  1.00 23.25     1DIK 231
ATOM    140  CD2 LEU    24      -9.211  43.126  29.281  1.00 15.42     1DIK 232
ATOM    141  N   TRP    25     -12.062  38.496  28.437  1.00 26.64     1DIK 233
ATOM    142  CA  TRP    25     -12.744  37.317  28.961  1.00 21.87     1DIK 234
ATOM    143  C   TRP    25     -11.811  36.148  29.357  1.00 22.59     1DIK 235
ATOM    144  O   TRP    25     -12.283  35.040  29.625  1.00 22.32     1DIK 236
ATOM    145  CB  TRP    25     -13.804  36.845  27.951  1.00 22.87     1DIK 237
ATOM    146  CG  TRP    25     -14.977  37.813  27.754  1.00 25.99     1DIK 238
ATOM    147  CD1 TRP    25     -15.376  38.805  28.615  1.00 22.03     1DIK 239
ATOM    148  CD2 TRP    25     -15.880  37.877  26.626  1.00 23.51     1DIK 240
ATOM    149  NE1 TRP    25     -16.459  39.475  28.094  1.00 22.08     1DIK 241
ATOM    150  CE2 TRP    25     -16.792  38.931  26.877  1.00 24.34     1DIK 242
ATOM    151  CE3 TRP    25     -16.004  37.150  25.425  1.00 25.98     1DIK 243
ATOM    152  CZ2 TRP    25     -17.821  39.280  25.973  1.00 20.60     1DIK 244
ATOM    153  CZ3 TRP    25     -17.034  37.500  24.517  1.00 21.02     1DIK 245
ATOM    154  CH2 TRP    25     -17.923  38.555  24.804  1.00 20.24     1DIK 246
ATOM    155  N   GLY    26     -10.499  36.384  29.403  1.00 20.85     1DIK 247
ATOM    156  CA  GLY    26      -9.566  35.322  29.757  1.00 21.54     1DIK 248
ATOM    157  C   GLY    26      -9.676  34.138  28.806  1.00 21.52     1DIK 249
ATOM    158  O   GLY    26      -9.642  34.319  27.590  1.00 19.25     1DIK 250
ATOM    159  N   GLN    27      -9.819  32.927  29.346  1.00 23.90     1DIK 251
ATOM    160  CA  GLN    27      -9.946  31.740  28.503  1.00 24.89     1DIK 252
ATOM    161  C   GLN    27     -11.340  31.566  27.902  1.00 24.51     1DIK 253
ATOM    162  O   GLN    27     -11.600  30.573  27.226  1.00 25.98     1DIK 254
ATOM    163  CB  GLN    27      -9.535  30.455  29.245  1.00 23.84     1DIK 255
ATOM    164  CG  GLN    27     -10.472  29.995  30.323  1.00 21.01     1DIK 256
ATOM    165  CD  GLN    27     -10.344  30.823  31.573  1.00 27.35     1DIK 257
ATOM    166  OE1 GLN    27      -9.452  31.671  31.694  1.00 31.10     1DIK 258
ATOM    167  NE2 GLN    27     -11.231  30.588  32.517  1.00 32.00     1DIK 259
ATOM    168  N   TYR    28     -12.241  32.516  28.156  1.00 25.51     1DIK 260
ATOM    169  CA  TYR    28     -13.592  32.472  27.578  1.00 23.43     1DIK 261
ATOM    170  C   TYR    28     -13.647  33.499  26.433  1.00 24.19     1DIK 262
ATOM    171  O   TYR    28     -14.716  33.779  25.867  1.00 24.91     1DIK 263
ATOM    172  CB  TYR    28     -14.673  32.787  28.624  1.00 20.52     1DIK 264
ATOM    173  CG  TYR    28     -14.797  31.767  29.727  1.00 21.45     1DIK 265
ATOM    174  CD1 TYR    28     -14.609  30.402  29.480  1.00 25.41     1DIK 266
ATOM    175  CD2 TYR    28     -15.091  32.164  31.027  1.00 26.26     1DIK 267
ATOM    176  CE1 TYR    28     -14.711  29.462  30.506  1.00 24.86     1DIK 268
ATOM    177  CE2 TYR    28     -15.194  31.238  32.056  1.00 28.46     1DIK 269
ATOM    178  CZ  TYR    28     -15.005  29.895  31.793  1.00 29.76     1DIK 270
ATOM    179  OH  TYR    28     -15.113  28.997  32.827  1.00 35.18     1DIK 271
ATOM    180  N   ALA    29     -12.480  34.061  26.111  1.00 21.55     1DIK 272
ATOM    181  CA  ALA    29     -12.340  35.025  25.029  1.00 21.69     1DIK 273
ATOM    182  C   ALA    29     -12.102  34.251  23.725  1.00 22.47     1DIK 274
ATOM    183  O   ALA    29     -11.401  33.233  23.720  1.00 22.07     1DIK 275
ATOM    184  CB  ALA    29     -11.139  35.944  25.305  1.00 12.96     1DIK 276
ATOM    185  N   PRO    30     -12.709  34.697  22.612  1.00 24.01     1DIK 277
ATOM    186  CA  PRO    30     -12.509  34.027  21.319  1.00 20.94     1DIK 278
```

FIG. 8-4

```
ATOM   187  C   PRO  30    -11.099  34.409  20.841  1.00  19.17   1DIK 279
ATOM   188  O   PRO  30    -10.608  35.498  21.155  1.00  18.52   1DIK 280
ATOM   189  CB  PRO  30    -13.568  34.671  20.414  1.00  20.61   1DIK 281
ATOM   190  CG  PRO  30    -14.540  35.324  21.362  1.00  24.76   1DIK 282
ATOM   191  CD  PRO  30    -13.651  35.819  22.480  1.00  25.47   1DIK 283
ATOM   192  N   PHE  31    -10.438  33.533  20.093  1.00  20.80   1DIK 284
ATOM   193  CA  PHE  31     -9.102  33.861  19.596  1.00  19.54   1DIK 285
ATOM   194  C   PHE  31     -9.077  35.195  18.814  1.00  20.93   1DIK 286
ATOM   195  O   PHE  31     -9.957  35.482  17.984  1.00  20.23   1DIK 287
ATOM   196  CB  PHE  31     -8.552  32.723  18.692  1.00  17.50   1DIK 288
ATOM   197  CG  PHE  31     -7.448  33.165  17.750  1.00  19.27   1DIK 289
ATOM   198  CD1 PHE  31     -6.119  33.222  18.181  1.00  21.10   1DIK 290
ATOM   199  CD2 PHE  31     -7.747  33.579  16.435  1.00  18.79   1DIK 291
ATOM   200  CE1 PHE  31     -5.105  33.692  17.318  1.00  21.44   1DIK 292
ATOM   201  CE2 PHE  31     -6.741  34.050  15.564  1.00  14.12   1DIK 293
ATOM   202  CZ  PHE  31     -5.426  34.108  16.005  1.00  17.15   1DIK 294
ATOM   203  N   PHE  32     -8.067  36.005  19.097  1.00  18.45   1DIK 295
ATOM   204  CA  PHE  32     -7.844  37.244  18.368  1.00  20.59   1DIK 296
ATOM   205  C   PHE  32     -6.324  37.260  18.121  1.00  20.82   1DIK 297
ATOM   206  O   PHE  32     -5.536  36.921  19.002  1.00  23.47   1DIK 298
ATOM   207  CB  PHE  32     -8.350  38.480  19.131  1.00  19.12   1DIK 299
ATOM   208  CG  PHE  32     -7.872  38.573  20.560  1.00  23.83   1DIK 300
ATOM   209  CD1 PHE  32     -8.508  37.845  21.577  1.00  20.95   1DIK 301
ATOM   210  CD2 PHE  32     -6.806  39.406  20.896  1.00  19.92   1DIK 302
ATOM   211  CE1 PHE  32     -8.095  37.946  22.896  1.00  20.93   1DIK 303
ATOM   212  CE2 PHE  32     -6.382  39.517  22.219  1.00  22.76   1DIK 304
ATOM   213  CZ  PHE  32     -7.032  38.783  23.226  1.00  23.83   1DIK 305
ATOM   214  N   SER  33     -5.914  37.623  16.915  1.00  20.87   1DIK 306
ATOM   215  CA  SER  33     -4.504  37.635  16.571  1.00  22.19   1DIK 307
ATOM   216  C   SER  33     -3.672  38.690  17.284  1.00  23.15   1DIK 308
ATOM   217  O   SER  33     -4.041  39.870  17.320  1.00  23.04   1DIK 309
ATOM   218  CB  SER  33     -4.329  37.796  15.060  1.00  22.81   1DIK 310
ATOM   219  OG  SER  33     -2.947  37.792  14.729  1.00  25.39   1DIK 311
ATOM   220  N   LEU  34     -2.544  38.263  17.846  1.00  23.77   1DIK 312
ATOM   221  CA  LEU  34     -1.638  39.188  18.523  1.00  25.51   1DIK 313
ATOM   222  C   LEU  34     -0.492  39.605  17.606  1.00  26.78   1DIK 314
ATOM   223  O   LEU  34      0.501  40.148  18.084  1.00  26.99   1DIK 315
ATOM   224  CB  LEU  34     -1.063  38.572  19.796  1.00  23.17   1DIK 316
ATOM   225  CG  LEU  34     -2.087  38.252  20.887  1.00  25.71   1DIK 317
ATOM   226  CD1 LEU  34     -1.395  37.465  21.984  1.00  23.09   1DIK 318
ATOM   227  CD2 LEU  34     -2.712  39.528  21.427  1.00  19.78   1DIK 319
ATOM   228  N   ALA  35     -0.639  39.365  16.301  1.00  27.00   1DIK 320
ATOM   229  CA  ALA  35      0.390  39.711  15.319  1.00  31.06   1DIK 321
ATOM   230  C   ALA  35      0.835  41.166  15.428  1.00  35.74   1DIK 322
ATOM   231  O   ALA  35      2.025  41.455  15.344  1.00  39.04   1DIK 323
ATOM   232  CB  ALA  35     -0.103  39.434  13.915  1.00  24.83   1DIK 324
ATOM   233  N   ASN  36     -0.118  42.075  15.623  1.00  39.86   1DIK 325
ATOM   234  CA  ASN  36      0.181  43.506  15.737  1.00  41.12   1DIK 326
ATOM   235  C   ASN  36      0.815  43.897  17.057  1.00  40.64   1DIK 327
ATOM   236  O   ASN  36      1.319  45.010  17.188  1.00  42.67   1DIK 328
ATOM   237  CB  ASN  36     -1.084  44.349  15.538  1.00  43.24   1DIK 329
ATOM   238  CG  ASN  36     -1.671  44.193  14.156  1.00  49.12   1DIK 330
ATOM   239  OD1 ASN  36     -0.945  44.021  13.172  1.00  50.49   1DIK 331
ATOM   240  ND2 ASN  36     -2.995  44.246  14.066  1.00  56.59   1DIK 332
ATOM   241  N   GLU  37      0.784  43.000  18.039  1.00  39.04   1DIK 333
ATOM   242  CA  GLU  37      1.380  43.287  19.347  1.00  39.87   1DIK 334
ATOM   243  C   GLU  37      2.788  42.722  19.440  1.00  37.45   1DIK 335
ATOM   244  O   GLU  37      3.506  42.963  20.411  1.00  38.65   1DIK 336
ATOM   245  CB  GLU  37      0.530  42.693  20.478  1.00  43.47   1DIK 337
ATOM   246  CG  GLU  37     -0.796  43.401  20.721  1.00  47.80   1DIK 338
ATOM   247  CD  GLU  37     -0.616  44.863  21.087  1.00  51.75   1DIK 339
ATOM   248  OE1 GLU  37      0.084  45.166  22.088  1.00  51.94   1DIK 340
ATOM   249  OE2 GLU  37     -1.183  45.710  20.357  1.00  55.20   1DIK 341
ATOM   250  N   SER  38      3.174  41.961  18.425  1.00  35.62   1DIK 342
ATOM   251  CA  SER  38      4.482  41.340  18.389  1.00  34.02   1DIK 343
ATOM   252  C   SER  38      5.565  42.357  17.986  1.00  34.45   1DIK 344
```

FIG. 8-5

| | | | | | | | | | |
|---|---|---|---|---|---|---|---|---|---|
| ATOM | 253 | O | SER | 38 | 5.428 | 43.061 | 16.985 | 1.00 35.65 | 1DIK 345 |
| ATOM | 254 | CB | SER | 38 | 4.454 | 40.163 | 17.404 | 1.00 33.07 | 1DIK 346 |
| ATOM | 255 | OG | SER | 38 | 5.561 | 39.292 | 17.583 | 1.00 28.90 | 1DIK 347 |
| ATOM | 256 | N | VAL | 39 | 6.632 | 42.420 | 18.782 | 1.00 33.51 | 1DIK 348 |
| ATOM | 257 | CA | VAL | 39 | 7.767 | 43.305 | 18.541 | 1.00 33.30 | 1DIK 349 |
| ATOM | 258 | C | VAL | 39 | 8.539 | 42.760 | 17.327 | 1.00 33.54 | 1DIK 350 |
| ATOM | 259 | O | VAL | 39 | 9.024 | 43.520 | 16.490 | 1.00 34.06 | 1DIK 351 |
| ATOM | 260 | CB | VAL | 39 | 8.690 | 43.356 | 19.801 | 1.00 37.39 | 1DIK 352 |
| ATOM | 261 | CG1 | VAL | 39 | 9.833 | 44.331 | 19.602 | 1.00 39.93 | 1DIK 353 |
| ATOM | 262 | CG2 | VAL | 39 | 7.884 | 43.774 | 21.018 | 1.00 38.16 | 1DIK 354 |
| ATOM | 263 | N | ILE | 40 | 8.645 | 41.434 | 17.239 | 1.00 32.27 | 1DIK 355 |
| ATOM | 264 | CA | ILE | 40 | 9.323 | 40.766 | 16.127 | 1.00 29.21 | 1DIK 356 |
| ATOM | 265 | C | ILE | 40 | 8.262 | 40.386 | 15.083 | 1.00 28.46 | 1DIK 357 |
| ATOM | 266 | O | ILE | 40 | 7.195 | 39.885 | 15.440 | 1.00 26.34 | 1DIK 358 |
| ATOM | 267 | CB | ILE | 40 | 10.059 | 39.494 | 16.624 | 1.00 29.64 | 1DIK 359 |
| ATOM | 268 | CG1 | ILE | 40 | 11.147 | 39.900 | 17.631 | 1.00 30.03 | 1DIK 360 |
| ATOM | 269 | CG2 | ILE | 40 | 10.633 | 38.721 | 15.436 | 1.00 26.81 | 1DIK 361 |
| ATOM | 270 | CD1 | ILE | 40 | 11.771 | 38.777 | 18.437 | 1.00 26.07 | 1DIK 362 |
| ATOM | 271 | N | SER | 41 | 8.548 | 40.626 | 13.806 | 1.00 29.09 | 1DIK 363 |
| ATOM | 272 | CA | SER | 41 | 7.594 | 40.302 | 12.737 | 1.00 30.76 | 1DIK 364 |
| ATOM | 273 | C | SER | 41 | 7.310 | 38.798 | 12.646 | 1.00 29.37 | 1DIK 365 |
| ATOM | 274 | O | SER | 41 | 8.234 | 37.990 | 12.552 | 1.00 28.10 | 1DIK 366 |
| ATOM | 275 | CB | SER | 41 | 8.113 | 40.802 | 11.386 | 1.00 29.99 | 1DIK 367 |
| ATOM | 276 | OG | SER | 41 | 7.148 | 40.555 | 10.379 | 1.00 32.70 | 1DIK 368 |
| ATOM | 227 | N | PRO | 42 | 6.021 | 38.410 | 12.664 | 1.00 31.46 | 1DIK 369 |
| ATOM | 278 | CA | PRO | 42 | 5.577 | 37.009 | 12.592 | 1.00 30.99 | 1DIK 370 |
| ATOM | 279 | C | PRO | 42 | 5.915 | 36.287 | 11.285 | 1.00 31.80 | 1DIK 371 |
| ATOM | 280 | O | PRO | 42 | 5.950 | 35.062 | 11.241 | 1.00 34.31 | 1DIK 372 |
| ATOM | 281 | CB | PRO | 42 | 4.056 | 37.109 | 12.791 | 1.00 28.85 | 1DIK 373 |
| ATOM | 282 | CG | PRO | 42 | 3.852 | 38.432 | 13.454 | 1.00 32.81 | 1DIK 374 |
| ATOM | 283 | CD | PRO | 42 | 4.863 | 39.312 | 12.766 | 1.00 31.32 | 1DIK 375 |
| ATOM | 284 | N | GLU | 43 | 6.160 | 37.047 | 10.226 | 1.00 34.83 | 1DIK 376 |
| ATOM | 285 | CA | GLU | 43 | 6.467 | 36.483 | 8.917 | 1.00 36.61 | 1DIK 377 |
| ATOM | 286 | C | GLU | 43 | 7.765 | 35.703 | 8.835 | 1.00 35.76 | 1DIK 378 |
| ATOM | 287 | O | GLU | 43 | 8.757 | 36.046 | 9.480 | 1.00 37.48 | 1DIK 379 |
| ATOM | 288 | CB | GLU | 43 | 6.516 | 37.586 | 7.867 | 1.00 45.46 | 1DIK 380 |
| ATOM | 289 | CG | GLU | 43 | 5.236 | 38.394 | 7.734 | 1.00 61.52 | 1DIK 381 |
| ATOM | 290 | CD | GLU | 43 | 5.488 | 39.889 | 7.891 | 1.00 71.53 | 1DIK 382 |
| ATOM | 291 | OE1 | GLU | 43 | 6.553 | 40.371 | 7.420 | 1.00 76.20 | 1DIK 383 |
| ATOM | 292 | OE2 | GLU | 43 | 4.624 | 40.581 | 8.487 | 1.00 75.49 | 1DIK 384 |
| ATOM | 293 | N | VAL | 44 | 7.739 | 34.654 | 8.020 | 1.00 35.15 | 1DIK 385 |
| ATOM | 294 | CA | VAL | 44 | 8.900 | 33.806 | 7.785 | 1.00 34.87 | 1DIK 386 |
| ATOM | 295 | C | VAL | 44 | 9.900 | 34.708 | 7.060 | 1.00 36.04 | 1DIK 387 |
| ATOM | 296 | O | VAL | 44 | 9.570 | 35.289 | 6.031 | 1.00 37.59 | 1DIK 388 |
| ATOM | 297 | CB | VAL | 44 | 8.529 | 32.582 | 6.883 | 1.00 33.01 | 1DIK 389 |
| ATOM | 298 | CG1 | VAL | 44 | 9.757 | 31.698 | 6.657 | 1.00 28.63 | 1DIK 390 |
| ATOM | 299 | CG2 | VAL | 44 | 7.398 | 31.773 | 7.522 | 1.00 26.10 | 1DIK 391 |
| ATOM | 300 | N | PRO | 45 | 11.131 | 34.837 | 7.590 | 1.00 38.73 | 1DIK 392 |
| ATOM | 301 | CA | PRO | 45 | 12.171 | 35.680 | 6.996 | 1.00 40.95 | 1DIK 393 |
| ATOM | 302 | C | PRO | 45 | 12.492 | 35.362 | 5.558 | 1.00 44.42 | 1DIK 394 |
| ATOM | 303 | O | PRO | 45 | 12.492 | 34.196 | 5.149 | 1.00 44.24 | 1DIK 395 |
| ATOM | 304 | CB | PRO | 45 | 13.382 | 35.431 | 7.893 | 1.00 39.65 | 1DIK 396 |
| ATOM | 305 | CG | PRO | 45 | 12.775 | 35.101 | 9.201 | 1.00 40.04 | 1DIK 397 |
| ATOM | 306 | CD | PRO | 45 | 11.645 | 34.183 | 8.806 | 1.00 40.88 | 1DIK 398 |
| ATOM | 307 | N | ALA | 46 | 12.769 | 36.418 | 4.798 | 1.00 48.71 | 1DIK 399 |
| ATOM | 308 | CA | ALA | 46 | 13.127 | 36.292 | 3.396 | 1.00 50.25 | 1DIK 400 |
| ATOM | 309 | C | ALA | 46 | 14.456 | 35.555 | 3.435 | 1.00 49.80 | 1DIK 401 |
| ATOM | 310 | O | ALA | 46 | 15.326 | 35.906 | 4.229 | 1.00 49.90 | 1DIK 402 |
| ATOM | 311 | CB | ALA | 46 | 13.304 | 37.677 | 2.777 | 1.00 50.74 | 1DIK 403 |
| ATOM | 312 | N | GLY | 47 | 14.613 | 34.533 | 2.600 | 1.00 47.13 | 1DIK 404 |
| ATOM | 313 | CA | GLY | 47 | 15.862 | 33.789 | 2.596 | 1.00 41.93 | 1DIK 405 |
| ATOM | 314 | C | GLY | 47 | 15.863 | 32.579 | 3.520 | 1.00 39.94 | 1DIK 406 |
| ATOM | 315 | O | GLY | 47 | 16.893 | 31.906 | 3.681 | 1.00 36.72 | 1DIK 407 |
| ATOM | 316 | N | CYS | 48 | 14.720 | 32.300 | 4.141 | 1.00 36.56 | 1DIK 408 |
| ATOM | 317 | CA | CYS | 48 | 14.609 | 31.139 | 5.012 | 1.00 34.94 | 1DIK 409 |
| ATOM | 318 | C | CYS | 48 | 13.549 | 30.237 | 4.434 | 1.00 34.24 | 1DIK 410 |

FIG. 8-6

```
ATOM    319  O   CYS    48      12.669  30.684   3.693  1.00 33.85      1DIK 411
ATOM    320  CB  CYS    48      14.232  31.528   6.435  1.00 29.09      1DIK 412
ATOM    321  SG  CYS    48      15.506  32.511   7.263  1.00 30.08      1DIK 413
ATOM    322  N   ARG    49      13.643  28.962   4.775  1.00 32.71      1DIK 414
ATOM    323  CA  ARG    49      12.707  27.965   4.293  1.00 31.47      1DIK 415
ATOM    324  C   ARG    49      12.307  27.093   5.496  1.00 29.98      1DIK 416
ATOM    325  O   ARG    49      13.181  26.547   6.196  1.00 24.89      1DIK 417
ATOM    326  CB  ARG    49      13.424  27.153   3.219  1.00 34.59      1DIK 418
ATOM    327  CG  ARG    49      12.615  26.104   2.516  1.00 45.38      1DIK 419
ATOM    328  CD  ARG    49      13.520  25.363   1.547  1.00 50.77      1DIK 420
ATOM    329  NE  ARG    49      14.760  24.899   2.185  1.00 53.82      1DIK 421
ATOM    330  CZ  ARG    49      15.024  23.626   2.479  1.00 54.48      1DIK 422
ATOM    331  NH1 ARG    49      14.132  22.680   2.199  1.00 54.38      1DIK 223
ATOM    332  NH2 ARG    49      16.178  23.297   3.054  1.00 53.78      1DIK 424
ATOM    333  N   VAL    50      11.001  26.975   5.747  1.00 26.52      1DIK 425
ATOM    334  CA  VAL    50      10.510  26.167   6.865  1.00 23.44      1DIK 426
ATOM    335  C   VAL    50      10.718  24.689   6.555  1.00 22.87      1DIK 427
ATOM    336  O   VAL    50      10.383  24.223   5.472  1.00 24.36      1DIK 428
ATOM    337  CB  VAL    50       9.012  26.441   7.157  1.00 22.39      1DIK 429
ATOM    338  CG1 VAL    50       8.518  25.564   8.318  1.00 22.32      1DIK 430
ATOM    339  CG2 VAL    50       8.817  27.903   7.506  1.00 18.72      1DIK 431
ATOM    340  N   THR    51      11.278  23.958   7.510  1.00 23.31      1DIK 432
ATOM    341  CA  THR    51      11.533  22.536   7.341  1.00 23.80      1DIK 433
ATOM    342  C   THR    51      10.764  21.649   8.332  1.00 25.07      1DIK 434
ATOM    343  O   THR    51      10.821  20.422   8.242  1.00 25.40      1DIK 435
ATOM    344  CB  THR    51      13.042  22.240   7.471  1.00 26.51      1DIK 436
ATOM    345  OG1 THR    51      13.516  22.691   8.745  1.00 27.16      1DIK 437
ATOM    346  OG2 THR    51      13.823  22.954   6.378  1.00 26.68      1DIK 438
ATOM    347  N   PHE    52      10.052  22.267   9.274  1.00 23.82      1DIK 439
ATOM    348  CA  PHE    52       9.280  21.543  10.285  1.00 18.63      1DIK 440
ATOM    349  C   PHE    52       8.264  22.527  10.821  1.00 19.14      1DIK 441
ATOM    350  O   PHE    52       8.559  23.710  10.993  1.00 19.73      1DIK 442
ATOM    351  CB  PHE    52      10.211  21.081  11.425  1.00 17.98      1DIK 443
ATOM    352  CG  PHE    52       9.497  20.552  12.661  1.00 19.23      1DIK 444
ATOM    353  CD1 PHE    52       9.006  21.424  13.636  1.00 18.19      1DIK 445
ATOM    354  CD2 PHE    52       9.328  19.185  12.854  1.00 18.71      1DIK 446
ATOM    355  CE1 PHE    52       8.359  20.941  14.783  1.00 15.91      1DIK 447
ATOM    356  CE2 PHE    52       8.682  18.690  14.001  1.00 20.50      1DIK 448
ATOM    357  CZ  PHE    52       8.198  19.576  14.964  1.00 16.11      1DIK 449
ATOM    358  N   ALA    53       7.061  22.053  11.072  1.00 16.93      1DIK 450
ATOM    359  CA  ALA    53       6.045  22.910  11.647  1.00 19.01      1DIK 451
ATOM    360  C   ALA    53       5.112  22.048  12.468  1.00 19.84      1DIK 452
ATOM    361  O   ALA    53       4.647  21.002  12.011  1.00 21.85      1DIK 453
ATOM    362  CB  ALA    53       5.265  23.658  10.563  1.00 17.27      1DIK 454
ATOM    363  N   GLN    54       4.866  22.479  13.696  1.00 19.97      1DIK 455
ATOM    364  CA  GLN    54       3.924  21.801  14.570  1.00 16.77      1DIK 456
ATOM    365  C   GLN    54       2.963  22.820  15.172  1.00 13.22      1DIK 457
ATOM    366  O   GLN    54       3.370  23.901  15.592  1.00 15.19      1DIK 458
ATOM    367  CB  GLN    54       4.619  21.072  15.711  1.00 18.35      1DIK 459
ATOM    368  CG  GLN    54       3.595  20.527  16.697  1.00 24.84      1DIK 460
ATOM    369  CD  GLN    54       4.138  19.486  17.607  1.00 27.27      1DIK 461
ATOM    370  OE1 GLN    54       4.891  18.614  17.195  1.00 28.71      1DIK 462
ATOM    371  NE2 GLN    54       3.758  19.561  18.863  1.00 33.46      1DIK 463
ATOM    372  N   VAL    55       1.686  22.486  15.206  1.00 13.93      1DIK 464
ATOM    373  CA  VAL    55       0.721  23.372  15.822  1.00 14.13      1DIK 465
ATOM    374  C   VAL    55       0.094  22.604  16.990  1.00 14.94      1DIK 466
ATOM    375  O   VAL    55      -0.192  21.404  16.878  1.00 13.02      1DIK 467
ATOM    376  CB  VAL    55      -0.377  23.842  14.812  1.00 14.68      1DIK 468
ATOM    377  CG1 VAL    55      -1.062  22.645  14.155  1.00  8.55      1DIK 469
ATOM    378  CG2 VAL    55      -1.407  24.739  15.521  1.00 15.11      1DIK 470
ATOM    379  N   LEU    56      -0.076  23.292  18.111  1.00 11.84      1DIK 471
ATOM    380  CA  LEU    56      -0.719  22.731  19.278  1.00 11.96      1DIK 472
ATOM    381  C   LEU    56      -1.896  23.694  19.426  1.00 14.67      1DIK 473
ATOM    382  O   LEU    56      -1.721  24.903  19.647  1.00 13.79      1DIK 474
ATOM    383  CB  LEU    56       0.197  22.771  20.503  1.00 17.28      1DIK 475
ATOM    384  CG  LEU    56      -0.513  22.538  21.842  1.00 17.00      1DIK 476
```

FIG. 8-7

```
ATOM    385  CD1 LEU   56      -1.065  21.122  21.949  1.00 13.43      1DIK 477
ATOM    386  CD2 LEU   56       0.472  22.817  22.938  1.00 17.28      1DIK 478
ATOM    387  N   SER   57      -3.095  23.162  19.277  1.00 16.89      1DIK 479
ATOM    388  CA  SER   57      -4.289  23.976  19.329  1.00 16.37      1DIK 480
ATOM    389  C   SER   57      -5.260  23.544  20.411  1.00 16.34      1DIK 481
ATOM    390  O   SER   57      -5.341  22.363  20.760  1.00 18.09      1DIK 482
ATOM    391  CB  SER   57      -4.984  23.906  17.960  1.00 15.08      1DIK 483
ATOM    392  OG  SER   57      -6.256  24.527  17.966  1.00 15.23      1DIK 484
ATOM    393  N   ARG   58      -5.986  24.514  20.946  1.00 14.89      1DIK 485
ATOM    394  CA  ARG   58      -7.015  24.257  21.934  1.00 16.34      1DIK 486
ATOM    395  C   ARG   58      -8.299  24.104  21.100  1.00 20.75      1DIK 487
ATOM    396  O   ARG   58      -8.352  24.546  19.940  1.00 20.55      1DIK 488
ATOM    397  CB  ARG   58      -7.159  25.457  22.874  1.00 14.15      1DIK 489
ATOM    398  CG  ARG   58      -8.315  25.320  23.835  1.00 13.80      1DIK 490
ATOM    399  CD  ARG   58      -8.411  26.468  24.791  1.00 15.28      1DIK 491
ATOM    400  NE  ARG   58      -9.551  26.299  25.692  1.00 16.96      1DIK 492
ATOM    401  CZ  ARG   58     -10.218  27.306  26.253  1.00 17.74      1DIK 493
ATOM    402  NH1 ARG   58      -9.863  28.564  26.021  1.00 19.32      1DIK 494
ATOM    403  NH2 ARG   58     -11.239  27.055  27.051  1.00 14.92      1DIK 495
ATOM    404  N   HIS   59      -9.326  23.478  21.673  1.00 22.89      1DIK 496
ATOM    405  CA  HIS   59     -10.620  23.324  20.993  1.00 21.80      1DIK 497
ATOM    406  C   HIS   59     -11.286  24.703  20.795  1.00 21.30      1DIK 498
ATOM    407  O   HIS   59     -10.860  25.693  21.403  1.00 20.60      1DIK 499
ATOM    408  CB  HIS   59     -11.537  22.407  21.809  1.00 20.25      1DIK 500
ATOM    409  CG  HIS   59     -11.767  22.867  23.218  1.00 21.97      1DIK 501
ATOM    410  ND1 HIS   59     -12.523  23.979  23.527  1.00 21.32      1DIK 502
ATOM    411  CD2 HIS   59     -11.350  22.356  24.400  1.00 18.14      1DIK 503
ATOM    412  CE1 HIS   59     -12.564  24.132  24.838  1.00 18.77      1DIK 504
ATOM    413  NE2 HIS   59     -11.860  23.161  25.390  1.00 19.93      1DIK 505
ATOM    414  N   GLY   60     -12.318  24.782  19.957  1.00 20.66      1DIK 506
ATOM    415  CA  GLY   60     -12.976  26.063  19.736  1.00 20.29      1DIK 507
ATOM    416  C   GLY   60     -13.950  26.442  20.847  1.00 21.51      1DIK 508
ATOM    417  O   GLY   60     -14.042  25.737  21.856  1.00 21.15      1DIK 509
ATOM    418  N   ALA   61     -14.669  27.549  20.659  1.00 20.16      1DIK 510
ATOM    419  CA  ALA   61     -15.664  28.047  21.618  1.00 20.00      1DIK 511
ATOM    420  C   ALA   61     -16.735  26.996  21.888  1.00 20.35      1DIK 512
ATOM    421  O   ALA   61     -17.247  26.366  20.954  1.00 21.69      1DIK 513
ATOM    422  CB  ALA   61     -16.326  29.320  21.079  1.00 15.53      1DIK 514
ATOM    423  N   ARG   62     -17.077  26.823  23.161  1.00 19.64      1DIK 515
ATOM    424  CA  ARG   62     -18.070  25.832  23.581  1.00 19.57      1DIK 516
ATOM    425  C   ARG   62     -19.162  26.420  24.482  1.00 21.60      1DIK 517
ATOM    426  O   ARG   62     -19.079  27.574  24.932  1.00 18.58      1DIK 518
ATOM    427  CB  ARG   62     -17.378  24.703  24.346  1.00 15.11      1DIK 519
ATOM    428  CG  ARG   62     -16.505  25.211  25.486  1.00 17.39      1DIK 520
ATOM    429  CD  ARG   62     -16.371  24.195  26.609  1.00 22.59      1DIK 521
ATOM    430  NE  ARG   62     -15.570  24.726  27.711  1.00 23.06      1DIK 522
ATOM    431  CZ  ARG   62     -16.067  25.234  28.839  1.00 25.28      1DIK 523
ATOM    432  NH1 ARG   62     -17.379  25.272  29.052  1.00 28.41      1DIK 524
ATOM    433  NH2 ARG   62     -15.244  25.704  29.766  1.00 27.40      1DIK 525
ATOM    434  N   TYR   63     -20.193  25.619  24.726  1.00 23.53      1DIK 526
ATOM    435  CA  TYR   63     -21.280  26.004  25.615  1.00 25.54      1DIK 527
ATOM    436  C   TYR   63     -20.729  25.786  27.033  1.00 28.59      1DIK 528
ATOM    437  O   TYR   63     -19.646  25.206  27.200  1.00 28.67      1DIK 529
ATOM    438  CB  TYR   63     -22.481  25.082  25.394  1.00 24.63      1DIK 530
ATOM    439  CG  TYR   63     -23.192  25.300  24.082  1.00 29.77      1DIK 531
ATOM    440  CD1 TYR   63     -23.806  26.529  23.795  1.00 29.27      1DIK 532
ATOM    441  CD2 TYR   63     -23.237  24.290  23.116  1.00 27.48      1DIK 533
ATOM    442  CE1 TYR   63     -24.444  26.748  22.576  1.00 31.57      1DIK 534
ATOM    443  CE2 TYR   63     -23.867  24.495  21.895  1.00 26.46      1DIK 535
ATOM    444  CZ  TYR   63     -24.468  25.727  21.626  1.00 34.26      1DIK 536
ATOM    445  OH  TYR   63     -25.067  25.950  20.398  1.00 35.58      1DIK 537
ATOM    446  N   PRO   64     -21.444  26.254  28.076  1.00 31.03      1DIK 538
ATOM    447  CA  PRO   64     -20.879  26.003  29.407  1.00 31.84      1DIK 539
ATOM    448  C   PRO   64     -20.849  24.482  29.625  1.00 32.43      1DIK 540
ATOM    449  O   PRO   64     -21.547  23.728  28.932  1.00 30.67      1DIK 541
ATOM    450  CB  PRO   64     -21.891  26.670  30.342  1.00 27.12      1DIK 542
```

FIG. 8-8

```
ATOM    451  CG  PRO    64     -22.524  27.706  29.487  1.00 30.89     1DIK 543
ATOM    452  CD  PRO    64     -22.706  27.004  28.181  1.00 27.90     1DIK 544
ATOM    453  N   THR    65     -20.042  24.011  30.564  1.00 35.27     1DIK 545
ATOM    454  CA  THR    65     -20.038  22.579  30.830  1.00 37.08     1DIK 546
ATOM    455  C   THR    65     -21.375  22.333  31.507  1.00 38.68     1DIK 547
ATOM    456  O   THR    65     -21.897  23.224  32.185  1.00 35.35     1DIK 548
ATOM    457  CB  THR    65     -18.897  22.170  31.774  1.00 35.91     1DIK 549
ATOM    458  OG1 THR    65     -18.997  22.906  32.999  1.00 40.63     1DIK 550
ATOM    459  CG2 THR    65     -17.544  22.438  31.116  1.00 35.54     1DIK 551
ATOM    460  N   ASP    66     -21.933  21.141  31.329  1.00 44.49     1DIK 552
ATOM    461  CA  ASP    66     -23.222  20.806  31.935  1.00 48.12     1DIK 553
ATOM    462  C   ASP    66     -23.305  21.205  33.418  1.00 48.96     1DIK 554
ATOM    463  O   ASP    66     -24.299  21.789  33.858  1.00 48.33     1DIK 555
ATOM    464  CB  ASP    66     -23.513  19.309  31.782  1.00 50.94     1DIK 556
ATOM    465  CG  ASP    66     -24.974  18.977  32.030  1.00 54.72     1DIK 557
ATOM    466  OD1 ASP    66     -25.838  19.495  31.280  1.00 55.38     1DIK 558
ATOM    467  OD2 ASP    66     -25.255  18.206  32.977  1.00 55.13     1DIK 559
ATOM    468  N   SER    67     -22.262  20.895  34.180  1.00 47.71     1DIK 560
ATOM    469  CA  SER    67     -22.233  21.247  35.587  1.00 46.65     1DIK 561
ATOM    470  C   SER    67     -22.525  22.751  35.796  1.00 45.82     1DIK 562
ATOM    471  O   SER    67     -23.477  23.102  36.501  1.00 47.90     1DIK 563
ATOM    472  CB  SER    67     -20.875  20.861  36.172  1.00 45.81     1DIK 564
ATOM    473  OG  SER    67     -20.769  21.285  37.516  1.00 51.18     1DIK 565
ATOM    474  N   LYS    68     -21.727  23.630  35.178  1.00 43.55     1DIK 566
ATOM    475  CA  LYS    68     -21.896  25.092  35.312  1.00 39.40     1DIK 567
ATOM    476  C   LYS    68     -23.201  25.626  34.753  1.00 37.75     1DIK 568
ATOM    477  O   LYS    68     -23.760  26.578  35.301  1.00 36.03     1DIK 569
ATOM    478  CB  LYS    68     -20.753  25.837  34.638  1.00 38.35     1DIK 570
ATOM    479  CG  LYS    68     -19.448  25.727  35.356  1.00 38.37     1DIK 571
ATOM    480  CD  LYS    68     -19.273  26.838  36.351  1.00 39.44     1DIK 572
ATOM    481  CE  LYS    68     -17.830  26.847  36.833  1.00 44.75     1DIK 573
ATOM    482  NZ  LYS    68     -17.376  28.222  37.198  1.00 52.53     1DIK 574
ATOM    483  N   GLY    69     -23.675  25.022  33.664  1.00 35.27     1DIK 575
ATOM    484  CA  GLY    69     -24.928  25.439  33.058  1.00 38.22     1DIK 576
ATOM    485  C   GLY    69     -26.073  25.358  34.054  1.00 41.32     1DIK 577
ATOM    486  O   GLY    69     -26.947  26.228  34.057  1.00 41.17     1DIK 578
ATOM    487  N   LYS    70     -26.059  24.313  34.891  1.00 42.89     1DIK 579
ATOM    488  CA  LYS    70     -27.071  24.092  35.934  1.00 44.02     1DIK 580
ATOM    489  C   LYS    70     -27.075  25.317  36.840  1.00 41.82     1DIK 581
ATOM    490  O   LYS    70     -28.110  25.959  37.043  1.00 42.10     1DIK 582
ATOM    491  CB  LYS    70     -26.717  22.892  36.835  1.00 49.51     1DIK 583
ATOM    492  CG  LYS    70     -26.624  21.513  36.195  1.00 53.72     1DIK 584
ATOM    493  CD  LYS    70     -27.976  20.920  35.867  1.00 56.10     1DIK 585
ATOM    494  CE  LYS    70     -27.822  19.444  35.549  1.00 56.46     1DIK 586
ATOM    495  NZ  LYS    70     -28.950  18.940  34.717  1.00 58.23     1DIK 587
ATOM    496  N   LYS    71     -25.901  25.625  37.382  1.00 34.23     1DIK 588
ATOM    497  CA  LYS    71     -25.735  26.752  38.278  1.00 32.70     1DIK 589
ATOM    498  C   LYS    71     -26.157  28.070  37.644  1.00 32.77     1DIK 590
ATOM    499  O   LYS    71     -26.839  28.867  38.283  1.00 34.19     1DIK 591
ATOM    500  CB  LYS    71     -24.294  26.814  38.743  1.00 34.32     1DIK 592
ATOM    501  CG  LYS    71     -23.848  25.549  39.465  1.00 38.15     1DIK 593
ATOM    502  CD  LYS    71     -22.365  25.606  39.758  1.00 42.92     1DIK 594
ATOM    503  CE  LYS    71     -21.904  24.450  40.639  1.00 47.95     1DIK 595
ATOM    504  NZ  LYS    71     -20.408  24.463  40.789  1.00 52.26     1DIK 596
ATOM    505  N   TYR    72     -25.764  28.298  36.393  1.00 31.69     1DIK 597
ATOM    506  CA  TYR    72     -26.128  29.526  35.676  1.00 31.22     1DIK 598
ATOM    507  C   TYR    72     -27.642  29.636  35.580  1.00 32.50     1DIK 599
ATOM    508  O   TYR    72     -28.232  30.663  35.916  1.00 31.20     1DIK 600
ATOM    509  CB  TYR    72     -25.550  29.524  34.254  1.00 28.26     1DIK 601
ATOM    510  CG  TYR    72     -24.045  29.680  34.164  1.00 24.30     1DIK 602
ATOM    511  CD1 TYR    72     -23.278  30.037  35.282  1.00 21.92     1DIK 603
ATOM    512  CD2 TYR    72     -23.383  29.475  32.951  1.00 26.92     1DIK 604
ATOM    513  CE1 TYR    72     -21.894  30.186  35.192  1.00 21.95     1DIK 605
ATOM    514  CE2 TYR    72     -21.999  29.623  32.850  1.00 25.41     1DIK 606
ATOM    515  CZ  TYR    72     -21.265  29.977  33.971  1.00 26.50     1DIK 607
ATOM    516  OH  TYR    72     -19.904  30.124  33.860  1.00 31.12     1DIK 608
```

FIG. 8-9

```
ATOM  517  N    SER  73   -28.262  28.562  35.114  1.00 34.91   1DIK 609
ATOM  518  CA   SER  73   -29.705  28.498  34.965  1.00 37.19   1DIK 610
ATOM  519  C    SER  73   -30.430  28.745  36.286  1.00 36.76   1DIK 611
ATOM  520  O    SER  73   -31.337  29.576  36.367  1.00 39.80   1DIK 612
ATOM  521  CB   SER  73   -30.100  27.133  34.421  1.00 37.82   1DIK 613
ATOM  522  OG   SER  73   -31.450  27.151  34.001  1.00 48.85   1DIK 614
ATOM  523  N    ALA  74   -30.027  28.017  37.321  1.00 36.25   1DIK 615
ATOM  524  CA   ALA  74   -30.627  28.143  38.645  1.00 32.75   1DIK 616
ATOM  525  C    ALA  74   -30.544  29.585  39.162  1.00 33.94   1DIK 617
ATOM  526  O    ALA  74   -31.544  30.156  39.607  1.00 37.43   1DIK 618
ATOM  527  CB   ALA  74   -29.929  27.196  39.612  1.00 27.83   1DIK 619
ATOM  528  N    LEU  75   -29.352  30.169  39.094  1.00 31.82   1DIK 620
ATOM  529  CA   LEU  75   -29.130  31.529  39.552  1.00 30.28   1DIK 621
ATOM  530  C    LEU  75   -30.043  32.526  38.855  1.00 32.18   1DIK 622
ATOM  531  O    LEU  75   -30.553  33.460  39.483  1.00 33.24   1DIK 623
ATOM  532  CB   LEU  75   -27.669  31.929  39.343  1.00 27.09   1DIK 624
ATOM  533  CG   LEU  75   -27.340  33.380  39.705  1.00 31.49   1DIK 625
ATOM  534  CD1  LEU  75   -27.680  33.616  41.182  1.00 32.22   1DIK 626
ATOM  535  CD2  LEU  75   -25.871  33.687  39.422  1.00 28.98   1DIK 627
ATOM  536  N    ILE  76   -30.253  32.334  37.559  1.00 34.42   1DIK 628
ATOM  537  CA   ILE  76   -31.107  33.235  36.800  1.00 35.51   1DIK 629
ATOM  538  C    ILE  76   -32.581  33.100  37.187  1.00 38.20   1DIK 630
ATOM  539  O    ILE  76   -33.287  34.104  37.290  1.00 37.73   1DIK 631
ATOM  540  CB   ILE  76   -30.897  33.040  35.271  1.00 35.44   1DIK 632
ATOM  541  CG1  ILE  76   -29.543  33.649  34.872  1.00 32.79   1DIK 633
ATOM  542  CG2  ILE  76   -32.051  33.665  34.467  1.00 30.04   1DIK 634
ATOM  543  CD1  ILE  76   -29.180  33.468  33.407  1.00 32.29   1DIK 635
ATOM  544  N    GLU  77   -33.050  31.876  37.409  1.00 41.02   1DIK 636
ATOM  545  CA   GLU  77   -34.440  31.683  37.801  1.00 45.17   1DIK 637
ATOM  546  C    GLU  77   -34.630  32.291  39.166  1.00 45.15   1DIK 638
ATOM  547  O    GLU  77   -35.655  32.926  39.434  1.00 46.76   1DIK 639
ATOM  548  CB   GLU  77   -34.800  30.209  37.861  1.00 51.95   1DIK 640
ATOM  549  CG   GLU  77   -34.891  29.564  36.499  1.00 66.31   1DIK 641
ATOM  550  CD   GLU  77   -35.578  28.203  36.531  1.00 74.99   1DIK 642
ATOM  551  OE1  GLU  77   -35.736  27.633  37.642  1.00 78.28   1DIK 643
ATOM  552  OE2  GLU  77   -35.960  27.702  35.443  1.00 79.43   1DIK 644
ATOM  553  N    GLU  78   -33.631  32.098  40.025  1.00 43.62   1DIK 645
ATOM  554  CA   GLU  78   -33.667  32.631  41.378  1.00 41.02   1DIK 646
ATOM  555  C    GLU  78   -33.758  34.155  41.364  1.00 38.09   1DIK 647
ATOM  556  O    GLU  78   -34.518  34.733  42.134  1.00 37.93   1DIK 648
ATOM  557  CB   GLU  78   -32.445  32.185  42.175  1.00 41.48   1DIK 649
ATOM  558  CG   GLU  78   -32.538  32.616  43.621  1.00 49.04   1DIK 650
ATOM  559  CD   GLU  78   -31.261  32.413  44.414  1.00 53.16   1DIK 651
ATOM  560  OE1  GLU  78   -30.551  31.404  44.174  1.00 56.49   1DIK 652
ATOM  561  OE2  GLU  78   -30.977  33.272  45.283  1.00 50.49   1DIK 653
ATOM  562  N    ILE  79   -32.989  34.810  40.501  1.00 36.46   1DIK 654
ATOM  563  CA   ILE  79   -33.059  36.265  40.400  1.00 37.33   1DIK 655
ATOM  564  C    ILE  79   -34.446  36.672  39.897  1.00 41.12   1DIK 656
ATOM  565  O    ILE  79   -35.034  37.648  40.374  1.00 43.28   1DIK 657
ATOM  566  CB   ILE  79   -32.003  36.829  39.418  1.00 36.22   1DIK 658
ATOM  567  CG1  ILE  79   -30.606  36.694  40.031  1.00 32.53   1DIK 659
ATOM  568  CG2  ILE  79   -32.341  38.300  39.057  1.00 30.60   1DIK 660
ATOM  569  CD1  ILE  79   -29.481  37.029  39.088  1.00 28.25   1DIK 661
ATOM  570  N    GLN  80   -34.965  35.918  38.934  1.00 41.53   1DIK 662
ATOM  571  CA   GLN  80   -36.276  36.201  38.375  1.00 43.98   1DIK 663
ATOM  572  C    GLN  80   -37.399  36.074  39.392  1.00 48.10   1DIK 664
ATOM  573  O    GLN  80   -38.450  36.687  39.228  1.00 51.13   1DIK 665
ATOM  574  CB   GLN  80   -36.549  35.290  37.186  1.00 40.14   1DIK 666
ATOM  575  CG   GLN  80   -35.828  35.733  35.933  1.00 41.38   1DIK 667
ATOM  576  CD   GLN  80   -35.983  34.751  34.792  1.00 42.01   1DIK 668
ATOM  577  OE1  GLN  80   -36.303  33.583  35.000  1.00 43.95   1DIK 669
ATOM  578  NE2  GLN  80   -35.753  35.220  33.577  1.00 40.77   1DIK 670
ATOM  579  N    GLN  81   -37.186  35.281  40.437  1.00 51.52   1DIK 671
ATOM  580  CA   GLN  81   -38.205  35.105  41.468  1.00 54.70   1DIK 672
ATOM  581  C    GLN  81   -38.099  36.109  42.611  1.00 54.45   1DIK 673
ATOM  582  O    GLN  81   -39.089  36.717  43.004  1.00 57.66   1DIK 674
```

FIG. 8-10

```
ATOM    583  CB  GLN    81     -38.139  33.699  42.050  1.00 58.18      1DIK 675
ATOM    584  CG  GLN    81     -38.560  32.607  41.093  1.00 70.29      1DIK 676
ATOM    585  CD  GLN    81     -38.505  31.233  41.746  1.00 78.03      1DIK 677
ATOM    586  OE1 GLN    81     -39.099  31.014  42.809  1.00 80.87      1DIK 678
ATOM    587  NE2 GLN    81     -37.790  30.300  41.116  1.00 80.03      1DIK 679
ATOM    588  N   ASN    82     -36.896  36.280  43.138  1.00 52.58      1DIK 680
ATOM    589  CA  ASN    82     -36.668  37.179  44.263  1.00 52.84      1DIK 681
ATOM    590  C   ASN    82     -36.717  38.688  44.013  1.00 53.31      1DIK 682
ATOM    591  O   ASN    82     -37.110  39.445  44.905  1.00 53.72      1DIK 683
ATOM    592  CB  ASN    82     -35.336  36.828  44.944  1.00 51.31      1DIK 684
ATOM    593  CG  ASN    82     -35.320  35.418  45.520  1.00 50.40      1DIK 685
ATOM    594  OD1 ASN    82     -36.250  34.629  45.312  1.00 46.50      1DIK 686
ATOM    595  ND2 ASN    82     -34.257  35.092  46.246  1.00 48.14      1DIK 687
ATOM    596  N   ALA    83     -36.316  39.133  42.823  1.00 55.26      1DIK 688
ATOM    597  CA  ALA    83     -36.300  40.566  42.518  1.00 54.90      1DIK 689
ATOM    598  C   ALA    83     -37.693  41.174  42.326  1.00 56.32      1DIK 690
ATOM    599  O   ALA    83     -38.545  40.619  41.617  1.00 52.96      1DIK 691
ATOM    600  CB  ALA    83     -35.417  40.846  41.296  1.00 51.72      1DIK 692
ATOM    601  N   THR    84     -37.905  42.320  42.974  1.00 58.60      1DIK 693
ATOM    602  CA  THR    84     -39.166  43.048  42.904  1.00 59.70      1DIK 694
ATOM    603  C   THR    84     -39.170  44.025  41.730  1.00 60.59      1DIK 695
ATOM    604  O   THR    84     -40.212  44.256  41.116  1.00 63.43      1DIK 696
ATOM    605  CB  THR    84     -39.452  43.835  44.223  1.00 61.01      1DIK 697
ATOM    606  OG1 THR    84     -38.308  44.638  44.574  1.00 61.94      1DIK 698
ATOM    607  CG2 THR    84     -39.786  42.871  45.375  1.00 57.54      1DIK 699
ATOM    608  N   THR    85     -38.011  44.595  41.410  1.00 60.26      1DIK 700
ATOM    609  CA  THR    85     -37.923  45.550  40.309  1.00 61.94      1DIK 701
ATOM    610  C   THR    85     -36.844  45.254  39.271  1.00 60.00      1DIK 702
ATOM    611  O   THR    85     -35.710  44.923  39.608  1.00 58.14      1DIK 703
ATOM    612  CB  THR    85     -37.714  46.973  40.844  1.00 64.54      1DIK 704
ATOM    613  OG1 THR    85     -36.901  46.916  42.027  1.00 68.74      1DIK 705
ATOM    614  CG2 THR    85     -39.062  47.627  41.167  1.00 64.69      1DIK 706
ATOM    615  N   PHE    86     -37.217  45.380  38.003  1.00 59.68      1DIK 707
ATOM    616  CA  PHE    86     -36.301  45.143  36.895  1.00 59.09      1DIK 708
ATOM    617  C   PHE    86     -36.308  46.366  35.988  1.00 58.32      1DIK 709
ATOM    618  O   PHE    86     -36.829  46.298  34.880  1.00 58.58      1DIK 710
ATOM    619  CB  PHE    86     -36.752  43.940  36.055  1.00 59.17      1DIK 711
ATOM    620  CG  PHE    86     -36.747  42.633  36.787  1.00 60.12      1DIK 712
ATOM    621  CD1 PHE    86     -35.566  41.917  36.952  1.00 60.09      1DIK 713
ATOM    622  CD2 PHE    86     -37.928  42.103  37.294  1.00 58.71      1DIK 714
ATOM    623  CE1 PHE    86     -35.564  40.685  37.614  1.00 62.46      1DIK 715
ATOM    624  CE2 PHE    86     -37.939  40.873  37.957  1.00 59.49      1DIK 716
ATOM    625  CZ  PHE    86     -36.756  40.162  38.117  1.00 59.88      1DIK 717
ATOM    626  N   ASP    87     -35.743  47.484  36.432  1.00 59.28      1DIK 718
ATOM    627  CA  ASP    87     -35.745  48.672  35.576  1.00 61.03      1DIK 719
ATOM    628  C   ASP    87     -34.390  49.050  34.977  1.00 58.67      1DIK 720
ATOM    629  O   ASP    87     -33.331  48.696  35.503  1.00 56.33      1DIK 721
ATOM    630  CB  ASP    87     -36.376  49.882  36.294  1.00 67.39      1DIK 722
ATOM    631  CG  ASP    87     -35.731  50.181  37.634  1.00 74.12      1DIK 723
ATOM    632  OD1 ASP    87     -34.542  50.581  37.654  1.00 77.08      1DIK 724
ATOM    633  OD2 ASP    87     -36.422  50.017  38.670  1.00 76.76      1DIK 725
ATOM    634  N   GLY    88     -34.438  49.775  33.864  1.00 56.11      1DIK 726
ATOM    635  CA  GLY    88     -33.223  50.193  33.195  1.00 52.64      1DIK 727
ATOM    636  C   GLY    88     -32.521  49.004  32.565  1.00 50.66      1DIK 728
ATOM    637  O   GLY    88     -33.161  48.140  31.950  1.00 48.22      1DIK 729
ATOM    638  N   LYS    89     -31.202  48.957  32.734  1.00 47.80      1DIK 730
ATOM    639  CA  LYS    89     -30.376  47.885  32.188  1.00 45.18      1DIK 731
ATOM    640  C   LYS    89     -30.681  46.482  32.744  1.00 44.09      1DIK 732
ATOM    641  O   LYS    89     -30.087  45.504  32.301  1.00 46.90      1DIK 733
ATOM    642  CB  LYS    89     -28.898  48.222  32.390  1.00 42.58      1DIK 734
ATOM    643  CG  LYS    89     -28.530  48.500  33.828  1.00 47.71      1DIK 735
ATOM    644  CD  LYS    89     -27.068  48.905  33.973  1.00 54.98      1DIK 736
ATOM    645  CE  LYS    89     -26.737  49.253  35.426  1.00 56.55      1DIK 737
ATOM    646  NZ  LYS    89     -25.293  49.611  35.610  1.00 61.03      1DIK 738
ATOM    647  N   TYR    90     -31.594  46.382  33.705  1.00 38.46      1DIK 739
ATOM    648  CA  TYR    90     -31.959  45.095  34.277  1.00 35.36      1DIK 740
```

FIG. 8-11

| | | | | | | | | | |
|---|---|---|---|---|---|---|---|---|---|
| ATOM | 649 | C | TYR | 90 | -33.269 | 44.568 | 33.699 | 1.00 38.19 | 1DIK 741 |
| ATOM | 650 | O | TYR | 90 | -33.709 | 43.469 | 34.042 | 1.00 36.65 | 1DIK 742 |
| ATOM | 651 | CB | TYR | 90 | -32.122 | 45.220 | 35.781 | 1.00 32.46 | 1DIK 743 |
| ATOM | 652 | CG | TYR | 90 | -30.873 | 45.633 | 36.506 | 1.00 31.81 | 1DIK 744 |
| ATOM | 653 | CD1 | TYR | 90 | -29.901 | 44.693 | 36.851 | 1.00 32.85 | 1DIK 745 |
| ATOM | 654 | CD2 | TYR | 90 | -30.668 | 46.959 | 36.866 | 1.00 32.53 | 1DIK 746 |
| ATOM | 655 | CE1 | TYR | 90 | -28.754 | 45.066 | 37.539 | 1.00 29.82 | 1DIK 747 |
| ATOM | 656 | CE2 | TYR | 90 | -29.528 | 47.351 | 37.553 | 1.00 32.39 | 1DIK 748 |
| ATOM | 657 | CZ | TYR | 90 | -28.574 | 46.400 | 37.887 | 1.00 34.71 | 1DIK 749 |
| ATOM | 658 | OH | TYR | 90 | -27.446 | 46.792 | 38.565 | 1.00 31.33 | 1DIK 750 |
| ATOM | 659 | N | ALA | 91 | -33.891 | 45.351 | 32.820 | 1.00 41.63 | 1DIK 751 |
| ATOM | 660 | CA | ALA | 91 | -35.168 | 44.978 | 32.218 | 1.00 40.63 | 1DIK 752 |
| ATOM | 661 | C | ALA | 91 | -35.159 | 43.631 | 31.510 | 1.00 40.55 | 1DIK 753 |
| ATOM | 662 | O | ALA | 91 | -36.105 | 42.858 | 31.641 | 1.00 41.26 | 1DIK 754 |
| ATOM | 663 | CB | ALA | 91 | -35.632 | 46.069 | 31.262 | 1.00 40.02 | 1DIK 755 |
| ATOM | 664 | N | PHE | 92 | -34.097 | 43.340 | 30.763 | 1.00 41.42 | 1DIK 756 |
| ATOM | 665 | CA | PHE | 92 | -34.010 | 42.069 | 30.036 | 1.00 39.95 | 1DIK 757 |
| ATOM | 666 | C | PHE | 92 | -34.164 | 40.849 | 30.938 | 1.00 38.42 | 1DIK 758 |
| ATOM | 667 | O | PHE | 92 | -34.726 | 39.836 | 30.526 | 1.00 36.46 | 1DIK 759 |
| ATOM | 668 | CB | PHE | 92 | -32.677 | 41.972 | 29.287 | 1.00 38.12 | 1DIK 760 |
| ATOM | 669 | CG | PHE | 92 | -31.499 | 41.624 | 30.163 | 1.00 36.18 | 1DIK 761 |
| ATOM | 670 | CD1 | PHE | 92 | -30.861 | 42.606 | 30.919 | 1.00 32.76 | 1DIK 762 |
| ATOM | 671 | CD2 | PHE | 92 | -31.018 | 40.314 | 30.215 | 1.00 34.57 | 1DIK 763 |
| ATOM | 672 | CE1 | PHE | 92 | -29.760 | 42.297 | 31.713 | 1.00 34.09 | 1DIK 764 |
| ATOM | 673 | CE2 | PHE | 92 | -29.917 | 39.991 | 31.006 | 1.00 33.52 | 1DIK 765 |
| ATOM | 674 | CZ | PHE | 92 | -29.284 | 40.988 | 31.759 | 1.00 34.32 | 1DIK 766 |
| ATOM | 675 | N | LEU | 93 | -33.657 | 40.961 | 32.164 | 1.00 39.65 | 1DIK 767 |
| ATOM | 676 | CA | LEU | 93 | -33.707 | 39.877 | 33.143 | 1.00 42.68 | 1DIK 768 |
| ATOM | 677 | C | LEU | 93 | -35.097 | 39.376 | 33.504 | 1.00 46.01 | 1DIK 769 |
| ATOM | 678 | O | LEU | 93 | -35.271 | 38.199 | 33.839 | 1.00 46.08 | 1DIK 770 |
| ATOM | 679 | CB | LEU | 93 | -32.981 | 40.284 | 34.428 | 1.00 39.70 | 1DIK 771 |
| ATOM | 680 | CG | LEU | 93 | -31.479 | 39.991 | 34.430 | 1.00 38.98 | 1DIK 772 |
| ATOM | 681 | CD1 | LEU | 93 | -30.805 | 40.641 | 35.632 | 1.00 37.62 | 1DIK 773 |
| ATOM | 682 | CD2 | LEU | 93 | -31.258 | 38.480 | 34.419 | 1.00 35.20 | 1DIK 774 |
| ATOM | 683 | N | LYS | 94 | -36.085 | 40.257 | 33.437 | 1.00 50.11 | 1DIK 775 |
| ATOM | 684 | CA | LYS | 94 | -37.445 | 39.874 | 33.780 | 1.00 54.55 | 1DIK 776 |
| ATOM | 685 | C | LYS | 94 | -37.938 | 38.709 | 32.915 | 1.00 54.53 | 1DIK 777 |
| ATOM | 686 | O | LYS | 94 | -38.651 | 37.831 | 33.402 | 1.00 56.72 | 1DIK 778 |
| ATOM | 687 | CB | LYS | 94 | -38.380 | 41.087 | 33.663 | 1.00 59.55 | 1DIK 779 |
| ATOM | 688 | CG | LYS | 94 | -39.736 | 40.899 | 34.322 | 1.00 66.52 | 1DIK 780 |
| ATOM | 689 | CD | LYS | 94 | -40.436 | 42.236 | 34.556 | 1.00 71.87 | 1DIK 781 |
| ATOM | 690 | CE | LYS | 94 | -41.818 | 42.031 | 35.189 | 1.00 75.09 | 1DIK 782 |
| ATOM | 691 | NZ | LYS | 94 | -42.493 | 43.320 | 35.533 | 1.00 75.30 | 1DIK 783 |
| ATOM | 692 | N | THR | 95 | -37.549 | 38.687 | 31.643 | 1.00 52.52 | 1DIK 784 |
| ATOM | 693 | CA | THR | 95 | -37.991 | 37.622 | 30.748 | 1.00 50.56 | 1DIK 785 |
| ATOM | 694 | C | THR | 95 | -36.902 | 36.850 | 30.009 | 1.00 49.46 | 1DIK 786 |
| ATOM | 695 | O | THR | 95 | -37.177 | 36.258 | 28.960 | 1.00 48.63 | 1DIK 787 |
| ATOM | 696 | CB | THR | 95 | -38.962 | 38.168 | 29.700 | 1.00 52.17 | 1DIK 788 |
| ATOM | 697 | OG1 | THR | 95 | -38.366 | 39.295 | 29.039 | 1.00 48.18 | 1DIK 789 |
| ATOM | 698 | CG2 | THR | 95 | -40.272 | 38.574 | 30.357 | 1.00 54.41 | 1DIK 790 |
| ATOM | 699 | N | TYR | 96 | -35.676 | 36.855 | 30.531 | 1.00 47.27 | 1DIK 791 |
| ATOM | 700 | CA | TYR | 96 | -34.582 | 36.119 | 29.894 | 1.00 44.27 | 1DIK 792 |
| ATOM | 701 | C | TYR | 96 | -34.863 | 34.613 | 29.997 | 1.00 44.70 | 1DIK 793 |
| ATOM | 702 | O | TYR | 96 | -35.227 | 34.107 | 31.060 | 1.00 43.58 | 1DIK 794 |
| ATOM | 703 | CB | TYR | 96 | -33.236 | 36.456 | 30.550 | 1.00 37.81 | 1DIK 795 |
| ATOM | 704 | CG | TYR | 96 | -32.071 | 35.699 | 29.957 | 1.00 34.72 | 1DIK 796 |
| ATOM | 705 | CD1 | TYR | 96 | -31.362 | 36.208 | 28.866 | 1.00 38.16 | 1DIK 797 |
| ATOM | 706 | CD2 | TYR | 96 | -31.683 | 34.465 | 30.474 | 1.00 35.36 | 1DIK 798 |
| ATOM | 707 | CE1 | TYR | 96 | -30.290 | 35.499 | 28.302 | 1.00 37.21 | 1DIK 799 |
| ATOM | 708 | CE2 | TYR | 96 | -30.620 | 33.747 | 29.923 | 1.00 37.79 | 1DIK 800 |
| ATOM | 709 | CZ | TYR | 96 | -29.929 | 34.269 | 28.839 | 1.00 39.34 | 1DIK 801 |
| ATOM | 710 | OH | TYR | 96 | -28.882 | 33.557 | 28.303 | 1.00 37.35 | 1DIK 802 |
| ATOM | 711 | N | ASN | 97 | -34.694 | 33.903 | 28.888 | 1.00 43.16 | 1DIK 803 |
| ATOM | 712 | CA | ASN | 97 | -34.937 | 32.471 | 28.859 | 1.00 45.14 | 1DIK 804 |
| ATOM | 713 | C | ASN | 97 | -33.617 | 31.744 | 28.554 | 1.00 45.53 | 1DIK 805 |
| ATOM | 714 | O | ASN | 97 | -33.097 | 31.838 | 27.436 | 1.00 46.50 | 1DIK 806 |

FIG. 8-12

```
ATOM    715  CB   ASN   97     -35.988  32.167  27.788  1.00  50.43      1DIK 807
ATOM    716  CG   ASN   97     -36.536  30.758  27.895  1.00  58.07      1DIK 808
ATOM    717  OD1  ASN   97     -36.630  30.191  28.991  1.00  62.08      1DIK 809
ATOM    718  ND2  ASN   97     -36.905  30.179  26.755  1.00  59.47      1DIK 810
ATOM    719  N    TYR   98     -33.079  31.035  29.550  1.00  42.20      1DIK 811
ATOM    720  CA   TYR   98     -31.814  30.308  29.413  1.00  39.67      1DIK 812
ATOM    721  C    TYR   98     -31.937  29.149  28.430  1.00  39.43      1DIK 813
ATOM    722  O    TYR   98     -32.589  28.156  28.719  1.00  42.93      1DIK 814
ATOM    723  CB   TYR   98     -31.357  29.772  30.775  1.00  35.56      1DIK 815
ATOM    724  CG   TYR   98     -29.955  29.201  30.763  1.00  34.67      1DIK 816
ATOM    725  CD1  TYR   98     -29.720  27.862  30.440  1.00  33.36      1DIK 817
ATOM    726  CD2  TYR   98     -28.857  30.004  31.067  1.00  30.84      1DIK 818
ATOM    727  CE1  TYR   98     -28.421  27.343  30.421  1.00  33.02      1DIK 819
ATOM    728  CE2  TYR   98     -27.564  29.496  31.053  1.00  31.68      1DIK 820
ATOM    729  CZ   TYR   98     -27.351  28.167  30.731  1.00  32.17      1DIK 821
ATOM    730  OH   TYR   98     -26.071  27.673  30.742  1.00  31.22      1DIK 822
ATOM    731  N    SER   99     -31.304  29.267  27.272  1.00  41.23      1DIK 823
ATOM    732  CA   SER   99     -31.395  28.211  26.277  1.00  42.13      1DIK 824
ATOM    733  C    SER   99     -30.043  27.782  25.699  1.00  41.05      1DIK 825
ATOM    734  O    SER   99     -29.972  27.293  24.572  1.00  39.39      1DIK 826
ATOM    735  CB   SER   99     -32.340  28.645  25.148  1.00  43.93      1DIK 827
ATOM    736  OG   SER   99     -31.869  29.828  24.518  1.00  44.91      1DIK 828
ATOM    737  N    LEU  100     -28.970  27.964  26.464  1.00  38.89      1DIK 829
ATOM    738  CA   LEU  100     -27.647  27.561  25.999  1.00  36.71      1DIK 830
ATOM    739  C    LEU  100     -27.555  26.038  26.067  1.00  35.82      1DIK 831
ATOM    740  O    LEU  100     -28.181  25.425  26.932  1.00  37.24      1DIK 832
ATOM    741  CB   LEU  100     -26.548  28.175  26.878  1.00  33.03      1DIK 833
ATOM    742  CG   LEU  100     -26.381  29.694  26.799  1.00  33.85      1DIK 834
ATOM    743  CD1  LEU  100     -25.272  30.149  27.725  1.00  30.27      1DIK 835
ATOM    744  CD2  LEU  100     -26.063  30.090  25.375  1.00  33.01      1DIK 836
ATOM    745  N    GLY  101     -26.789  25.437  25.153  1.00  34.71      1DIK 837
ATOM    746  CA   GLY  101     -26.585  23.999  25.169  1.00  29.13      1DIK 838
ATOM    747  C    GLY  101     -25.572  23.673  26.270  1.00  31.41      1DIK 839
ATOM    748  O    GLY  101     -25.410  24.443  27.227  1.00  28.98      1DIK 840
ATOM    749  N    ALA  102     -24.875  22.547  26.163  1.00  30.11      1DIK 841
ATOM    750  CA   ALA  102     -23.892  22.208  27.180  1.00  29.75      1DIK 842
ATOM    751  C    ALA  102     -22.745  21.409  26.581  1.00  29.60      1DIK 843
ATOM    752  O    ALA  102     -22.943  20.675  25.622  1.00  32.26      1DIK 844
ATOM    753  CB   ALA  102     -24.556  21.423  28.318  1.00  26.45      1DIK 845
ATOM    754  N    ASP  103     -21.553  21.578  27.148  1.00  29.83      1DIK 846
ATOM    755  CA   ASP  103     -20.329  20.868  26.756  1.00  31.04      1DIK 847
ATOM    756  C    ASP  103     -19.817  20.909  25.318  1.00  29.41      1DIK 848
ATOM    757  O    ASP  103     -18.603  20.919  25.093  1.00  26.94      1DIK 849
ATOM    758  CB   ASP  103     -20.425  19.391  27.175  1.00  32.82      1DIK 850
ATOM    759  CG   ASP  103     -20.685  19.213  28.665  1.00  37.87      1DIK 851
ATOM    760  OD1  ASP  103     -19.906  19.738  29.490  1.00  39.37      1DIK 852
ATOM    761  OD2  ASP  103     -21.677  18.540  29.013  1.00  39.81      1DIK 853
ATOM    762  N    ASP  104     -20.723  20.924  24.351  1.00  28.43      1DIK 854
ATOM    763  CA   ASP  104     -20.356  20.891  22.954  1.00  29.73      1DIK 855
ATOM    764  C    ASP  104     -19.720  22.127  22.382  1.00  30.60      1DIK 856
ATOM    765  O    ASP  104     -19.830  23.226  22.925  1.00  32.58      1DIK 857
ATOM    766  CB   ASP  104     -21.581  20.573  22.096  1.00  37.28      1DIK 858
ATOM    767  CG   ASP  104     -22.117  19.176  22.321  1.00  43.64      1DIK 859
ATOM    768  OD1  ASP  104     -21.308  18.243  22.545  1.00  45.93      1DIK 860
ATOM    769  OD2  ASP  104     -23.358  19.019  22.268  1.00  49.65      1DIK 861
ATOM    770  N    LEU  105     -19.053  21.915  21.257  1.00  27.70      1DIK 862
ATOM    771  CA   LEU  105     -18.432  22.973  20.491  1.00  27.87      1DIK 863
ATOM    772  C    LEU  105     -19.642  23.744  19.933  1.00  29.06      1DIK 864
ATOM    773  O    LEU  105     -20.626  23.116  19.531  1.00  27.73      1DIK 865
ATOM    774  CB   LEU  105     -17.668  22.327  19.334  1.00  27.40      1DIK 866
ATOM    775  CG   LEU  105     -16.474  23.040  18.736  1.00  27.83      1DIK 867
ATOM    776  CD1  LEU  105     -15.518  23.368  19.855  1.00  33.80      1DIK 868
ATOM    777  CD2  LEU  105     -15.790  22.162  17.716  1.00  27.39      1DIK 869
ATOM    778  N    THR  106     -19.599  25.075  19.917  1.00  28.75      1DIK 870
ATOM    779  CA   THR  106     -20.714  25.848  19.358  1.00  28.71      1DIK 871
ATOM    780  C    THR  106     -20.462  26.060  17.858  1.00  31.52      1DIK 872
```

FIG. 8-13

```
ATOM    781  O    THR   106     -19.338  25.863  17.369  1.00 32.15      1DIK 873
ATOM    782  CB   THR   106     -20.849  27.256  20.001  1.00 29.41      1DIK 874
ATOM    783  OG1  THR   106     -19.691  28.044  19.698  1.00 28.94      1DIK 875
ATOM    784  CG2  THR   106     -21.034  27.164  21.496  1.00 27.82      1DIK 876
ATOM    785  N    PRO   107     -21.503  26.448  17.098  1.00 30.71      1DIK 877
ATOM    786  CA   PRO   107     -21.312  26.680  15.658  1.00 28.88      1DIK 878
ATOM    787  C    PRO   107     -20.169  27.693  15.406  1.00 27.50      1DIK 879
ATOM    788  O    PRO   107     -19.381  27.531  14.464  1.00 30.80      1DIK 880
ATOM    789  CB   PRO   107     -22.679  27.203  15.218  1.00 25.78      1DIK 881
ATOM    790  CG   PRO   107     -23.610  26.495  16.163  1.00 27.66      1DIK 882
ATOM    791  CD   PRO   107     -22.910  26.662  17.481  1.00 28.45      1DIK 883
ATOM    792  N    PHE   108     -20.082  28.727  16.245  1.00 23.11      1DIK 884
ATOM    793  CA   PHE   108     -19.015  29.729  16.151  1.00 22.62      1DIK 885
ATOM    794  C    PHE   108     -17.644  29.059  16.383  1.00 25.28      1DIK 886
ATOM    795  O    PHE   108     -16.657  29.356  15.670  1.00 25.00      1DIK 887
ATOM    796  CB   PHE   108     -19.226  30.837  17.195  1.00 20.26      1DIK 888
ATOM    797  CG   PHE   108     -18.063  31.794  17.312  1.00 25.13      1DIK 889
ATOM    798  CD1  PHE   108     -17.819  32.743  16.325  1.00 24.81      1DIK 890
ATOM    799  CD2  PHE   108     -17.196  31.737  18.410  1.00 28.22      1DIK 891
ATOM    800  CE1  PHE   108     -16.726  33.617  16.430  1.00 26.50      1DIK 892
ATOM    801  CE2  PHE   108     -16.101  32.609  18.521  1.00 25.64      1DIK 893
ATOM    802  CZ   PHE   108     -15.868  33.546  17.531  1.00 22.77      1DIK 894
ATOM    803  N    GLY   109     -17.597  28.164  17.380  1.00 21.53      1DIK 895
ATOM    804  CA   GLY   109     -16.383  27.428  17.704  1.00 21.31      1DIK 896
ATOM    805  C    GLY   109     -15.917  26.535  16.562  1.00 22.06      1DIK 897
ATOM    806  O    GLY   109     -14.713  26.384  16.338  1.00 22.23      1DIK 898
ATOM    807  N    GLU   110     -16.869  25.941  15.842  1.00 20.87      1DIK 899
ATOM    808  CA   GLU   110     -16.565  25.108  14.687  1.00 18.70      1DIK 900
ATOM    809  C    GLU   110     -15.908  25.975  13.623  1.00 19.56      1DIK 901
ATOM    810  O    GLU   110     -14.895  25.590  13.019  1.00 20.43      1DIK 902
ATOM    811  CB   GLU   110     -17.843  24.513  14.123  1.00 19.80      1DIK 903
ATOM    812  CG   GLU   110     -18.563  23.605  15.104  1.00 22.70      1DIK 904
ATOM    813  CD   GLU   110     -19.803  22.983  14.520  1.00 23.25      1DIK 905
ATOM    814  OE1  GLU   110     -20.346  23.513  13.524  1.00 27.96      1DIK 906
ATOM    815  OE2  GLU   110     -20.237  21.955  15.063  1.00 26.17      1DIK 907
ATOM    816  N    GLN   111     -16.489  27.153  13.402  1.00 18.95      1DIK 908
ATOM    817  CA   GLN   111     -15.963  28.094  12.427  1.00 20.74      1DIK 909
ATOM    818  C    GLN   111     -14.541  28.523  12.791  1.00 21.64      1DIK 910
ATOM    819  O    GLN   111     -13.679  28.651  11.908  1.00 21.26      1DIK 911
ATOM    820  CB   GLN   111     -16.868  29.321  12.319  1.00 26.01      1DIK 912
ATOM    821  CG   GLN   111     -16.527  30.222  11.144  1.00 32.20      1DIK 913
ATOM    822  CD   GLN   111     -16.503  29.455   9.825  1.00 37.67      1DIK 914
ATOM    823  OE1  GLN   111     -17.440  28.718   9.511  1.00 42.78      1DIK 915
ATOM    824  NE2  GLN   111     -15.432  29.620   9.051  1.00 34.61      1DIK 916
ATOM    825  N    GLU   112     -14.292  28.743  14.084  1.00 20.80      1DIK 917
ATOM    826  CA   GLU   112     -12.960  29.137  14.550  1.00 19.26      1DIK 918
ATOM    827  C    GLU   112     -11.875  28.135  14.133  1.00 19.50      1DIK 919
ATOM    828  O    GLU   112     -10.777  28.537  13.705  1.00 14.92      1DIK 920
ATOM    829  CB   GLU   112     -12.923  29.262  16.075  1.00 19.60      1DIK 921
ATOM    830  CG   GLU   112     -13.535  30.522  16.669  1.00 19.22      1DIK 922
ATOM    831  CD   GLU   112     -13.276  30.607  18.157  1.00 19.02      1DIK 923
ATOM    832  OE1  GLU   112     -13.712  29.691  18.878  1.00 19.03      1DIK 924
ATOM    833  OE2  GLU   112     -12.636  31.576  18.611  1.00 19.54      1DIK 925
ATOM    834  N    LEU   113     -12.177  26.841  14.262  1.00 15.87      1DIK 926
ATOM    835  CA   LEU   113     -11.213  25.803  13.908  1.00 18.95      1DIK 927
ATOM    836  C    LEU   113     -11.023  25.666  12.398  1.00 19.66      1DIK 928
ATOM    837  O    LEU   113      -9.907  25.411  11.929  1.00 19.09      1DIK 929
ATOM    838  CB   LEU   113     -11.592  24.471  14.559  1.00 19.94      1DIK 930
ATOM    839  CG   LEU   113     -11.016  24.283  15.966  1.00 19.61      1DIK 931
ATOM    840  CD1  LEU   113      -9.550  23.910  15.842  1.00 17.82      1DIK 932
ATOM    841  CD2  LEU   113     -11.190  25.552  16.819  1.00 15.58      1DIK 933
ATOM    842  N    VAL   114     -12.104  25.840  11.641  1.00 20.06      1DIK 934
ATOM    843  CA   VAL   114     -12.020  25.801  10.183  1.00 18.34      1DIK 935
ATOM    844  C    VAL   114     -11.039  26.916   9.779  1.00 19.73      1DIK 936
ATOM    845  O    VAL   114     -10.108  26.692   9.003  1.00 20.73      1DIK 937
ATOM    846  CB   VAL   114     -13.411  26.071   9.526  1.00 21.09      1DIK 938
```

FIG. 8-14

```
ATOM    847  CG1 VAL   114     -13.246  26.333   8.048  1.00 11.01      1DIK 939
ATOM    848  CG2 VAL   114     -14.361  24.877   9.747  1.00 14.20      1DIK 940
ATOM    849  N   ASN   115     -11.245  28.115  10.322  1.00 19.62      1DIK 941
ATOM    850  CA  ASN   115     -10.371  29.255  10.031  1.00 19.27      1DIK 942
ATOM    851  C   ASN   115      -8.909  28.985  10.398  1.00 20.48      1DIK 943
ATOM    852  O   ASN   115      -7.993  29.371   9.673  1.00 19.85      1DIK 944
ATOM    853  CB  ASN   115     -10.844  30.494  10.776  1.00 19.96      1DIK 945
ATOM    854  CG  ASN   115     -12.094  31.109  10.175  1.00 21.18      1DIK 946
ATOM    855  OD1 ASN   115     -12.671  30.593   9.226  1.00 22.64      1DIK 947
ATOM    856  ND2 ASN   115     -12.516  32.227  10.733  1.00 19.58      1DIK 948
ATOM    857  N   SER   116      -8.699  28.327  11.532  1.00 22.03      1DIK 949
ATOM    858  CA  SER   116      -7.358  27.966  12.004  1.00 20.45      1DIK 950
ATOM    859  C   SER   116      -6.696  26.987  11.000  1.00 20.54      1DIK 951
ATOM    860  O   SER   116      -5.489  27.078  10.725  1.00 19.21      1DIK 952
ATOM    861  CB  SER   116      -7.465  27.330  13.407  1.00 20.16      1DIK 953
ATOM    862  OG  SER   116      -6.199  27.086  13.987  1.00 15.09      1DIK 954
ATOM    863  N   GLY   117      -7.484  26.059  10.458  1.00 17.37      1DIK 955
ATOM    864  CA  GLY   117      -6.963  25.112   9.485  1.00 18.31      1DIK 956
ATOM    865  C   GLY   117      -6.507  25.807   8.209  1.00 19.33      1DIK 957
ATOM    866  O   GLY   117      -5.468  25.455   7.647  1.00 22.20      1DIK 958
ATOM    867  N   ILE   118      -7.294  26.784   7.759  1.00 18.87      1DIK 959
ATOM    868  CA  ILE   118      -6.998  27.585   6.567  1.00 19.05      1DIK 960
ATOM    869  C   ILE   118      -5.690  28.347   6.739  1.00 19.38      1DIK 961
ATOM    870  O   ILE   118      -4.831  28.365   5.848  1.00 20.03      1DIK 962
ATOM    871  CB  ILE   118      -8.105  28.640   6.316  1.00 18.22      1DIK 963
ATOM    872  CG1 ILE   118      -9.392  27.959   5.860  1.00 16.45      1DIK 964
ATOM    873  CG2 ILE   118      -7.627  29.688   5.310  1.00 13.65      1DIK 965
ATOM    874  CD1 ILE   118     -10.549  28.901   5.792  1.00 12.46      1DIK 966
ATOM    875  N   LYS   119      -5.555  28.979   7.900  1.00 21.72      1DIK 967
ATOM    876  CA  LYS   119      -4.381  29.775   8.225  1.00 21.99      1DIK 968
ATOM    877  C   LYS   119      -3.095  28.955   8.340  1.00 22.12      1DIK 969
ATOM    878  O   LYS   119      -2.034  29.404   7.881  1.00 22.21      1DIK 970
ATOM    879  CB  LYS   119      -4.636  30.574   9.503  1.00 22.43      1DIK 971
ATOM    880  CG  LYS   119      -3.536  31.557   9.789  1.00 27.62      1DIK 972
ATOM    881  CD  LYS   119      -4.020  32.690  10.649  1.00 29.86      1DIK 973
ATOM    882  CE  LYS   119      -2.986  33.798  10.646  1.00 29.14      1DIK 974
ATOM    883  NZ  LYS   119      -3.311  34.827  11.667  1.00 30.24      1DIK 975
ATOM    884  N   PHE   120      -3.191  27.765   8.942  1.00 19.44      1DIK 976
ATOM    885  CA  PHE   120      -2.034  26.879   9.084  1.00 20.52      1DIK 977
ATOM    886  C   PHE   120      -1.561  26.429   7.694  1.00 22.99      1DIK 978
ATOM    887  O   PHE   120      -0.355  26.404   7.415  1.00 21.56      1DIK 979
ATOM    888  CB  PHE   120      -2.381  25.647   9.927  1.00 18.62      1DIK 980
ATOM    889  CG  PHE   120      -1.208  24.727  10.163  1.00 25.65      1DIK 981
ATOM    890  CD1 PHE   120      -0.192  25.083  11.059  1.00 23.32      1DIK 982
ATOM    891  CD2 PHE   120      -1.114  23.504   9.493  1.00 25.43      1DIK 983
ATOM    892  CE1 PHE   120       0.894  24.243  11.284  1.00 18.73      1DIK 984
ATOM    893  CE2 PHE   120      -0.025  22.651   9.712  1.00 22.55      1DIK 985
ATOM    894  CZ  PHE   120       0.981  23.021  10.610  1.00 20.53      1DIK 986
ATOM    895  N   TYR   121      -2.515  26.074   6.830  1.00 20.17      1DIK 987
ATOM    896  CA  TYR   121      -2.179  25.656   5.482  1.00 19.95      1DIK 988
ATOM    897  C   TYR   121      -1.450  26.766   4.718  1.00 21.59      1DIK 989
ATOM    898  O   TYR   121      -0.402  26.528   4.112  1.00 19.41      1DIK 990
ATOM    899  CB  TYR   121      -3.427  25.271   4.668  1.00 19.72      1DIK 991
ATOM    900  CG  TYR   121      -3.029  24.865   3.265  1.00 20.01      1DIK 992
ATOM    901  CD1 TYR   121      -2.859  25.819   2.240  1.00 18.79      1DIK 993
ATOM    902  CD2 TYR   121      -2.721  23.537   2.983  1.00 20.66      1DIK 994
ATOM    903  CE1 TYR   121      -2.381  25.445   0.976  1.00 19.33      1DIK 995
ATOM    904  CE2 TYR   121      -2.246  23.152   1.730  1.00 23.50      1DIK 996
ATOM    905  CZ  TYR   121      -2.074  24.097   0.737  1.00 23.64      1DIK 997
ATOM    906  OH  TYR   121      -1.593  23.670  -0.472  1.00 22.79      1DIK 998
ATOM    907  N   GLN   122      -2.021  27.969   4.734  1.00 23.17      1DIK 999
ATOM    908  CA  GLN   122      -1.447  29.104   4.022  1.00 22.67      1DIK1000
ATOM    909  C   GLN   122      -0.085  29.549   4.527  1.00 22.41      1DIK1001
ATOM    910  O   GLN   122       0.799  29.860   3.735  1.00 25.99      1DIK1002
ATOM    911  CB  GLN   122      -2.387  30.296   4.071  1.00 26.42      1DIK1103
ATOM    912  CG  GLN   122      -3.691  30.133   3.323  1.00 27.92      1DIK1004
```

FIG. 8-15

```
ATOM    913  CD   GLN  122    -4.623  31.333   3.531  1.00  34.41      1DIK1005
ATOM    914  OE1  GLN  122    -4.531  32.066   4.537  1.00  33.16      1DIK1006
ATOM    915  NE2  GLN  122    -5.528  31.538   2.582  1.00  36.14      1DIK1007
ATOM    916  N    ARG  123     0.089  29.586   5.841  1.00  22.55      1DIK1008
ATOM    917  CA   ARG  123     1.359  30.011   6.416  1.00  21.19      1DIK1009
ATOM    918  C    ARG  123     2.541  29.106   6.012  1.00  23.05      1DIK1010
ATOM    919  O    ARG  123     3.652  29.582   5.785  1.00  23.96      1DIK1011
ATOM    920  CB   ARG  123     1.225  30.083   7.947  1.00  20.65      1DIK1012
ATOM    921  CG   ARG  123     2.485  30.519   8.653  1.00  19.56      1DIK1013
ATOM    922  CD   ARG  123     2.297  30.672  10.146  1.00  21.87      1DIK1014
ATOM    923  NE   ARG  123     3.580  30.973  10.789  1.00  24.63      1DIK1015
ATOM    924  CZ   ARG  123     4.173  32.174  10.802  1.00  28.06      1DIK1016
ATOM    925  NH1  ARG  123     3.605  33.236  10.232  1.00  18.64      1DIK1017
ATOM    926  NH2  ARG  123     5.349  32.319  11.402  1.00  24.13      1DIK1018
ATOM    927  N    TYR  124     2.298  27.803   5.915  1.00  24.21      1DIK1019
ATOM    928  CA   TYR  124     3.346  26.852   5.572  1.00  24.48      1DIK1020
ATOM    929  C    TYR  124     3.125  26.182   4.222  1.00  26.16      1DIK1021
ATOM    930  O    TYR  124     3.486  25.016   4.049  1.00  24.40      1DIK1022
ATOM    931  CB   TYR  124     3.444  25.790   6.679  1.00  22.35      1DIK1023
ATOM    932  CG   TYR  124     3.696  26.398   8.040  1.00  24.40      1DIK1024
ATOM    933  CD1  TYR  124     4.946  26.923   8.360  1.00  20.62      1DIK1025
ATOM    934  CD2  TYR  124     2.677  26.484   8.998  1.00  25.42      1DIK1026
ATOM    935  CE1  TYR  124     5.186  27.515   9.579  1.00  20.04      1DIK1027
ATOM    936  CE2  TYR  124     2.907  27.082  10.236  1.00  22.59      1DIK1028
ATOM    937  CZ   TYR  124     4.176  27.600  10.521  1.00  22.79      1DIK1029
ATOM    938  OH   TYR  124     4.450  28.205  11.737  1.00  16.28      1DIK1030
ATOM    939  N    GLU  125     2.548  26.921   3.273  1.00  27.83      1DIK1031
ATOM    940  CA   GLU  125     2.242  26.406   1.931  1.00  31.93      1DIK1032
ATOM    941  C    GLU  125     3.321  25.534   1.276  1.00  31.07      1DIK1033
ATOM    942  O    GLU  125     3.008  24.504   0.680  1.00  31.87      1DIK1034
ATOM    943  CB   GLU  125     1.875  27.566   0.985  1.00  35.88      1DIK1035
ATOM    944  CG   GLU  125     1.226  27.149  -0.360  1.00  46.46      1DIK1036
ATOM    945  CD   GLU  125     2.239  26.814  -1.475  1.00  54.36      1DIK1037
ATOM    946  OE1  GLU  125     3.343  27.412  -1.491  1.00  58.38      1DIK1038
ATOM    947  OE2  GLU  125     1.937  25.955  -2.343  1.00  54.70      1DIK1039
ATOM    948  N    SER  126     4.583  25.929   1.383  1.00  28.00      1DIK1040
ATOM    949  CA   SER  126     5.651  25.161   0.755  1.00  31.00      1DIK1041
ATOM    950  C    SER  126     5.733  23.711   1.249  1.00  31.74      1DIK1042
ATOM    951  O    SER  126     6.217  22.831   0.525  1.00  32.26      1DIK1043
ATOM    952  CB   SER  126     6.992  25.881   0.936  1.00  33.57      1DIK1044
ATOM    953  OG   SER  126     7.256  26.134   2.308  1.00  41.28      1DIK1045
ATOM    954  N    LEU  127     5.262  23.476   2.477  1.00  28.17      1DIK1046
ATOM    955  CA   LEU  127     5.246  22.148   3.087  1.00  23.13      1DIK1047
ATOM    956  C    LEU  127     3.879  21.466   2.981  1.00  22.92      1DIK1048
ATOM    957  O    LEU  127     3.781  20.304   2.584  1.00  24.92      1DIK1049
ATOM    958  CB   LEU  127     5.601  22.236   4.569  1.00  21.37      1DIK1050
ATOM    959  CG   LEU  127     7.017  22.618   4.969  1.00  24.27      1DIK1051
ATOM    960  CD1  LEU  127     7.125  22.582   6.485  1.00  17.41      1DIK1052
ATOM    961  CD2  LEU  127     8.006  21.652   4.316  1.00  20.13      1DIK1053
ATOM    962  N    THR  128     2.833  22.198   3.352  1.00  22.22      1DIK1054
ATOM    963  CA   THR  128     1.461  21.701   3.357  1.00  21.36      1DIK1055
ATOM    964  C    THR  128     0.935  21.259   1.989  1.00  25.64      1DIK1056
ATOM    965  O    THR  128     0.016  20.429   1.907  1.00  26.78      1DIK1057
ATOM    966  CB   THR  128     0.502  22.765   3.941  1.00  18.91      1DIK1058
ATOM    967  OG1  THR  128     0.687  24.008   3.248  1.00  16.25      1DIK1059
ATOM    968  CG2  THR  128     0.771  22.971   5.413  1.00   8.45      1DIK1060
ATOM    969  N    ARG  129     1.510  21.803   0.917  1.00  27.58      1DIK1061
ATOM    970  CA   ARG  129     1.070  21.436  -0.423  1.00  27.49      1DIK1062
ATOM    971  C    ARG  129     1.303  19.975  -0.790  1.00  24.39      1DIK1063
ATOM    972  O    ARG  129     0.612  19.448  -1.652  1.00  25.81      1DIK1064
ATOM    973  CB   ARG  129     1.673  22.351  -1.484  1.00  28.84      1DIK1065
ATOM    974  CG   ARG  129     3.139  22.218  -1.685  1.00  31.94      1DIK1066
ATOM    975  CD   ARG  129     3.536  23.072  -2.860  1.00  46.51      1DIK1067
ATOM    976  NE   ARG  129     4.899  22.774  -3.270  1.00  59.18      1DIK1068
ATOM    977  CZ   ARG  129     5.879  23.669  -3.295  1.00  67.18      1DIK1069
ATOM    978  NH1  ARG  129     5.643  24.936  -2.948  1.00  66.97      1DIK1070
```

FIG. 8-16

```
ATOM    979  NH2 ARG 129     7.098  23.294  -3.672  1.00 69.63    1DIK1071
ATOM    980  N   ASN 130     2.266  19.306  -0.166  1.00 26.81    1DIK1072
ATOM    981  CA  ASN 130     2.456  17.883  -0.470  1.00 29.49    1DIK1073
ATOM    982  C   ASN 130     2.819  16.977   0.691  1.00 25.25    1DIK1074
ATOM    983  O   ASN 130     3.369  15.904   0.489  1.00 22.37    1DIK1075
ATOM    984  CB  ASN 130     3.407  17.643  -1.657  1.00 33.67    1DIK1076
ATOM    985  CG  ASN 130     4.679  18.415  -1.550  1.00 35.85    1DIK1077
ATOM    986  OD1 ASN 130     5.242  18.561  -0.472  1.00 41.17    1DIK1078
ATOM    987  ND2 ASN 130     5.148  18.926  -2.678  1.00 36.92    1DIK1079
ATOM    988  N   ILE 131     2.499  17.409   1.905  1.00 23.74    1DIK1080
ATOM    989  CA  ILE 131     2.729  16.600   3.087  1.00 22.76    1DIK1081
ATOM    990  C   ILE 131     1.405  16.555   3.857  1.00 22.22    1DIK1082
ATOM    991  O   ILE 131     0.706  17.568   3.994  1.00 20.81    1DIK1083
ATOM    992  CB  ILE 131     3.864  17.171   3.974  1.00 25.01    1DIK1084
ATOM    993  CG1 ILE 131     5.196  17.051   3.237  1.00 22.26    1DIK1085
ATOM    994  CG2 ILE 131     3.966  16.383   5.296  1.00 25.81    1DIK1086
ATOM    995  CD1 ILE 131     6.264  18.012   3.705  1.00 19.55    1DIK1087
ATOM    996  N   VAL 132     1.052  15.368   4.336  1.00 21.56    1DIK1088
ATOM    997  CA  VAL 132    -0.173  15.184   5.113  1.00 21.17    1DIK1089
ATOM    998  C   VAL 132     0.285  15.221   6.575  1.00 20.81    1DIK1090
ATOM    999  O   VAL 132     1.137  14.422   6.979  1.00 20.82    1DIK1091
ATOM   1000  CB  VAL 132    -0.841  13.807   4.803  1.00 18.52    1DIK1092
ATOM   1001  CG1 VAL 132    -2.123  13.651   5.597  1.00 14.56    1DIK1093
ATOM   1002  CG2 VAL 132    -1.126  13.686   3.320  1.00 13.43    1DIK1094
ATOM   1003  N   PRO 133    -0.260  16.151   7.383  1.00 20.75    1DIK1095
ATOM   1004  CA  PRO 133     0.116  16.273   8.798  1.00 17.17    1DIK1096
ATOM   1005  C   PRO 133    -0.288  15.036   9.585  1.00 20.37    1DIK1097
ATOM   1006  O   PRO 133    -1.268  14.364   9.229  1.00 19.54    1DIK1098
ATOM   1007  CB  PRO 133    -0.684  17.488   9.277  1.00 17.52    1DIK1099
ATOM   1008  CG  PRO 133    -1.029  18.231   8.029  1.00 19.74    1DIK1100
ATOM   1009  CD  PRO 133    -1.278  17.151   7.020  1.00 21.29    1DIK1101
ATOM   1010  N   PHE 134     0.467  14.721  10.641  1.00 20.95    1DIK1102
ATOM   1011  CA  PHE 134     0.131  13.596  11.514  1.00 18.61    1DIK1103
ATOM   1012  C   PHE 134    -0.583  14.285  12.677  1.00 17.69    1DIK1104
ATOM   1013  O   PHE 134    -0.016  15.175  13.310  1.00 17.93    1DIK1105
ATOM   1014  CB  PHE 134     1.368  12.847  12.003  1.00 17.50    1DIK1106
ATOM   1015  CG  PHE 134     1.040  11.715  12.941  1.00 17.28    1DIK1107
ATOM   1016  CD1 PHE 134     0.616  10.478  12.443  1.00 11.84    1DIK1108
ATOM   1017  CD2 PHE 134     1.133  11.888  14.324  1.00 13.50    1DIK1109
ATOM   1018  CE1 PHE 134     0.285   9.423  13.310  1.00 11.64    1DIK1110
ATOM   1019  CE2 PHE 134     0.804  10.837  15.203  1.00 12.13    1DIK1111
ATOM   1020  CZ  PHE 134     0.379   9.607  14.693  1.00 15.07    1DIK1112
ATOM   1021  N   ILE 135    -1.816  13.863  12.949  1.00 15.82    1DIK1113
ATOM   1022  CA  ILE 135    -2.670  14.495  13.953  1.00 13.71    1DIK1114
ATOM   1023  C   ILE 135    -3.088  13.644  15.156  1.00 14.35    1DIK1115
ATOM   1024  O   ILE 135    -3.425  12.461  15.015  1.00 16.80    1DIK1116
ATOM   1025  CB  ILE 135    -3.952  15.018  13.243  1.00 11.04    1DIK1117
ATOM   1026  CG1 ILE 135    -3.568  15.994  12.134  1.00  9.94    1DIK1118
ATOM   1027  CG2 ILE 135    -4.906  15.690  14.222  1.00 15.43    1DIK1119
ATOM   1028  CD1 ILE 135    -4.731  16.360  11.245  1.00 11.33    1DIK1120
ATOM   1029  N   ARG 136    -3.074  14.259  16.335  1.00 13.24    1DIK1121
ATOM   1030  CA  ARG 136    -3.480  13.593  17.571  1.00 15.19    1DIK1122
ATOM   1031  C   ARG 136    -4.451  14.511  18.296  1.00 16.07    1DIK1123
ATOM   1032  O   ARG 136    -4.355  15.734  18.190  1.00 16.44    1DIK1124
ATOM   1033  CB  ARG 136    -2.289  13.322  18.487  1.00 13.97    1DIK1125
ATOM   1034  CG  ARG 136    -1.203  12.434  17.905  1.00 12.99    1DIK1126
ATOM   1035  CD  ARG 136    -0.176  12.079  18.973  1.00 14.14    1DIK1127
ATOM   1036  NE  ARG 136     0.441  13.277  19.540  1.00 22.30    1DIK1128
ATOM   1037  CZ  ARG 136     1.335  13.288  20.525  1.00 20.79    1DIK1129
ATOM   1038  NH1 ARG 136     1.743  12.150  21.081  1.00 17.01    1DIK1130
ATOM   1039  NH2 ARG 136     1.819  14.450  20.951  1.00 17.84    1DIK1131
ATOM   1040  N   SER 137    -5.378  13.918  19.035  1.00 16.59    1DIK1132
ATOM   1041  CA  SER 137    -6.381  14.663  19.789  1.00 14.27    1DIK1133
ATOM   1042  C   SER 137    -6.624  13.982  21.147  1.00 17.11    1DIK1134
ATOM   1043  O   SER 137    -6.549  12.754  21.272  1.00 16.51    1DIK1135
ATOM   1044  CB  SER 137    -7.682  14.703  18.966  1.00 13.24    1DIK1136
```

FIG. 8-17

```
ATOM   1045  OG  SER  137   -8.804  15.178  19.690  1.00 13.55      1DIK1137
ATOM   1046  N   SER  138   -6.898  14.782  22.169  1.00 18.79      1DIK1138
ATOM   1047  CA  SER  138   -7.212  14.246  23.486  1.00 18.47      1DIK1139
ATOM   1048  C   SER  138   -8.651  13.714  23.338  1.00 20.67      1DIK1140
ATOM   1049  O   SER  138   -9.436  14.261  22.557  1.00 21.12      1DIK1141
ATOM   1050  CB  SER  138   -7.123  15.360  24.526  1.00 19.25      1DIK1142
ATOM   1051  OG  SER  138   -7.161  14.832  25.831  1.00 19.54      1DIK1143
ATOM   1052  N   GLY  139   -9.005  12.660  24.070  1.00 24.07      1DIK1144
ATOM   1053  CA  GLY  139  -10.326  12.064  23.923  1.00 23.86      1DIK1145
ATOM   1054  C   GLY  139  -11.511  12.774  24.550  1.00 26.14      1DIK1146
ATOM   1055  O   GLY  139  -12.114  12.261  25.491  1.00 33.68      1DIK1147
ATOM   1056  N   SER  140  -11.853  13.946  24.046  1.00 23.95      1DIK1148
ATOM   1057  CA  SER  140  -12.976  14.715  24.553  1.00 18.34      1DIK1149
ATOM   1058  C   SER  140  -13.709  15.148  23.296  1.00 21.76      1DIK1150
ATOM   1059  O   SER  140  -13.084  15.655  22.356  1.00 22.25      1DIK1151
ATOM   1060  CB  SER  140  -12.479  15.925  25.319  1.00 17.99      1DIK1152
ATOM   1061  OG  SER  140  -13.543  16.819  25.617  1.00 22.47      1DIK1153
ATOM   1062  N   SER  141  -15.024  14.959  23.274  1.00 19.07      1DIK1154
ATOM   1063  CA  SER  141  -15.825  15.278  22.097  1.00 21.60      1DIK1155
ATOM   1064  C   SER  141  -15.592  16.644  21.496  1.00 22.01      1DIK1156
ATOM   1065  O   SER  141  -15.468  16.764  20.275  1.00 23.16      1DIK1157
ATOM   1066  CB  SER  141  -17.303  15.111  22.399  1.00 23.43      1DIK1158
ATOM   1067  OG  SER  141  -17.480  14.054  23.319  1.00 40.45      1DIK1159
ATOM   1068  N   ARG  142  -15.526  17.675  22.335  1.00 19.81      1DIK1160
ATOM   1069  CA  ARG  142  -15.325  19.010  21.809  1.00 18.48      1DIK1161
ATOM   1070  C   ARG  142  -13.951  19.187  21.180  1.00 18.52      1DIK1162
ATOM   1071  O   ARG  142  -13.779  19.999  20.264  1.00 17.81      1DIK1163
ATOM   1072  CB  ARG  142  -15.580  20.072  22.885  1.00 17.69      1DIK1164
ATOM   1073  CG  ARG  142  -14.661  20.050  24.069  1.00 20.10      1DIK1165
ATOM   1074  CD  ARG  142  -14.952  21.269  24.913  1.00 23.72      1DIK1166
ATOM   1075  NE  ARG  142  -14.441  21.157  26.280  1.00 27.97      1DIK1167
ATOM   1076  CZ  ARG  142  -15.100  20.586  27.292  1.00 28.86      1DIK1168
ATOM   1077  NH1 ARG  142  -16.301  20.053  27.106  1.00 28.91      1DIK1169
ATOM   1078  NH2 ARG  142  -14.552  20.543  28.499  1.00 29.64      1DIK1170
ATOM   1079  N   VAL  143  -12.973  18.424  21.662  1.00 18.71      1DIK1171
ATOM   1080  CA  VAL  143  -11.620  18.516  21.137  1.00 16.09      1DIK1172
ATOM   1081  C   VAL  143  -11.561  17.777  19.799  1.00 19.00      1DIK1173
ATOM   1082  O   VAL  143  -11.031  18.303  18.802  1.00 19.96      1DIK1174
ATOM   1083  CB  VAL  143  -10.604  17.962  22.152  1.00 14.17      1DIK1175
ATOM   1084  CG1 VAL  143   -9.179  18.106  21.630  1.00 13.33      1DIK1176
ATOM   1085  CG2 VAL  143  -10.746  18.717  23.450  1.00 11.92      1DIK1177
ATOM   1086  N   ILE  144  -12.132  16.576  19.778  1.00 17.56      1DIK1178
ATOM   1087  CA  ILE  144  -12.177  15.752  18.582  1.00 17.36      1DIK1179
ATOM   1088  C   ILE  144  -12.882  16.490  17.431  1.00 19.27      1DIK1180
ATOM   1089  O   ILE  144  -12.400  16.492  16.281  1.00 20.66      1DIK1181
ATOM   1090  CB  ILE  144  -12.874  14.422  18.911  1.00 21.52      1DIK1182
ATOM   1091  CG1 ILE  144  -11.943  13.584  19.789  1.00 21.60      1DIK1183
ATOM   1092  CG2 ILE  144  -13.274  13.677  17.637  1.00 18.16      1DIK1184
ATOM   1093  CD1 ILE  144  -12.628  12.446  20.491  1.00 28.65      1DIK1185
ATOM   1094  N   ALA  145  -14.013  17.123  17.742  1.00 17.39      1DIK1186
ATOM   1095  CA  ALA  145  -14.780  17.889  16.752  1.00 15.97      1DIK1187
ATOM   1096  C   ALA  145  -13.951  19.066  16.243  1.00 18.18      1DIK1188
ATOM   1097  O   ALA  145  -14.049  19.436  15.073  1.00 20.54      1DIK1189
ATOM   1098  CB  ALA  145  -16.080  18.397  17.362  1.00 11.92      1DIK1190
ATOM   1099  N   SER  146  -13.141  19.654  17.125  1.00 17.49      1DIK1191
ATOM   1110  CA  SER  146  -12.273  20.768  16.759  1.00 18.53      1DIK1192
ATOM   1101  C   SER  146  -11.188  20.288  15.788  1.00 17.95      1DIK1193
ATOM   1102  O   SER  146  -10.843  20.988  14.823  1.00 15.32      1DIK1194
ATOM   1103  CB  SER  146  -11.648  21.379  18.015  1.00 20.60      1DIK1195
ATOM   1104  OG  SER  146  -12.654  21.966  18.836  1.00 18.35      1DIK1196
ATOM   1105  N   GLY  147  -10.668  19.088  16.047  1.00 17.16      1DIK1197
ATOM   1106  CA  GLY  147   -9.658  18.498  15.182  1.00 15.76      1DIK1198
ATOM   1107  C   GLY  147  -10.229  18.313  13.782  1.00 18.06      1DIK1199
ATOM   1108  O   GLY  147   -9.582  18.643  12.786  1.00 17.79      1DIK1200
ATOM   1109  N   LYS  148  -11.450  17.790  13.702  1.00 17.79      1DIK1201
ATOM   1110  CA  LYS  148  -12.123  17.585  12.422  1.00 16.21      1DIK1202
```

FIG. 8-18

```
ATOM  1111  C    LYS  148  -12.423  18.870  11.651  1.00  17.80  1DIK1203
ATOM  1112  O    LYS  148  -12.351  18.871  10.414  1.00  16.69  1DIK1204
ATOM  1113  CB   LYS  148  -13.422  16.821  12.631  1.00  20.50  1DIK1205
ATOM  1114  CG   LYS  148  -13.219  15.389  13.023  1.00  22.63  1DIK1206
ATOM  1115  CD   LYS  148  -14.539  14.722  13.227  1.00  27.17  1DIK1207
ATOM  1116  CE   LYS  148  -14.342  13.245  13.427  1.00  34.56  1DIK1208
ATOM  1117  NZ   LYS  148  -15.652  12.546  13.477  1.00  43.70  1DIK1209
ATOM  1118  N    LYS  149  -12.765  19.956  12.355  1.00  16.53  1DIK1210
ATOM  1119  CA   LYS  149  -13.049  21.221  11.680  1.00  19.05  1DIK1211
ATOM  1120  C    LYS  149  -11.756  21.821  11.132  1.00  19.26  1DIK1212
ATOM  1121  O    LYS  149  -11.747  22.412  10.050  1.00  19.18  1DIK1213
ATOM  1122  CB   LYS  149  -13.725  22.234  12.608  1.00  19.43  1DIK1214
ATOM  1123  CG   LYS  149  -15.018  21.775  13.196  1.00  25.49  1DIK1215
ATOM  1124  CD   LYS  149  -15.954  21.157  12.163  1.00  24.15  1DIK1216
ATOM  1125  CE   LYS  149  -16.677  22.178  11.350  1.00  24.54  1DIK1217
ATOM  1126  NZ   LYS  149  -17.717  21.492  10.530  1.00  23.29  1DIK1218
ATOM  1127  N    PHE  150  -10.672  21.677  11.885  1.00  17.03  1DIK1219
ATOM  1128  CA   PHE  150   -9.368  22.178  11.462  1.00  17.33  1DIK1220
ATOM  1129  C    PHE  150   -8.992  21.469  10.163  1.00  18.46  1DIK1221
ATOM  1130  O    PHE  150   -8.540  22.104   9.222  1.00  20.65  1DIK1222
ATOM  1131  CB   PHE  150   -8.321  21.892  12.555  1.00  17.32  1DIK1223
ATOM  1132  CG   PHE  150   -6.916  22.282  12.185  1.00  17.15  1DIK1224
ATOM  1133  CD1  PHE  150   -6.110  21.428  11.433  1.00  15.76  1DIK1225
ATOM  1134  CD2  PHE  150   -6.387  23.491  12.601  1.00  16.86  1DIK1226
ATOM  1135  CE1  PHE  150   -4.803  21.769  11.102  1.00  13.21  1DIK1227
ATOM  1136  CE2  PHE  150   -5.075  23.841  12.274  1.00  18.79  1DIK1228
ATOM  1137  CZ   PHE  150   -4.283  22.973  11.521  1.00  18.15  1DIK1229
ATOM  1138  N    ILE  151   -9.186  20.151  10.123  1.00  18.70  1DIK1230
ATOM  1139  CA   ILE  151   -8.887  19.337   8.949  1.00  16.84  1DIK1231
ATOM  1140  C    ILE  151   -9.700  19.829   7.751  1.00  21.25  1DIK1232
ATOM  1141  O    ILE  151   -9.212  19.895   6.621  1.00  22.35  1DIK1233
ATOM  1142  CB   ILE  151   -9.205  17.858   9.229  1.00  19.09  1DIK1234
ATOM  1143  CG1  ILE  151   -8.109  17.255  10.109  1.00  15.35  1DIK1235
ATOM  1144  CG2  ILE  151   -9.324  17.067   7.938  1.00  15.46  1DIK1236
ATOM  1145  CD1  ILE  151   -8.418  15.850  10.569  1.00  15.29  1DIK1237
ATOM  1146  N    GLU  152  -10.948  20.181   8.001  1.00  22.78  1DIK1238
ATOM  1147  CA   GLU  152  -11.821  20.692   6.954  1.00  22.06  1DIK1239
ATOM  1148  C    GLU  152  -11.208  21.958   6.339  1.00  22.51  1DIK1240
ATOM  1149  O    GLU  152  -11.019  22.033   5.125  1.00  27.84  1DIK1241
ATOM  1150  CB   GLU  152  -13.186  20.998   7.560  1.00  23.89  1DIK1242
ATOM  1151  CG   GLU  152  -14.321  21.169   6.578  1.00  27.41  1DIK1243
ATOM  1152  CD   GLU  152  -15.650  21.403   7.293  1.00  27.55  1DIK1244
ATOM  1153  OE1  GLU  152  -15.975  20.635   8.241  1.00  21.35  1DIK1245
ATOM  1154  OE2  GLU  152  -16.357  22.358   6.897  1.00  28.87  1DIK1246
ATOM  1155  N    GLY  153  -10.892  22.943   7.176  1.00  20.57  1DIK1247
ATOM  1156  CA   GLY  153  -10.305  24.177   6.693  1.00  19.76  1DIK1248
ATOM  1157  C    GLY  153   -8.990  23.965   5.955  1.00  23.46  1DIK1249
ATOM  1158  O    GLY  153   -8.773  24.528   4.886  1.00  25.73  1DIK1250
ATOM  1159  N    PHE  154   -8.114  23.145   6.528  1.00  22.50  1DIK1251
ATOM  1160  CA   PHE  154   -6.803  22.835   5.958  1.00  18.12  1DIK1252
ATOM  1161  C    PHE  154   -6.921  22.181   4.570  1.00  21.03  1DIK1253
ATOM  1162  O    PHE  154   -6.275  22.606   3.595  1.00  16.52  1DIK1254
ATOM  1163  CB   PHE  154   -6.048  21.909   6.937  1.00  16.95  1DIK1255
ATOM  1164  CG   PHE  154   -4.730  21.407   6.422  1.00  14.32  1DIK1256
ATOM  1165  CD1  PHE  154   -4.666  20.253   5.635  1.00  13.33  1DIK1257
ATOM  1166  CD2  PHE  154   -3.548  22.093   6.713  1.00  14.60  1DIK1258
ATOM  1167  CE1  PHE  154   -3.432  19.781   5.134  1.00  13.26  1DIK1259
ATOM  1168  CE2  PHE  154   -2.308  21.639   6.224  1.00  15.41  1DIK1260
ATOM  1169  CZ   PHE  154   -2.250  20.483   5.432  1.00  15.03  1DIK1261
ATOM  1170  N    GLN  155   -7.757  21.152   4.479  1.00  20.29  1DIK1262
ATOM  1171  CA   GLN  155   -7.921  20.441   3.231  1.00  21.66  1DIK1263
ATOM  1172  C    GLN  155   -8.626  21.290   2.170  1.00  25.36  1DIK1264
ATOM  1173  O    GLN  155   -8.255  21.256   0.983  1.00  26.48  1DIK1265
ATOM  1174  CB   GLN  155   -8.653  19.118   3.475  1.00  21.80  1DIK1266
ATOM  1175  CG   GLN  155   -8.471  18.085   2.369  1.00  27.70  1DIK1267
ATOM  1176  CD   GLN  155   -7.001  17.785   2.056  1.00  32.63  1DIK1268
```

FIG. 8-19

```
ATOM   1177  OE1 GLN   155      -6.105  18.052   2.859  1.00 34.93      1DIK1269
ATOM   1178  NE2 GLN   155      -6.753  17.229   0.883  1.00 32.41      1DIK1270
ATOM   1179  N   SER   156      -9.628  22.059   2.581  1.00 22.38      1DIK1271
ATOM   1180  CA  SER   156     -10.355  22.911   1.632  1.00 27.24      1DIK1272
ATOM   1181  C   SER   156      -9.474  23.925   0.912  1.00 26.37      1DIK1273
ATOM   1182  O   SER   156      -9.733  24.273  -0.246  1.00 26.94      1DIK1274
ATOM   1183  CB  SER   156     -11.477  23.644   2.347  1.00 25.77      1DIK1275
ATOM   1184  OG  SER   156     -12.392  22.686   2.834  1.00 38.06      1DIK1276
ATOM   1185  N   THR   157      -8.442  24.400   1.610  1.00 25.19      1DIK1277
ATOM   1186  CA  THR   157      -7.499  25.365   1.062  1.00 22.52      1DIK1278
ATOM   1187  C   THR   157      -6.535  24.632   0.123  1.00 24.65      1DIK1279
ATOM   1188  O   THR   157      -6.147  25.163  -0.928  1.00 23.24      1DIK1280
ATOM   1189  CB  THR   157      -6.702  26.040   2.189  1.00 21.15      1DIK1281
ATOM   1190  OG1 THR   157      -7.599  26.414   3.238  1.00 24.29      1DIK1282
ATOM   1191  CG2 THR   157      -6.012  27.292   1.679  1.00 16.11      1DIK1283
ATOM   1192  N   LYS   158      -6.161  23.411   0.509  1.00 21.14      1DIK1284
ATOM   1193  CA  LYS   158      -5.254  22.599  -0.279  1.00 22.69      1DIK1285
ATOM   1194  C   LYS   158      -5.848  22.241  -1.656  1.00 22.91      1DIK1286
ATOM   1195  O   LYS   158      -5.131  22.216  -2.655  1.00 20.40      1DIK1287
ATOM   1196  CB  LYS   158      -4.890  21.335   0.495  1.00 20.54      1DIK1288
ATOM   1197  CG  LYS   158      -3.806  20.504  -0.174  1.00 20.74      1DIK1289
ATOM   1198  CD  LYS   158      -3.200  19.556   0.829  1.00 24.06      1DIK1290
ATOM   1199  CE  LYS   158      -2.215  18.618   0.187  1.00 20.01      1DIK1291
ATOM   1200  NZ  LYS   158      -1.529  17.800   1.220  1.00 21.14      1DIK1292
ATOM   1201  N   LEU   159      -7.151  21.972  -1.703  1.00 22.71      1DIK1293
ATOM   1202  CA  LEU   159      -7.819  21.638  -2.959  1.00 24.27      1DIK1294
ATOM   1203  C   LEU   159      -7.784  22.786  -3.940  1.00 26.47      1DIK1295
ATOM   1204  O   LEU   159      -7.781  22.558  -5.144  1.00 29.65      1DIK1296
ATOM   1205  CB  LEU   159      -9.286  21.297  -2.743  1.00 21.63      1DIK1297
ATOM   1206  CG  LEU   159      -9.611  20.081  -1.913  1.00 25.68      1DIK1298
ATOM   1207  CD1 LEU   159     -11.110  20.032  -1.750  1.00 29.97      1DIK1299
ATOM   1208  CD2 LEU   159      -9.069  18.832  -2.571  1.00 25.43      1DIK1300
ATOM   1209  N   LYS   160      -7.781  24.015  -3.428  1.00 27.67      1DIK1301
ATOM   1210  CA  LYS   160      -7.759  25.196  -4.281  1.00 27.18      1DIK1302
ATOM   1211  C   LYS   160      -6.343  25.615  -4.632  1.00 27.06      1DIK1303
ATOM   1212  O   LYS   160      -6.161  26.651  -5.268  1.00 31.28      1DIK1304
ATOM   1213  CB  LYS   160      -8.426  26.383  -3.592  1.00 29.62      1DIK1305
ATOM   1214  CG  LYS   160      -9.827  26.183  -3.080  1.00 31.58      1DIK1306
ATOM   1215  CD  LYS   160     -10.152  27.402  -2.228  1.00 41.75      1DIK1307
ATOM   1216  CE  LYS   160     -11.463  27.266  -1.482  1.00 49.39      1DIK1308
ATOM   1217  NZ  LYS   160     -11.817  28.556  -0.806  1.00 51.98      1DIK1309
ATOM   1218  N   ASP   161      -5.343  24.840  -4.223  1.00 25.13      1DIK1310
ATOM   1219  CA  ASP   161      -3.954  25.193  -4.506  1.00 27.83      1DIK1311
ATOM   1220  C   ASP   161      -3.416  24.467  -5.758  1.00 30.73      1DIK1312
ATOM   1221  O   ASP   161      -3.237  23.250  -5.753  1.00 29.13      1DIK1313
ATOM   1222  CB  ASP   161      -3.082  24.897  -3.276  1.00 27.42      1DIK1314
ATOM   1223  CG  ASP   161      -1.642  25.368  -3.442  1.00 30.76      1DIK1315
ATOM   1224  OD1 ASP   161      -1.314  25.998  -4.468  1.00 38.67      1DIK1316
ATOM   1225  OD2 ASP   161      -0.819  25.114  -2.542  1.00 29.87      1DIK1317
ATOM   1226  N   PRO   162      -3.134  25.222  -6.842  1.00 33.61      1DIK1318
ATOM   1227  CA  PRO   162      -2.622  24.685  -8.110  1.00 33.28      1DIK1319
ATOM   1228  C   PRO   162      -1.352  23.853  -7.960  1.00 33.91      1DIK1320
ATOM   1229  O   PRO   162      -1.148  22.886  -8.684  1.00 34.55      1DIK1321
ATOM   1230  CB  PRO   162      -2.354  25.947  -8.932  1.00 33.55      1DIK1322
ATOM   1231  CG  PRO   162      -3.370  26.919  -8.413  1.00 33.99      1DIK1323
ATOM   1232  CD  PRO   162      -3.274  26.690  -6.927  1.00 34.27      1DIK1324
ATOM   1233  N   ARG   163      -0.502  24.231  -7.017  1.00 36.00      1DIK1325
ATOM   1234  CA  ARG   163       0.758  23.529  -6.799  1.00 36.01      1DIK1326
ATOM   1235  C   ARG   163       0.664  22.345  -5.833  1.00 34.24      1DIK1327
ATOM   1236  O   ARG   163       1.669  21.693  -5.548  1.00 31.55      1DIK1328
ATOM   1237  CB  ARG   163       1.802  24.525  -6.310  1.00 42.55      1DIK1329
ATOM   1238  CG  ARG   163       1.929  25.753  -7.205  1.00 53.77      1DIK1330
ATOM   1239  CD  ARG   163       3.014  26.683  -6.704  1.00 63.94      1DIK1331
ATOM   1240  NE  ARG   163       4.304  25.997  -6.634  1.00 74.87      1DIK1332
ATOM   1241  CZ  ARG   163       5.337  26.386  -5.886  1.00 79.93      1DIK1333
ATOM   1242  NH1 ARG   163       5.258  27.468  -5.123  1.00 82.39      1DIK1334
```

FIG. 8-20

| | | | | | | | | | |
|---|---|---|---|---|---|---|---|---|---|
| ATOM | 1243 | NH2 | ARG | 163 | 6.464 | 25.685 | -5.902 | 1.00 84.40 | 1DIK1335 |
| ATOM | 1244 | N | ALA | 164 | -0.539 | 22.072 | -5.331 | 1.00 33.77 | 1DIK1336 |
| ATOM | 1245 | CA | ALA | 164 | -0.762 | 20.962 | -4.407 | 1.00 34.08 | 1DIK1337 |
| ATOM | 1246 | C | ALA | 164 | -0.656 | 19.630 | -5.149 | 1.00 35.29 | 1DIK1338 |
| ATOM | 1247 | O | ALA | 164 | -0.984 | 19.540 | -6.325 | 1.00 36.67 | 1DIK1339 |
| ATOM | 1248 | CB | ALA | 164 | -2.130 | 21.087 | -3.744 | 1.00 33.17 | 1DIK1340 |
| ATOM | 1249 | N | GLN | 165 | -0.197 | 18.593 | -4.460 | 1.00 38.92 | 1DIK1341 |
| ATOM | 1250 | CA | GLN | 165 | -0.035 | 17.283 | -5.076 | 1.00 38.56 | 1DIK1342 |
| ATOM | 1251 | C | GLN | 165 | -1.336 | 16.530 | -5.281 | 1.00 35.34 | 1DIK1343 |
| ATOM | 1252 | O | GLN | 165 | -2.031 | 16.207 | -4.319 | 1.00 38.47 | 1DIK1344 |
| ATOM | 1253 | CB | GLN | 165 | 0.895 | 16.422 | -4.248 | 1.00 42.23 | 1DIK1345 |
| ATOM | 1254 | CG | GLN | 165 | 1.155 | 15.104 | -4.907 | 1.00 52.03 | 1DIK1346 |
| ATOM | 1255 | CD | GLN | 165 | 2.472 | 14.565 | -4.502 | 1.00 57.76 | 1DIK1347 |
| ATOM | 1256 | OE1 | GLN | 165 | 3.461 | 14.718 | -5.224 | 1.00 62.19 | 1DIK1348 |
| ATOM | 1257 | NE2 | GLN | 165 | 2.516 | 13.932 | -3.332 | 1.00 58.19 | 1DIK1349 |
| ATOM | 1258 | N | PRO | 166 | -1.664 | 16.207 | -6.542 | 1.00 33.99 | 1DIK1350 |
| ATOM | 1259 | CA | PRO | 166 | -2.902 | 15.485 | -6.886 | 1.00 31.51 | 1DIK1351 |
| ATOM | 1260 | C | PRO | 166 | -3.006 | 14.057 | -6.326 | 1.00 28.15 | 1DIK1352 |
| ATOM | 1261 | O | PRO | 166 | -2.010 | 13.348 | -6.240 | 1.00 30.43 | 1DIK1353 |
| ATOM | 1262 | CB | PRO | 166 | -2.889 | 15.502 | -8.420 | 1.00 28.29 | 1DIK1354 |
| ATOM | 1263 | CG | PRO | 166 | -1.405 | 15.492 | -8.737 | 1.00 29.54 | 1DIK1355 |
| ATOM | 1264 | CD | PRO | 166 | -0.854 | 16.486 | -7.747 | 1.00 28.70 | 1DIK1356 |
| ATOM | 1265 | N | GLY | 167 | -4.215 | 13.656 | -5.940 | 1.00 24.69 | 1DIK1357 |
| ATOM | 1266 | CA | GLY | 167 | -4.453 | 12.313 | -5.437 | 1.00 21.00 | 1DIK1358 |
| ATOM | 1267 | C | GLY | 167 | -3.990 | 11.986 | -4.032 | 1.00 25.28 | 1DIK1359 |
| ATOM | 1268 | O | GLY | 167 | -4.190 | 10.867 | -3.550 | 1.00 27.36 | 1DIK1360 |
| ATOM | 1269 | N | GLN | 168 | -3.372 | 12.951 | -3.367 | 1.00 24.69 | 1DIK1361 |
| ATOM | 1270 | CA | GLN | 168 | -2.882 | 12.759 | -2.010 | 1.00 24.46 | 1DIK1362 |
| ATOM | 1271 | C | GLN | 168 | -4.065 | 12.534 | -1.062 | 1.00 24.95 | 1DIK1363 |
| ATOM | 1272 | O | GLN | 168 | -5.177 | 13.035 | -1.295 | 1.00 24.47 | 1DIK1364 |
| ATOM | 1273 | CB | GLN | 168 | -2.081 | 13.987 | -1.596 | 1.00 26.68 | 1DIK1365 |
| ATOM | 1274 | CG | GLN | 168 | -1.155 | 13.744 | -0.439 | 1.00 30.05 | 1DIK1366 |
| ATOM | 1275 | CD | GLN | 168 | -0.012 | 14.736 | -0.405 | 1.00 33.87 | 1DIK1367 |
| ATOM | 1276 | OE1 | GLN | 168 | -0.185 | 15.937 | -0.685 | 1.00 29.61 | 1DIK1368 |
| ATOM | 1277 | NE2 | GLN | 168 | 1.176 | 14.239 | -0.064 | 1.00 30.19 | 1DIK1369 |
| ATOM | 1278 | N | SER | 169 | -3.853 | 11.781 | 0.005 | 1.00 23.60 | 1DIK1370 |
| ATOM | 1279 | CA | SER | 169 | -4.958 | 11.530 | 0.916 | 1.00 26.25 | 1DIK1371 |
| ATOM | 1280 | C | SER | 169 | -5.214 | 12.673 | 1.896 | 1.00 25.94 | 1DIK1372 |
| ATOM | 1281 | O | SER | 169 | -4.342 | 13.503 | 2.146 | 1.00 29.04 | 1DIK1373 |
| ATOM | 1282 | CB | SER | 169 | -4.737 | 10.205 | 1.652 | 1.00 26.64 | 1DIK1374 |
| ATOM | 1283 | OG | SER | 169 | -3.432 | 10.135 | 2.184 | 1.00 35.33 | 1DIK1375 |
| ATOM | 1284 | N | SER | 170 | -6.418 | 12.724 | 2.444 | 1.00 25.08 | 1DIK1376 |
| ATOM | 1285 | CA | SER | 170 | -6.756 | 13.759 | 3.414 | 1.00 23.05 | 1DIK1377 |
| ATOM | 1286 | C | SER | 170 | -6.169 | 13.440 | 4.791 | 1.00 21.06 | 1DIK1378 |
| ATOM | 1287 | O | SER | 170 | -5.867 | 12.280 | 5.101 | 1.00 19.23 | 1DIK1379 |
| ATOM | 1288 | CB | SER | 170 | -8.273 | 13.838 | 3.586 | 1.00 20.90 | 1DIK1380 |
| ATOM | 1289 | OG | SER | 170 | -8.909 | 14.154 | 2.380 | 1.00 31.58 | 1DIK1381 |
| ATOM | 1290 | N | PRO | 171 | -5.993 | 14.463 | 5.637 | 1.00 20.40 | 1DIK1382 |
| ATOM | 1291 | CA | PRO | 171 | -5.461 | 14.175 | 6.967 | 1.00 19.96 | 1DIK1383 |
| ATOM | 1292 | C | PRO | 171 | -6.650 | 13.566 | 7.727 | 1.00 20.25 | 1DIK1384 |
| ATOM | 1293 | O | PRO | 171 | -7.788 | 13.548 | 7.228 | 1.00 16.51 | 1DIK1385 |
| ATOM | 1294 | CB | PRO | 171 | -5.147 | 15.566 | 7.531 | 1.00 22.09 | 1DIK1386 |
| ATOM | 1295 | CG | PRO | 171 | -5.169 | 16.491 | 6.329 | 1.00 21.91 | 1DIK1387 |
| ATOM | 1296 | CD | PRO | 171 | -6.236 | 15.905 | 5.471 | 1.00 22.51 | 1DIK1388 |
| ATOM | 1297 | N | LYS | 172 | -6.397 | 13.076 | 8.931 | 1.00 20.67 | 1DIK1389 |
| ATOM | 1298 | CA | LYS | 172 | -7.458 | 12.515 | 9.764 | 1.00 20.50 | 1DIK1390 |
| ATOM | 1299 | C | LYS | 172 | -6.873 | 12.446 | 11.164 | 1.00 19.29 | 1DIK1391 |
| ATOM | 1300 | O | LYS | 172 | -5.686 | 12.709 | 11.362 | 1.00 19.22 | 1DIK1392 |
| ATOM | 1301 | CB | LYS | 172 | -7.867 | 11.114 | 9.286 | 1.00 18.29 | 1DIK1393 |
| ATOM | 1302 | CG | LYS | 172 | -6.703 | 10.172 | 9.177 | 1.00 18.63 | 1DIK1394 |
| ATOM | 1303 | CD | LYS | 172 | -7.122 | 8.761 | 9.350 | 1.00 23.30 | 1DIK1395 |
| ATOM | 1304 | CE | LYS | 172 | -5.885 | 7.903 | 9.304 | 1.00 30.02 | 1DIK1396 |
| ATOM | 1305 | NZ | LYS | 172 | -6.233 | 6.492 | 9.627 | 1.00 44.40 | 1DIK1397 |
| ATOM | 1306 | N | ILE | 173 | -7.698 | 12.100 | 12.136 | 1.00 16.98 | 1DIK1398 |
| ATOM | 1307 | CA | ILE | 173 | -7.218 | 11.998 | 13.493 | 1.00 19.06 | 1DIK1399 |
| ATOM | 1308 | C | ILE | 173 | -6.583 | 10.614 | 13.635 | 1.00 22.40 | 1DIK1400 |

FIG. 8-21

```
ATOM   1309  O    ILE  173   -7.266   9.593  13.768  1.00 21.26      1DIK1401
ATOM   1310  CB   ILE  173   -8.371  12.274  14.475  1.00 19.92      1DIK1402
ATOM   1311  CG1  ILE  173   -8.868  13.715  14.232  1.00 18.99      1DIK1403
ATOM   1312  CG2  ILE  173   -7.902  12.109  15.921  1.00 20.59      1DIK1404
ATOM   1313  CD1  ILE  173  -10.087  14.103  14.987  1.00 16.15      1DIK1405
ATOM   1314  N    ASP  174   -5.256  10.599  13.588  1.00 19.22      1DIK1406
ATOM   1315  CA   ASP  174   -4.504   9.366  13.667  1.00 18.78      1DIK1407
ATOM   1316  C    ASP  174   -4.495   8.689  15.021  1.00 20.21      1DIK1408
ATOM   1317  O    ASP  174   -4.507   7.463  15.087  1.00 23.44      1DIK1409
ATOM   1318  CB   ASP  174   -3.074   9.606  13.213  1.00 16.70      1DIK1410
ATOM   1319  CG   ASP  174   -3.001  10.130  11.793  1.00 21.97      1DIK1411
ATOM   1320  OD1  ASP  174   -3.185   9.320  10.853  1.00 28.66      1DIK1412
ATOM   1321  OD2  ASP  174   -2.763  11.348  11.618  1.00 15.14      1DIK1413
ATOM   1322  N    VAL  175   -4.464   9.470  16.099  1.00 19.64      1DIK1414
ATOM   1323  CA   VAL  175   -4.453   8.903  17.449  1.00 15.74      1DIK1415
ATOM   1324  C    VAL  175   -5.381   9.700  18.364  1.00 19.16      1DIK1416
ATOM   1325  O    VAL  175   -5.346  10.942  18.361  1.00 22.21      1DIK1417
ATOM   1326  CB   VAL  175   -3.016   8.940  18.088  1.00 15.96      1DIK1418
ATOM   1327  CG1  VAL  175   -3.013   8.205  19.427  1.00 11.79      1DIK1419
ATOM   1328  CG2  VAL  175   -1.967   8.323  17.154  1.00 15.25      1DIK1420
ATOM   1329  N    VAL  176   -6.220   9.009  19.135  1.00 16.60      1DIK1421
ATOM   1330  CA   VAL  176   -7.078   9.696  20.099  1.00 18.96      1DIK1422
ATOM   1331  C    VAL  176   -6.630   9.238  21.484  1.00 18.63      1DIK1423
ATOM   1332  O    VAL  176   -6.837   8.084  21.849  1.00 19.14      1DIK1424
ATOM   1333  CB   VAL  176   -8.585   9.390  19.923  1.00 19.70      1DIK1425
ATOM   1334  CG1  VAL  176   -9.382  10.058  21.050  1.00 18.39      1DIK1426
ATOM   1335  CG2  VAL  176   -9.071   9.919  18.580  1.00 17.14      1DIK1427
ATOM   1336  N    ILE  177   -6.017  10.135  22.249  1.00 16.49      1DIK1428
ATOM   1337  CA   ILE  177   -5.528   9.790  23.578  1.00 18.84      1DIK1429
ATOM   1338  C    ILE  177   -6.626   9.871  24.646  1.00 22.64      1DIK1430
ATOM   1339  O    ILE  177   -7.233  10.926  24.877  1.00 21.84      1DIK1431
ATOM   1340  CB   ILE  177   -4.331  10.669  23.959  1.00 17.93      1DIK1432
ATOM   1341  CG1  ILE  177   -3.258  10.548  22.876  1.00 21.31      1DIK1433
ATOM   1342  CG2  ILE  177   -3.747  10.209  25.293  1.00 13.33      1DIK1434
ATOM   1343  CD1  ILE  177   -2.129  11.530  23.031  1.00 24.99      1DIK1435
ATOM   1344  N    SER  178   -6.879   8.740  25.293  1.00 22.92      1DIK1436
ATOM   1345  CA   SER  178   -7.913   8.664  26.308  1.00 22.43      1DIK1437
ATOM   1346  C    SER  178   -7.692   9.620  27.469  1.00 23.70      1DIK1438
ATOM   1347  O    SER  178   -6.562   9.880  27.896  1.00 19.07      1DIK1439
ATOM   1348  CB   SER  178   -8.019   7.234  26.832  1.00 24.76      1DIK1440
ATOM   1349  OG   SER  178   -8.931   7.149  27.918  1.00 26.50      1DIK1441
ATOM   1350  N    GLU  179   -8.802  10.138  27.975  1.00 23.30      1DIK1442
ATOM   1351  CA   GLU  179   -8.763  11.032  29.109  1.00 24.10      1DIK1443
ATOM   1352  C    GLU  179   -9.145  10.299  30.390  1.00 26.08      1DIK1444
ATOM   1353  O    GLU  179   -9.372  10.930  31.424  1.00 28.11      1DIK1445
ATOM   1354  CB   GLU  179   -9.683  12.219  28.875  1.00 20.32      1DIK1446
ATOM   1355  CG   GLU  179   -9.046  13.277  28.013  1.00 19.78      1DIK1447
ATOM   1356  CD   GLU  179   -9.975  14.413  27.679  1.00 21.33      1DIK1448
ATOM   1357  OE1  GLU  179  -11.081  14.507  28.248  1.00 28.21      1DIK1449
ATOM   1358  OE2  GLU  179   -9.595  15.224  26.832  1.00 24.31      1DIK1450
ATOM   1359  N    ALA  180   -9.220   8.970  30.326  1.00 27.12      1DIK1451
ATOM   1360  CA   ALA  180   -9.554   8.166  31.501  1.00 28.40      1DIK1452
ATOM   1361  C    ALA  180   -8.508   8.476  32.578  1.00 29.95      1DIK1453
ATOM   1362  O    ALA  180   -7.325   8.664  32.271  1.00 28.75      1DIK1454
ATOM   1363  CB   ALA  180   -9.542   6.694  31.151  1.00 22.95      1DIK1455
ATOM   1364  N    SER  181   -8.944   8.525  33.831  1.00 31.85      1DIK1456
ATOM   1365  CA   SER  181   -8.049   8.866  34.939  1.00 35.04      1DIK1457
ATOM   1366  C    SER  181   -6.762   8.047  35.009  1.00 31.72      1DIK1458
ATOM   1367  O    SER  181   -5.755   8.525  35.525  1.00 33.94      1DIK1459
ATOM   1368  CB   SER  181   -8.806   8.770  36.260  1.00 36.11      1DIK1460
ATOM   1369  OG   SER  181   -9.377   7.479  36.373  1.00 46.40      1DIK1461
ATOM   1370  N    SER  182   -6.798   6.821  34.500  1.00 27.14      1DIK1462
ATOM   1371  CA   SER  182   -5.615   5.963  34.488  1.00 29.83      1DIK1463
ATOM   1372  C    SER  182   -4.792   6.051  33.181  1.00 30.65      1DIK1464
ATOM   1373  O    SER  182   -3.808   5.329  33.013  1.00 35.32      1DIK1465
ATOM   1374  CB   SER  182   -6.023   4.496  34.726  1.00 32.11      1DIK1466
```

FIG. 8-22

```
ATOM   1375  OG   SER   182     -6.967   4.032  33.757  1.00  33.33      1DIK1467
ATOM   1376  N    SER   183     -5.187   6.924  32.261  1.00  26.39      1DIK1468
ATOM   1377  CA   SER   183     -4.499   7.049  30.986  1.00  21.35      1DIK1469
ATOM   1378  C    SER   183     -3.268   7.953  30.986  1.00  18.80      1DIK1470
ATOM   1379  O    SER   183     -3.263   9.002  31.621  1.00  18.57      1DIK1471
ATOM   1380  CB   SER   183     -5.499   7.547  29.952  1.00  23.15      1DIK1472
ATOM   1381  OG   SER   183     -4.884   7.739  28.702  1.00  22.70      1DIK1473
ATOM   1382  N    ASN   184     -2.216   7.545  30.281  1.00  21.24      1DIK1474
ATOM   1383  CA   ASN   184     -1.012   8.383  30.160  1.00  22.85      1DIK1475
ATOM   1384  C    ASN   184     -1.287   9.264  28.942  1.00  22.55      1DIK1476
ATOM   1385  O    ASN   184     -1.275   8.786  27.805  1.00  21.64      1DIK1477
ATOM   1386  CB   ASN   184      0.233   7.542  29.918  1.00  25.23      1DIK1478
ATOM   1387  CG   ASN   184      0.476   6.547  31.027  1.00  29.76      1DIK1479
ATOM   1388  OD1  ASN   184      0.631   6.927  32.186  1.00  25.74      1DIK1480
ATOM   1389  ND2  ASN   184      0.505   5.259  30.680  1.00  31.61      1DIK1481
ATOM   1390  N    ASN   185     -1.536  10.546  29.197  1.00  20.70      1DIK1482
ATOM   1391  CA   ASN   185     -1.903  11.526  28.177  1.00  18.51      1DIK1483
ATOM   1392  C    ASN   185     -1.015  12.775  28.289  1.00  18.05      1DIK1484
ATOM   1393  O    ASN   185     -1.179  13.567  29.209  1.00  19.30      1DIK1485
ATOM   1394  CB   ASN   185     -3.386  11.879  28.421  1.00  17.92      1DIK1486
ATOM   1395  CG   ASN   185     -3.990  12.809  27.376  1.00  20.11      1DIK1487
ATOM   1396  OD1  ASN   185     -5.199  12.965  27.331  1.00  25.61      1DIK1488
ATOM   1397  ND2  ASN   185     -3.174  13.421  26.543  1.00  23.70      1DIK1489
ATOM   1398  N    THR   186     -0.089  12.962  27.350  1.00  18.02      1DIK1490
ATOM   1399  CA   THR   186      0.809  14.116  27.383  1.00  19.61      1DIK1491
ATOM   1400  C    THR   186      0.117  15.452  27.104  1.00  23.05      1DIK1492
ATOM   1401  O    THR   186      0.619  16.513  27.477  1.00  24.23      1DIK1493
ATOM   1402  CB   THR   186      1.959  13.971  26.367  1.00  20.27      1DIK1494
ATOM   1403  OG1  THR   186      1.410  13.772  25.062  1.00  19.57      1DIK1495
ATOM   1404  CG2  THR   186      2.871  12.815  26.731  1.00  15.78      1DIK1496
ATOM   1405  N    LEU   187     -1.030  15.398  26.443  1.00  22.21      1DIK1497
ATOM   1406  CA   LEU   187     -1.772  16.597  26.092  1.00  21.72      1DIK1498
ATOM   1407  C    LEU   187     -2.549  17.208  27.259  1.00  23.64      1DIK1499
ATOM   1408  O    LEU   187     -2.797  18.410  27.282  1.00  22.02      1DIK1500
ATOM   1409  CB   LEU   187     -2.716  16.276  24.933  1.00  23.09      1DIK1501
ATOM   1410  CG   LEU   187     -2.063  15.798  23.623  1.00  23.80      1DIK1502
ATOM   1411  CD1  LEU   187     -3.140  15.295  22.673  1.00  19.98      1DIK1503
ATOM   1412  CD2  LEU   187     -1.262  16.926  22.984  1.00  19.12      1DIK1504
ATOM   1413  N    ASP   188     -2.934  16.376  28.218  1.00  24.87      1DIK1505
ATOM   1414  CA   ASP   188     -3.684  16.815  29.399  1.00  28.75      1DIK1506
ATOM   1415  C    ASP   188     -3.540  15.688  30.424  1.00  27.51      1DIK1507
ATOM   1416  O    ASP   188     -4.431  14.851  30.584  1.00  30.17      1DIK1508
ATOM   1417  CB   ASP   188     -5.165  17.042  29.041  1.00  34.58      1DIK1509
ATOM   1418  CG   ASP   188     -5.958  17.724  30.171  1.00  41.42      1DIK1510
ATOM   1419  OD1  ASP   188     -5.474  18.727  30.765  1.00  42.84      1DIK1511
ATOM   1420  OD2  ASP   188     -7.079  17.246  30.461  1.00  42.36      1DIK1512
ATOM   1421  N    PRO   189     -2.398  15.653  31.129  1.00  26.10      1DIK1513
ATOM   1422  CA   PRO   189     -2.107  14.622  32.137  1.00  25.17      1DIK1514
ATOM   1423  C    PRO   189     -3.063  14.609  33.322  1.00  26.14      1DIK1515
ATOM   1424  O    PRO   189     -3.442  15.671  33.825  1.00  27.85      1DIK1516
ATOM   1425  CB   PRO   189     -0.677  14.959  32.579  1.00  21.04      1DIK1517
ATOM   1426  CG   PRO   189     -0.113  15.765  31.425  1.00  21.36      1DIK1518
ATOM   1427  CD   PRO   189     -1.286  16.615  31.026  1.00  22.23      1DIK1519
ATOM   1428  N    GLY   190     -3.442  13.413  33.766  1.00  24.92      1DIK1520
ATOM   1429  CA   GLY   190     -4.325  13.296  34.910  1.00  24.73      1DIK1521
ATOM   1430  C    GLY   190     -3.783  12.314  35.934  1.00  29.33      1DIK1522
ATOM   1431  O    GLY   190     -4.457  12.016  36.917  1.00  32.88      1DIK1523
ATOM   1432  N    THR   191     -2.563  11.824  35.722  1.00  26.97      1DIK1524
ATOM   1433  CA   THR   191     -1.964  10.826  36.603  1.00  26.69      1DIK1525
ATOM   1434  C    THR   191     -1.040  11.316  37.725  1.00  30.17      1DIK1526
ATOM   1435  O    THR   191     -0.535  10.507  38.518  1.00  32.24      1DIK1527
ATOM   1436  CB   THR   191     -1.202   9.781  35.776  1.00  25.25      1DIK1528
ATOM   1437  OG1  THR   191     -0.258  10.449  34.927  1.00  25.22      1DIK1529
ATOM   1438  CG2  THR   191     -2.170   8.967  34.918  1.00  24.37      1DIK1530
ATOM   1439  N    CYS   192     -0.805  12.621  37.800  1.00  29.82      1DIK1531
ATOM   1440  CA   CYS   192      0.055  13.164  38.847  1.00  29.63      1DIK1532
```

FIG. 8-23

```
ATOM   1441  C   CYS 192  -0.783 13.395 40.101 1.00 29.84   1DIK1533
ATOM   1442  O   CYS 192  -1.282 14.507 40.330 1.00 26.80   1DIK1534
ATOM   1443  CB  CYS 192   0.699 14.466 38.387 1.00 28.28   1DIK1535
ATOM   1444  SG  CYS 192   1.766 15.227 39.646 1.00 30.95   1DIK1536
ATOM   1445  N   THR 193  -0.924 12.333 40.900 1.00 31.00   1DIK1537
ATOM   1446  CA  THR 193  -1.719 12.331 42.134 1.00 30.54   1DIK1538
ATOM   1447  C   THR 193  -1.679 13.595 42.998 1.00 28.74   1DIK1539
ATOM   1448  O   THR 193  -2.718 14.231 43.213 1.00 26.01   1DIK1540
ATOM   1449  CB  THR 193  -1.371 11.117 43.018 1.00 34.12   1DIK1541
ATOM   1450  OG1 THR 193  -1.408  9.919 42.231 1.00 39.67   1DIK1542
ATOM   1451  CG2 THR 193  -2.386 10.976 44.130 1.00 35.19   1DIK1543
ATOM   1452  N   VAL 194  -0.503 13.969 43.489 1.00 27.22   1DIK1544
ATOM   1453  CA  VAL 194  -0.415 15.157 44.323 1.00 30.44   1DIK1545
ATOM   1454  C   VAL 194  -0.953 16.406 43.614 1.00 33.87   1DIK1546
ATOM   1455  O   VAL 194  -1.705 17.178 44.211 1.00 37.21   1DIK1547
ATOM   1456  CB  VAL 194   1.022 15.387 44.829 1.00 31.50   1DIK1548
ATOM   1457  CG1 VAL 194   1.175 16.793 45.390 1.00 27.45   1DIK1549
ATOM   1458  CG2 VAL 194   1.339 14.382 45.914 1.00 26.96   1DIK1550
ATOM   1459  N   PHE 195  -0.587 16.600 42.349 1.00 33.70   1DIK1551
ATOM   1460  CA  PHE 195  -1.049 17.768 41.598 1.00 32.23   1DIK1552
ATOM   1461  C   PHE 195  -2.575 17.802 41.485 1.00 33.46   1DIK1553
ATOM   1462  O   PHE 195  -3.195 18.853 41.665 1.00 34.15   1DIK1554
ATOM   1463  CB  PHE 195  -0.429 17.803 40.192 1.00 28.54   1DIK1555
ATOM   1464  CG  PHE 195  -0.987 18.890 39.311 1.00 24.30   1DIK1556
ATOM   1465  CD1 PHE 195  -0.563 20.207 39.457 1.00 21.84   1DIK1557
ATOM   1466  CD2 PHE 195  -1.952 18.595 38.344 1.00 22.84   1DIK1558
ATOM   1467  CE1 PHE 195  -1.087 21.237 38.650 1.00 28.26   1DIK1559
ATOM   1468  CE2 PHE 195  -2.486 19.610 37.529 1.00 26.40   1DIK1560
ATOM   1469  CZ  PHE 195  -2.051 20.940 37.684 1.00 23.76   1DIK1561
ATOM   1470  N   GLU 196  -3.174 16.656 41.188 1.00 33.59   1DIK1562
ATOM   1471  CA  GLU 196  -4.618 16.574 41.048 1.00 34.08   1DIK1563
ATOM   1472  C   GLU 196  -5.357 16.966 42.328 1.00 35.44   1DIK1564
ATOM   1473  O   GLU 196  -6.497 17.411 42.266 1.00 35.61   1DIK1565
ATOM   1474  CB  GLU 196  -5.026 15.165 40.602 1.00 34.98   1DIK1566
ATOM   1475  CG  GLU 196  -4.509 14.774 39.211 1.00 37.27   1DIK1567
ATOM   1476  CD  GLU 196  -5.098 15.638 38.094 1.00 40.35   1DIK1568
ATOM   1477  OE1 GLU 196  -6.338 15.806 38.053 1.00 45.20   1DIK1569
ATOM   1478  OE2 GLU 196  -4.332 16.154 37.256 1.00 33.72   1DIK1570
ATOM   1479  N   ASP 197  -4.715 16.807 43.483 1.00 38.29   1DIK1571
ATOM   1480  CA  ASP 197  -5.352 17.160 44.758 1.00 40.02   1DIK1572
ATOM   1481  C   ASP 197  -5.141 18.621 45.173 1.00 38.28   1DIK1573
ATOM   1482  O   ASP 197  -5.770 19.093 46.110 1.00 38.49   1DIK1574
ATOM   1483  CB  ASP 197  -4.862 16.234 45.887 1.00 43.17   1DIK1575
ATOM   1484  CG  ASP 197  -5.402 14.805 45.766 1.00 48.76   1DIK1576
ATOM   1485  OD1 ASP 197  -6.582 14.630 45.373 1.00 50.32   1DIK1577
ATOM   1486  OD2 ASP 197  -4.640 13.853 46.069 1.00 49.19   1DIK1578
ATOM   1487  N   SER 198  -4.261 19.327 44.470 1.00 38.44   1DIK1579
ATOM   1488  CA  SER 198  -3.928 20.724 44.763 1.00 38.19   1DIK1580
ATOM   1489  C   SER 198  -5.131 21.675 44.824 1.00 39.35   1DIK1581
ATOM   1490  O   SER 198  -6.001 21.639 43.952 1.00 38.20   1DIK1582
ATOM   1491  CB  SER 198  -2.929 21.231 43.713 1.00 34.00   1DIK1583
ATOM   1492  OG  SER 198  -2.404 22.508 44.049 1.00 37.33   1DIK1584
ATOM   1493  N   GLU 199  -5.175 22.530 45.848 1.00 40.37   1DIK1585
ATOM   1494  CA  GLU 199  -6.262 23.505 45.981 1.00 42.79   1DIK1586
ATOM   1495  C   GLU 199  -5.735 24.932 45.904 1.00 41.90   1DIK1587
ATOM   1496  O   GLU 199  -6.453 25.886 46.228 1.00 41.14   1DIK1588
ATOM   1497  CB  GLU 199  -7.010 23.322 47.295 1.00 47.81   1DIK1589
ATOM   1498  CG  GLU 199  -7.935 22.127 47.334 1.00 56.13   1DIK1590
ATOM   1499  CD  GLU 199  -8.400 21.817 48.752 1.00 62.12   1DIK1591
ATOM   1500  OE1 GLU 199  -7.533 21.713 49.663 1.00 60.51   1DIK1592
ATOM   1501  OE2 GLU 199  -9.631 21.680 48.952 1.00 64.72   1DIK1593
ATOM   1502  N   LEU 200  -4.485 25.079 45.465 1.00 39.80   1DIK1594
ATOM   1503  CA  LEU 200  -3.861 26.391 45.356 1.00 38.33   1DIK1595
ATOM   1504  C   LEU 200  -4.700 27.405 44.565 1.00 40.30   1DIK1596
ATOM   1505  O   LEU 200  -4.924 28.526 45.027 1.00 41.57   1DIK1597
ATOM   1506  CB  LEU 200  -2.469 26.260 44.740 1.00 34.44   1DIK1598
```

FIG. 8-24

```
ATOM   1507  CG   LEU  200      -1.659  27.564  44.728  1.00  38.04      1DIK1599
ATOM   1508  CD1  LEU  200      -1.503  28.104  46.144  1.00  29.88      1DIK1600
ATOM   1509  CD2  LEU  200      -0.297  27.334  44.087  1.00  36.27      1DIK1601
ATOM   1510  N    ALA  201      -5.170  27.012  43.384  1.00  39.72      1DIK1602
ATOM   1511  CA   ALA  201      -5.974  27.901  42.549  1.00  38.07      1DIK1603
ATOM   1512  C    ALA  201      -7.230  28.400  43.247  1.00  39.57      1DIK1604
ATOM   1513  O    ALA  201      -7.623  29.541  43.048  1.00  41.56      1DIK1605
ATOM   1514  CB   ALA  201      -6.354  27.211  41.249  1.00  33.45      1DIK1606
ATOM   1515  N    ASP  202      -7.863  27.557  44.060  1.00  42.79      1DIK1607
ATOM   1516  CA   ASP  202      -9.089  27.949  44.767  1.00  46.09      1DIK1608
ATOM   1517  C    ASP  202      -8.812  29.026  45.804  1.00  46.30      1DIK1609
ATOM   1518  O    ASP  202      -9.596  29.968  45.962  1.00  48.14      1DIK1610
ATOM   1519  CB   ASP  202      -9.719  26.748  45.461  1.00  52.71      1DIK1611
ATOM   1520  CG   ASP  202     -10.027  25.624  44.503  1.00  62.26      1DIK1612
ATOM   1521  OD1  ASP  202     -10.673  25.892  43.457  1.00  62.64      1DIK1613
ATOM   1522  OD2  ASP  202      -9.617  24.476  44.804  1.00  68.25      1DIK1614
ATOM   1523  N    THR  203      -7.693  28.875  46.507  1.00  42.43      1DIK1615
ATOM   1524  CA   THR  203      -7.283  29.828  47.524  1.00  40.28      1DIK1616
ATOM   1525  C    THR  203      -7.020  31.183  46.875  1.00  38.82      1DIK1617
ATOM   1526  O    THR  203      -7.475  32.212  47.370  1.00  40.38      1DIK1618
ATOM   1527  CB   THR  203      -6.010  29.334  48.243  1.00  41.33      1DIK1619
ATOM   1528  OG1  THR  203      -6.318  28.139  48.976  1.00  42.61      1DIK1620
ATOM   1529  CG2  THR  203      -5.469  30.397  49.192  1.00  37.55      1DIK1621
ATOM   1530  N    VAL  204      -6.291  31.170  45.762  1.00  37.98      1DIK1622
ATOM   1531  CA   VAL  204      -5.953  32.386  45.021  1.00  36.13      1DIK1623
ATOM   1532  C    VAL  204      -7.209  33.048  44.454  1.00  34.77      1DIK1624
ATOM   1533  O    VAL  204      -7.372  34.265  44.544  1.00  35.20      1DIK1625
ATOM   1534  CB   VAL  204      -4.939  32.070  43.888  1.00  36.51      1DIK1626
ATOM   1535  CG1  VAL  204      -4.675  33.291  43.036  1.00  33.64      1DIK1627
ATOM   1536  CG2  VAL  204      -3.638  31.577  44.496  1.00  30.96      1DIK1628
ATOM   1537  N    GLU  205      -8.101  32.248  43.885  1.00  34.36      1DIK1629
ATOM   1538  CA   GLU  205      -9.343  32.778  43.331  1.00  36.22      1DIK1630
ATOM   1539  C    GLU  205     -10.125  33.501  44.414  1.00  36.92      1DIK1631
ATOM   1540  O    GLU  205     -10.662  34.580  44.182  1.00  40.62      1DIK1632
ATOM   1541  CB   GLU  205     -10.201  31.655  42.750  1.00  33.02      1DIK1633
ATOM   1542  CG   GLU  205     -11.607  32.094  42.365  1.00  39.52      1DIK1634
ATOM   1543  CD   GLU  205     -12.312  31.094  41.454  1.00  46.03      1DIK1635
ATOM   1544  OE1  GLU  205     -12.076  29.875  41.597  1.00  48.84      1DIK1636
ATOM   1545  OE2  GLU  205     -13.105  31.526  40.585  1.00  53.38      1DIK1637
ATOM   1546  N    ALA  206     -10.179  32.897  45.597  1.00  39.03      1DIK1638
ATOM   1547  CA   ALA  206     -10.898  33.464  46.731  1.00  37.04      1DIK1639
ATOM   1548  C    ALA  206     -10.262  34.787  47.160  1.00  36.03      1DIK1640
ATOM   1549  O    ALA  206     -10.954  35.803  47.316  1.00  32.23      1DIK1641
ATOM   1550  CB   ALA  206     -10.909  32.472  47.891  1.00  32.31      1DIK1642
ATOM   1551  N    ASN  207      -8.946  34.774  47.335  1.00  35.44      1DIK1643
ATOM   1552  CA   ASN  207      -8.231  35.971  47.754  1.00  40.04      1DIK1644
ATOM   1553  C    ASN  207      -8.484  37.150  46.836  1.00  39.71      1DIK1645
ATOM   1554  O    ASN  207      -8.838  38.235  47.307  1.00  42.35      1DIK1646
ATOM   1555  CB   ASN  207      -6.716  35.722  47.841  1.00  43.98      1DIK1647
ATOM   1556  CG   ASN  207      -6.331  34.791  48.992  1.00  48.43      1DIK1648
ATOM   1557  OD1  ASN  207      -7.115  34.557  49.922  1.00  46.90      1DIK1649
ATOM   1558  ND2  ASN  207      -5.111  34.252  48.930  1.00  50.65      1DIK1650
ATOM   1559  N    PHE  208      -8.318  36.946  45.531  1.00  37.95      1DIK1651
ATOM   1560  CA   PHE  208      -8.499  38.044  44.591  1.00  34.08      1DIK1652
ATOM   1561  C    PHE  208      -9.925  38.528  44.400  1.00  32.61      1DIK1653
ATOM   1562  O    PHE  208     -10.156  39.739  44.401  1.00  32.67      1DIK1654
ATOM   1563  CB   PHE  208      -7.878  37.726  43.229  1.00  32.46      1DIK1655
ATOM   1564  CG   PHE  208      -7.841  38.915  42.287  1.00  32.48      1DIK1656
ATOM   1565  CD1  PHE  208      -6.951  39.966  42.506  1.00  30.74      1DIK1657
ATOM   1566  CD2  PHE  208      -8.713  38.991  41.193  1.00  28.48      1DIK1658
ATOM   1567  CE1  PHE  208      -6.929  41.081  41.650  1.00  29.80      1DIK1659
ATOM   1568  CE2  PHE  208      -8.700  40.090  40.339  1.00  26.94      1DIK1660
ATOM   1569  CZ   PHE  208      -7.805  41.140  40.568  1.00  30.80      1DIK1661
ATOM   1570  N    THR  209     -10.887  37.620  44.238  1.00  31.39      1DIK1662
ATOM   1571  CA   THR  209     -12.259  38.074  44.026  1.00  33.60      1DIK1663
ATOM   1572  C    THR  209     -12.678  38.987  45.171  1.00  34.71      1DIK1664
```

FIG. 8-25

```
ATOM   1573  O    THR  209   -13.415  39.954  44.963  1.00  36.94      1DIK 1665
ATOM   1574  CB   THR  209   -13.280  36.904  43.844  1.00  32.70      1DIK 1666
ATOM   1575  OG1  THR  209   -13.295  36.072  45.004  1.00  36.54      1DIK 1667
ATOM   1576  CG2  THR  209   -12.919  36.057  42.631  1.00  31.98      1DIK 1668
ATOM   1577  N    ALA  210   -12.193  38.693  46.376  1.00  37.10      1DIK 1669
ATOM   1578  CA   ALA  210   -12.504  39.505  47.557  1.00  37.69      1DIK 1670
ATOM   1579  C    ALA  210   -12.126  40.977  47.342  1.00  39.15      1DIK 1671
ATOM   1580  O    ALA  210   -12.801  41.876  47.849  1.00  42.92      1DIK 1672
ATOM   1581  CB   ALA  210   -11.781  38.954  48.770  1.00  31.71      1DIK 1673
ATOM   1582  N    THR  211   -11.067  41.222  46.576  1.00  36.88      1DIK 1674
ATOM   1583  CA   THR  211   -10.610  42.581  46.310  1.00  36.47      1DIK 1675
ATOM   1584  C    THR  211   -11.462  43.431  45.341  1.00  35.57      1DIK 1676
ATOM   1585  O    THR  211   -11.188  44.629  45.192  1.00  37.01      1DIK 1677
ATOM   1586  CB   THR  211    -9.170  42.583  45.769  1.00  37.77      1DIK 1678
ATOM   1587  OG1  THR  211    -9.190  42.206  44.388  1.00  40.97      1DIK 1679
ATOM   1588  CG2  THR  211    -8.297  41.590  46.537  1.00  35.34      1DIK 1680
ATOM   1589  N    PHE  212   -12.473  42.858  44.683  1.00  29.14      1DIK 1681
ATOM   1590  CA   PHE  212   -13.280  43.659  43.749  1.00  24.90      1DIK 1682
ATOM   1591  C    PHE  212   -14.736  43.224  43.559  1.00  27.12      1DIK 1683
ATOM   1592  O    PHE  212   -15.577  44.041  43.190  1.00  31.27      1DIK 1684
ATOM   1593  CB   PHE  212   -12.583  43.755  42.371  1.00  25.16      1DIK 1685
ATOM   1594  CG   PHE  212   -12.772  42.534  41.491  1.00  26.99      1DIK 1686
ATOM   1595  CD1  PHE  212   -12.017  41.382  41.689  1.00  24.61      1DIK 1687
ATOM   1596  CD2  PHE  212   -13.724  42.538  40.469  1.00  29.36      1DIK 1688
ATOM   1597  CE1  PHE  212   -12.213  40.252  40.883  1.00  26.98      1DIK 1689
ATOM   1598  CE2  PHE  212   -13.926  41.417  39.661  1.00  23.41      1DIK 1690
ATOM   1599  CZ   PHE  212   -13.170  40.273  39.869  1.00  24.28      1DIK 1691
ATOM   1600  N    VAL  213   -15.045  41.954  43.798  1.00  26.22      1DIK 1692
ATOM   1601  CA   VAL  213   -16.414  41.458  43.637  1.00  26.85      1DIK 1693
ATOM   1602  C    VAL  213   -17.424  41.996  44.676  1.00  31.61      1DIK 1694
ATOM   1603  O    VAL  213   -18.554  42.341  44.322  1.00  30.84      1DIK 1695
ATOM   1604  CB   VAL  213   -16.449  39.905  43.611  1.00  22.75      1DIK 1696
ATOM   1605  CG1  VAL  213   -17.854  39.405  43.418  1.00  16.76      1DIK 1697
ATOM   1606  CG2  VAL  213   -15.592  39.403  42.489  1.00  20.78      1DIK 1698
ATOM   1607  N    PRO  214   -17.041  42.076  45.966  1.00  33.45      1DIK 1699
ATOM   1608  CA   PRO  214   -17.969  42.585  46.989  1.00  33.40      1DIK 1700
ATOM   1609  C    PRO  214   -18.707  43.889  46.624  1.00  31.74      1DIK 1701
ATOM   1610  O    PRO  214   -19.922  43.978  46.813  1.00  34.40      1DIK 1702
ATOM   1611  CB   PRO  214   -17.067  42.749  48.207  1.00  36.14      1DIK 1703
ATOM   1612  CG   PRO  214   -16.114  41.600  48.040  1.00  37.34      1DIK 1704
ATOM   1613  CD   PRO  214   -15.753  41.702  46.578  1.00  34.24      1DIK 1705
ATOM   1614  N    SER  215   -17.992  44.887  46.103  1.00  29.66      1DIK 1706
ATOM   1615  CA   SER  215   -18.619  46.154  45.698  1.00  31.11      1DIK 1707
ATOM   1616  C    SER  215   -19.661  45.910  44.615  1.00  30.62      1DIK 1708
ATOM   1617  O    SER  215   -20.767  46.451  44.671  1.00  29.20      1DIK 1709
ATOM   1618  CB   SER  215   -17.584  47.123  45.136  1.00  33.71      1DIK 1710
ATOM   1619  OG   SER  215   -16.463  47.219  45.991  1.00  47.07      1DIK 1711
ATOM   1620  N    ILE  216   -19.297  45.093  43.627  1.00  29.96      1DIK 1712
ATOM   1621  CA   ILE  216   -20.199  44.757  42.529  1.00  27.85      1DIK 1713
ATOM   1622  C    ILE  216   -21.446  44.086  43.104  1.00  29.12      1DIK 1714
ATOM   1623  O    ILE  216   -22.578  44.429  42.734  1.00  28.40      1DIK 1715
ATOM   1624  CB   ILE  216   -19.532  43.797  41.512  1.00  24.43      1DIK 1716
ATOM   1625  CG1  ILE  216   -18.194  44.372  41.032  1.00  25.18      1DIK 1717
ATOM   1626  CG2  ILE  216   -20.446  43.596  40.334  1.00  24.08      1DIK 1718
ATOM   1627  CD1  ILE  216   -17.423  43.463  40.073  1.00  19.59      1DIK 1719
ATOM   1628  N    ARG  217   -21.231  43.136  44.016  1.00  32.27      1DIK 1720
ATOM   1629  CA   ARG  217   -22.326  42.415  44.661  1.00  33.05      1DIK 1721
ATOM   1630  C    ARG  217   -23.283  43.390  45.348  1.00  34.41      1DIK 1722
ATOM   1631  O    ARG  217   -24.508  43.263  45.220  1.00  34.77      1DIK 1723
ATOM   1632  CB   ARG  217   -21.798  41.415  45.689  1.00  32.26      1DIK 1724
ATOM   1633  CG   ARG  217   -22.910  40.737  46.468  1.00  28.72      1DIK 1725
ATOM   1634  CD   ARG  217   -22.379  39.772  47.495  1.00  33.69      1DIK 1726
ATOM   1635  NE   ARG  217   -21.418  40.352  48.438  1.00  37.21      1DIK 1727
ATOM   1636  CZ   ARG  217   -21.677  41.336  49.303  1.00  38.84      1DIK 1728
ATOM   1637  NH1  ARG  217   -22.879  41.908  49.355  1.00  34.37      1DIK 1729
ATOM   1638  NH2  ARG  217   -20.713  41.754  50.120  1.00  35.90      1DIK 1730
```

FIG. 8-26

```
ATOM   1639  N   GLN   218     -22.729  44.359  46.073  1.00 32.95      1DIK1731
ATOM   1640  CA  GLN   218     -23.562  45.352  46.749  1.00 36.19      1DIK1732
ATOM   1641  C   GLN   218     -24.392  46.172  45.763  1.00 36.45      1DIK1733
ATOM   1642  O   GLN   218     -25.565  46.450  46.026  1.00 36.62      1DIK1734
ATOM   1643  CB  GLN   218     -22.715  46.275  47.617  1.00 37.01      1DIK1735
ATOM   1644  CG  GLN   218     -22.118  45.574  48.819  1.00 42.03      1DIK1736
ATOM   1645  CD  GLN   218     -21.371  46.519  49.727  1.00 44.82      1DIK1737
ATOM   1646  OE1 GLN   218     -21.019  47.631  49.335  1.00 47.97      1DIK1738
ATOM   1647  NE2 GLN   218     -21.123  46.083  50.955  1.00 49.64      1DIK1739
ATOM   1648  N   ARG   219     -23.799  46.548  44.629  1.00 34.39      1DIK1740
ATOM   1649  CA  ARG   219     -24.529  47.313  43.624  1.00 31.62      1DIK1741
ATOM   1650  C   ARG   219     -25.691  46.487  43.091  1.00 33.49      1DIK1742
ATOM   1651  O   ARG   219     -26.813  46.984  42.982  1.00 34.34      1DIK1743
ATOM   1652  CB  ARG   219     -23.618  47.722  42.470  1.00 29.81      1DIK1744
ATOM   1653  CG  ARG   219     -24.290  48.626  41.446  1.00 27.77      1DIK1745
ATOM   1654  CD  ARG   219     -23.291  49.121  40.410  1.00 28.23      1DIK1746
ATOM   1655  NE  ARG   219     -22.904  48.071  39.462  1.00 27.67      1DIK1747
ATOM   1656  CZ  ARG   219     -21.656  47.650  39.254  1.00 29.17      1DIK1748
ATOM   1657  NH1 ARG   219     -20.638  48.169  39.933  1.00 21.50      1DIK1749
ATOM   1658  NH2 ARG   219     -21.423  46.698  38.360  1.00 32.18      1DIK1750
ATOM   1659  N   LEU   220     -25.437  45.223  42.765  1.00 32.50      1DIK1751
ATOM   1660  CA  LEU   220     -26.504  44.377  42.243  1.00 33.49      1DIK1752
ATOM   1661  C   LEU   220     -27.609  44.104  43.260  1.00 32.41      1DIK1753
ATOM   1662  O   LEU   220     -28.790  44.123  42.901  1.00 29.58      1DIK1754
ATOM   1663  CB  LEU   220     -25.948  43.043  41.727  1.00 34.41      1DIK1755
ATOM   1664  CG  LEU   220     -25.043  43.081  40.494  1.00 36.51      1DIK1756
ATOM   1665  CD1 LEU   220     -24.636  41.657  40.138  1.00 35.97      1DIK1757
ATOM   1666  CD2 LEU   220     -25.758  43.753  39.331  1.00 27.80      1DIK1758
ATOM   1667  N   GLU   221     -27.233  43.848  44.517  1.00 35.98      1DIK1759
ATOM   1668  CA  GLU   221     -28.213  43.560  45.576  1.00 38.20      1DIK1760
ATOM   1669  C   GLU   221     -29.100  44.771  45.795  1.00 39.87      1DIK1761
ATOM   1670  O   GLU   221     -30.302  44.646  46.042  1.00 40.20      1DIK1762
ATOM   1671  CB  GLU   221     -27.519  43.179  46.881  1.00 35.73      1DIK1763
ATOM   1672  CG  GLU   221     -26.800  41.848  46.816  1.00 39.22      1DIK1764
ATOM   1673  CD  GLU   221     -26.340  41.346  48.176  1.00 42.91      1DIK1765
ATOM   1674  OE1 GLU   221     -25.555  42.054  48.861  1.00 43.49      1DIK1766
ATOM   1675  OE2 GLU   221     -26.770  40.234  48.557  1.00 41.59      1DIK1767
ATOM   1676  N   ASN   222     -28.486  45.943  45.689  1.00 41.49      1DIK1768
ATOM   1677  CA  ASN   222     -29.182  47.208  45.841  1.00 45.54      1DIK1769
ATOM   1678  C   ASN   222     -30.139  47.515  44.672  1.00 43.33      1DIK1770
ATOM   1679  O   ASN   222     -31.257  47.971  44.903  1.00 45.33      1DIK1771
ATOM   1680  CB  ASN   222     -28.158  48.329  46.017  1.00 54.00      1DIK1772
ATOM   1681  CG  ASN   222     -28.797  49.701  46.091  1.00 62.65      1DIK1773
ATOM   1682  OD1 ASN   222     -28.256  50.675  45.558  1.00 68.49      1DIK1774
ATOM   1683  ND2 ASN   222     -29.951  49.793  46.752  1.00 66.30      1DIK1775
ATOM   1684  N   ASP   223     -29.715  47.268  43.433  1.00 41.09      1DIK1776
ATOM   1685  CA  ASP   223     -30.562  47.521  42.256  1.00 37.20      1DIK1777
ATOM   1686  C   ASP   223     -31.655  46.482  42.022  1.00 38.11      1DIK1778
ATOM   1687  O   ASP   223     -32.712  46.809  41.482  1.00 39.42      1DIK1779
ATOM   1688  CB  ASP   223     -29.717  47.636  40.990  1.00 35.50      1DIK1780
ATOM   1689  CG  ASP   223     -28.772  48.821  41.017  1.00 38.50      1DIK1781
ATOM   1690  OD1 ASP   223     -28.977  49.753  41.826  1.00 40.58      1DIK1782
ATOM   1691  OD2 ASP   223     -27.811  48.827  40.220  1.00 41.14      1DIK1783
ATOM   1692  N   LEU   224     -31.412  45.231  42.405  1.00 40.35      1DIK1784
ATOM   1693  CA  LEU   224     -32.427  44.188  42.232  1.00 45.31      1DIK1785
ATOM   1694  C   LEU   224     -32.971  43.798  43.604  1.00 49.10      1DIK1786
ATOM   1695  O   LEU   224     -32.732  42.685  44.077  1.00 52.62      1DIK1787
ATOM   1696  CB  LEU   224     -31.835  42.956  41.543  1.00 42.30      1DIK1788
ATOM   1697  CG  LEU   224     -31.389  43.069  40.086  1.00 40.02      1DIK1789
ATOM   1698  CD1 LEU   224     -30.443  41.925  39.770  1.00 37.89      1DIK1790
ATOM   1699  CD2 LEU   224     -32.594  43.046  39.173  1.00 37.37      1DIK1791
ATOM   1700  N   SER   225     -33.701  44.721  44.232  1.00 50.58      1DIK1792
ATOM   1701  CA  SER   225     -34.283  44.522  45.564  1.00 49.16      1DIK1793
ATOM   1702  C   SER   225     -34.977  43.185  45.737  1.00 45.74      1DIK1794
ATOM   1703  O   SER   225     -35.844  42.816  44.944  1.00 45.28      1DIK1795
ATOM   1704  CB  SER   225     -35.280  45.639  45.880  1.00 51.40      1DIK1796
```

FIG. 8-27

```
ATOM   1705  OG   SER  225   -34.660  46.909  45.793  1.00  58.48      1DIK1797
ATOM   1706  N    GLY  226   -34.591  42.465  46.781  1.00  42.17      1DIK1798
ATOM   1707  CA   GLY  226   -35.196  41.173  47.040  1.00  43.89      1DIK1799
ATOM   1708  C    GLY  226   -34.226  40.060  46.731  1.00  44.37      1DIK1800
ATOM   1709  O    GLY  226   -34.461  38.900  47.051  1.00  47.89      1DIK1801
ATOM   1710  N    VAL  227   -33.119  40.422  46.108  1.00  42.94      1DIK1802
ATOM   1711  CA   VAL  227   -32.108  39.465  45.727  1.00  43.07      1DIK1803
ATOM   1712  C    VAL  227   -30.903  39.493  46.670  1.00  41.79      1DIK1804
ATOM   1713  O    VAL  227   -30.485  40.560  47.135  1.00  41.57      1DIK1805
ATOM   1714  CB   VAL  227   -31.676  39.750  44.252  1.00  45.33      1DIK1806
ATOM   1715  CG1  VAL  227   -30.316  39.167  43.947  1.00  44.28      1DIK1807
ATOM   1716  CG2  VAL  227   -32.721  39.189  43.297  1.00  44.62      1DIK1808
ATOM   1717  N    THR  228   -30.371  38.307  46.963  1.00  40.83      1DIK1809
ATOM   1718  CA   THR  228   -29.166  38.159  47.785  1.00  39.67      1DIK1810
ATOM   1719  C    THR  228   -28.234  37.336  46.893  1.00  37.22      1DIK1811
ATOM   1720  O    THR  228   -28.679  36.394  46.235  1.00  33.46      1DIK1812
ATOM   1721  CB   THR  228   -29.412  37.398  49.124  1.00  41.63      1DIK1813
ATOM   1722  OG1  THR  228   -29.990  36.116  48.867  1.00  44.83      1DIK1814
ATOM   1723  CG2  THR  228   -30.339  38.177  50.021  1.00  43.36      1DIK1845
ATOM   1724  N    LEU  229   -26.957  37.689  46.862  1.00  36.42      1DIK1816
ATOM   1725  CA   LEU  229   -25.991  36.988  46.022  1.00  35.85      1DIK1817
ATOM   1726  C    LEU  229   -24.689  36.735  46.771  1.00  36.00      1DIK1818
ATOM   1727  O    LEU  229   -24.302  37.520  47.630  1.00  37.29      1DIK1819
ATOM   1728  CB   LEU  229   -25.664  37.848  44.799  1.00  35.69      1DIK1820
ATOM   1729  CG   LEU  229   -26.790  38.240  43.850  1.00  31.77      1DIK1821
ATOM   1730  CD1  LEU  229   -26.254  39.233  42.860  1.00  32.31      1DIK1822
ATOM   1731  CD2  LEU  229   -27.334  37.014  43.143  1.00  31.68      1DIK1823
ATOM   1732  N    THR  230   -24.011  35.643  46.447  1.00  33.91      1DIK1824
ATOM   1733  CA   THR  230   -22.729  35.359  47.072  1.00  34.10      1DIK1825
ATOM   1734  C    THR  230   -21.743  35.959  46.083  1.00  34.69      1DIK1826
ATOM   1735  O    THR  230   -22.119  36.265  44.944  1.00  32.68      1DIK1827
ATOM   1736  CB   THR  230   -22.466  33.838  47.178  1.00  34.26      1DIK1828
ATOM   1737  OG1  THR  230   -22.463  33.260  45.870  1.00  30.93      1DIK1829
ATOM   1738  CG2  THR  230   -23.552  33.151  47.997  1.00  31.47      1DIK1830
ATOM   1739  N    ASP  231   -20.493  36.131  46.494  1.00  37.66      1DIK1831
ATOM   1740  CA   ASP  231   -19.478  36.674  45.592  1.00  39.60      1DIK1832
ATOM   1741  C    ASP  231   -19.312  35.794  44.344  1.00  40.76      1DIK1833
ATOM   1742  O    ASP  231   -19.186  36.303  43.227  1.00  43.31      1DIK1834
ATOM   1743  CB   ASP  231   -18.138  36.827  46.313  1.00  39.61      1DIK1835
ATOM   1744  CG   ASP  231   -18.147  37.956  47.321  1.00  44.99      1DIK1836
ATOM   1745  OD1  ASP  231   -19.042  38.825  47.233  1.00  45.50      1DIK1837
ATOM   1746  OD2  ASP  231   -17.254  37.976  48.202  1.00  49.54      1DIK1838
ATOM   1747  N    THR  232   -19.324  34.479  44.544  1.00  38.28      1DIK1839
ATOM   1748  CA   THR  232   -19.188  33.520  43.458  1.00  34.10      1DIK1840
ATOM   1749  C    THR  232   -20.280  33.679  42.416  1.00  32.21      1DIK1841
ATOM   1750  O    THR  232   -19.994  33.663  41.222  1.00  34.55      1DIK1842
ATOM   1751  CB   THR  232   -19.210  32.075  44.010  1.00  34.37      1DIK1843
ATOM   1752  OG1  THR  232   -18.074  31.896  44.856  1.00  35.55      1DIK1844
ATOM   1753  CG2  THR  232   -19.163  31.037  42.894  1.00  26.21      1DIK1845
ATOM   1754  N    GLU  233   -21.525  33.835  42.856  1.00  28.27      1DIK1846
ATOM   1755  CA   GLU  233   -22.637  33.978  41.919  1.00  29.61      1DIK1847
ATOM   1756  C    GLU  233   -22.500  35.196  41.016  1.00  27.81      1DIK1848
ATOM   1757  O    GLU  233   -22.923  35.162  39.872  1.00  30.27      1DIK1849
ATOM   1758  CB   GLU  233   -23.970  34.029  42.660  1.00  32.29      1DIK1850
ATOM   1759  CG   GLU  233   -24.262  32.784  43.483  1.00  38.65      1DIK1851
ATOM   1760  CD   GLU  233   -25.539  32.893  44.298  1.00  41.41      1DIK1852
ATOM   1761  OE1  GLU  233   -25.716  33.897  45.041  1.00  39.47      1DIK1853
ATOM   1762  OE2  GLU  233   -26.366  31.961  44.188  1.00  43.44      1DIK1854
ATOM   1763  N    VAL  234   -21.916  36.270  41.529  1.00  26.78      1DIK1855
ATOM   1764  CA   VAL  234   -21.718  37.471  40.730  1.00  27.81      1DIK1856
ATOM   1765  C    VAL  234   -20.779  37.131  39.555  1.00  28.07      1DIK1857
ATOM   1766  O    VAL  234   -21.031  37.532  38.409  1.00  27.61      1DIK1858
ATOM   1767  CB   VAL  234   -21.139  38.631  41.599  1.00  29.25      1DIK1859
ATOM   1768  CG1  VAL  234   -20.669  39.790  40.719  1.00  26.00      1DIK1860
ATOM   1769  CG2  VAL  234   -22.202  39.114  42.574  1.00  23.62      1DIK1861
ATOM   1770  N    THR  235   -19.712  36.383  39.830  1.00  25.71      1DIK1862
```

FIG. 8-28

```
ATOM   1771  CA   THR   235     -18.784  35.991  38.773  1.00  27.53      1DIK1863
ATOM   1772  C    THR   235     -19.506  35.104  37.728  1.00  28.27      1DIK1864
ATOM   1773  O    THR   235     -19.098  35.065  36.565  1.00  27.05      1DIK1865
ATOM   1774  CB   THR   235     -17.513  35.272  39.329  1.00  26.76      1DIK1866
ATOM   1775  OG1  THR   235     -17.866  33.998  39.876  1.00  28.53      1DIK1867
ATOM   1776  CG2  THR   235     -16.859  36.104  40.416  1.00  27.73      1DIK1868
ATOM   1777  N    TYR   236     -20.575  34.406  38.129  1.00  27.79      1DIK1869
ATOM   1778  CA   TYR   236     -21.339  33.577  37.188  1.00  27.49      1DIK1870
ATOM   1779  C    TYR   236     -22.024  34.490  36.171  1.00  28.77      1DIK1871
ATOM   1780  O    TYR   236     -22.106  34.165  34.980  1.00  30.28      1DIK1872
ATOM   1781  CB   TYR   236     -22.405  32.741  37.908  1.00  28.51      1DIK1873
ATOM   1782  CG   TYR   236     -21.873  31.589  38.735  1.00  31.65      1DIK1874
ATOM   1783  CD1  TYR   236     -20.517  31.243  38.711  1.00  32.72      1DIK1875
ATOM   1784  CD2  TYR   236     -22.733  30.838  39.546  1.00  33.46      1DIK1876
ATOM   1785  CE1  TYR   236     -20.030  30.181  39.471  1.00  33.24      1DIK1877
ATOM   1786  CE2  TYR   236     -22.258  29.768  40.315  1.00  35.17      1DIK1878
ATOM   7187  CZ   TYR   236     -20.904  29.446  40.271  1.00  39.13      1DIK1879
ATOM   1788  OH   TYR   236     -20.422  28.393  41.025  1.00  43.32      1DIK1880
ATOM   1789  N    LEU   237     -22.513  35.632  36.656  1.00  29.13      1DIK1881
ATOM   1790  CA   LEU   237     -23.179  36.634  35.818  1.00  27.63      1DIK1882
ATOM   1791  C    LEU   237     -22.173  37.237  34.842  1.00  27.17      1DIK1883
ATOM   1792  O    LEU   237     -22.506  37.527  33.699  1.00  30.67      1DIK1884
ATOM   1793  CB   LEU   237     -23.813  37.734  36.682  1.00  25.77      1DIK1885
ATOM   1794  CG   LEU   237     -25.081  37.327  37.447  1.00  22.88      1DIK1886
ATOM   1795  CD1  LEU   237     -25.528  38.415  38.421  1.00  24.36      1DIK1887
ATOM   1796  CD2  LEU   237     -26.165  37.036  36.455  1.00  17.71      1DIK1888
ATOM   1797  N    MET   238     -20.940  37.423  35.286  1.00  24.39      1DIK1889
ATOM   1798  CA   MET   238     -19.918  37.948  34.403  1.00  25.37      1DIK1890
ATOM   1799  C    MET   238     -19.575  36.882  33.359  1.00  28.12      1DIK1891
ATOM   1800  O    MET   238     -19.335  37.210  32.195  1.00  31.98      1DIK1892
ATOM   1801  CB   MET   238     -18.684  38.358  35.203  1.00  21.01      1DIK1893
ATOM   1802  CG   MET   238     -18.967  39.504  36.148  1.00  18.56      1DIK1894
ATOM   1803  SD   MET   238     -17.500  40.183  36.915  1.00  26.85      1DIK1895
ATOM   1804  CE   MET   238     -16.964  41.396  35.681  1.00  20.81      1DIK1896
ATOM   1805  N    ASP   239     -19.562  35.608  33.764  1.00  29.27      1DIK1897
ATOM   1806  CA   ASP   239     -19.268  34.497  32.838  1.00  28.12      1DIK1898
ATOM   1807  C    ASP   239     -20.314  34.486  31.727  1.00  26.51      1DIK1899
ATOM   1808  O    ASP   239     -20.003  34.210  30.577  1.00  27.19      1DIK1900
ATOM   1809  CB   ASP   239     -19.340  33.129  33.542  1.00  27.22      1DIK1901
ATOM   1810  CG   ASP   239     -18.144  32.836  34.448  1.00  24.04      1DIK1902
ATOM   1811  OD1  ASP   239     -17.162  33.602  34.461  1.00  22.09      1DIK1903
ATOM   1812  OD2  ASP   239     -18.194  31.807  35.162  1.00  27.85      1DIK1904
ATOM   1813  N    MET   240     -21.557  34.784  32.089  1.00  24.64      1DIK1905
ATOM   1814  CA   MET   240     -22.664  34.800  31.141  1.00  26.17      1DIK1906
ATOM   1815  C    MET   240     -22.509  35.815  30.018  1.00  26.18      1DIK1907
ATOM   1816  O    MET   240     -23.034  35.621  28.924  1.00  25.09      1DIK1908
ATOM   1817  CB   MET   240     -23.984  35.039  31.877  1.00  29.12      1DIK1909
ATOM   1818  CG   MET   240     -24.519  33.809  32.591  1.00  28.59      1DIK1910
ATOM   1819  SD   MET   240     -24.873  32.469  31.404  1.00  34.30      1DIK1911
ATOM   1820  CE   MET   240     -26.354  33.141  30.505  1.00  25.69      1DIK1912
ATOM   1821  N    CYS   241     -21.793  36.899  30.280  1.00  25.30      1DIK1913
ATOM   1822  CA   CYS   241     -21.581  37.910  29.254  1.00  27.89      1DIK1914
ATOM   1823  C    CYS   241     -20.931  37.244  28.032  1.00  25.49      1DIK1915
ATOM   1824  O    CYS   241     -21.348  37.459  26.892  1.00  26.76      1DIK1916
ATOM   1825  CB   CYS   241     -20.710  39.049  29.814  1.00  24.99      1DIK1917
ATOM   1826  SG   CYS   241     -19.856  40.115  28.598  1.00  27.44      1DIK1918
ATOM   1827  N    SER   242     -19.924  36.420  28.291  1.00  25.28      1DIK1919
ATOM   1828  CA   SER   242     -19.197  35.698  27.256  1.00  25.73      1DIK1920
ATOM   1829  C    SER   242     -20.072  34.679  26.507  1.00  26.63      1DIK1921
ATOM   1830  O    SER   242     -20.275  34.786  25.289  1.00  25.57      1DIK1922
ATOM   1831  CB   SER   242     -18.003  34.989  27.897  1.00  27.44      1DIK1923
ATOM   1832  OG   SER   242     -17.294  34.219  26.949  1.00  39.33      1DIK1924
ATOM   1833  N    PHE   243     -20.594  33.697  27.238  1.00  26.85      1DIK1925
ATOM   1834  CA   PHE   243     -21.419  32.642  26.648  1.00  26.10      1DIK1926
ATOM   1835  C    PHE   243     -22.663  33.140  25.941  1.00  27.04      1DIK1927
ATOM   1836  O    PHE   243     -23.021  32.637  24.872  1.00  26.53      1DIK1928
```

FIG. 8-29

```
ATOM  1837  CB   PHE  243   -21.818  31.617  27.714  1.00  25.98      1DIK1929
ATOM  1838  CG   PHE  243   -20.655  30.845  28.277  1.00  26.19      1DIK1930
ATOM  1839  CD1  PHE  243   -20.075  29.805  27.549  1.00  23.12      1DIK1931
ATOM  1840  CD2  PHE  243   -20.129  31.168  29.530  1.00  21.56      1DIK1932
ATOM  1841  CE1  PHE  243   -18.978  29.093  28.066  1.00  25.40      1DIK1933
ATOM  1842  CE2  PHE  243   -19.042  30.469  30.052  1.00  22.05      1DIK1934
ATOM  1843  CZ   PHE  243   -18.461  29.427  29.319  1.00  21.32      1DIK1935
ATOM  1844  N    ASP  244   -23.330  34.126  26.529  1.00  27.71      1DIK1936
ATOM  1845  CA   ASP  244   -24.537  34.643  25.907  1.00  30.62      1DIK1937
ATOM  1846  C    ASP  244   -24.235  35.494  24.666  1.00  32.18      1DIK1938
ATOM  1847  O    ASP  244   -25.120  35.741  23.854  1.00  34.05      1DIK1939
ATOM  1848  CB   ASP  244   -25.379  35.428  26.917  1.00  27.50      1DIK1940
ATOM  1849  CG   ASP  244   -26.785  35.723  26.404  1.00  28.82      1DIK1941
ATOM  1850  OD1  ASP  244   -27.531  34.777  26.077  1.00  24.13      1DIK1942
ATOM  1851  OD2  ASP  244   -27.149  36.910  26.323  1.00  30.15      1DIK1943
ATOM  1852  N    THR  245   -22.996  35.944  24.510  1.00  32.39      1DIK1944
ATOM  1853  CA   THR  245   -22.658  36.740  23.343  1.00  33.50      1DIK1945
ATOM  1854  C    THR  245   -22.282  35.850  22.153  1.00  38.87      1DIK1946
ATOM  1855  O    THR  245   -22.911  35.918  21.091  1.00  37.64      1DIK1947
ATOM  1856  CB   THR  245   -21.511  37.706  23.647  1.00  32.72      1DIK1948
ATOM  1857  OG1  THR  245   -21.940  38.652  24.631  1.00  37.51      1DIK1949
ATOM  1858  CG2  THR  245   -21.084  38.446  22.394  1.00  28.33      1DIK1950
ATOM  1859  N    ILE  246   -21.268  35.008  22.335  1.00  40.95      1DIK1951
ATOM  1860  CA   ILE  246   -20.803  34.140  21.262  1.00  43.89      1DIK1952
ATOM  1861  C    ILE  246   -21.590  32.847  21.034  1.00  48.67      1DIK1953
ATOM  1862  O    ILE  246   -21.151  31.992  20.262  1.00  48.67      1DIK1954
ATOM  1863  CB   ILE  246   -19.279  33.826  21.419  1.00  41.80      1DIK1955
ATOM  1864  CG1  ILE  246   -18.988  33.144  22.757  1.00  37.29      1DIK1956
ATOM  1865  CG2  ILE  246   -18.464  35.125  21.329  1.00  43.70      1DIK1957
ATOM  1866  CD1  ILE  246   -17.508  33.098  23.087  1.00  29.59      1DIK1958
ATOM  1867  N    SER  247   -22.747  32.710  21.688  1.00  56.97      1DIK1959
ATOM  1868  CA   SER  247   -23.601  31.523  21.534  1.00  63.90      1DIK1960
ATOM  1869  C    SER  247   -24.145  31.424  20.107  1.00  70.33      1DIK1961
ATOM  1870  O    SER  247   -24.503  30.328  19.662  1.00  73.70      1DIK1962
ATOM  1871  CB   SER  247   -24.787  31.567  22.499  1.00  67.11      1DIK1963
ATOM  1872  OG   SER  247   -25.783  32.483  22.058  1.00  66.63      1DIK1964
ATOM  1873  N    THR  248   -24.213  32.569  19.411  1.00  74.67      1DIK1965
ATOM  1874  CA   THR  248   -24.683  32.671  18.015  1.00  74.94      1DIK1966
ATOM  1875  C    THR  248   -23.546  33.054  17.049  1.00  76.44      1DIK1967
ATOM  1876  O    THR  248   -23.272  34.241  16.808  1.00  77.32      1DIK1968
ATOM  1877  CB   THR  248   -25.810  33.719  17.893  1.00  74.59      1DIK1969
ATOM  1878  OG1  THR  248   -26.917  33.299  18.699  1.00  74.12      1DIK1970
ATOM  1879  CG2  THR  248   -26.262  33.888  16.427  1.00  72.58      1DIK1971
ATOM  1880  N    THR  253   -23.919  38.646  16.591  1.00  49.08      1DIK1972
ATOM  1881  CA   THR  253   -24.110  39.972  15.999  1.00  51.56      1DIK1973
ATOM  1882  C    THR  253   -24.258  41.028  17.100  1.00  49.54      1DIK1974
ATOM  1883  O    THR  253   -23.757  42.146  16.965  1.00  49.39      1DIK1975
ATOM  1884  CB   THR  253   -25.394  40.051  15.103  1.00  52.26      1DIK1976
ATOM  1885  OG1  THR  253   -25.489  38.881  14.282  1.00  61.78      1DIK1977
ATOM  1886  CG2  THR  253   -25.344  41.284  14.189  1.00  51.28      1DIK1978
ATOM  1887  N    LYS  254   -24.941  40.670  18.185  1.00  46.23      1DIK1979
ATOM  1888  CA   LYS  254   -25.170  41.610  19.275  1.00  45.73      1DIK1980
ATOM  1889  C    LYS  254   -24.562  41.222  20.618  1.00  42.99      1DIK1981
ATOM  1890  O    LYS  254   -24.470  40.044  20.939  1.00  45.43      1DIK1982
ATOM  1891  CB   LYS  254   -26.664  41.864  19.410  1.00  46.12      1DIK1983
ATOM  1892  CG   LYS  254   -27.214  42.520  18.157  1.00  51.91      1DIK1984
ATOM  1893  CD   LYS  254   -28.671  42.840  18.273  1.00  56.51      1DIK1985
ATOM  1894  CE   LYS  254   -29.168  43.456  16.987  1.00  60.44      1DIK1986
ATOM  1895  NZ   LYS  254   -30.576  43.918  17.160  1.00  67.71      1DIK1987
ATOM  1896  N    LEU  255   -24.141  42.226  21.387  1.00  38.90      1DIK1988
ATOM  1897  CA   LEU  255   -23.533  42.022  22.705  1.00  33.29      1DIK1989
ATOM  1898  C    LEU  255   -24.584  41.661  23.751  1.00  32.90      1DIK1990
ATOM  1899  O    LEU  255   -25.637  42.288  23.825  1.00  33.07      1DIK1991
ATOM  1900  CB   LEU  255   -22.797  43.286  23.141  1.00  25.06      1DIK1992
ATOM  1901  CG   LEU  255   -21.856  43.213  24.344  1.00  26.05      1DIK1993
ATOM  1902  CD1  LEU  255   -20.707  42.242  24.095  1.00  21.04      1DIK1994
```

FIG. 8-30

```
ATOM   1903  CD2 LEU  255   -21.326  44.595  24.608  1.00  22.14      1DIK1995
ATOM   1904  N   SER  256   -24.293  40.647  24.558  1.00  32.93      1DIK1996
ATOM   1905  CA  SER  256   -25.212  40.207  25.598  1.00  31.52      1DIK1997
ATOM   1906  C   SER  256   -25.489  41.293  26.643  1.00  32.01      1DIK1998
ATOM   1907  O   SER  256   -24.574  42.013  27.082  1.00  30.64      1DIK1999
ATOM   1908  CB  SER  256   -24.650  38.965  26.306  1.00  30.76      1DIK2000
ATOM   1909  OG  SER  256   -25.446  38.602  27.430  1.00  27.78      1DIK2001
ATOM   1910  N   PRO  257   -26.766  41.432  27.051  1.00  32.46      1DIK2002
ATOM   1911  CA  PRO  257   -27.131  42.434  28.060  1.00  32.73      1DIK2003
ATOM   1912  C   PRO  257   -26.372  42.191  29.379  1.00  31.79      1DIK2004
ATOM   1913  O   PRO  257   -26.136  43.130  30.138  1.00  35.33      1DIK2005
ATOM   1914  CB  PRO  257   -28.644  42.239  28.209  1.00  32.20      1DIK2006
ATOM   1915  CG  PRO  257   -29.053  41.696  26.861  1.00  31.42      1DIK2007
ATOM   1916  CD  PRO  257   -27.960  40.701  26.587  1.00  30.36      1DIK2008
ATOM   1917  N   PHE  258   -25.984  40.941  29.646  1.00  27.64      1DIK2009
ATOM   1918  CA  PHE  258   -25.221  40.617  30.859  1.00  25.04      1DIK2010
ATOM   1919  C   PHE  258   -23.910  41.407  30.928  1.00  24.80      1DIK2011
ATOM   1920  O   PHE  258   -23.389  41.661  32.011  1.00  22.95      1DIK2012
ATOM   1921  CB  PHE  258   -24.877  39.122  30.911  1.00  25.72      1DIK2013
ATOM   1922  CG  PHE  258   -26.033  38.239  31.253  1.00  24.20      1DIK2014
ATOM   1923  CD1 PHE  258   -26.455  38.105  32.569  1.00  23.98      1DIK2015
ATOM   1924  CD2 PHE  258   -26.712  37.544  30.257  1.00  26.82      1DIK2016
ATOM   1925  CE1 PHE  258   -27.543  37.288  32.890  1.00  23.72      1DIK2017
ATOM   1926  CE2 PHE  258   -27.806  36.721  30.565  1.00  24.56      1DIK2018
ATOM   1927  CZ  PHE  258   -28.220  36.594  31.879  1.00  24.85      1DIK2019
ATOM   1928  N   CYS  259   -23.375  41.790  29.772  1.00  24.43      1DIK2020
ATOM   1929  CA  CYS  259   -22.119  42.536  29.731  1.00  27.30      1DIK2021
ATOM   1930  C   CYS  259   -22.323  43.952  30.207  1.00  29.38      1DIK2022
ATOM   1931  O   CYS  259   -21.420  44.565  30.771  1.00  29.68      1DIK2023
ATOM   1932  CB  CYS  259   -21.564  42.591  28.307  1.00  26.45      1DIK2024
ATOM   1933  SG  CYS  259   -21.348  40.968  27.516  1.00  30.19      1DIK2025
ATOM   1934  N   ASP  260   -23.527  44.460  29.975  1.00  31.11      1DIK2026
ATOM   1935  CA  ASP  260   -23.879  45.821  30.326  1.00  33.64      1DIK2027
ATOM   1936  C   ASP  260   -24.002  46.070  31.815  1.00  32.59      1DIK2028
ATOM   1937  O   ASP  260   -24.054  47.212  32.246  1.00  34.03      1DIK2029
ATOM   1938  CB  ASP  060   -25.194  46.201  29.645  1.00  39.78      1DIK2030
ATOM   1939  CG  ASP  260   -25.246  47.667  29.252  1.00  44.26      1DIK2031
ATOM   1940  OD1 ASP  260   -24.190  48.185  28.834  1.00  45.01      1DIK2032
ATOM   1941  OD2 ASP  260   -26.328  48.292  29.362  1.00  42.47      1DIK2033
ATOM   1942  N   LEU  261   -24.051  45.007  32.603  1.00  33.47      1DIK2034
ATOM   1943  CA  LEU  261   -24.200  45.149  34.043  1.00  29.07      1DIK2035
ATOM   1944  C   LEU  261   -22.887  45.446  34.736  1.00  29.71      1DIK2036
ATOM   1945  O   LEU  261   -22.867  45.747  35.929  1.00  33.17      1DIK2037
ATOM   1946  CB  LEU  261   -24.816  43.880  34.629  1.00  28.55      1DIK2038
ATOM   1947  CG  LEU  261   -26.103  43.405  33.947  1.00  27.56      1DIK2039
ATOM   1948  CD1 LEU  261   -26.541  42.089  34.534  1.00  25.79      1DIK2040
ATOM   1949  CD2 LEU  261   -27.197  44.441  34.130  1.00  27.02      1DIK2041
ATOM   1950  N   PHE  262   -21.786  45.376  33.997  1.00  29.05      1DIK2042
ATOM   1951  CA  PHE  262   -20.471  45.607  34.586  1.00  27.80      1DIK2043
ATOM   1952  C   PHE  262   -19.709  46.685  33.837  1.00  29.74      1DIK2044
ATOM   1953  O   PHE  262   -19.869  46.846  32.622  1.00  35.51      1DIK2045
ATOM   1954  CB  PHE  262   -19.685  44.280  34.621  1.00  24.44      1DIK2046
ATOM   1955  CG  PHE  262   -20.478  43.146  35.192  1.00  21.66      1DIK2047
ATOM   1956  CD1 PHE  262   -20.589  42.987  36.572  1.00  18.94      1DIK2048
ATOM   1957  CD2 PHE  262   -21.176  42.277  34.348  1.00  20.22      1DIK2049
ATOM   1958  CE1 PHE  262   -21.396  41.976  37.106  1.00  21.42      1DIK2050
ATOM   1959  CE2 PHE  262   -21.985  41.265  34.865  1.00  19.46      1DIK2051
ATOM   1960  CZ  PHE  262   -22.099  41.112  36.250  1.00  21.48      1DIK2052
ATOM   1961  N   THR  263   -18.881  47.428  34.564  1.00  30.27      1DIK2053
ATOM   1962  CA  THR  263   -18.113  48.502  33.967  1.00  29.94      1DIK2054
ATOM   1963  C   THR  263   -16.811  47.961  33.425  1.00  29.54      1DIK2055
ATOM   1964  O   THR  263   -16.466  46.805  33.671  1.00  31.34      1DIK2056
ATOM   1965  CB  THR  263   -17.860  49.648  34.985  1.00  32.12      1DIK2057
ATOM   1966  OG1 THR  263   -16.998  49.193  36.036  1.00  29.58      1DIK2058
ATOM   1967  CG2 THR  263   -19.183  50.112  35.589  1.00  22.67      1DIK2059
ATOM   1968  N   HIS  264   -16.087  48.802  32.693  1.00  30.02      1DIK2060
```

FIG. 8-31

```
ATOM   1969  CA   HIS  264   -14.829  48.400  32.090  1.00  28.00      1DIK2061
ATOM   1970  C    HIS  264   -13.717  47.984  33.052  1.00  30.02      1DIK2062
ATOM   1971  O    HIS  264   -12.998  47.015  32.774  1.00  31.35      1DIK2063
ATOM   1972  CB   HIS  264   -14.314  49.480  31.143  1.00  27.91      1DIK2064
ATOM   1973  CG   HIS  264   -13.111  49.048  30.370  1.00  34.68      1DIK2065
ATOM   1974  ND1  HIS  264   -13.186  48.157  29.318  1.00  31.27      1DIK2066
ATOM   1975  CD2  HIS  264   -11.795  49.339  30.527  1.00  35.74      1DIK2067
ATOM   1976  CE1  HIS  264   -11.969  47.916  28.863  1.00  37.49      1DIK2068
ATOM   1977  NE2  HIS  264   -11.108  48.620  29.579  1.00  38.67      1DIK2069
ATOM   1978  N    ASP  265   -13.560  48.703  34.167  1.00  31.42      1DIK2070
ATOM   1979  CA   ASP  265   -12.533  48.371  35.172  1.00  29.27      1DIK2071
ATOM   1980  C    ASP  265   -12.831  47.030  35.859  1.00  27.71      1DIK2072
ATOM   1981  O    ASP  265   -11.923  46.352  36.346  1.00  25.15      1DIK2073
ATOM   1982  CB   ASP  265   -12.421  49.481  36.222  1.00  36.26      1DIK2074
ATOM   1983  CG   ASP  265   -13.745  49.764  36.921  1.00  44.48      1DIK2075
ATOM   1984  OD1  ASP  265   -14.671  50.307  36.267  1.00  43.98      1DIK2076
ATOM   1985  OD2  ASP  265   -13.860  49.441  38.128  1.00  49.77      1DIK2077
ATOM   1986  N    GLU  266   -14.108  46.651  35.896  1.00  26.27      1DIK2078
ATOM   1987  CA   GLU  266   -14.502  45.378  36.484  1.00  26.01      1DIK2079
ATOM   1988  C    GLU  266   -14.093  44.272  35.517  1.00  27.04      1DIK2080
ATOM   1989  O    GLU  266   -13.665  43.205  35.956  1.00  28.64      1DIK2081
ATOM   1990  CB   GLU  266   -15.997  45.359  36.785  1.00  24.19      1DIK2082
ATOM   1991  CG   GLU  266   -16.336  46.287  37.939  1.00  24.01      1DIK2083
ATOM   1992  CD   GLU  266   -17.824  46.521  38.139  1.00  28.94      1DIK2084
ATOM   1993  OE1  GLU  266   -18.647  46.091  37.299  1.00  30.18      1DIK2085
ATOM   1994  OE2  GLU  266   -18.175  47.150  39.160  1.00  32.29      1DIK2086
ATOM   1995  N    TRP  267   -14.207  44.521  34.210  1.00  24.96      1DIK2087
ATOM   1996  CA   TRP  267   -13.765  43.535  33.221  1.00  24.91      1DIK2088
ATOM   1997  C    TRP  267   -12.243  43.380  33.306  1.00  24.45      1DIK2089
ATOM   1998  O    TRP  267   -11.723  42.269  33.202  1.00  25.00      1DIK2090
ATOM   1999  CB   TRP  267   -14.210  43.915  31.801  1.00  22.45      1DIK2091
ATOM   2000  CG   TRP  267   -15.684  43.646  31.596  1.00  22.28      1DIK2092
ATOM   2001  CD1  TRP  267   -16.661  44.567  31.355  1.00  20.97      1DIK2093
ATOM   2002  CD2  TRP  267   -16.349  42.370  31.684  1.00  20.83      1DIK2094
ATOM   2003  NE1  TRP  267   -17.889  43.952  31.293  1.00  23.15      1DIK2095
ATOM   2004  CE2  TRP  267   -17.726  42.604  31.493  1.00  23.26      1DIK2096
ATOM   2005  CE3  TRP  267   -15.913  41.055  31.914  1.00  18.67      1DIK2097
ATOM   2006  CZ2  TRP  267   -18.672  41.569  31.529  1.00  22.56      1DIK2098
ATOM   2007  CZ3  TRP  267   -16.849  40.032  31.951  1.00  15.00      1DIK2099
ATOM   2008  CH2  TRP  267   -18.211  40.294  31.761  1.00  18.10      1DIK2100
ATOM   2009  N    ILE  268   -11.526  44.479  33.517  1.00  23.42      1DIK2101
ATOM   2010  CA   ILE  268   -10.073  44.399  33.647  1.00  25.35      1DIK2102
ATOM   2011  C    ILE  268    -9.721  43.461  34.801  1.00  27.88      1DIK2103
ATOM   2012  O    ILE  268    -8.776  42.673  34.714  1.00  28.12      1DIK2104
ATOM   2013  CB   ILE  268    -9.460  45.786  33.889  1.00  27.94      1DIK2105
ATOM   2014  CG1  ILE  268    -9.515  46.575  32.579  1.00  27.22      1DIK2106
ATOM   2015  CG2  ILE  268    -8.031  45.659  34.457  1.00  19.33      1DIK2107
ATOM   2016  CD1  ILE  268    -9.124  48.027  32.704  1.00  36.44      1DIK2108
ATOM   2017  N    ASN  269   -10.495  43.553  35.877  1.00  27.63      1DIK2109
ATOM   2018  CA   ASN  269   -10.290  42.704  37.039  1.00  27.33      1DIK2110
ATOM   2019  C    ASN  269   -10.656  41.259  36.739  1.00  26.62      1DIK2111
ATOM   2020  O    ASN  269    -9.918  40.348  37.108  1.00  27.01      1DIK2112
ATOM   2021  CB   ASN  269   -11.110  43.206  38.226  1.00  32.36      1DIK2113
ATOM   2022  CG   ASN  269   -10.427  44.332  38.966  1.00  32.62      1DIK2114
ATOM   2023  OD1  ASN  269    -9.287  44.208  39.423  1.00  29.54      1DIK2115
ATOM   2024  ND2  ASN  269   -11.120  45.443  39.088  1.00  38.68      1DIK2116
ATOM   2025  N    TYR  270   -11.794  41.052  36.075  1.00  22.76      1DIK2117
ATOM   2026  CA   TYR  270   -12.245  39.708  35.712  1.00  22.97      1DIK2118
ATOM   2027  C    TYR  270   -11.168  39.013  34.866  1.00  25.78      1DIK2119
ATOM   2028  O    TYR  270   -10.788  37.868  35.135  1.00  27.56      1DIK2120
ATOM   2029  CB   TYR  270   -13.559  39.800  34.934  1.00  22.99      1DIK2121
ATOM   2030  CG   TYR  270   -14.101  38.485  34.386  1.00  25.74      1DIK2122
ATOM   2031  CD1  TYR  270   -14.989  37.699  35.134  1.00  26.53      1DIK2123
ATOM   2032  CD2  TYR  270   -13.761  38.050  33.099  1.00  23.95      1DIK2124
ATOM   2033  CE1  TYR  270   -15.528  36.511  34.607  1.00  23.23      1DIK2125
ATOM   2034  CE2  TYR  270   -14.288  36.878  32.570  1.00  23.85      1DIK2126
```

FIG. 8-32

```
ATOM  2035  CZ   TYR  270  -15.173  36.113  33.327  1.00  25.13  1DIK2127
ATOM  2036  OH   TYR  270  -15.705  34.964  32.790  1.00  23.62  1DIK2128
ATOM  2037  N    ASP  271  -10.678  39.714  33.847  1.00  23.05  1DIK2129
ATOM  2038  CA   ASP  271   -9.651  39.186  32.975  1.00  21.40  1DIK2130
ATOM  2039  C    ASP  271   -8.449  38.727  33.810  1.00  24.98  1DIK2131
ATOM  2040  O    ASP  271   -7.903  37.632  33.587  1.00  23.79  1DIK2132
ATOM  2041  CB   ASP  271   -9.214  40.259  31.972  1.00  19.82  1DIK2133
ATOM  2042  CG   ASP  271   -8.135  39.762  31.028  1.00  25.01  1DIK2134
ATOM  2043  OD1  ASP  271   -8.467  38.997  30.098  1.00  25.69  1DIK2135
ATOM  2044  OD2  ASP  271   -6.955  40.130  31.215  1.00  22.99  1DIK2136
ATOM  2045  N    TYR  272   -8.042  39.565  34.766  1.00  26.52  1DIK2137
ATOM  2046  CA   TYR  272   -6.912  39.257  35.627  1.00  24.36  1DIK2138
ATOM  2047  C    TYR  272   -7.201  38.031  36.498  1.00  25.48  1DIK2139
ATOM  2048  O    TYR  272   -6.308  37.209  36.738  1.00  27.60  1DIK2140
ATOM  2049  CB   TYR  272   -6.546  40.458  36.501  1.00  25.93  1DIK2141
ATOM  2050  CG   TYR  272   -5.236  40.246  37.210  1.00  24.39  1DIK2142
ATOM  2051  CD1  TYR  272   -4.042  40.250  36.495  1.00  24.69  1DIK2143
ATOM  2052  CD2  TYR  272   -5.186  40.001  38.587  1.00  24.58  1DIK2144
ATOM  2053  CE1  TYR  272   -2.825  40.014  37.120  1.00  24.93  1DIK2145
ATOM  2054  CE2  TYR  272   -3.970  39.762  39.230  1.00  23.27  1DIK2146
ATOM  2055  CZ   TYR  272   -2.794  39.770  38.482  1.00  25.13  1DIK2147
ATOM  2056  OH   TYR  272   -1.577  39.541  39.073  1.00  27.21  1DIK2148
ATOM  2057  N    LEU  273   -8.441  37.900  36.969  1.00  24.96  1DIK2149
ATOM  2058  CA   LEU  273   -8.834  36.743  37.778  1.00  24.02  1DIK2150
ATOM  2059  C    LEU  273   -8.624  35.455  36.964  1.00  25.27  1DIK2151
ATOM  2060  O    LEU  273   -8.159  34.454  37.503  1.00  29.71  1DIK2152
ATOM  2061  CB   LEU  273  -10.302  36.858  38.214  1.00  20.23  1DIK2153
ATOM  2062  CG   LEU  273  -10.976  35.622  38.826  1.00  23.41  1DIK2154
ATOM  2063  CD1  LEU  273  -10.254  35.191  40.104  1.00  20.60  1DIK2155
ATOM  2064  CD2  LEU  273  -12.440  35.922  39.108  1.00  17.70  1DIK2156
ATOM  2065  N    GLN  274   -8.962  35.478  35.672  1.00  23.99  1DIK2157
ATOM  2066  CA   GLN  274   -8.778  34.303  34.811  1.00  21.73  1DIK2158
ATOM  2067  C    GLN  274   -7.290  33.944  34.655  1.00  21.38  1DIK2159
ATOM  2068  O    GLN  274   -6.928  32.763  34.650  1.00  19.72  1DIK2160
ATOM  2069  CB   GLN  274   -9.415  34.530  33.442  1.00  20.31  1DIK2161
ATOM  2070  CG   GLN  274  -10.881  34.906  33.505  1.00  23.01  1DIK2162
ATOM  2071  CD   GLN  274  -11.710  34.017  34.424  1.00  25.47  1DIK2163
ATOM  2072  OE1  GLN  274  -11.536  32.805  34.477  1.00  23.72  1DIK2164
ATOM  2073  NE2  GLN  274  -12.622  34.629  35.154  1.00  32.39  1DIK2165
ATOM  2074  N    SER  275   -6.436  34.961  34.526  1.00  20.92  1DIK2166
ATOM  2075  CA   SER  275   -4.991  34.751  34.433  1.00  20.81  1DIK2167
ATOM  2076  C    SER  275   -4.472  34.099  35.725  1.00  24.14  1DIK2168
ATOM  2077  O    SER  275   -3.612  33.208  35.684  1.00  27.93  1DIK2169
ATOM  2078  CB   SER  275   -4.271  36.078  34.205  1.00  15.74  1DIK2170
ATOM  2079  OG   SER  275   -4.640  36.626  32.950  1.00  24.68  1DIK2171
ATOM  2080  N    LEU  276   -4.991  34.537  36.873  1.00  25.40  1DIK2172
ATOM  2081  CA   LEU  276   -4.571  33.969  38.157  1.00  25.08  1DIK2173
ATOM  2082  C    LEU  276   -4.956  32.500  38.259  1.00  22.91  1DIK2174
ATOM  2083  O    LEU  276   -4.132  31.675  38.619  1.00  24.12  1DIK2175
ATOM  2084  CB   LEU  276   -5.173  34.753  39.333  1.00  25.80  1DIK2176
ATOM  2085  CG   LEU  276   -4.558  36.123  39.596  1.00  23.07  1DIK2177
ATOM  2086  CD1  LEU  276   -5.418  36.893  40.560  1.00  23.03  1DIK2178
ATOM  2087  CD2  LEU  276   -3.158  35.948  40.144  1.00  24.41  1DIK2179
ATOM  2088  N    LYS  277   -6.204  32.174  37.943  1.00  24.32  1DIK2180
ATOM  2089  CA   LYS  277   -6.656  30.790  38.001  1.00  25.45  1DIK2181
ATOM  2090  C    LYS  277   -5.722  29.874  37.204  1.00  24.92  1DIK2182
ATOM  2091  O    LYS  277   -5.302  28.835  37.703  1.00  26.63  1DIK2183
ATOM  2092  CB   LYS  277   -8.049  30.647  37.417  1.00  26.65  1DIK2184
ATOM  2093  CG   LYS  277   -9.226  31.126  38.222  1.00  30.58  1DIK2185
ATOM  2094  CD   LYS  277  -10.424  30.639  37.399  1.00  36.27  1DIK2186
ATOM  2095  CE   LYS  277  -11.754  31.247  37.737  1.00  39.17  1DIK2187
ATOM  2096  NZ   LYS  277  -12.677  30.913  36.604  1.00  37.60  1DIK2188
ATOM  2097  N    LYS  278   -5.408  30.250  35.964  1.00  24.38  1DIK2189
ATOM  2098  CA   LYS  278   -4.523  29.440  35.111  1.00  24.41  1DIK2190
ATOM  2099  C    LYS  278   -3.073  29.414  35.598  1.00  24.27  1DIK2191
ATOM  2100  O    LYS  278   -2.429  28.360  35.590  1.00  24.08  1DIK2192
```

FIG. 8-33

```
ATOM   2101  CB  LYS 278     -4.544  29.948  33.658  1.00 23.48      1DIK2193
ATOM   2102  CG  LYS 278     -5.880  29.828  32.975  1.00 20.48      1DIK2194
ATOM   2103  CD  LYS 278     -6.423  28.428  33.097  1.00 19.64      1DIK2195
ATOM   2104  CE  LYS 278     -7.859  28.389  32.661  1.00 24.74      1DIK2196
ATOM   2105  NZ  LYS 278     -8.431  27.043  32.798  1.00 22.55      1DIK2197
ATOM   2106  N   TYR 279     -2.565  30.573  36.016  1.00 22.37      1DIK2198
ATOM   2107  CA  TYR 279     -1.194  30.686  36.488  1.00 22.48      1DIK2199
ATOM   2108  C   TYR 279     -0.880  29.887  37.749  1.00 24.45      1DIK2200
ATOM   2109  O   TYR 279      0.165  29.237  37.826  1.00 25.51      1DIK2201
ATOM   2110  CB  TYR 279     -0.828  32.141  36.724  1.00 23.08      1DIK2202
ATOM   2111  CG  TYR 279      0.618  32.318  37.123  1.00 25.86      1DIK2203
ATOM   2112  CD1 TYR 279      1.631  32.222  36.179  1.00 21.81      1DIK2204
ATOM   2113  CD2 TYR 279      0.973  32.570  38.452  1.00 24.65      1DIK2205
ATOM   2114  CE1 TYR 279      2.956  32.368  36.540  1.00 26.71      1DIK2206
ATOM   2115  CE2 TYR 279      2.294  32.718  38.824  1.00 21.38      1DIK2207
ATOM   2116  CZ  TYR 279      3.281  32.616  37.863  1.00 25.91      1DIK2208
ATOM   2117  OH  TYR 279      4.596  32.746  38.217  1.00 28.30      1DIK2209
ATOM   2118  N   TYR 280     -1.764  29.938  38.740  1.00 24.59      1DIK2210
ATOM   2119  CA  TYR 280     -1.536  29.208  39.981  1.00 26.07      1DIK2211
ATOM   2120  C   TYR 280     -2.136  27.822  39.951  1.00 26.49      1DIK2212
ATOM   2121  O   TYR 280     -1.889  27.011  40.845  1.00 28.70      1DIK2213
ATOM   2122  CB  TYR 280     -2.045  30.002  41.188  1.00 25.05      1DIK2214
ATOM   2123  CG  TYR 280     -1.148  31.180  41.507  1.00 28.69      1DIK2215
ATOM   2124  CD1 TYR 280      0.047  30.997  42.214  1.00 24.61      1DIK2216
ATOM   2125  CD2 TYR 280     -1.466  32.475  41.065  1.00 27.52      1DIK2217
ATOM   2126  CE1 TYR 280      0.911  32.069  42.466  1.00 25.31      1DIK2218
ATOM   2127  CE2 TYR 280     -0.608  33.556  41.313  1.00 28.66      1DIK2219
ATOM   2128  CZ  TYR 280      0.578  33.342  42.011  1.00 28.71      1DIK2220
ATOM   2129  OH  TYR 280      1.444  34.385  42.212  1.00 29.16      1DIK2221
ATOM   2130  N   GLY 281     -2.922  27.548  38.916  1.00 26.31      1DIK2222
ATOM   2131  CA  GLY 281     -3.530  26.240  38.780  1.00 22.80      1DIK2223
ATOM   2132  C   GLY 281     -2.680  25.285  37.960  1.00 25.18      1DIK2224
ATOM   2133  O   GLY 281     -2.512  24.122  38.342  1.00 29.22      1DIK2225
ATOM   2134  N   HIS 282     -2.141  25.771  36.841  1.00 22.24      1DIK2226
ATOM   2135  CA  HIS 282     -1.342  24.943  35.939  1.00 24.32      1DIK2227
ATOM   2136  C   HIS 282     -0.042  25.561  35.448  1.00 26.33      1DIK2228
ATOM   2137  O   HIS 282      0.770  24.877  34.817  1.00 27.62      1DIK2229
ATOM   2138  CB  HIS 282     -2.190  24.543  34.733  1.00 21.27      1DIK2230
ATOM   2139  CG  HIS 282     -3.524  23.985  35.112  1.00 29.02      1DIK2231
ATOM   2140  ND1 HIS 282     -3.765  22.631  35.222  1.00 29.69      1DIK2232
ATOM   2141  CD2 HIS 282     -4.685  24.602  35.444  1.00 29.92      1DIK2233
ATOM   2142  CE1 HIS 282     -5.015  22.437  35.605  1.00 30.68      1DIK2234
ATOM   2143  NE2 HIS 282     -5.595  23.617  35.747  1.00 30.72      1DIK2235
ATOM   2144  N   GLY 283      0.155  26.846  35.722  1.00 27.84      1DIK2236
ATOM   2145  CA  GLY 283      1.370  27.508  35.292  1.00 26.80      1DIK2237
ATOM   2146  C   GLY 283      2.436  27.399  36.365  1.00 30.11      1DIK2238
ATOM   2147  O   GLY 283      2.324  26.566  37.272  1.00 26.73      1DIK2239
ATOM   2148  N   ALA 284      3.461  28.249  36.259  1.00 31.03      1DIK2240
ATOM   2149  CA  ALA 284      4.579  28.284  37.196  1.00 28.74      1DIK2241
ATOM   2150  C   ALA 284      4.178  28.654  38.621  1.00 32.24      1DIK2242
ATOM   2151  O   ALA 284      4.955  28.464  39.553  1.00 36.63      1DIK2243
ATOM   2152  CB  ALA 284      5.626  29.240  36.702  1.00 26.23      1DIK2244
ATOM   2153  N   GLY 285      2.974  29.182  38.800  1.00 31.80      1DIK2245
ATOM   2154  CA  GLY 285      2.534  29.541  40.133  1.00 30.04      1DIK2246
ATOM   2155  C   GLY 285      2.289  28.305  40.969  1.00 32.15      1DIK2247
ATOM   2156  O   GLY 285      2.274  28.364  42.201  1.00 39.54      1DIK2248
ATOM   2157  N   ASN 286      2.090  27.174  40.307  1.00 29.49      1DIK2249
ATOM   2158  CA  ASN 286      1.844  25.921  41.001  1.00 26.41      1DIK2250
ATOM   2159  C   ASN 286      3.140  25.106  41.045  1.00 28.02      1DIK2251
ATOM   2160  O   ASN 286      3.825  24.958  40.031  1.00 29.27      1DIK2252
ATOM   2161  CB  ASN 286      0.747  25.148  40.278  1.00 22.60      1DIK2253
ATOM   2162  CG  ASN 286      0.176  24.038  41.118  1.00 25.66      1DIK2254
ATOM   2163  OD1 ASN 286      0.822  23.009  41.330  1.00 27.94      1DIK2255
ATOM   2164  ND2 ASN 286     -1.039  24.236  41.611  1.00 22.58      1DIK2256
ATOM   2165  N   PRO 287      3.506  24.576  42.225  1.00 30.51      1DIK2257
ATOM   2166  CA  PRO 287      4.739  23.780  42.340  1.00 31.36      1DIK2258
```

FIG. 8-34

```
ATOM   2167  C    PRO   287       4.852   22.670   41.288  1.00 31.71      1DIK2259
ATOM   2168  O    PRO   287       5.931   22.427   40.750  1.00 34.15      1DIK2260
ATOM   2169  CB   PRO   287       4.658   23.221   43.762  1.00 29.15      1DIK2261
ATOM   2170  CG   PRO   287       3.923   24.320   44.499  1.00 32.66      1DIK2262
ATOM   2171  CD   PRO   287       2.821   24.691   43.527  1.00 29.14      1DIK2263
ATOM   2172  N    LEU   288       3.741   22.000   40.992  1.00 31.66      1DIK2264
ATOM   2173  CA   LEU   288       3.734   20.926   39.999  1.00 30.96      1DIK2265
ATOM   2174  C    LEU   288       3.054   21.320   38.673  1.00 31.70      1DIK2266
ATOM   2175  O    LEU   288       2.710   20.447   37.861  1.00 32.44      1DIK2267
ATOM   2176  CB   LEU   288       3.071   19.673   40.584  1.00 27.59      1DIK2268
ATOM   2177  CG   LEU   288       3.854   19.025   41.731  1.00 27.62      1DIK2269
ATOM   2178  CD1  LEU   288       3.039   17.913   42.364  1.00 28.75      1DIK2270
ATOM   2179  CD2  LEU   288       5.177   18.502   41.206  1.00 25.46      1DIK2271
ATOM   2180  N    GLY   289       2.877   22.626   38.458  1.00 29.27      1DIK2272
ATOM   2181  CA   GLY   289       2.240   23.121   37.245  1.00 28.87      1DIK2273
ATOM   2182  C    GLY   289       3.038   22.806   35.990  1.00 28.45      1DIK2274
ATOM   2183  O    GLY   289       2.591   22.015   35.152  1.00 25.00      1DIK2275
ATOM   2184  N    PRO   290       4.227   23.414   35.827  1.00 26.67      1DIK2276
ATOM   2185  CA   PRO   290       5.075   23.169   34.654  1.00 27.05      1DIK2277
ATOM   2186  C    PRO   290       5.420   21.667   34.473  1.00 27.87      1DIK2278
ATOM   2187  O    PRO   290       5.590   21.194   33.349  1.00 28.39      1DIK2279
ATOM   2188  CB   PRO   290       6.312   24.034   34.945  1.00 25.95      1DIK2280
ATOM   2189  CG   PRO   290       5.756   25.161   35.778  1.00 22.17      1DIK2281
ATOM   2190  CD   PRO   290       4.851   24.402   36.728  1.00 24.69      1DIK2282
ATOM   2191  N    THR   291       5.521   20.925   35.576  1.00 28.55      1DIK2283
ATOM   2192  CA   THR   291       5.807   19.495   35.525  1.00 23.19      1DIK2284
ATOM   2193  C    THR   291       4.778   18.742   34.668  1.00 23.08      1DIK2285
ATOM   2194  O    THR   291       5.106   17.718   34.067  1.00 23.15      1DIK2286
ATOM   2195  CB   THR   291       5.862   18.902   36.958  1.00 21.42      1DIK2287
ATOM   2196  OG1  THR   291       7.129   19.213   37.530  1.00 19.92      1DIK2288
ATOM   2197  CG2  THR   291       5.684   17.395   36.968  1.00 14.25      1DIK2289
ATOM   2197  N    GLN   292       3.543   19.243   34.599  1.00 22.57      1DIK2290
ATOM   2198  CA   GLN   292       2.509   18.584   33.791  1.00 21.65      1DIK2291
ATOM   2199  C    GLN   292       2.805   18.650   32.283  1.00 19.91      1DIK2292
ATOM   2201  O    GLN   292       2.227   17.904   31.494  1.00 23.11      1DIK2293
ATOM   2202  CB   GLN   292       1.119   19.190   34.046  1.00 18.92      1DIK2294
ATOM   2203  CG   GLN   292       0.656   19.202   35.487  1.00 23.26      1DIK2295
ATOM   2204  CD   GLN   292       0.821   17.867   36.187  1.00 24.01      1DIK2296
ATOM   2205  OE1  GLN   292       0.122   16.902   35.892  1.00 25.86      1DIK2297
ATOM   2206  NE2  GLN   292       1.752   17.809   37.127  1.00 26.50      1DIK2298
ATOM   2207  N    GLY   293       3.709   19.528   31.879  1.00 17.82      1DIK2299
ATOM   2208  CA   GLY   293       3.993   19.650   30.472  1.00 17.52      1DIK2300
ATOM   2209  C    GLY   293       5.284   19.050   29.990  1.00 21.21      1DIK2301
ATOM   2210  O    GLY   293       5.581   19.184   28.799  1.00 23.37      1DIK2302
ATOM   2211  N    VAL   294       6.054   18.391   30.859  1.00 19.02      1DIK2303
ATOM   2212  CA   VAL   294       7.329   17.838   30.403  1.00 17.89      1DIK2304
ATOM   2213  C    VAL   294       7.202   16.680   29.426  1.00 18.74      1DIK2305
ATOM   2214  O    VAL   294       8.009   16.588   28.495  1.00 25.27      1DIK2306
ATOM   2215  CB   VAL   294       8.292   17.477   31.558  1.00 18.75      1DIK2307
ATOM   2216  CG1  VAL   294       8.596   18.722   32.382  1.00 19.92      1DIK2308
ATOM   2217  CG2  VAL   294       7.707   16.415   32.425  1.00 24.87      1DIK2309
ATOM   2218  N    GLY   295       6.205   15.815   26.609  1.00 17.01      1DIK2310
ATOM   2219  CA   GLY   295       6.003   14.701   28.692  1.00 16.78      1DIK2311
ATOM   2220  C    GLY   295       5.870   15.193   27.258  1.00 21.51      1DIK2312
ATOM   2221  O    GLY   295       6.561   14.697   26.345  1.00 20.80      1DIK2313
ATOM   2222  N    TYR   296       4.988   16.177   27.055  1.00 16.60      1DIK2314
ATOM   2223  CA   TYR   296       4.780   16.767   25.739  1.00 16.58      1DIK2315
ATOM   2224  C    TYR   296       6.063   17.410   25.193  1.00 20.08      1DIK2316
ATOM   2225  O    TYR   296       6.371   17.314   23.996  1.00 20.96      1DIK2317
ATOM   2226  CB   TYR   296       3.686   17.823   25.803  1.00 17.05      1DIK2318
ATOM   2227  CG   TYR   296       3.273   18.295   24.437  1.00 16.86      1DIK2319
ATOM   2228  CD1  TYR   296       2.388   17.541   23.676  1.00 17.02      1DIK2320
ATOM   2229  CD2  TYR   296       3.774   19.483   23.896  1.00 15.90      1DIK2321
ATOM   2230  CE1  TYR   296       2.006   17.942   22.418  1.00 16.51      1DIK2322
ATOM   2231  CE2  TYR   296       3.399   19.897   22.637  1.00 17.02      1DIK2323
ATOM   2232  CZ   TYR   296       2.510   19.117   21.899  1.00 20.60      1DIK2324
```

FIG. 8-35

```
ATOM  2233  OH   TYR  296    2.101  19.495  20.640  1.00  22.06    1DIK2325
ATOM  2234  N    ALA  297    6.798  18.076  26.081  1.00  20.78    1DIK2326
ATOM  2235  CA   ALA  297    8.054  18.726  25.730  1.00  20.65    1DIK2327
ATOM  2236  C    ALA  297    9.079  17.698  25.239  1.00  18.75    1DIK2328
ATOM  2237  O    ALA  297    9.795  17.942  24.267  1.00  20.26    1DIK2329
ATOM  2238  CB   ALA  297    8.599  19.487  26.934  1.00  20.11    1DIK2330
ATOM  2239  N    ASN  298    9.156  16.549  25.904  1.00  14.67    1DIK2331
ATOM  2240  CA   ASN  298   10.088  15.507  25.479  1.00  15.91    1DIK2332
ATOM  2241  C    ASN  298    9.656  14.898  24.146  1.00  17.04    1DIK2333
ATOM  2242  O    ASN  298   10.498  14.429  23.373  1.00  18.62    1DIK2334
ATOM  2243  CB   ASN  298   10.226  14.433  26.553  1.00  16.51    1DIK2335
ATOM  2244  CG   ASN  298   11.093  14.888  27.702  1.00  19.39    1DIK2336
ATOM  2245  OD1  ASN  298   12.127  15.533  27.494  1.00  18.34    1DIK2337
ATOM  2246  ND2  ASN  298   10.686  14.559  28.919  1.00  10.95    1DIK2338
ATOM  2247  N    GLU  299    8.348  14.900  23.879  1.00  18.29    1DIK2339
ATOM  2248  CA   GLU  299    7.828  14.403  22.608  1.00  20.08    1DIK2340
ATOM  2249  C    GLU  299    8.214  15.404  21.515  1.00  19.66    1DIK2341
ATOM  2250  O    GLU  299    8.519  15.012  20.385  1.00  18.23    1DIK2342
ATOM  2251  CB   GLU  299    6.309  14.226  22.649  1.00  17.35    1DIK2343
ATOM  2252  CG   GLU  299    5.877  13.046  23.478  1.00  20.50    1DIK2344
ATOM  2253  CD   GLU  299    4.383  12.754  23.393  1.00  24.46    1DIK2345
ATOM  2254  OE1  GLU  299    3.576  13.690  23.181  1.00  17.82    1DIK2346
ATOM  2255  OE2  GLU  299    4.013  11.572  23.542  1.00  22.37    1DIK2347
ATOM  2256  N    LEU  300    8.206  16.693  21.859  1.00  19.59    1DIK2348
ATOM  2257  CA   LEU  300    8.596  17.739  20.917  1.00  20.13    1DIK2349
ATOM  2258  C    LEU  300   10.095  17.600  20.593  1.00  20.28    1DIK2350
ATOM  2259  O    LEU  300   10.487  17.665  19.422  1.00  22.61    1DIK2351
ATOM  2260  CB   LEU  300    8.289  19.125  21.488  1.00  21.25    1DIK2352
ATOM  2261  CG   LEU  300    8.649  20.287  20.559  1.00  24.96    1DIK2353
ATOM  2262  CD1  LEU  300    7.930  20.151  19.230  1.00  24.02    1DIK2354
ATOM  2263  CD2  LEU  300    8.269  21.578  21.219  1.00  16.85    1DIK2355
ATOM  2264  N    ILE  301   10.926  17.400  21.624  1.00  18.80    1DIK2356
ATOM  2265  CA   ILE  301   12.373  17.213  21.444  1.00  15.04    1DIK2357
ATOM  2266  C    ILE  301   12.587  16.017  20.484  1.00  20.56    1DIK2358
ATOM  2267  O    ILE  301   13.429  16.056  19.575  1.00  18.58    1DIK2359
ATOM  2268  CB   ILE  301   13.059  16.937  22.812  1.00  16.02    1DIK2360
ATOM  2269  CG1  ILE  301   13.004  18.194  23.686  1.00  17.32    1DIK2361
ATOM  2270  CG2  ILE  301   14.498  16.487  22.626  1.00   6.56    1DIK2362
ATOM  2271  CD1  ILE  301   13.594  18.005  25.064  1.00  14.26    1DIK2363
ATOM  2272  N    ALA  302   11.806  14.958  20.685  1.00  20.02    1DIK2364
ATOM  2273  CA   ALA  302   11.891  13.776  19.840  1.00  20.23    1DIK2365
ATOM  2274  C    ALA  302   11.610  14.139  18.375  1.00  21.81    1DIK2366
ATOM  2275  O    ALA  302   12.326  13.708  17.470  1.00  19.81    1DIK2367
ATOM  2276  CB   ALA  302   10.912  12.718  20.327  1.00  20.45    1DIK2368
ATOM  2277  N    ARG  303   10.577  14.943  18.138  1.00  20.13    1DIK2369
ATOM  2278  CA   ARG  303   10.227  15.329  16.774  1.00  17.34    1DIK2370
ATOM  2279  C    ARG  303   11.245  16.267  16.093  1.00  19.34    1DIK2371
ATOM  2280  O    ARG  303   11.569  16.095  14.907  1.00  15.37    1DIK2372
ATOM  2281  CB   ARG  303    8.816  15.934  16.750  1.00  15.85    1DIK2373
ATOM  2282  CG   ARG  303    7.715  14.914  17.021  1.00  12.30    1DIK2374
ATOM  2283  CD   ARG  303    6.353  15.572  17.215  1.00  11.98    1DIK2375
ATOM  2284  NE   ARG  303    5.287  14.572  17.315  1.00  11.60    1DIK2376
ATOM  2285  CZ   ARG  303    3.989  14.836  17.456  1.00  15.17    1DIK2377
ATOM  2286  NH1  ARG  303    3.538  16.088  17.540  1.00  11.46    1DIK2378
ATOM  2287  NH2  ARG  303    3.132  13.830  17.519  1.00  15.32    1DIK2379
ATOM  2288  N    LEU  304   11.752  17.247  16.838  1.00  16.06    1DIK2380
ATOM  2289  CA   LEU  304   12.722  18.188  16.289  1.00  18.27    1DIK2381
ATOM  2290  C    LEU  304   14.026  17.480  15.922  1.00  20.93    1DIK2382
ATOM  2291  O    LEU  304   14.638  17.772  14.897  1.00  23.62    1DIK2383
ATOM  2292  CB   LEU  304   13.020  19.309  17.292  1.00  12.77    1DIK2384
ATOM  2293  CG   LEU  304   11.882  20.262  17.643  1.00  20.49    1DIK2385
ATOM  2294  CD1  LEU  304   12.289  21.157  18.805  1.00  17.27    1DIK2386
ATOM  2295  CD2  LEU  304   11.509  21.083  16.416  1.00  22.28    1DIK2387
ATOM  2296  N    THR  305   14.450  16.546  16.763  1.00  21.43    1DIK2388
ATOM  2297  CA   THR  305   15.686  15.823  16.518  1.00  22.45    1DIK2389
ATOM  2298  C    THR  305   15.510  14.475  15.803  1.00  23.67    1DIK2390
```

FIG. 8-36

```
ATOM   2299  O   THR   305      16.491  13.788  15.552  1.00 25.10      1DIK2391
ATOM   2300  CB  THR   305      16.429  15.589  17.843  1.00 21.99      1DIK2392
ATOM   2301  OG1 THR   305      15.622  14.782  18.711  1.00 26.81      1DIK2393
ATOM   2302  CG2 THR   305      16.712  16.906  18.530  1.00 16.41      1DIK2394
ATOM   2303  N   HIS   306      14.276  14.100  15.476  1.00 24.74      1DIK2395
ATOM   2304  CA  HIS   306      13.982  12.815  14.815  1.00 28.44      1DIK2396
ATOM   2305  C   HIS   306      14.566  11.628  15.600  1.00 27.46      1DIK2397
ATOM   2306  O   HIS   306      15.122  10.704  15.012  1.00 33.56      1DIK2398
ATOM   2307  CB  HIS   306      14.519  12.796  13.374  1.00 27.83      1DIK2399
ATOM   2308  CG  HIS   306      14.236  14.053  12.613  1.00 33.95      1DIK2400
ATOM   2309  ND1 HIS   306      12.959  14.447  12.268  1.00 35.48      1DIK2401
ATOM   2310  CD2 HIS   306      15.065  15.022  12.155  1.00 32.87      1DIK2402
ATOM   2311  CE1 HIS   306      13.013  15.604  11.633  1.00 35.66      1DIK2403
ATOM   2312  NE2 HIS   306      14.280  15.974  11.552  1.00 35.02      1DIK2404
ATOM   2313  N   SER   307      14.429  11.654  16.919  1.00 22.90      1DIK2405
ATOM   2314  CA  SER   307      14.956  10.606  17.779  1.00 24.39      1DIK2406
ATOM   2315  C   SER   307      13.858  10.081  18.684  1.00 27.25      1DIK2407
ATOM   2316  O   SER   307      12.864  10.768  18.920  1.00 31.56      1DIK2408
ATOM   2317  CB  SER   307      16.050  11.175  18.662  1.00 22.96      1DIK2409
ATOM   2318  OG  SER   307      16.779  12.147  17.948  1.00 39.77      1DIK2410
ATOM   2319  N   PRO   308      14.014   8.845  19.201  1.00 28.75      1DIK2411
ATOM   2320  CA  PRO   308      13.004   8.260  20.094  1.00 26.08      1DIK2412
ATOM   2321  C   PRO   308      12.764   9.127  21.322  1.00 23.85      1DIK2413
ATOM   2322  O   PRO   308      13.614   9.921  21.711  1.00 22.93      1DIK2414
ATOM   2323  CB  PRO   308      13.609   6.899  20.450  1.00 25.36      1DIK2415
ATOM   2324  CG  PRO   308      14.416   6.567  19.204  1.00 24.66      1DIK2416
ATOM   2325  CD  PRO   308      15.109   7.886  18.963  1.00 25.37      1DIK2417
ATOM   2326  N   VAL   309      11.601   8.968  21.932  1.00 25.92      1DIK2418
ATOM   2327  CA  VAL   309      11.250   9.744  23.105  1.00 23.97      1DIK2419
ATOM   2328  C   VAL   309      11.959   9.207  24.348  1.00 28.96      1DIK2420
ATOM   2329  O   VAL   309      12.050   7.990  24.554  1.00 28.02      1DIK2421
ATOM   2330  CB  VAL   309       9.725   9.692  23.367  1.00 19.99      1DIK2422
ATOM   2331  CG1 VAL   309       9.351  10.630  24.506  1.00 14.96      1DIK2423
ATOM   2332  CG2 VAL   309       8.963  10.053  22.112  1.00 21.23      1DIK2424
ATOM   2333  N   HIS   310      12.480  10.118  25.166  1.00 32.25      1DIK2425
ATOM   2334  CA  HIS   310      13.101   9.751  26.433  1.00 30.63      1DIK2426
ATOM   2335  C   HIS   310      12.270  10.503  27.447  1.00 28.25      1DIK2427
ATOM   2336  O   HIS   310      12.459  11.699  27.668  1.00 29.12      1DIK2428
ATOM   2337  CB  HIS   310      14.573  10.160  26.502  1.00 35.26      1DIK2429
ATOM   2338  CG  HIS   310      15.477   9.219  25.772  1.00 46.85      1DIK2430
ATOM   2339  ND1 HIS   310      15.732   9.329  24.418  1.00 53.75      1DIK2431
ATOM   2340  CD2 HIS   310      16.148   8.117  26.191  1.00 52.66      1DIK2432
ATOM   2341  CE1 HIS   310      16.517   8.339  24.032  1.00 54.18      1DIK2433
ATOM   2342  NE2 HIS   310      16.784   7.588  25.089  1.00 57.76      1DIK2434
ATOM   2343  N   ASP   311      11.326   9.795  28.047  1.00 25.80      1DIK2435
ATOM   2344  CA  ASP   311      10.450  10.404  29.019  1.00 24.79      1DIK2436
ATOM   2345  C   ASP   311       9.947   9.348  29.959  1.00 26.98      1DIK2437
ATOM   2346  O   ASP   311       9.707   8.212  29.564  1.00 29.31      1DIK2438
ATOM   2347  CB  ASP   311       9.257  11.064  28.317  1.00 25.99      1DIK2439
ATOM   2348  CG  ASP   311       8.239  11.619  29.292  1.00 24.92      1DIK2440
ATOM   2349  OD1 ASP   311       8.498  12.703  29.844  1.00 24.37      1DIK2441
ATOM   2350  OD2 ASP   311       7.184  10.982  29.512  1.00 21.07      1DIK2442
ATOM   2351  N   ASP   312       9.779   9.740  31.210  1.00 29.33      1DIK2443
ATOM   2352  CA  ASP   312       9.269   8.849  32.217  1.00 29.81      1DIK2444
ATOM   2353  C   ASP   312       8.262   9.626  33.072  1.00 32.06      1DIK2445
ATOM   2354  O   ASP   312       8.201   9.465  34.294  1.00 33.19      1DIK2446
ATOM   2355  CB  ASP   312      10.422   8.309  33.061  1.00 32.29      1DIK2447
ATOM   2356  CG  ASP   312      10.034   7.062  33.861  1.00 40.96      1DIK2448
ATOM   2357  OD1 ASP   312       8.902   6.523  33.695  1.00 37.90      1DIK2449
ATOM   2358  OD2 ASP   312      10.882   6.616  34.668  1.00 46.83      1DIK2450
ATOM   2359  N   THR   313       7.470  10.475  32.424  1.00 28.45      1DIK2451
ATOM   2360  CA  THR   313       6.472  11.250  33.143  1.00 26.99      1DIK2452
ATOM   2361  C   THR   313       5.040  10.924  32.685  1.00 27.21      1DIK2453
ATOM   2362  O   THR   313       4.455   9.940  33.145  1.00 25.95      1DIK2454
ATOM   2363  CB  THR   313       6.762  12.771  33.043  1.00 27.49      1DIK2455
ATOM   2364  OG1 THR   313       6.694  13.193  31.671  1.00 21.29      1DIK2456
```

FIG. 8-37

```
ATOM   2365  CG2 THR 313      8.164  13.075  33.597  1.00 23.59      1DIK2457
ATOM   2366  N   SER 314      4.476  11.726  31.785  1.00 24.25      1DIK2458
ATOM   2367  CA  SER 314      3.105  11.510  31.326  1.00 20.48      1DIK2459
ATOM   2368  C   SER 314      2.936  10.702  30.042  1.00 20.74      1DIK2460
ATOM   2369  O   SER 314      1.821  10.289  29.712  1.00 20.71      1DIK2461
ATOM   2370  CB  SER 314      2.409  12.867  31.160  1.00 20.21      1DIK2462
ATOM   2371  OG  SER 314      3.137  13.722  30.286  1.00 23.16      1DIK2463
ATOM   2372  N   SER 315      4.028  10.468  29.317  1.00 21.85      1DIK2464
ATOM   2373  CA  SER 315      3.923   9.757  28.055  1.00 20.97      1DIK2465
ATOM   2374  C   SER 315      3.568   8.288  28.141  1.00 23.67      1DIK2466
ATOM   2375  O   SER 315      3.890   7.593  29.111  1.00 26.91      1DIK2467
ATOM   2376  CB  SER 315      5.187   9.953  27.200  1.00 18.40      1DIK2468
ATOM   2377  OG  SER 315      6.313   9.245  27.685  1.00 18.66      1DIK2469
ATOM   2378  N   ASN 316      2.885   7.830  27.102  1.00 23.83      1DIK2470
ATOM   2379  CA  ASN 316      2.489   6.440  26.964  1.00 24.79      1DIK2471
ATOM   2380  C   ASN 316      3.689   5.793  26.225  1.00 23.66      1DIK2472
ATOM   2381  O   ASN 316      3.929   6.088  25.047  1.00 24.08      1DIK2473
ATOM   2382  CB  ASN 316      1.205   6.394  26.130  1.00 24.17      1DIK2474
ATOM   2383  CG  ASN 316      0.621   5.012  26.011  1.00 20.87      1DIK2475
ATOM   2384  OD1 ASN 316      1.331   4.026  25.849  1.00 26.91      1DIK2476
ATOM   2385  ND2 ASN 316     -0.690   4.936  26.081  1.00 24.90      1DIK2477
ATOM   2386  N   HIS 317      4.439   4.930  26.918  1.00 19.55      1DIK2478
ATOM   2387  CA  HIS 317      5.627   4.274  26.341  1.00 17.40      1DIK2479
ATOM   2388  C   HIS 317      5.289   3.406  25.149  1.00 18.22      1DIK2480
ATOM   2389  O   HIS 317      6.015   3.392  24.152  1.00 21.43      1DIK2481
ATOM   2390  CB  HIS 317      6.341   3.401  27.380  1.00 19.52      1DIK2482
ATOM   2391  CG  HIS 317      6.708   4.125  28.640  1.00 25.20      1DIK2483
ATOM   2392  ND1 HIS 317      7.379   5.332  28.643  1.00 28.94      1DIK2484
ATOM   2393  CD2 HIS 317      6.503   3.808  29.940  1.00 26.03      1DIK2485
ATOM   2394  CE1 HIS 317      7.571   5.728  29.888  1.00 27.28      1DIK2486
ATOM   2395  NE2 HIS 317      7.049   4.821  30.694  1.00 31.03      1DIK2487
ATOM   2396  N   THR 318      4.187   2.670  25.255  1.00 18.44      1DIK2488
ATOM   2397  CA  THR 318      3.740   1.800  24.180  1.00 18.99      1DIK2489
ATOM   2398  C   THR 318      3.329   2.644  22.978  1.00 21.41      1DIK2490
ATOM   2399  O   THR 318      3.764   2.399  21.851  1.00 20.04      1DIK2491
ATOM   2400  CB  THR 318      2.544   0.955  24.632  1.00 18.88      1DIK2492
ATOM   2401  OG1 THR 318      2.889   0.310  25.857  1.00 18.06      1DIK2493
ATOM   2402  CG2 THR 318      2.188  -0.116  23.594  1.00 14.25      1DIK2494
ATOM   2403  N   LEU 319      2.500   3.650  23.221  1.00 20.99      1DIK2495
ATOM   2404  CA  LEU 319      2.030   4.509  22.151  1.00 21.53      1DIK2496
ATOM   2405  C   LEU 319      3.171   5.205  21.383  1.00 25.80      1DIK2497
ATOM   2406  O   LEU 319      3.091   5.371  20.165  1.00 25.17      1DIK2498
ATOM   2407  CB  LEU 319      1.085   5.541  22.733  1.00 20.62      1DIK2499
ATOM   2408  CG  LEU 319      0.100   6.148  21.761  1.00 22.28      1DIK2500
ATOM   2409  CD1 LEU 319     -0.686   5.029  21.099  1.00 23.07      1DIK2501
ATOM   2410  CD2 LEU 319     -0.819   7.079  22.522  1.00 20.45      1DIK2502
ATOM   2411  N   ASP 320      4.234   5.603  22.085  1.00 24.35      1DIK2503
ATOM   2412  CA  ASP 320      5.360   6.297  21.445  1.00 22.47      1DIK2504
ATOM   2413  C   ASP 320      6.493   5.459  20.884  1.00 21.00      1DIK2505
ATOM   2414  O   ASP 320      7.437   6.005  20.317  1.00 17.90      1DIK2506
ATOM   2415  CB  ASP 320      5.956   7.325  22.403  1.00 19.58      1DIK2507
ATOM   2416  CG  ASP 320      5.061   8.531  22.582  1.00 22.62      1DIK2508
ATOM   2417  OD1 ASP 320      3.909   8.509  22.092  1.00 22.05      1DIK2509
ATOM   2418  OD2 ASP 320      5.509   9.505  23.214  1.00 18.12      1DIK2510
ATOM   2419  N   SER 321      6.407   4.143  21.024  1.00 22.21      1DIK2511
ATOM   2420  CA  SER 321      7.477   3.271  20.556  1.00 25.24      1DIK2512
ATOM   2421  C   SER 321      7.416   2.869  19.082  1.00 25.75      1DIK2513
ATOM   2422  O   SER 321      8.382   2.315  18.539  1.00 25.63      1DIK2514
ATOM   2423  CB  SER 321      7.496   2.023  21.417  1.00 23.95      1DIK2515
ATOM   2424  OG  SER 321      6.265   1.358  21.278  1.00 33.89      1DIK2516
ATOM   2425  N   SER 322      6.288   3.155  18.441  1.00 27.36      1DIK2517
ATOM   2426  CA  SER 322      6.084   2.776  17.053  1.00 27.84      1DIK2518
ATOM   2427  C   SER 322      5.695   3.928  16.118  1.00 27.85      1DIK2519
ATOM   2428  O   SER 322      4.948   4.838  16.502  1.00 26.35      1DIK2520
ATOM   2429  CB  SER 322      5.016   1.677  17.007  1.00 27.18      1DIK2521
ATOM   2430  OG  SER 322      4.568   1.439  15.688  1.00 34.11      1DIK2522
```

FIG. 8-38

```
ATOM   2431  N   PRO  323    6.206   3.895  14.872  1.00 27.40    1DIK2523
ATOM   2432  CA  PRO  323    5.967   4.880  13.807  1.00 27.34    1DIK2524
ATOM   2433  C   PRO  323    4.471   5.053  13.496  1.00 26.66    1DIK2525
ATOM   2434  O   PRO  323    4.037   6.111  13.049  1.00 29.69    1DIK2526
ATOM   2435  CB  PRO  323    6.713   4.276  12.611  1.00 27.47    1DIK2527
ATOM   2436  CG  PRO  323    7.827   3.522  13.251  1.00 26.17    1DIK2528
ATOM   2437  CD  PRO  323    7.121   2.840  14.398  1.00 25.07    1DIK2529
ATOM   2438  N   ALA  324    3.685   4.014  13.732  1.00 23.94    1DIK2530
ATOM   2439  CA  ALA  324    2.258   4.086  13.465  1.00 24.16    1DIK2531
ATOM   2440  C   ALA  324    1.558   5.072  14.381  1.00 21.32    1DIK2532
ATOM   2441  O   ALA  324    0.598   5.712  13.984  1.00 24.85    1DIK2533
ATOM   2442  CB  ALA  324    1.615   2.709  13.615  1.00 23.92    1DIK2534
ATOM   2443  N   THR  325    2.024   5.194  15.612  1.00 19.68    1DIK2535
ATOM   2444  CA  THR  325    1.379   6.097  16.537  1.00 18.15    1DIK2536
ATOM   2445  C   THR  325    2.260   7.256  16.940  1.00 20.32    1DIK2537
ATOM   2446  O   THR  325    1.791   8.183  17.602  1.00 20.91    1DIK2538
ATOM   2447  CB  THR  325    0.898   5.350  17.764  1.00 18.83    1DIK2539
ATOM   2448  OG1 THR  325    1.907   4.428  18.161  1.00 23.06    1DIK2540
ATOM   2449  CG2 THR  325   -0.375   4.579  17.451  1.00 18.83    1DIK2541
ATOM   2450  N   PHE  326    3.532   7.202  16.548  1.00 19.80    1DIK2542
ATOM   2451  CA  PHE  326    4.467   8.282  16.824  1.00 18.01    1DIK2543
ATOM   2452  C   PHE  326    5.605   8.328  15.787  1.00 18.87    1DIK2544
ATOM   2453  O   PHE  326    6.725   7.875  16.046  1.00 20.23    1DIK2545
ATOM   2454  CB  PHE  326    5.024   8.183  18.256  1.00 22.80    1DIK2546
ATOM   2455  CG  PHE  326    5.620   9.478  18.761  1.00 20.42    1DIK2547
ATOM   2456  CD1 PHE  326    4.810  10.445  19.362  1.00 19.30    1DIK2548
ATOM   2457  CD2 PHE  326    6.979   9.755  18.595  1.00 15.81    1DIK2549
ATOM   2458  CE1 PHE  326    5.340  11.680  19.790  1.00 12.22    1DIK2550
ATOM   2459  CE2 PHE  326    7.515  10.984  19.018  1.00 18.58    1DIK2551
ATOM   2460  CZ  PHE  326    6.686  11.948  19.617  1.00 14.93    1DIK2552
ATOM   2461  N   PRO  327    5.323   8.876  14.588  1.00 18.42    1DIK2553
ATOM   2462  CA  PRO  327    6.270   9.017  13.473  1.00 19.53    1DIK2554
ATOM   2463  C   PRO  327    7.260  10.121  13.791  1.00 21.71    1DIK2555
ATOM   2464  O   PRO  327    6.875  11.203  14.245  1.00 21.90    1DIK2556
ATOM   2465  CB  PRO  327    5.388   9.449  12.300  1.00 16.34    1DIK2557
ATOM   2466  CG  PRO  327    3.995   9.168  12.745  1.00 17.33    1DIK2558
ATOM   2467  CD  PRO  327    4.013   9.422  14.211  1.00 16.80    1DIK2559
ATOM   2468  N   LEU  328    8.532   9.855  13.539  1.00 24.26    1DIK2560
ATOM   2469  CA  LEU  328    9.569  10.836  13.812  1.00 23.81    1DIK2561
ATOM   2470  C   LEU  328    9.967  11.618  12.566  1.00 24.00    1DIK2562
ATOM   2471  O   LEU  328   10.721  12.580  12.654  1.00 26.13    1DIK2563
ATOM   2472  CB  LEU  328   10.801  10.135  14.384  1.00 22.63    1DIK2564
ATOM   2473  CG  LEU  328   10.576   9.272  15.625  1.00 25.54    1DIK2565
ATOM   2474  CD1 LEU  328   11.869   8.560  15.990  1.00 24.58    1DIK2566
ATOM   2475  CD2 LEU  328   10.092  10.137  16.782  1.00 22.69    1DIK2567
ATOM   2476  N   ASN  329    9.473  11.220  11.403  1.00 26.61    1DIK2568
ATOM   2477  CA  ASN  329    9.865  11.919  10.198  1.00 29.63    1DIK2569
ATOM   2478  C   ASN  329    8.759  12.578   9.413  1.00 27.72    1DIK2570
ATOM   2479  O   ASN  329    8.941  12.876   8.243  1.00 32.13    1DIK2571
ATOM   2480  CB  ASN  329   10.686  11.001   9.288  1.00 36.18    1DIK2572
ATOM   2481  CG  ASN  329   12.075  10.733   9.843  1.00 48.05    1DIK2573
ATOM   2482  OD1 ASN  329   12.927  11.632   9.873  1.00 52.99    1DIK2574
ATOM   2483  ND2 ASN  329   12.315   9.494  10.290  1.00 53.32    1DIK2575
ATOM   2484  N   SER  330    7.601  12.797  10.020  1.00 28.90    1DIK2576
ATOM   2485  CA  SER  330    6.550  13.530   9.313  1.00 30.10    1DIK2577
ATOM   2486  C   SER  330    7.141  14.938   9.429  1.00 33.67    1DIK2578
ATOM   2487  O   SER  330    8.041  15.193  10.257  1.00 39.71    1DIK2579
ATOM   2488  CB  SER  330    5.212  13.489  10.054  1.00 27.33    1DIK2580
ATOM   2489  OG  SER  330    4.824  12.169  10.372  1.00 30.99    1DIK2581
ATOM   2490  N   THR  331    6.670  15.869   8.633  1.00 29.23    1DIK2582
ATOM   2491  CA  THR  331    7.260  17.198   8.729  1.00 29.49    1DIK2583
ATOM   2492  C   THR  331    6.303  18.150   9.420  1.00 25.32    1DIK2584
ATOM   2493  O   THR  331    6.714  19.147  10.005  1.00 22.51    1DIK2585
ATOM   2494  CB  THR  331    7.590  17.690   7.321  1.00 31.50    1DIK2586
ATOM   2495  OG1 THR  331    8.453  16.737   6.705  1.00 27.95    1DIK2587
ATOM   2496  CG2 THR  331    8.242  19.035   7.343  1.00 36.14    1DIK2588
```

FIG. 8-39

```
ATOM   2497  N    LEU   332      5.021   17.804    9.334  1.00 24.55     1DIK2589
ATOM   2498  CA   LEU   332      3.930   18.578    9.885  1.00 23.43     1DIK2590
ATOM   2499  C    LEU   332      3.168   17.760   10.916  1.00 21.17     1DIK2591
ATOM   2500  O    LEU   332      2.814   16.606   10.655  1.00 20.55     1DIK2592
ATOM   2501  CB   LEU   332      2.965   18.972    8.756  1.00 23.10     1DIK2593
ATOM   2502  CG   LEU   332      3.542   19.823    7.625  1.00 25.75     1DIK2594
ATOM   2503  CD1  LEU   332      2.598   19.836    6.431  1.00 21.25     1DIK2595
ATOM   2504  CD2  LEU   332      3.802   21.223    8.145  1.00 19.61     1DIK2596
ATOM   2505  N    TYR   333      2.916   18.361   12.076  1.00 19.69     1DIK2597
ATOM   2506  CA   TYR   333      2.154   17.720   13.152  1.00 17.57     1DIK2598
ATOM   2507  C    TYR   333      1.101   18.691   13.706  1.00 14.59     1DIK2599
ATOM   2508  O    TYR   333      1.304   19.910   13.718  1.00 17.04     1DIK2600
ATOM   2509  CB   TYR   333      3.076   17.317   14.301  1.00 16.40     1DIK2601
ATOM   2510  CG   TYR   333      4.150   16.329   13.944  1.00 15.46     1DIK2602
ATOM   2511  CD1  TYR   333      3.927   14.962   14.058  1.00 16.50     1DIK2603
ATOM   2512  CD2  TYR   333      5.399   16.758   13.519  1.00 15.19     1DIK2604
ATOM   2513  CE1  TYR   333      4.929   14.039   13.758  1.00 19.21     1DIK2605
ATOM   2514  CE2  TYR   333      6.412   15.845   13.214  1.00 19.07     1DIK2606
ATOM   2515  CZ   TYR   333      6.170   14.487   13.338  1.00 20.05     1DIK2607
ATOM   2516  OH   TYR   333      7.165   13.580   13.056  1.00 20.29     1DIK2608
ATOM   2517  N    ALA   334     -0.022   18.154   14.161  1.00 11.62     1DIK2609
ATOM   2518  CA   ALA   334     -1.072   18.971   14.764  1.00 14.11     1DIK2610
ATOM   2519  C    ALA   334     -1.642   18.190   15.952  1.00 17.81     1DIK2611
ATOM   2520  O    ALA   334     -2.001   17.014   15.808  1.00 20.52     1DIK2612
ATOM   2521  CB   ALA   334     -2.169   19.291   13.763  1.00  6.64     1DIK2613
ATOM   2522  N    ASP   335     -1.706   18.842   17.117  1.00 15.89     1DIK2614
ATOM   2523  CA   ASP   335     -2.234   18.234   18.334  1.00 15.85     1DIK2615
ATOM   2524  C    ASP   335     -3.350   19.116   18.877  1.00 19.02     1DIK2616
ATOM   2525  O    ASP   335     -3.261   20.350   18.823  1.00 17.86     1DIK2617
ATOM   2526  CB   ASP   335     -1.126   18.059   19.392  1.00 16.00     1DIK2618
ATOM   2527  CG   ASP   335     -0.099   16.997   19.001  1.00 20.47     1DIK2619
ATOM   2528  OD1  ASP   335     -0.502   15.948   18.466  1.00 22.42     1DIK2620
ATOM   2529  OD2  ASP   335      1.112   17.201   19.224  1.00 20.56     1DIK2621
ATOM   2530  N    PHE   336     -4.402   18.481   19.395  1.00 18.17     1DIK2622
ATOM   2531  CA   PHE   336     -5.543   19.200   19.937  1.00 17.35     1DIK2623
ATOM   2532  C    PHE   336     -5.774   18.839   21.402  1.00 19.88     1DIK2624
ATOM   2533  O    PHE   336     -5.815   17.655   21.776  1.00 19.43     1DIK2625
ATOM   2534  CB   PHE   336     -6.778   18.940   19.066  1.00 17.54     1DIK2626
ATOM   2535  CG   PHE   336     -6.594   19.394   17.655  1.00 14.71     1DIK2627
ATOM   2536  CD1  PHE   336     -5.954   18.577   16.728  1.00 14.86     1DIK2628
ATOM   2537  CD2  PHE   336     -6.978   20.676   17.271  1.00 14.13     1DIK2629
ATOM   2538  CE1  PHE   336     -5.688   19.036   15.434  1.00 19.47     1DIK2630
ATOM   2539  CE2  PHE   336     -6.721   21.148   15.987  1.00 13.80     1DIK2631
ATOM   2540  CZ   PHE   336     -6.072   20.328   15.065  1.00 15.97     1DIK2632
ATOM   2541  N    SER   337     -5.933   19.881   22.219  1.00 16.75     1DIK2633
ATOM   2542  CA   SER   337     -6.096   19.713   23.642  1.00 15.92     1DIK2634
ATOM   2543  C    SER   337     -6.962   20.793   24.331  1.00 17.12     1DIK2635
ATOM   2544  O    SER   337     -7.708   21.549   23.684  1.00 15.10     1DIK2636
ATOM   2545  CB   SER   337     -4.696   19.692   24.251  1.00 13.71     1DIK2637
ATOM   2546  OG   SER   337     -4.698   18.968   25.455  1.00 18.65     1DIK2638
ATOM   2547  N    HIS   338     -6.843   20.836   25.658  1.00 16.73     1DIK2639
ATOM   2548  CA   HIS   338     -7.546   21.772   26.536  1.00 18.64     1DIK2640
ATOM   2549  C    HIS   338     -6.616   22.900   26.998  1.00 20.65     1DIK2641
ATOM   2550  O    HIS   338     -5.392   22.785   26.917  1.00 23.22     1DIK2642
ATOM   2551  CB   HIS   338     -8.055   21.039   27.785  1.00 17.35     1DIK2643
ATOM   2552  CG   HIS   338     -8.942   19.871   27.483  1.00 21.37     1DIK2644
ATOM   2553  ND1  HIS   338    -10.309   19.990   27.345  1.00 21.44     1DIK2645
ATOM   2554  CD2  HIS   338     -8.654   18.566   27.265  1.00 16.55     1DIK2646
ATOM   2555  CE1  HIS   338    -10.824   18.809   27.053  1.00 21.79     1DIK2647
ATOM   2556  NE2  HIS   338     -9.841   17.931   26.998  1.00 19.02     1DIK2648
ATOM   2557  N    ASP   339     -7.204   23.981   27.504  1.00 21.52     1DIK2649
ATOM   2558  CA   ASP   339     -6.436   25.120   27.983  1.00 19.43     1DIK2650
ATOM   2559  C    ASP   339     -5.452   24.739   29.079  1.00 18.53     1DIK2651
ATOM   2560  O    ASP   339     -4.301   25.170   29.052  1.00 22.28     1DIK2652
ATOM   2561  CB   ASP   339     -7.364   26.275   28.452  1.00 23.01     1DIK2653
ATOM   2562  CG   ASP   339     -8.397   25.856   29.528  1.00 25.24     1DIK2654
```

FIG. 8-40

```
ATOM   2563  OD1 ASP   339     -8.560  24.654  29.838  1.00 27.53      1DIK2655
ATOM   2564  OD2 ASP   339     -9.066  26.759  30.075  1.00 27.85      1DIK2656
ATOM   2565  N   ASN   340     -5.892  23.922  30.032  1.00 16.85      1DIK2657
ATOM   2566  CA  ASN   340     -5.035  23.514  31.141  1.00 17.73      1DIK2658
ATOM   2567  C   ASN   340     -3.750  22.830  30.712  1.00 19.02      1DIK2659
ATOM   2568  O   ASN   340     -2.666  23.210  31.161  1.00 21.77      1DIK2660
ATOM   2569  CB  ASN   340     -5.810  22.643  32.111  1.00 19.49      1DIK2661
ATOM   2570  CG  ASN   340     -6.815  23.443  32.908  1.00 22.56      1DIK2662
ATOM   2571  OD1 ASN   340     -6.752  24.662  32.945  1.00 25.89      1DIK2663
ATOM   2572  ND2 ASN   340     -7.743  22.762  33.552  1.00 28.53      1DIK2664
ATOM   2573  N   GLY   341     -3.858  21.831  29.845  1.00 17.89      1DIK2665
ATOM   2574  CA  GLY   341     -2.665  21.160  29.364  1.00 15.63      1DIK2666
ATOM   2575  C   GLY   341     -1.764  22.118  28.600  1.00 11.99      1DIK2667
ATOM   2576  O   GLY   341     -0.549  22.077  28.735  1.00 16.11      1DIK2668
ATOM   2577  N   ILE   342     -2.344  22.996  27.797  1.00 13.11      1DIK2669
ATOM   2578  CA  ILE   342     -1.525  23.941  27.036  1.00 17.14      1DIK2670
ATOM   2579  C   ILE   342     -0.755  24.910  27.946  1.00 17.23      1DIK2671
ATOM   2580  O   ILE   342      0.410  25.214  27.694  1.00 17.60      1DIK2672
ATOM   2581  CB  ILE   342     -2.399  24.690  25.990  1.00 16.48      1DIK2673
ATOM   2582  CG1 ILE   342     -2.982  23.663  25.015  1.00 11.17      1DIK2674
ATOM   2583  CG2 ILE   342     -1.574  25.710  25.221  1.00 12.60      1DIK2675
ATOM   2584  CD1 ILE   342     -4.052  24.199  24.138  1.00 14.25      1DIK2676
ATOM   2585  N   ILE   343     -1.397  25.384  29.010  1.00 20.72      1DIK2677
ATOM   2586  CA  ILE   343     -0.747  26.296  29.948  1.00 20.28      1DIK2678
ATOM   2587  C   ILE   343      0.531  25.647  30.503  1.00 21.94      1DIK2679
ATOM   2588  O   ILE   343      1.617  26.243  30.467  1.00 23.12      1DIK2680
ATOM   2589  CB  ILE   343     -1.703  26.677  31.124  1.00 17.08      1DIK2681
ATOM   2590  CG1 ILE   343     -2.757  27.671  30.638  1.00 12.06      1DIK2682
ATOM   2591  CG2 ILE   343     -0.911  27.321  32.277  1.00 12.92      1DIK2683
ATOM   2592  CD1 ILE   343     -2.152  29.042  30.271  1.00 11.66      1DIK2684
ATOM   2593  N   SER   344      0.394  24.424  31.006  1.00 20.30      1DIK2685
ATOM   2594  CA  SER   344      1.519  23.690  31.564  1.00 17.86      1DIK2686
ATOM   2595  C   SER   344      2.636  23.482  30.544  1.00 20.31      1DIK2687
ATOM   2596  O   SER   344      3.825  23.604  30.881  1.00 19.02      1DIK2688
ATOM   2597  CB  SER   344      1.036  22.344  32.081  1.00 18.82      1DIK2689
ATOM   2598  OG  SER   344      0.137  22.512  33.164  1.00 19.78      1DIK2690
ATOM   2599  N   ILE   345      2.248  23.170  29.302  1.00 19.86      1DIK2691
ATOM   2600  CA  ILE   345      3.194  22.940  28.205  1.00 19.61      1DIK2692
ATOM   2601  C   ILE   345      3.990  24.211  27.877  1.00 22.16      1DIK2693
ATOM   2602  O   ILE   345      5.211  24.156  27.678  1.00 21.36      1DIK2694
ATOM   2603  CB  ILE   345      2.460  22.420  26.936  1.00 17.67      1DIK2695
ATOM   2604  CG1 ILE   345      1.926  21.009  27.194  1.00 17.47      1DIK2696
ATOM   2605  CG2 ILE   345      3.389  22.402  25.738  1.00 10.81      1DIK2697
ATOM   2606  CD1 ILE   345      1.129  20.443  26.052  1.00 20.20      1DIK2698
ATOM   2607  N   LEU   346      3.290  25.347  27.828  1.00 21.51      1DIK2699
ATOM   2608  CA  LEU   346      3.906  26.645  27.558  1.00 21.18      1DIK2700
ATOM   2609  C   LEU   346      4.987  26.936  28.610  1.00 19.82      1DIK2701
ATOM   2610  O   LEU   346      6.078  27.401  28.281  1.00 22.60      1DIK2702
ATOM   2611  CB  LEU   346      2.838  27.754  27.559  1.00 21.21      1DIK2703
ATOM   2612  CG  LEU   346      1.787  27.761  26.430  1.00 25.27      1DIK2704
ATOM   2613  CD1 LEU   346      0.797  28.905  26.655  1.00 22.27      1DIK2705
ATOM   2614  CD2 LEU   346      2.457  27.910  25.067  1.00 19.78      1DIK2706
ATOM   2615  N   PHE   347      4.694  26.658  29.875  1.00 21.86      1DIK2707
ATOM   2616  CA  PHE   347      5.679  26.878  30.929  1.00 21.46      1DIK2708
ATOM   2617  C   PHE   347      6.825  25.881  30.884  1.00 24.47      1DIK2709
ATOM   2618  O   PHE   347      7.981  26.282  31.064  1.00 23.78      1DIK2710
ATOM   2619  CB  PHE   347      5.006  26.903  32.300  1.00 22.55      1DIK2711
ATOM   2620  CG  PHE   347      4.289  28.189  32.566  1.00 19.15      1DIK2712
ATOM   2621  CD1 PHE   347      4.977  29.283  33.088  1.00 19.76      1DIK2713
ATOM   2622  CD2 PHE   347      2.953  28.332  32.233  1.00 17.59      1DIK2714
ATOM   2623  CE1 PHE   347      4.341  30.508  33.268  1.00 18.90      1DIK2715
ATOM   2624  CE2 PHE   347      2.311  29.542  32.407  1.00 21.97      1DIK2716
ATOM   2625  CZ  PHE   347      3.007  30.638  32.926  1.00 20.72      1DIK2717
ATOM   2626  N   ALA   348      6.517  24.599  30.634  1.00 25.00      1DIK2718
ATOM   2627  CA  ALA   348      7.547  23.551  30.533  1.00 23.63      1DIK2719
ATOM   2628  C   ALA   348      8.523  23.830  29.374  1.00 23.94      1DIK2720
```

FIG. 8-41

```
ATOM   2629  O    ALA  348      9.647  23.327  29.368  1.00 22.81      1DIK2721
ATOM   2630  CB   ALA  348      6.909  22.175  30.360  1.00 18.75      1DIK2722
ATOM   2631  N    LEU  349      8.096  24.624  28.394  1.00 23.18      1DIK2723
ATOM   2632  CA   LEU  349      8.969  24.977  27.279  1.00 24.76      1DIK2724
ATOM   2633  C    LEU  349      9.725  26.227  27.606  1.00 25.45      1DIK2725
ATOM   2634  O    LEU  349     10.538  26.708  26.760  1.00 26.63      1DIK2726
ATOM   2635  CB   LEU  349      8.11   25.197  25.990  1.00 24.37      1DIK2727
ATOM   2636  CG   LEU  349      7.530  23.958  25.332  1.00 27.98      1DIK2728
ATOM   2637  CD1  LEU  349      6.813  24.399  24.054  1.00 24.59      1DIK2729
ATOM   2638  CD2  LEU  349      8.578  22.871  25.023  1.00 19.81      1DIK2730
ATOM   2639  N    GLY  350      9.625  26.745  28.827  1.00 25.68      1DIK2731
ATOM   2640  CA   GLY  350     10.370  27.916  29.269  1.00 27.97      1DIK2732
ATOM   2641  C    GLY  350     10.009  29.236  28.611  1.00 30.96      1DIK2733
ATOM   2642  O    GLY  350     10.781  30.197  28.671  1.00 31.89      1DIK2734
ATOM   2643  N    LEU  351      8.830  29.292  27.997  1.00 31.09      1DIK2735
ATOM   2644  CA   LEU  351      8.367  30.486  27.301  1.00 29.39      1DIK2736
ATOM   2645  C    LEU  351      8.048  31.700  28.184  1.00 30.29      1DIK2737
ATOM   2646  O    LEU  351      8.092  32.841  27.722  1.00 28.55      1DIK2738
ATOM   2647  CB   LEU  351      7.147  30.132  26.456  1.00 31.14      1DIK2739
ATOM   2648  CG   LEU  351      7.359  28.989  25.467  1.00 29.30      1DIK2740
ATOM   2649  CD1  LEU  351      6.063  28.718  24.722  1.00 28.64      1DIK2741
ATOM   2650  CD2  LEU  351      8.483  29.347  24.501  1.00 25.72      1DIK2742
ATOM   2651  N    TYR  352      7.731  31.474  29.453  1.00 31.04      1DIK2743
ATOM   2652  CA   TYR  352      7.410  32.594  30.325  1.00 31.74      1DIK2744
ATOM   2653  C    TYR  352      8.350  32.747  31.502  1.00 34.72      1DIK2745
ATOM   2654  O    TYR  352      7.942  33.102  32.613  1.00 33.44      1DIK2746
ATOM   2655  CB   TYR  352      5.953  32.484  30.752  1.00 26.97      1DIK2747
ATOM   2656  CG   TYR  352      5.090  32.667  29.552  1.00 28.46      1DIK2748
ATOM   2657  CD1  TYR  352      4.916  33.932  29.003  1.00 27.92      1DIK2749
ATOM   2658  CD2  TYR  352      4.506  31.574  28.910  1.00 29.60      1DIK2750
ATOM   2659  CE1  TYR  352      4.190  34.118  27.846  1.00 30.02      1DIK2751
ATOM   2660  CE2  TYR  352      3.773  31.745  27.745  1.00 30.26      1DIK2752
ATOM   2661  CZ   TYR  352      3.622  33.029  27.220  1.00 32.93      1DIK2753
ATOM   2662  OH   TYR  352      2.903  33.228  26.067  1.00 33.54      1DIK2754
ATOM   2663  N    ASN  353      9.626  32.484  31.236  1.00 40.74      1DIK2755
ATOM   2664  CA   ASN  353     10.669  32.582  32.251  1.00 47.39      1DIK2756
ATOM   2665  C    ASN  353     10.941  34.011  32.729  1.00 47.72      1DIK2757
ATOM   2666  O    ASN  353     11.505  34.206  33.802  1.00 46.72      1DIK2758
ATOM   2667  CB   ASN  353     11.966  31.932  31.749  1.00 49.39      1DIK2759
ATOM   2668  CG   ASN  353     11.931  30.406  31.832  1.00 53.90      1DIK2760
ATOM   2669  OD1  ASN  353     10.895  29.801  32.155  1.00 51.32      1DIK2761
ATOM   2670  ND2  ASN  353     13.071  29.774  31.537  1.00 57.79      1DIK2762
ATOM   2671  N    GLY  354     10.535  35.002  31.937  1.00 48.40      1DIK2763
ATOM   2672  CA   GLY  354     10.741  36.390  32.319  1.00 49.75      1DIK2764
ATOM   2673  C    GLY  354      9.531  36.974  33.032  1.00 49.81      1DIK2765
ATOM   2674  O    GLY  354      9.424  38.193  33.203  1.00 55.38      1DIK2766
ATOM   2675  N    THR  355      8.622  36.101  33.449  1.00 46.75      1DIK2767
ATOM   2676  CA   THR  355      7.396  36.496  34.135  1.00 46.22      1DIK2768
ATOM   2677  C    THR  355      7.536  36.191  35.631  1.00 47.74      1DIK2769
ATOM   2678  O    THR  355      7.789  35.042  36.007  1.00 47.46      1DIK2770
ATOM   2679  CB   THR  355      6.180  35.691  33.556  1.00 42.82      1DIK2771
ATOM   2680  OG1  THR  355      6.147  35.847  32.131  1.00 43.08      1DIK2772
ATOM   2681  CG2  THR  355      4.853  36.160  34.154  1.00 35.74      1DIK2773
ATOM   2682  N    LYS  356      7.388  37.202  36.486  1.00 44.73      1DIK2774
ATOM   2683  CA   LYS  356      7.478  36.960  37.926  1.00 42.43      1DIK2775
ATOM   2684  C    LYS  356      6.116  36.530  38.437  1.00 40.86      1DIK2776
ATOM   2685  O    LYS  356      5.103  36.849  37.813  1.00 42.40      1DIK2777
ATOM   2686  CB   LYS  356      7.942  38.210  38.664  1.00 41.47      1DIK2778
ATOM   2687  CG   LYS  356      9.438  38.349  38.668  1.00 42.08      1DIK2779
ATOM   2688  CD   LYS  356      9.866  39.579  39.406  1.00 42.64      1DIK2780
ATOM   2689  CE   LYS  356     11.351  39.719  39.346  1.00 42.34      1DIK2781
ATOM   2690  NZ   LYS  356     11.693  41.124  39.631  1.00 48.71      1DIK2782
ATOM   2691  N    PRO  357      6.069  35.806  39.577  1.00 38.87      1DIK2783
ATOM   2692  CA   PRO  357      4.777  35.358  40.120  1.00 39.88      1DIK2784
ATOM   2693  C    PRO  357      3.771  36.512  40.134  1.00 42.03      1DIK2785
ATOM   2694  O    PRO  357      4.092  37.629  40.564  1.00 44.16      1DIK2786
```

FIG. 8-42

```
ATOM   2695  CB   PRO   357      5.149  34.869  41.517  1.00  38.17      1DIK2787
ATOM   2696  CG   PRO   357      6.526  34.306  41.295  1.00  34.95      1DIK2788
ATOM   2697  CD   PRO   357      7.183  35.366  40.438  1.00  33.26      1DIK2789
ATOM   2698  N    LEU   358      2.562  36.252  39.649  1.00  40.53      1DIK2790
ATOM   2699  CA   LEU   358      1.555  37.298  39.584  1.00  39.23      1DIK2791
ATOM   2700  C    LEU   358      1.075  37.682  40.975  1.00  40.76      1DIK2792
ATOM   2701  O    LEU   358      0.861  36.815  41.821  1.00  40.81      1DIK2793
ATOM   2702  CB   LEU   358      0.355  36.864  38.732  1.00  37.58      1DIK2794
ATOM   2703  CG   LEU   358      0.499  36.397  37.283  1.00  34.63      1DIK2795
ATOM   2704  CD1  LEU   358     -0.862  36.528  36.631  1.00  32.21      1DIK2796
ATOM   2705  CD2  LEU   358      1.512  37.210  36.528  1.00  33.59      1DIK2797
ATOM   2706  N    SER   359      0.900  38.979  41.205  1.00  39.69      1DIK2798
ATOM   2707  CA   SER   359      0.432  39.461  42.494  1.00  40.29      1DIK2799
ATOM   2708  C    SER   359     -0.963  38.910  42.687  1.00  38.32      1DIK2800
ATOM   2709  O    SER   359     -1.763  38.923  41.758  1.00  38.66      1DIK2801
ATOM   2710  CB   SER   359      0.376  40.989  42.515  1.00  43.59      1DIK2802
ATOM   2711  OG   SER   359     -0.234  41.445  43.720  1.00  51.02      1DIK2803
ATOM   2712  N    THR   360     -1.254  38.432  43.889  1.00  37.92      1DIK2804
ATOM   2713  CA   THR   360     -2.564  37.870  44.189  1.00  40.16      1DIK2805
ATOM   2714  C    THR   360     -3.564  38.907  44.709  1.00  39.58      1DIK2806
ATOM   2715  O    THR   360     -4.736  38.589  44.952  1.00  38.55      1DIK2807
ATOM   2716  CB   THR   360     -2.425  36.709  45.206  1.00  42.37      1DIK2808
ATOM   2717  OG1  THR   360     -1.519  37.095  46.255  1.00  47.97      1DIK2809
ATOM   2718  CG2  THR   360     -1.877  35.462  44.515  1.00  40.43      1DIK2810
ATOM   2719  N    THR   361     -3.104  40.144  44.875  1.00  40.07      1DIK2811
ATOM   2720  CA   THR   361     -3.964  41.214  45.381  1.00  42.85      1DIK2812
ATOM   2721  C    THR   361     -4.164  42.376  44.414  1.00  44.11      1DIK2813
ATOM   2722  O    THR   361     -5.183  43.053  44.469  1.00  44.52      1DIK2814
ATOM   2723  CB   THR   361     -3.432  41.787  46.728  1.00  42.66      1DIK2815
ATOM   2724  OG1  THR   361     -1.993  41.834  46.720  1.00  42.42      1DIK2816
ATOM   2725  CG2  THR   361     -3.909  40.934  47.877  1.00  45.08      1DIK2817
ATOM   2726  N    THR   362     -3.201  42.595  43.524  1.00  45.47      1DIK2818
ATOM   2727  CA   THR   362     -3.272  43.703  42.582  1.00  45.00      1DIK2819
ATOM   2728  C    THR   362     -3.134  43.247  41.138  1.00  42.73      1DIK2820
ATOM   2729  O    THR   362     -2.368  42.332  40.846  1.00  43.39      1DIK2821
ATOM   2730  CB   THR   362     -2.142  44.689  42.867  1.00  49.03      1DIK2822
ATOM   2731  OG1  THR   362     -2.006  44.846  44.287  1.00  56.76      1DIK2823
ATOM   2732  CG2  THR   362     -2.434  46.036  42.227  1.00  50.37      1DIK2824
ATOM   2733  N    VAL   363     -3.879  43.901  40.249  1.00  40.72      1DIK2825
ATOM   2734  CA   VAL   363     -3.860  43.616  38.815  1.00  37.30      1DIK2826
ATOM   2735  C    VAL   363     -2.524  44.081  38.243  1.00  39.07      1DIK2827
ATOM   2736  O    VAL   363     -2.045  45.160  38.603  1.00  40.33      1DIK2828
ATOM   2737  CB   VAL   363     -4.982  44.402  38.070  1.00  34.35      1DIK2829
ATOM   2738  CG1  VAL   363     -4.928  44.143  36.562  1.00  33.50      1DIK2830
ATOM   2739  CG2  VAL   363     -6.332  44.034  38.625  1.00  32.51      1DIK2831
ATOM   2740  N    GLU   364     -1.934  43.269  37.366  1.00  38.65      1DIK2832
ATOM   2741  CA   GLU   364     -0.676  43.602  36.694  1.00  40.15      1DIK2833
ATOM   2742  C    GLU   364     -0.961  43.550  35.199  1.00  41.61      1DIK2834
ATOM   2743  O    GLU   364     -1.619  42.628  34.714  1.00  42.19      1DIK2835
ATOM   2744  CB   GLU   364      0.421  42.606  37.040  1.00  39.16      1DIK2836
ATOM   2745  CG   GLU   364      0.621  42.449  38.515  1.00  45.46      1DIK2837
ATOM   2746  CD   GLU   364      1.956  41.863  38.842  1.00  46.24      1DIK2838
ATOM   2747  OE1  GLU   364      2.953  42.609  38.751  1.00  54.58      1DIK2839
ATOM   2748  OE2  GLU   364      2.013  40.666  39.187  1.00  43.12      1DIK2840
ATOM   2749  N    ASN   365     -0.475  44.540  34.466  1.00  41.88      1DIK2841
ATOM   2750  CA   ASN   365     -0.727  44.587  33.037  1.00  41.03      1DIK2842
ATOM   2751  C    ASN   365      0.218  43.661  32.288  1.00  39.55      1DIK2843
ATOM   2752  O    ASN   365      1.181  43.141  32.866  1.00  34.92      1DIK2844
ATOM   2753  CB   ASN   365     -0.615  46.025  32.513  1.00  46.26      1DIK2845
ATOM   2754  CG   ASN   365      0.786  46.589  32.649  1.00  49.70      1DIK2846
ATOM   2755  OD1  ASN   365      1.646  46.361  31.798  1.00  52.55      1DIK2847
ATOM   2756  ND2  ASN   365      1.024  47.323  33.719  1.00  56.03      1DIK2848
ATOM   2757  N    ILE   366     -0.075  43.481  30.999  1.00  38.20      1DIK2849
ATOM   2758  CA   ILE   366      0.671  42.603  30.103  1.00  36.15      1DIK2850
ATOM   2759  C    ILE   366      2.160  42.944  29.939  1.00  37.55      1DIK2851
ATOM   2760  O    ILE   366      2.947  42.107  29.489  1.00  38.87      1DIK2852
```

FIG. 8-43

| | | | | | | | | | |
|---|---|---|---|---|---|---|---|---|---|
| ATOM | 2761 | CB | ILE | 366 | -0.068 | 42.489 | 28.713 | 1.00 33.38 | 1DIK2853 |
| ATOM | 2762 | CG1 | ILE | 366 | 0.239 | 41.136 | 28.084 | 1.00 29.94 | 1DIK2854 |
| ATOM | 2763 | CG2 | ILE | 366 | 0.273 | 43.652 | 27.786 | 1.00 24.77 | 1DIK2855 |
| ATOM | 2764 | CD1 | ILE | 366 | -0.332 | 39.987 | 28.874 | 1.00 22.62 | 1DIK2856 |
| ATOM | 2765 | N | THR | 367 | 2.542 | 44.165 | 30.302 | 1.00 37.95 | 1DIK2857 |
| ATOM | 2766 | CA | THR | 367 | 3.944 | 44.592 | 30.243 | 1.00 40.36 | 1DIK2858 |
| ATOM | 2767 | C | THR | 367 | 4.654 | 44.030 | 31.486 | 1.00 40.59 | 1DIK2859 |
| ATOM | 2768 | O | THR | 367 | 5.775 | 43.512 | 31.406 | 1.00 40.36 | 1DIK2860 |
| ATOM | 2769 | CB | THR | 367 | 4.058 | 46.149 | 30.248 | 1.00 41.59 | 1DIK2861 |
| ATOM | 2770 | OG1 | THR | 367 | 3.625 | 46.663 | 28.983 | 1.00 38.58 | 1DIK2862 |
| ATOM | 2771 | CG2 | THR | 367 | 5.488 | 46.602 | 30.535 | 1.00 43.44 | 1DIK2863 |
| ATOM | 2772 | N | GLN | 368 | 3.985 | 44.135 | 32.630 | 1.00 39.60 | 1DIK2864 |
| ATOM | 2773 | CA | GLN | 368 | 4.532 | 43.647 | 33.880 | 1.00 42.39 | 1DIK2865 |
| ATOM | 2774 | C | GLN | 368 | 4.656 | 42.133 | 33.876 | 1.00 43.99 | 1DIK2866 |
| ATOM | 2775 | O | GLN | 368 | 5.613 | 41.598 | 34.438 | 1.00 47.07 | 1DIK2867 |
| ATOM | 2776 | CB | GLN | 368 | 3.650 | 44.055 | 35.050 | 1.00 46.02 | 1DIK2868 |
| ATOM | 2777 | CG | GLN | 368 | 3.575 | 45.543 | 35.313 | 1.00 52.12 | 1DIK2869 |
| ATOM | 2778 | CD | GLN | 368 | 2.605 | 45.854 | 36.439 | 1.00 55.80 | 1DIK2870 |
| ATOM | 2779 | OE1 | GLN | 368 | 1.553 | 46.460 | 36.223 | 1.00 53.21 | 1DIK2871 |
| ATOM | 2780 | NE2 | GLN | 368 | 2.953 | 45.432 | 37.649 | 1.00 58.79 | 1DIK2872 |
| ATOM | 2781 | N | THR | 369 | 3.691 | 41.447 | 33.250 | 1.00 42.31 | 1DIK2873 |
| ATOM | 2782 | CA | THR | 369 | 3.691 | 39.980 | 33.195 | 1.00 37.86 | 1DIK2874 |
| ATOM | 2783 | C | THR | 369 | 4.457 | 39.399 | 32.018 | 1.00 35.95 | 1DIK2875 |
| ATOM | 2784 | O | THR | 369 | 4.415 | 38.186 | 31.776 | 1.00 32.63 | 1DIK2876 |
| ATOM | 2785 | CB | THR | 369 | 2.273 | 39.404 | 33.156 | 1.00 37.12 | 1DIK2877 |
| ATOM | 2786 | OG1 | THR | 369 | 1.626 | 39.815 | 31.940 | 1.00 40.70 | 1DIK2878 |
| ATOM | 2787 | CG2 | THR | 369 | 1.475 | 39.871 | 34.368 | 1.00 28.31 | 1DIK2879 |
| ATOM | 2788 | N | ASP | 370 | 5.149 | 40.269 | 31.291 | 1.00 33.39 | 1DIK2880 |
| ATOM | 2789 | CA | ASP | 370 | 5.954 | 39.864 | 30.153 | 1.00 32.87 | 1DIK2881 |
| ATOM | 2790 | C | ASP | 370 | 5.170 | 39.043 | 29.104 | 1.00 31.05 | 1DIK2882 |
| ATOM | 2791 | O | ASP | 370 | 5.608 | 37.979 | 28.656 | 1.00 31.02 | 1DIK2883 |
| ATOM | 2792 | CB | ASP | 370 | 7.191 | 39.099 | 30.655 | 1.00 35.44 | 1DIK2884 |
| ATOM | 2793 | CG | ASP | 370 | 8.319 | 39.065 | 29.629 | 1.00 40.37 | 1DIK2885 |
| ATOM | 2794 | OD1 | ASP | 370 | 8.469 | 40.065 | 28.893 | 1.00 35.88 | 1DIK2886 |
| ATOM | 2795 | OD2 | ASP | 370 | 9.052 | 38.043 | 29.558 | 1.00 39.79 | 1DIK2887 |
| ATOM | 2796 | N | GLY | 371 | 4.003 | 39.548 | 28.721 | 1.00 29.15 | 1DIK2888 |
| ATOM | 2797 | CA | GLY | 371 | 3.203 | 38.883 | 27.717 | 1.00 26.42 | 1DIK2889 |
| ATOM | 2798 | C | GLY | 371 | 2.322 | 37.745 | 28.178 | 1.00 29.16 | 1DIK2890 |
| ATOM | 2799 | O | GLY | 371 | 1.686 | 37.105 | 27.350 | 1.00 31.15 | 1DIK2891 |
| ATOM | 2800 | N | PHE | 372 | 2.260 | 37.470 | 29.475 | 1.00 29.53 | 1DIK2892 |
| ATOM | 2801 | CA | PHE | 372 | 1.397 | 36.390 | 29.921 | 1.00 26.79 | 1DIK2893 |
| ATOM | 2802 | C | PHE | 372 | 0.035 | 36.824 | 30.426 | 1.00 28.06 | 1DIK2894 |
| ATOM | 2803 | O | PHE | 372 | -0.065 | 37.740 | 31.243 | 1.00 32.94 | 1DIK2895 |
| ATOM | 2804 | CB | PHE | 372 | 2.038 | 35.542 | 31.025 | 1.00 23.34 | 1DIK2896 |
| ATOM | 2805 | CG | PHE | 372 | 1.130 | 34.436 | 31.508 | 1.00 24.56 | 1DIK2897 |
| ATOM | 2806 | CD1 | PHE | 372 | 0.994 | 33.257 | 30.772 | 1.00 22.68 | 1DIK2898 |
| ATOM | 2807 | CD2 | PHE | 372 | 0.355 | 34.601 | 32.648 | 1.00 22.77 | 1DIK2899 |
| ATOM | 2808 | CE1 | PHE | 372 | 0.095 | 32.268 | 31.161 | 1.00 23.69 | 1DIK2900 |
| ATOM | 2809 | CE2 | PHE | 372 | -0.553 | 33.614 | 33.048 | 1.00 26.64 | 1DIK2901 |
| ATOM | 2810 | CZ | PHE | 372 | -0.684 | 32.447 | 32.303 | 1.00 24.28 | 1DIK2902 |
| ATOM | 2811 | N | SER | 373 | -1.006 | 36.149 | 29.941 | 1.00 27.69 | 1DIK2903 |
| ATOM | 2812 | CA | SER | 373 | -2.394 | 36.361 | 30.377 | 1.00 24.96 | 1DIK2904 |
| ATOM | 2813 | C | SER | 373 | -3.191 | 35.201 | 29.772 | 1.00 25.82 | 1DIK2905 |
| ATOM | 2814 | O | SER | 373 | -2.776 | 34.638 | 28.753 | 1.00 26.67 | 1DIK2906 |
| ATOM | 2815 | CB | SER | 373 | -2.945 | 37.716 | 29.914 | 1.00 20.86 | 1DIK2907 |
| ATOM | 2816 | OG | SER | 373 | -3.520 | 37.661 | 28.620 | 1.00 26.28 | 1DIK2908 |
| ATOM | 2817 | N | SER | 374 | -4.310 | 34.820 | 30.378 | 1.00 23.66 | 1DIK2909 |
| ATOM | 2818 | CA | SER | 374 | -5.092 | 33.728 | 29.816 | 1.00 23.58 | 1DIK2910 |
| ATOM | 2819 | C | SER | 374 | -5.576 | 34.063 | 28.418 | 1.00 21.38 | 1DIK2911 |
| ATOM | 2820 | O | SER | 374 | -5.596 | 33.201 | 27.552 | 1.00 24.01 | 1DIK2912 |
| ATOM | 2821 | CB | SER | 374 | -6.295 | 33.404 | 30.688 | 1.00 24.78 | 1DIK2913 |
| ATOM | 2822 | OG | SER | 374 | -5.868 | 32.729 | 31.846 | 1.00 36.24 | 1DIK2914 |
| ATOM | 2823 | N | ALA | 375 | -5.965 | 35.316 | 28.209 | 1.00 19.17 | 1DIK2915 |
| ATOM | 2824 | CA | ALA | 375 | -6.462 | 35.774 | 26.919 | 1.00 18.77 | 1DIK2916 |
| ATOM | 2825 | C | ALA | 375 | -5.377 | 35.768 | 25.839 | 1.00 19.10 | 1DIK2917 |

FIG. 8-44

```
ATOM   2826  O    ALA   375      -5.674  35.603  24.662  1.00 17.13           1DIK2918
ATOM   2827  CB   ALA   375      -7.066  37.176  27.060  1.00 17.12           1DIK2919
ATOM   2828  N    TRP   376      -4.124  35.948  26.241  1.00 18.21           1DIK2920
ATOM   2829  CA   TRP   376      -3.028  35.956  25.285  1.00 20.78           1DIK2921
ATOM   2830  C    TRP   376      -2.419  34.585  25.036  1.00 22.76           1DIK2922
ATOM   2831  O    TRP   376      -1.724  34.391  24.032  1.00 24.41           1DIK2923
ATOM   2832  CB   TRP   376      -1.922  36.932  25.720  1.00 20.50           1DIK2924
ATOM   2833  CG   TRP   376      -2.236  38.359  25.406  1.00 21.91           1DIK2925
ATOM   2834  CD1  TRP   376      -3.465  38.941  25.432  1.00 21.75           1DIK2926
ATOM   2835  CD2  TRP   376      -1.309  39.389  25.017  1.00 23.53           1DIK2927
ATOM   2836  NE1  TRP   376      -3.368  40.265  25.085  1.00 23.80           1DIK2928
ATOM   2837  CE2  TRP   376      -2.060  40.572  24.824  1.00 24.79           1DIK2929
ATOM   2838  CE3  TRP   376       0.082  39.429  24.814  1.00 26.46           1DIK2930
ATOM   2839  CZ2  TRP   376      -1.468  41.794  24.435  1.00 25.72           1DIK2931
ATOM   2840  CZ3  TRP   376       0.676  40.649  24.425  1.00 24.82           1DIK2932
ATOM   2841  CH2  TRP   376      -0.106  41.812  24.242  1.00 24.72           1DIK2933
ATOM   2842  N    THR   377      -2.670  33.631  25.931  1.00 23.05           1DIK2934
ATOM   2843  CA   THR   377      -2.105  32.296  25.770  1.00 20.73           1DIK2935
ATOM   2844  C    THR   377      -3.128  31.212  25.438  1.00 21.78           1DIK2936
ATOM   2845  O    THR   377      -2.917  30.422  24.499  1.00 22.28           1DIK2937
ATOM   2846  CB   THR   377      -1.282  31.891  27.015  1.00 21.05           1DIK2938
ATOM   2847  OG1  THR   377      -2.125  31.885  28.181  1.00 20.07           1DIK2939
ATOM   2848  OG2  THR   377      -0.122  32.871  27.215  1.00 17.56           1DIK2940
ATOM   2849  N    VAL   378      -4.232  31.177  26.187  1.00 19.66           1DIK2941
ATOM   2850  CA   VAL   378      -5.266  30.173  25.960  1.00 17.69           1DIK2942
ATOM   2851  C    VAL   378      -6.712  30.611  25.663  1.00 19.05           1DIK2943
ATOM   2852  O    VAL   378      -7.657  30.160  26.323  1.00 18.97           1DIK2944
ATOM   2853  CB   VAL   378      -5.290  29.124  27.103  1.00 19.46           1DIK2945
ATOM   2854  CG1  VAL   378      -4.018  28.291  27.061  1.00 16.35           1DIK2946
ATOM   2855  CG2  VAL   378      -5.461  29.811  28.459  1.00 17.47           1DIK2947
ATOM   2856  N    PRO   379      -6.909  31.510  24.681  1.00 19.03           1DIK2948
ATOM   2857  CA   PRO   379      -8.300  31.878  24.405  1.00 17.80           1DIK2949
ATOM   2858  C    PRO   379      -8.910  30.654  23.696  1.00 19.39           1DIK2950
ATOM   2859  O    PRO   379      -8.215  29.655  23.472  1.00 21.31           1DIK2951
ATOM   2860  CB   PRO   379      -8.149  33.045  23.438  1.00 16.10           1DIK2952
ATOM   2861  CG   PRO   379      -6.877  32.691  22.677  1.00 17.21           1DIK2953
ATOM   2862  CD   PRO   379      -5.979  32.249  23.798  1.00 19.06           1DIK2954
ATOM   2863  N    PHE   380     -10.188  30.704  23.344  1.00 18.52           1DIK2955
ATOM   2864  CA   PHE   380     -10.784  29.588  22.608  1.00 18.85           1DIK2956
ATOM   2865  C    PHE   380     -10.052  29.506  21.263  1.00 21.10           1DIK2957
ATOM   2866  O    PHE   380      -9.733  30.535  20.669  1.00 24.26           1DIK2958
ATOM   2867  CB   PHE   380     -12.260  29.843  22.329  1.00 17.78           1DIK2959
ATOM   2868  CG   PHE   380     -13.150  29.637  23.509  1.00 20.97           1DIK2960
ATOM   2869  CD1  PHE   380     -13.089  28.461  24.247  1.00 18.51           1DIK2961
ATOM   2870  CD2  PHE   380     -14.084  30.615  23.868  1.00 22.13           1DIK2962
ATOM   2871  CE1  PHE   380     -13.945  28.252  25.327  1.00 23.16           1DIK2963
ATOM   2872  CE2  PHE   380     -14.942  30.419  24.941  1.00 20.92           1DIK2964
ATOM   2873  CZ   PHE   380     -14.874  29.229  25.677  1.00 18.80           1DIK2965
ATOM   2874  N    ALA   381      -9.790  28.296  20.785  1.00 19.83           1DIK2966
ATOM   2875  CA   ALA   381      -9.106  28.103  19.514  1.00 17.83           1DIK2967
ATOM   2876  C    ALA   381      -7.703  28.731  19.476  1.00 21.42           1DIK2968
ATOM   2877  O    ALA   381      -7.225  29.148  18.414  1.00 23.62           1DIK2969
ATOM   2878  CB   ALA   381      -9.968  28.641  18.369  1.00 16.06           1DIK2970
ATOM   2879  N    SER   382      -7.035  28.809  20.622  1.00 16.01           1DIK2971
ATOM   2880  CA   SER   382      -5.699  29.359  20.625  1.00 16.41           1DIK2972
ATOM   2881  C    SER   382      -4.814  28.403  19.850  1.00 16.99           1DIK2973
ATOM   2882  O    SER   382      -5.165  27.240  19.674  1.00 21.80           1DIK2974
ATOM   2883  CB   SER   382      -5.170  29.462  22.046  1.00 18.69           1DIK2975
ATOM   2884  OG   SER   382      -5.083  28.174  22.612  1.00 19.41           1DIK2976
ATOM   2885  N    ARG   383      -3.666  28.882  19.383  1.00 19.86           1DIK2977
ATOM   2886  CA   ARG   383      -2.724  28.025  18.678  1.00 16.82           1DIK2978
ATOM   2887  C    ARG   383      -1.299  28.454  18.979  1.00 19.46           1DIK2979
ATOM   2888  O    ARG   383      -1.000  29.648  19.103  1.00 22.02           1DIK2980
ATOM   2889  CB   ARG   383      -2.971  28.002  17.153  1.00 17.09           1DIK2981
ATOM   2890  CG   ARG   383      -2.591  29.257  16.352  1.00 17.29           1DIK2982
ATOM   2891  CD   ARG   383      -3.451  30.487  16.688  1.00 16.60           1DIK2983
```

FIG. 8-45

```
ATOM   2892  NE   ARG   383    -4.896  30.223  16.669  1.00 15.07      1DIK2984
ATOM   2893  CZ   ARG   383    -5.716  30.480  15.645  1.00 14.92      1DIK2985
ATOM   2894  NH1  ARG   383    -5.272  31.002  14.508  1.00  8.26      1DIK2986
ATOM   2895  NH2  ARG   383    -7.005  30.209  15.757  1.00 12.00      1DIK2987
ATOM   2896  N    LEU   384    -0.432  27.456  19.113  1.00 20.14      1DIK2988
ATOM   2897  CA   LEU   384     0.982  27.640  19.361  1.00 15.15      1DIK2989
ATOM   2898  C    LEU   384     1.632  26.976  18.156  1.00 17.51      1DIK2990
ATOM   2899  O    LEU   384     1.239  25.859  17.776  1.00 17.66      1DIK2991
ATOM   2900  CB   LEU   384     1.384  26.904  20.641  1.00 14.47      1DIK2992
ATOM   2901  CG   LEU   384     2.834  26.416  20.797  1.00 23.97      1DIK2993
ATOM   2902  CD1  LEU   384     3.761  27.555  21.205  1.00 22.30      1DIK2994
ATOM   2903  CD2  LEU   384     2.880  25.312  21.859  1.00 26.10      1DIK2995
ATOM   2904  N    TYR   385     2.601  27.658  17.546  1.00 17.61      1DIK2996
ATOM   2905  CA   TYR   385     3.336  27.110  16.402  1.00 14.96      1DIK2997
ATOM   2906  C    TYR   385     4.794  26.962  16.803  1.00 17.08      1DIK2998
ATOM   2907  O    TYR   385     5.379  27.860  17.428  1.00 15.24      1DIK2999
ATOM   2908  CB   TYR   385     3.341  28.047  15.186  1.00 12.27      1DIK3000
ATOM   2909  CG   TYR   385     2.021  28.338  14.532  1.00 14.64      1DIK3001
ATOM   2910  CD1  TYR   385     1.004  27.383  14.479  1.00 15.16      1DIK3002
ATOM   2911  CD2  TYR   385     1.795  29.580  13.942  1.00 17.04      1DIK3003
ATOM   2912  CE1  TYR   385    -0.209  27.657  13.854  1.00 16.98      1DIK3004
ATOM   2913  CE2  TYR   385     0.584  29.870  13.309  1.00 18.46      1DIK3005
ATOM   2914  CZ   TYR   385    -0.418  28.910  13.265  1.00 21.91      1DIK3006
ATOM   2915  OH   TYR   385    -1.620  29.216  12.637  1.00 13.55      1DIK3007
ATOM   2916  N    VAL   386     5.381  25.829  16.448  1.00 18.39      1DIK3008
ATOM   2917  CA   VAL   386     6.793  25.606  16.681  1.00 16.56      1DIK3009
ATOM   2918  C    VAL   386     7.285  25.311  15.279  1.00 17.90      1DIK3010
ATOM   2919  O    VAL   386     6.893  24.298  14.680  1.00 20.76      1DIK3011
ATOM   2920  CB   VAL   386     7.067  24.404  17.577  1.00 16.14      1DIK3012
ATOM   2921  CG1  VAL   386     8.572  24.270  17.787  1.00  6.88      1DIK3013
ATOM   2922  CG2  VAL   386     6.346  24.565  18.910  1.00 15.11      1DIK3014
ATOM   2923  N    GLU   387     8.116  26.198  14.745  1.00 17.38      1DIK3015
ATOM   2924  CA   GLU   387     8.656  26.029  13.400  1.00 19.62      1DIK3016
ATOM   2925  C    GLU   387    10.169  25.935  13.407  1.00 19.53      1DIK3017
ATOM   2926  O    GLU   387    10.834  26.508  14.269  1.00 21.49      1DIK3018
ATOM   2927  CB   GLU   387     8.211  27.185  12.488  1.00 19.65      1DIK3019
ATOM   2928  CG   GLU   387     8.456  28.572  13.064  1.00 24.89      1DIK3020
ATOM   2929  CD   GLU   387     7.839  29.707  12.237  1.00 25.32      1DIK3021
ATOM   2930  OE1  GLU   387     6.675  29.590  11.802  1.00 18.28      1DIK3022
ATOM   2931  OE2  GLU   387     8.531  30.726  12.030  1.00 24.15      1DIK3023
ATOM   2932  N    MET   388    10.708  25.196  12.448  1.00 22.89      1DIK3024
ATOM   2933  CA   MET   388    12.148  25.047  12.306  1.00 24.50      1DIK3025
ATOM   2934  C    MET   388    12.420  25.506  10.872  1.00 25.97      1DIK3026
ATOM   2935  O    MET   388    11.629  25.226   9.962  1.00 24.86      1DIK3027
ATOM   2936  CB   MET   388    12.564  23.596  12.542  1.00 24.86      1DIK3028
ATOM   2937  CG   MET   388    14.045  23.405  12.736  1.00 28.49      1DIK3029
ATOM   2938  SD   MET   388    14.420  21.945  13.737  1.00 32.00      1DIK3030
ATOM   2939  CE   MET   388    13.569  20.648  12.835  1.00 25.36      1DIK3031
ATOM   2940  N    MET   389    13.517  26.233  10.673  1.00 26.04      1DIK3032
ATOM   2941  CA   MET   389    13.863  26.749   9.351  1.00 27.38      1DIK3033
ATOM   2942  C    MET   389    15.354  26.673   9.063  1.00 31.05      1DIK3034
ATOM   2943  O    MET   389    16.186  26.532   9.970  1.00 28.80      1DIK3035
ATOM   2944  CB   MET   389    13.388  28.200   9.188  1.00 21.65      1DIK3036
ATOM   2945  CG   MET   389    13.986  29.170  10.190  1.00 20.31      1DIK3037
ATOM   2946  SD   MET   389    13.301  30.826  10.047  1.00 27.29      1DIK3038
ATOM   2947  CE   MET   389    11.760  30.668  10.980  1.00 23.61      1DIK3039
ATOM   2948  N    GLN   390    15.683  26.752   7.782  1.00 33.50      1DIK3040
ATOM   2949  CA   GLN   390    17.064  26.722   7.352  1.00 39.30      1DIK3041
ATOM   2950  C    GLN   390    17.218  28.001   6.560  1.00 37.68      1DIK3042
ATOM   2951  O    GLN   390    16.399  28.306   5.687  1.00 38.67      1DIK3043
ATOM   2952  CB   GLN   390    17.336  25.488   6.493  1.00 42.00      1DIK3044
ATOM   2953  CG   GLN   390    18.614  24.779   6.890  1.00 53.74      1DIK3045
ATOM   2954  CD   GLN   390    18.668  23.361   6.364  1.00 63.83      1DIK3046
ATOM   2955  OE1  GLN   390    18.355  23.105   5.191  1.00 68.11      1DIK3047
ATOM   2956  NE2  GLN   390    19.065  22.421   7.224  1.00 63.91      1DIK3048
```

FIG. 8-46

```
ATOM   2957  N   CYS   391      18.250  28.767   6.876  1.00  40.00      1DIK3049
ATOM   2958  CA  CYS   391      18.462  30.027   6.186  1.00  45.20      1DIK3050
ATOM   2959  C   CYS   391      19.823  30.061   5.521  1.00  49.70      1DIK3051
ATOM   2960  O   CYS   391      20.750  29.371   5.932  1.00  49.75      1DIK3052
ATOM   2961  CB  CYS   391      18.301  31.213   7.149  1.00  39.14      1DIK3053
ATOM   2962  SG  CYS   391      16.773  31.195   8.142  1.00  30.19      1DIK3054
ATOM   2963  N   GLN   392      19.917  30.883   4.488  1.00  59.92      1DIK3055
ATOM   2964  CA  GLN   392      21.121  31.044   3.685  1.00  68.58      1DIK3056
ATOM   2965  C   GLN   392      22.430  31.262   4.455  1.00  71.02      1DIK3057
ATOM   2966  O   GLN   392      23.442  30.618   4.166  1.00  72.41      1DIK3058
ATOM   2967  CB  GLN   392      20.883  32.199   2.724  1.00  73.43      1DIK3059
ATOM   2968  CG  GLN   392      21.760  32.223   1.498  1.00  80.79      1DIK3060
ATOM   2969  CD  GLN   392      21.489  33.465   0.686  1.00  83.73      1DIK3061
ATOM   2970  OE1 GLN   392      20.888  34.420   1.193  1.00  85.73      1DIK3062
ATOM   2971  NE2 GLN   392      21.920  33.471  -0.571  1.00  84.40      1DIK3063
ATOM   2972  N   ALA   393      22.408  32.169   5.425  1.00  72.05      1DIK3064
ATOM   2973  CA  ALA   393      23.604  32.467   6.207  1.00  74.09      1DIK3065
ATOM   2974  C   ALA   393      23.989  31.392   7.241  1.00  74.58      1DIK3066
ATOM   2975  O   ALA   393      25.159  31.020   7.345  1.00  74.91      1DIK3067
ATOM   2976  CB  ALA   393      23.440  33.820   6.895  1.00  75.97      1DIK3068
ATOM   2977  N   GLU   394      23.007  30.905   7.998  1.00  73.28      1DIK3069
ATOM   2978  CA  GLU   394      23.229  29.902   9.041  1.00  72.21      1DIK3070
ATOM   2979  C   GLU   394      23.418  28.461   8.528  1.00  70.24      1DIK3071
ATOM   2980  O   GLU   394      22.973  28.131   7.437  1.00  72.41      1DIK3072
ATOM   2981  CB  GLU   394      22.055  29.955  10.018  1.00  74.31      1DIK3073
ATOM   2982  CG  GLU   394      22.266  29.170  11.307  1.00  81.75      1DIK3074
ATOM   2983  CD  GLU   394      23.361  29.761  12.187  1.00  84.86      1DIK3075
ATOM   2984  OE1 GLU   394      23.242  30.948  12.578  1.00  86.06      1DIK3076
ATOM   2985  OE2 GLU   394      24.338  29.038  12.489  1.00  86.34      1DIK3077
ATOM   2986  N   GLN   395      24.077  27.608   9.314  1.00  67.62      1DIK3078
ATOM   2987  CA  GLN   395      24.296  26.203   8.924  1.00  67.27      1DIK3079
ATOM   2988  C   GLN   395      23.313  25.261   9.625  1.00  64.99      1DIK3080
ATOM   2989  O   GLN   395      22.818  24.294   9.034  1.00  65.93      1DIK3081
ATOM   2990  CB  GLN   395      25.704  25.752   9.288  1.00  70.58      1DIK3082
ATOM   2991  CG  GLN   395      26.799  26.627   8.760  1.00  80.49      1DIK3083
ATOM   2992  CD  GLN   395      28.085  26.437   9.542  1.00  86.58      1DIK3084
ATOM   2993  OE1 GLN   395      28.185  25.537  10.385  1.00  87.92      1DIK3085
ATOM   2994  NE2 GLN   395      29.077  27.280   9.272  1.00  90.05      1DIK3086
ATOM   2995  N   GLU   396      23.051  25.546  10.900  1.00  59.17      1DIK3087
ATOM   2996  CA  GLU   396      22.127  24.760  11.707  1.00  52.18      1DIK3088
ATOM   2997  C   GLU   396      20.694  25.250  11.536  1.00  45.17      1DIK3089
ATOM   2998  O   GLU   396      20.450  26.432  11.232  1.00  42.88      1DIK3090
ATOM   2999  CB  GLU   396      22.442  24.917  13.192  1.00  58.64      1DIK3091
ATOM   3000  CG  GLU   396      23.637  24.200  13.749  1.00  65.48      1DIK3092
ATOM   3001  CD  GLU   396      23.588  24.204  15.279  1.00  72.96      1DIK3093
ATOM   3002  OE1 GLU   396      22.721  23.485  15.849  1.00  75.18      1DIK3094
ATOM   3003  OE2 GLU   396      24.402  24.925  15.908  1.00  73.08      1DIK3095
ATOM   3004  N   PRO   397      19.723  24.344  11.708  1.00  37.24      1DIK3096
ATOM   3005  CA  PRO   397      18.346  24.817  11.572  1.00  33.03      1DIK3097
ATOM   3006  C   PRO   397      18.015  25.696  12.806  1.00  27.77      1DIK3098
ATOM   3007  O   PRO   397      18.547  25.491  13.912  1.00  23.86      1DIK3099
ATOM   3008  CB  PRO   397      17.537  23.515  11.499  1.00  30.60      1DIK3100
ATOM   3009  CG  PRO   397      18.343  22.572  12.325  1.00  34.10      1DIK3101
ATOM   3010  CD  PRO   397      19.779  22.897  11.975  1.00  33.21      1DIK3102
ATOM   3011  N   LEU   398      17.151  26.680  12.599  1.00  24.89      1DIK3103
ATOM   3012  CA  LEU   398      16.743  27.603  13.644  1.00  22.58      1DIK3104
ATOM   3013  C   LEU   398      15.287  27.333  14.072  1.00  23.54      1DIK3105
ATOM   3014  O   LEU   398      14.420  27.074  13.239  1.00  23.76      1DIK3106
ATOM   3015  CB  LEU   398      16.904  29.033  13.129  1.00  19.29      1DIK3107
ATOM   3016  CG  LEU   398      18.296  29.357  12.572  1.00  21.68      1DIK3108
ATOM   3017  CD1 LEU   398      18.210  30.505  11.590  1.00  21.80      1DIK3109
ATOM   3018  CD2 LEU   398      19.252  29.681  13.695  1.00  17.36      1DIK3110
ATOM   3019  N   VAL   399      15.039  27.395  15.374  1.00  23.51      1DIK3111
ATOM   3020  CA  VAL   399      13.727  27.149  15.959  1.00  23.57      1DIK3112
ATOM   3021  C   VAL   399      13.084  28.478  16.379  1.00  25.60      1DIK3113
ATOM   3022  O   VAL   399      13.767  29.398  16.832  1.00  28.79      1DIK3114
```

FIG. 8-47

| | | | | | | | | | |
|---|---|---|---|---|---|---|---|---|---|
| ATOM | 3023 | CB  | VAL | 399 | 13.864 | 26.226 | 17.220 | 1.00 23.92 | 1DIK3115 |
| ATOM | 3024 | CG1 | VAL | 399 | 12.510 | 25.978 | 17.867 | 1.00 19.35 | 1DIK3116 |
| ATOM | 3025 | CG2 | VAL | 399 | 14.525 | 24.906 | 16.844 | 1.00 19.06 | 1DIK3117 |
| ATOM | 3026 | N   | ARG | 400 | 11.770 | 28.576 | 16.223 | 1.00 24.81 | 1DIK3118 |
| ATOM | 3027 | CA  | ARG | 400 | 11.038 | 29.766 | 16.612 | 1.00 20.32 | 1DIK3119 |
| ATOM | 3028 | C   | ARG | 400 | 9.642  | 29.348 | 17.060 | 1.00 20.66 | 1DIK3120 |
| ATOM | 3029 | O   | ARG | 400 | 9.065  | 28.407 | 16.511 | 1.00 21.08 | 1DIK3121 |
| ATOM | 3030 | CB  | ARG | 400 | 10.950 | 30.754 | 15.457 | 1.00 21.26 | 1DIK3122 |
| ATOM | 3031 | CG  | ARG | 400 | 10.227 | 32.002 | 15.867 | 1.00 24.84 | 1DIK3123 |
| ATOM | 3032 | CD  | ARG | 400 | 10.446 | 33.098 | 14.903 | 1.00 22.49 | 1DIK3124 |
| ATOM | 3033 | NE  | ARG | 400 | 9.769  | 32.864 | 13.643 | 1.00 24.64 | 1DIK3125 |
| ATOM | 3034 | CZ  | ARG | 400 | 9.536  | 33.835 | 12.763 | 1.00 33.02 | 1DIK3126 |
| ATOM | 3035 | NH1 | ARG | 400 | 9.930  | 35.079 | 13.042 | 1.00 30.42 | 1DIK3127 |
| ATOM | 3036 | NH2 | ARG | 400 | 8.915  | 33.576 | 11.614 | 1.00 30.09 | 1DIK3128 |
| ATOM | 3037 | N   | VAL | 401 | 9.109  | 30.044 | 18.058 | 1.00 19.00 | 1DIK3129 |
| ATOM | 3038 | CA  | VAL | 401 | 7.795  | 29.757 | 18.606 | 1.00 18.61 | 1DIK3130 |
| ATOM | 3039 | C   | VAL | 401 | 6.882  | 30.980 | 18.554 | 1.00 21.25 | 1DIK3131 |
| ATOM | 3040 | O   | VAL | 401 | 7.260  | 32.059 | 19.003 | 1.00 23.23 | 1DIK3132 |
| ATOM | 3041 | CB  | VAL | 401 | 7.908  | 29.318 | 20.087 | 1.00 20.03 | 1DIK3133 |
| ATOM | 3042 | CG1 | VAL | 401 | 6.529  | 29.173 | 20.701 | 1.00 17.45 | 1DIK3134 |
| ATOM | 3043 | CG2 | VAL | 401 | 8.673  | 28.006 | 20.195 | 1.00 16.44 | 1DIK3135 |
| ATOM | 3044 | N   | LEU | 402 | 5.683  | 30.812 | 18.006 | 1.00 20.98 | 1DIK3136 |
| ATOM | 3045 | CA  | LEU | 402 | 4.701  | 31.888 | 17.948 | 1.00 17.41 | 1DIK3137 |
| ATOM | 3046 | C   | LEU | 402 | 3.540  | 31.418 | 18.804 | 1.00 19.37 | 1DIK3138 |
| ATOM | 3047 | O   | LEU | 402 | 3.165  | 30.249 | 18.728 | 1.00 22.64 | 1DIK3139 |
| ATOM | 3048 | CB  | LEU | 402 | 4.206  | 32.128 | 16.519 | 1.00 14.63 | 1DIK3140 |
| ATOM | 3049 | CG  | LEU | 402 | 5.213  | 32.709 | 15.523 | 1.00 17.85 | 1DIK3141 |
| ATOM | 3050 | CD1 | LEU | 402 | 6.046  | 31.608 | 14.893 | 1.00 12.36 | 1DIK3142 |
| ATOM | 3051 | CD2 | LEU | 402 | 4.464  | 33.480 | 14.461 | 1.00 15.05 | 1DIK3143 |
| ATOM | 3052 | N   | VAL | 403 | 2.984  | 32.305 | 19.626 | 1.00 18.51 | 1DIK3144 |
| ATOM | 3053 | CA  | VAL | 403 | 1.831  | 31.962 | 20.472 | 1.00 18.78 | 1DIK3145 |
| ATOM | 3054 | C   | VAL | 403 | 0.710  | 32.925 | 20.081 | 1.00 21.06 | 1DIK3146 |
| ATOM | 3055 | O   | VAL | 403 | 0.793  | 34.129 | 20.357 | 1.00 20.63 | 1DIK3147 |
| ATOM | 3056 | CB  | VAL | 403 | 2.150  | 32.111 | 21.993 | 1.00 17.73 | 1DIK3148 |
| ATOM | 3057 | CG1 | VAL | 403 | 0.904  | 31.836 | 22.840 | 1.00 12.73 | 1DIK3149 |
| ATOM | 3058 | CG2 | VAL | 403 | 3.266  | 31.146 | 22.388 | 1.00 16.54 | 1DIK3150 |
| ATOM | 3059 | N   | ASN | 404 | -0.327 | 32.397 | 19.429 | 1.00 18.48 | 1DIK3151 |
| ATOM | 3060 | CA  | ASN | 404 | -1.455 | 33.216 | 18.967 | 1.00 21.00 | 1DIK3152 |
| ATOM | 3061 | C   | ASN | 404 | -0.986 | 34.403 | 18.116 | 1.00 21.42 | 1DIK3153 |
| ATOM | 3062 | O   | ASN | 404 | -1.507 | 35.522 | 18.221 | 1.00 18.49 | 1DIK3154 |
| ATOM | 3063 | CB  | ASN | 404 | -2.323 | 33.679 | 20.142 | 1.00 17.93 | 1DIK3155 |
| ATOM | 3064 | CG  | ASN | 404 | -3.007 | 32.525 | 20.825 | 1.00 16.64 | 1DIK3156 |
| ATOM | 3065 | OD1 | ASN | 404 | -3.675 | 31.726 | 20.177 | 1.00 18.50 | 1DIK3157 |
| ATOM | 3066 | ND2 | ASN | 404 | -2.841 | 32.421 | 22.132 | 1.00 13.25 | 1DIK3158 |
| ATOM | 3067 | N   | ASP | 405 | 0.011  | 34.103 | 17.277 | 1.00 20.77 | 1DIK3159 |
| ATOM | 3068 | CA  | ASP | 405 | 0.657  | 35.003 | 16.317 | 1.00 21.55 | 1DIK3160 |
| ATOM | 3069 | C   | ASP | 405 | 1.704  | 35.960 | 16.838 | 1.00 24.70 | 1DIK3161 |
| ATOM | 3070 | O   | ASP | 405 | 2.244  | 36.765 | 16.078 | 1.00 27.69 | 1DIK3162 |
| ATOM | 3071 | CB  | ASP | 405 | -0.374 | 35.753 | 15.481 | 1.00 19.33 | 1DIK3163 |
| ATOM | 3072 | CG  | ASP | 405 | -1.249 | 34.821 | 14.694 | 1.00 21.06 | 1DIK3164 |
| ATOM | 3073 | OD1 | ASP | 405 | -0.824 | 33.668 | 14.469 | 1.00 22.07 | 1DIK3165 |
| ATOM | 3074 | OD2 | ASP | 405 | -2.359 | 35.231 | 14.303 | 1.00 23.53 | 1DIK3166 |
| ATOM | 3075 | N   | ARG | 406 | 1.999  | 35.874 | 18.126 | 1.00 24.97 | 1DIK3167 |
| ATOM | 3076 | CA  | ARG | 406 | 3.022  | 36.732 | 18.709 | 1.00 25.69 | 1DIK3168 |
| ATOM | 3077 | C   | ARG | 406 | 4.317  | 35.917 | 18.738 | 1.00 24.24 | 1DIK3169 |
| ATOM | 3078 | O   | ARG | 406 | 4.313  | 34.767 | 19.213 | 1.00 24.35 | 1DIK3170 |
| ATOM | 3079 | CB  | ARG | 406 | 2.619  | 37.141 | 20.139 | 1.00 26.35 | 1DIK3171 |
| ATOM | 3080 | CG  | ARG | 406 | 3.618  | 38.049 | 20.840 | 1.00 26.41 | 1DIK3172 |
| ATOM | 3081 | CD  | ARG | 406 | 3.315  | 38.224 | 22.331 | 1.00 28.94 | 1DIK3173 |
| ATOM | 3082 | NE  | ARG | 406 | 4.501  | 38.715 | 23.031 | 1.00 32.36 | 1DIK3174 |
| ATOM | 3083 | CZ  | ARG | 406 | 5.099  | 38.092 | 24.047 | 1.00 36.19 | 1DIK3175 |
| ATOM | 3084 | NH1 | ARG | 406 | 4.613  | 36.950 | 24.521 | 1.00 35.65 | 1DIK3176 |
| ATOM | 3085 | NH2 | ARG | 406 | 6.188  | 38.618 | 24.601 | 1.00 38.62 | 1DIK3177 |
| ATOM | 3086 | N   | VAL | 407 | 5.410  | 36.483 | 18.226 | 1.00 20.04 | 1DIK3178 |
| ATOM | 3087 | CA  | VAL | 407 | 6.689  | 35.779 | 18.266 | 1.00 19.32 | 1DIK3179 |

FIG. 8-48

```
ATOM   3088  C    VAL  407    7.183  35.895  19.710  1.00  22.20    1DIK3180
ATOM   3089  O    VAL  407    7.481  36.974  20.198  1.00  26.19    1DIK3181
ATOM   3090  CB   VAL  407    7.743  36.372  17.276  1.00  17.66    1DIK3182
ATOM   3091  CG1  VAL  407    9.143  35.815  17.606  1.00  12.58    1DIK3183
ATOM   3092  CG2  VAL  407    7.367  36.031  15.826  1.00   8.62    1DIK3184
ATOM   3093  N    VAL  408    7.245  34.767  20.391  1.00  27.04    1DIK3185
ATOM   3094  CA   VAL  408    7.682  34.718  21.779  1.00  30.49    1DIK3186
ATOM   3095  C    VAL  408    9.169  34.371  21.845  1.00  33.80    1DIK3187
ATOM   3096  O    VAL  408    9.576  33.273  21.468  1.00  36.38    1DIK3188
ATOM   3097  CB   VAL  408    6.869  33.645  22.575  1.00  27.31    1DIK3189
ATOM   3098  CG1  VAL  408    7.310  33.590  24.026  1.00  26.14    1DIK3190
ATOM   3099  CG2  VAL  408    5.392  33.950  22.493  1.00  25.33    1DIK3191
ATOM   3100  N    PRO  409   10.007  35.312  22.298  1.00  39.45    1DIK3192
ATOM   3101  CA   PRO  409   11.453  35.048  22.405  1.00  39.88    1DIK3193
ATOM   3102  C    PRO  409   11.740  33.855  23.348  1.00  38.92    1DIK3194
ATOM   3103  O    PRO  409   11.135  33.707  24.423  1.00  36.45    1DIK3195
ATOM   3104  CB   PRO  409   12.005  36.368  22.948  1.00  42.97    1DIK3196
ATOM   3105  CG   PRO  409   10.992  37.396  22.418  1.00  44.48    1DIK3197
ATOM   3106  CD   PRO  409    9.688  36.692  22.702  1.00  40.36    1DIK3198
ATOM   3107  N    LEU  410   12.668  33.009  22.921  1.00  38.46    1DIK3199
ATOM   3108  CA   LEU  410   13.041  31.814  23.660  1.00  34.48    1DIK3200
ATOM   3109  C    LEU  410   13.959  32.117  24.846  1.00  33.51    1DIK3201
ATOM   3110  O    LEU  410   14.710  33.092  24.839  1.00  31.11    1DIK3202
ATOM   3111  CB   LEU  410   13.707  30.810  22.697  1.00  32.83    1DIK3203
ATOM   3112  CG   LEU  410   12.875  30.372  21.476  1.00  29.37    1DIK3204
ATOM   3113  CD1  LEU  410   13.725  29.543  20.528  1.00  28.62    1DIK3205
ATOM   3114  CD2  LEU  410   11.661  29.584  21.937  1.00  24.58    1DIK3206
ATOM   3115  N    HIS  411   13.888  31.275  25.867  1.00  32.47    1DIK3207
ATOM   3116  CA   HIS  411   14.725  31.432  27.041  1.00  34.54    1DIK3208
ATOM   3117  C    HIS  411   15.585  30.188  27.209  1.00  33.85    1DIK3209
ATOM   3118  O    HIS  411   15.168  29.088  26.854  1.00  36.81    1DIK3210
ATOM   3119  CB   HIS  411   13.865  31.652  28.288  1.00  40.62    1DIK3211
ATOM   3120  CG   HIS  411   13.249  33.012  28.352  1.00  43.65    1DIK3212
ATOM   3121  ND1  HIS  411   11.994  33.287  27.854  1.00  46.21    1DIK3213
ATOM   3122  CD2  HIS  411   13.371  34.185  28.822  1.00  43.54    1DIK3214
ATOM   3123  CE1  HIS  411   11.731  34.571  28.012  1.00  46.39    1DIK3215
ATOM   3124  NE2  HIS  411   12.771  35.138  28.598  1.00  43.29    1DIK3216
ATOM   3125  N    GLY  412   16.786  30.372  27.747  1.00  32.45    1DIK3217
ATOM   3126  CA   GLY  412   17.690  29.258  27.961  1.00  27.18    1DIK3218
ATOM   3127  C    GLY  412   18.642  29.036  26.807  1.00  28.45    1DIK3219
ATOM   3128  O    GLY  412   19.530  28.180  26.880  1.00  32.18    1DIK3220
ATOM   3129  N    CYS  413   18.470  29.797  25.734  1.00  25.33    1DIK3221
ATOM   3130  CA   CYS  413   19.334  29.669  24.570  1.00  24.44    1DIK3222
ATOM   3131  C    CYS  413   19.542  31.073  24.032  1.00  23.08    1DIK3223
ATOM   3132  O    CYS  413   18.723  31.967  24.278  1.00  23.15    1DIK3224
ATOM   3133  CB   CYS  413   18.691  28.751  23.511  1.00  26.97    1DIK3225
ATOM   3134  SG   CYS  413   17.010  29.217  22.959  1.00  26.06    1DIK3226
ATOM   3135  N    PRO  414   20.640  31.289  23.299  1.00  22.53    1DIK3227
ATOM   3136  CA   PRO  414   21.000  32.586  22.706  1.00  25.51    1DIK3228
ATOM   3137  C    PRO  414   20.086  32.989  21.542  1.00  26.43    1DIK3229
ATOM   3138  O    PRO  414   20.303  32.531  20.415  1.00  24.37    1DIK3230
ATOM   3139  CB   PRO  414   22.438  32.359  22.202  1.00  27.32    1DIK3231
ATOM   3140  CG   PRO  414   22.904  31.083  22.891  1.00  26.89    1DIK3232
ATOM   3141  CD   PRO  414   21.649  30.264  22.972  1.00  25.24    1DIK3233
ATOM   3142  N    VAL  415   19.080  33.829  21.801  1.00  24.39    1DIK3234
ATOM   3143  CA   VAL  415   18.180  34.258  20.732  1.00  23.17    1DIK3235
ATOM   3144  C    VAL  415   18.762  35.328  19.817  1.00  23.33    1DIK3236
ATOM   3145  O    VAL  415   19.498  36.213  20.262  1.00  23.01    1DIK3237
ATOM   3146  CB   VAL  415   16.827  34.801  21.256  1.00  20.98    1DIK3238
ATOM   3147  CG1  VAL  415   15.937  33.675  21.666  1.00  22.55    1DIK3239
ATOM   3148  CG2  VAL  415   17.051  35.763  22.391  1.00  26.59    1DIK3240
ATOM   3149  N    ASP  416   18.434  35.236  18.532  1.00  21.89    1DIK3241
ATOM   3150  CA   ASP  416   18.881  36.224  17.569  1.00  23.29    1DIK3242
ATOM   3151  C    ASP  416   17.798  37.307  17.436  1.00  25.15    1DIK3243
ATOM   3152  O    ASP  416   16.739  37.209  18.070  1.00  23.71    1DIK3244
```

FIG. 8-49

```
ATOM  3153  CB   ASP  416   19.265  35.579  16.207  1.00  22.64    1DIK3245
ATOM  3154  CG   ASP  416   18.085  34.947  15.445  1.00  25.90    1DIK3246
ATOM  3155  OD1  ASP  416   16.896  35.237  15.713  1.00  28.90    1DIK3247
ATOM  3156  OD2  ASP  416   18.366  34.135  14.540  1.00  24.59    1DIK3248
ATOM  3157  N    ALA  417   18.062  38.327  16.619  1.00  25.89    1DIK3249
ATOM  3158  CA   ALA  417   17.137  39.443  16.411  1.00  26.04    1DIK3250
ATOM  3159  C    ALA  417   15.717  39.053  15.986  1.00  27.35    1DIK3251
ATOM  3160  O    ALA  417   14.779  39.837  16.165  1.00  28.16    1DIK3252
ATOM  3161  CB   ALA  417   17.738  40.443  15.403  1.00  22.45    1DIK3253
ATOM  3162  N    LEU  418   15.553  37.852  15.428  1.00  28.60    1DIK3254
ATOM  3163  CA   LEU  418   14.238  37.384  14.991  1.00  26.36    1DIK3255
ATOM  3164  C    LEU  418   13.552  36.391  15.952  1.00  26.54    1DIK3256
ATOM  3165  O    LEU  418   12.533  35.795  15.608  1.00  26.72    1DIK3257
ATOM  3166  CB   LEU  418   14.329  36.829  13.564  1.00  25.45    1DIK3258
ATOM  3167  CG   LEU  418   14.649  37.875  12.474  1.00  28.70    1DIK3259
ATOM  3168  CD1  LEU  418   14.842  37.187  11.139  1.00  27.85    1DIK3260
ATOM  3169  CD2  LEU  418   13.525  38.908  12.354  1.00  23.85    1DIK3261
ATOM  3170  N    GLY  419   14.118  36.234  17.154  1.00  27.13    1DIK3262
ATOM  3171  CA   GLY  419   13.556  35.364  18.182  1.00  22.28    1DIK3263
ATOM  3172  C    GLY  419   13.913  33.894  18.094  1.00  25.13    1DIK3264
ATOM  3173  O    GLY  419   13.347  33.077  18.827  1.00  29.64    1DIK3265
ATOM  3174  N    ARG  420   14.852  33.555  17.218  1.00  18.88    1DIK3266
ATOM  3175  CA   ARG  420   15.252  32.173  17.004  1.00  21.64    1DIK3267
ATOM  3176  C    ARG  420   16.483  31.695  17.768  1.00  23.83    1DIK3268
ATOM  3177  O    ARG  420   17.306  32.495  18.193  1.00  26.72    1DIK3269
ATOM  3178  CB   ARG  420   15.504  31.959  15.515  1.00  23.45    1DIK3270
ATOM  3179  CG   ARG  420   14.413  32.532  14.623  1.00  27.05    1DIK3271
ATOM  3180  CD   ARG  420   14.827  32.520  13.166  1.00  25.37    1DIK3272
ATOM  3181  NE   ARG  420   16.019  33.333  12.915  1.00  30.86    1DIK3273
ATOM  3182  CZ   ARG  420   16.435  33.730  11.708  1.00  28.82    1DIK3274
ATOM  3183  NH1  ARG  420   15.775  33.407  10.599  1.00  25.15    1DIK3275
ATOM  3184  NH2  ARG  420   17.528  34.463  11.608  1.00  28.95    1DIK3276
ATOM  3185  N    CYS  421   16.590  30.377  17.927  1.00  24.78    1DIK3277
ATOM  3186  CA   CYS  421   17.726  29.704  18.570  1.00  22.57    1DIK3278
ATOM  3187  C    CYS  421   18.039  28.519  17.679  1.00  23.03    1DIK3279
ATOM  3188  O    CYS  421   17.144  27.988  17.035  1.00  22.43    1DIK3280
ATOM  3189  CB   CYS  421   17.366  29.144  19.944  1.00  22.26    1DIK3281
ATOM  3190  SG   CYS  421   17.337  30.349  21.302  1.00  27.11    1DIK3282
ATOM  3191  N    THR  422   19.294  28.098  17.623  1.00  26.80    1DIK3283
ATOM  3192  CA   THR  422   19.624  26.935  16.816  1.00  26.97    1DIK3284
ATOM  3193  C    THR  422   18.879  25.795  17.511  1.00  30.20    1DIK3285
ATOM  3194  O    THR  422   18.636  25.857  18.731  1.00  30.05    1DIK3286
ATOM  3195  CB   THR  422   21.146  26.649  16.799  1.00  25.67    1DIK3287
ATOM  3196  OG1  THR  422   21.615  26.400  18.133  1.00  25.43    1DIK3288
ATOM  3197  CG2  THR  422   21.895  27.827  16.200  1.00  23.71    1DIK3289
ATOM  3198  N    ARG  423   18.505  24.767  16.752  1.00  30.48    1DIK3290
ATOM  3199  CA   ARG  423   17.781  23.650  17.331  1.00  28.62    1DIK3291
ATOM  3200  C    ARG  423   18.528  23.048  18.518  1.00  29.61    1DIK3292
ATOM  3201  O    ARG  423   17.934  22.791  19.567  1.00  29.29    1DIK3293
ATOM  3202  CB   ARG  423   17.536  22.573  16.281  1.00  27.71    1DIK3294
ATOM  3203  CG   ARG  423   16.711  21.420  16.820  1.00  30.71    1DIK3295
ATOM  3204  CD   ARG  423   16.689  20.273  15.857  1.00  31.47    1DIK3296
ATOM  3205  NE   ARG  423   18.046  19.852  15.553  1.00  33.67    1DIK3297
ATOM  3206  CZ   ASP  423   18.406  19.262  14.422  1.00  33.99    1DIK3298
ATOM  3207  NH1  ASP  423   17.510  19.012  13.476  1.00  35.49    1DIK3299
ATOM  3208  NH2  ASP  423   19.671  18.921  14.241  1.00  38.78    1DIK3300
ATOM  3209  N    ASP  424   19.830  22.838  18.351  1.00  29.32    1DIK3301
ATOM  3210  CA   ASP  424   20.654  22.238  19.393  1.00  32.19    1DIK3302
ATOM  3211  C    ASP  424   20.729  22.998  20.704  1.00  30.97    1DIK3303
ATOM  3212  O    ASP  424   20.614  22.391  21.772  1.00  35.15    1DIK3304
ATOM  3213  CB   ASP  424   22.057  21.954  18.858  1.00  37.79    1DIK3305
ATOM  3214  CG   ASP  424   22.087  20.758  17.900  1.00  49.74    1DIK3306
ATOM  3215  OD1  ASP  424   21.108  20.531  17.136  1.00  52.55    1DIK3307
ATOM  3216  OD2  ASP  424   23.101  20.034  17.911  1.00  52.75    1DIK3308
ATOM  3217  N    SER  425   20.919  24.311  24.653  1.00  28.34    1DIK3309
```

FIG. 8-50

```
ATOM   3218  CA   SER  425      20.976  25.071  21.893  1.00  28.79      1DIK3310
ATOM   3219  C    SER  425      19.568  25.148  22.504  1.00  28.14      1DIK3311
ATOM   3220  O    SER  425      19.422  25.177  23.731  1.00  27.74      1DIK3312
ATOM   3221  CB   SER  425      21.584  26.470  21.674  1.00  27.42      1DIK3313
ATOM   3222  OG   SER  425      20.849  27.235  20.742  1.00  31.04      1DIK3314
ATOM   3223  N    PHE  426      18.538  25.170  21.651  1.00  26.40      1DIK3315
ATOM   3224  CA   PHE  426      17.152  25.203  22.129  1.00  26.40      1DIK3316
ATOM   3225  C    PHE  426      16.839  23.931  22.941  1.00  26.61      1DIK3317
ATOM   3226  O    PHE  426      16.311  23.996  24.064  1.00  23.72      1DIK3318
ATOM   3227  CB   PHE  426      16.149  25.327  20.961  1.00  24.80      1DIK3319
ATOM   3228  CG   PHE  426      14.698  25.227  21.399  1.00  24.49      1DIK3320
ATOM   3229  CD1  PHE  426      14.123  26.225  22.185  1.00  23.07      1DIK3321
ATOM   3230  CD2  PHE  426      13.925  24.117  21.061  1.00  22.45      1DIK3322
ATOM   3231  CE1  PHE  426      12.809  26.112  22.632  1.00  20.13      1DIK3323
ATOM   3232  CE2  PHE  426      12.609  23.999  21.506  1.00  19.45      1DIK3324
ATOM   3233  CZ   PHE  426      12.053  24.993  22.293  1.00  20.49      1DIK3325
ATOM   3234  N    VAL  427      17.161  22.780  22.354  1.00  27.03      1DIK3326
ATOM   3235  CA   VAL  427      16.948  21.491  22.996  1.00  27.17      1DIK3327
ATOM   3236  C    VAL  427      17.788  21.444  24.267  1.00  29.37      1DIK3328
ATOM   3237  O    VAL  427      17.327  21.011  25.323  1.00  32.09      1DIK3329
ATOM   3238  CB   VAL  427      17.348  20.346  22.047  1.00  28.39      1DIK3330
ATOM   3239  CG1  VAL  427      17.439  19.022  22.809  1.00  26.94      1DIK3331
ATOM   3240  CG2  VAL  427      16.326  20.256  20.901  1.00  24.93      1DIK3332
ATOM   3241  N    ARG  428      19.024  21.909  24.160  1.00  31.56      1DIK3333
ATOM   3242  CA   ARG  428      19.931  21.947  25.292  1.00  33.59      1DIK3334
ATOM   3243  C    ARG  428      19.331  22.797  26.426  1.00  32.27      1DIK3335
ATOM   3244  O    ARG  428      19.489  22.472  27.598  1.00  31.56      1DIK3336
ATOM   3245  CB   ARG  428      21.257  22.518  24.819  1.00  40.23      1DIK3337
ATOM   3246  CG   ARG  428      22.404  22.306  25.750  1.00  55.44      1DIK3338
ATOM   3247  CD   ARG  428      23.706  22.643  25.043  1.00  69.03      1DIK3339
ATOM   3248  NE   ARG  428      24.726  23.025  26.013  1.00  83.02      1DIK3340
ATOM   3249  CZ   ARG  428      25.632  23.981  25.819  1.00  88.04      1DIK3341
ATOM   3250  NH1  ARG  428      25.659  24.656  24.674  1.00  89.88      1DIK3342
ATOM   3251  NH2  ARG  428      26.516  24.260  26.777  1.00  89.48      1DIK3343
ATOM   3252  N    GLY  429      18.634  23.875  26.068  1.00  31.73      1DIK3344
ATOM   3253  CA   GLY  429      18.011  24.754  27.049  1.00  29.88      1DIK3345
ATOM   3254  C    GLY  429      16.814  24.187  27.816  1.00  31.65      1DIK3346
ATOM   3255  O    GLY  429      16.434  24.718  28.871  1.00  29.27      1DIK3347
ATOM   3256  N    LEU  430      16.208  23.115  27.308  1.00  32.28      1DIK3348
ATOM   3257  CA   LEU  430      15.057  22.495  27.977  1.00  31.40      1DIK3349
ATOM   3258  C    LEU  430      15.546  21.456  29.009  1.00  30.50      1DIK3350
ATOM   3259  O    LEU  430      15.093  20.307  29.033  1.00  30.10      1DIK3351
ATOM   3260  CB   LEU  430      14.144  21.836  26.930  1.00  27.85      1DIK3352
ATOM   3261  CG   LEU  430      13.635  22.755  25.819  1.00  27.51      1DIK3353
ATOM   3262  CD1  LEU  430      12.980  21.956  24.702  1.00  21.48      1DIK3354
ATOM   3263  CD2  LEU  430      12.672  23.751  26.420  1.00  21.75      1DIK3355
ATOM   3264  N    SER  431      16.468  21.869  29.869  1.00  29.03      1DIK3356
ATOM   3265  CA   SER  431      17.028  20.960  30.864  1.00  31.21      1DIK3357
ATOM   3266  C    SER  431      15.991  20.465  31.871  1.00  28.76      1DIK3358
ATOM   3267  O    SER  431      16.037  19.308  32.290  1.00  29.64      1DIK3359
ATOM   3268  CB   SER  431      18.212  21.623  31.580  1.00  31.70      1DIK3360
ATOM   3269  OG   SER  431      17.837  22.857  32.169  1.00  36.73      1DIK3361
ATOM   3270  N    PHE  432      15.059  21.334  32.254  1.00  25.33      1DIK3362
ATOM   3271  CA   PHE  432      14.016  20.969  33.207  1.00  26.36      1DIK3363
ATOM   3272  C    PHE  432      13.170  19.796  32.681  1.00  30.38      1DIK3364
ATOM   3273  O    PHE  432      12.904  18.822  33.404  1.00  29.32      1DIK3365
ATOM   3274  CB   PHE  432      13.133  22.186  33.487  1.00  21.52      1DIK3366
ATOM   3275  CG   PHE  432      11.908  21.885  34.315  1.00  24.46      1DIK3367
ATOM   3276  CD1  PHE  432      12.022  21.567  35.670  1.00  22.91      1DIK3368
ATOM   3277  CD2  PHE  432      10.636  21.941  33.739  1.00  19.38      1DIK3369
ATOM   3278  CE1  PHE  432      10.883  21.311  36.441  1.00  24.30      1DIK3370
ATOM   3279  CE2  PHE  432       9.489  21.688  34.495  1.00  22.66      1DIK3371
ATOM   3280  CZ   PHE  432       9.606  21.372  35.846  1.00  26.15      1DIK3372
ATOM   3281  N    ALA  433      12.752  19.896  31.421  1.00  27.75      1DIK3373
ATOM   3282  CA   ALA  433      11.958  18.850  30.796  1.00  26.55      1DIK3374
```

FIG. 8-51

| | | | | | | | | | | |
|---|---|---|---|---|---|---|---|---|---|---|
| ATOM | 3283 | C   | ALA | 433 | 12.789 | 17.577 | 30.597 | 1.00 | 25.17 | 1DIK3375 |
| ATOM | 3284 | O   | ALA | 433 | 12.350 | 16.492 | 30.974 | 1.00 | 28.47 | 1DIK3376 |
| ATOM | 3285 | CB  | ALA | 433 | 11.411 | 19.336 | 29.460 | 1.00 | 23.17 | 1DIK3377 |
| ATOM | 3286 | N   | ARG | 434 | 13.982 | 17.710 | 30.018 | 1.00 | 23.09 | 1DIK3378 |
| ATOM | 3287 | CA  | ARG | 434 | 14.849 | 16.557 | 29.754 | 1.00 | 24.40 | 1DIK3379 |
| ATOM | 3288 | C   | ARG | 434 | 15.156 | 15.725 | 30.992 | 1.00 | 24.98 | 1DIK3380 |
| ATOM | 3289 | O   | ARG | 434 | 15.416 | 14.525 | 30.889 | 1.00 | 25.10 | 1DIK3381 |
| ATOM | 3290 | CB  | ARG | 434 | 16.163 | 16.991 | 29.087 | 1.00 | 22.29 | 1DIK3382 |
| ATOM | 3291 | CG  | ARG | 434 | 16.013 | 17.379 | 27.610 | 1.00 | 27.82 | 1DIK3383 |
| ATOM | 3292 | CD  | ARG | 434 | 17.363 | 17.590 | 26.910 | 1.00 | 29.10 | 1DIK3384 |
| ATOM | 3293 | NE  | ARG | 434 | 18.090 | 18.741 | 27.446 | 1.00 | 36.82 | 1DIK3385 |
| ATOM | 3294 | CZ  | ARG | 434 | 19.087 | 18.664 | 28.332 | 1.00 | 39.13 | 1DIK3386 |
| ATOM | 3295 | NH1 | ARG | 434 | 19.487 | 17.480 | 28.784 | 1.00 | 39.16 | 1DIK3387 |
| ATOM | 3296 | NH2 | ARG | 434 | 19.688 | 19.770 | 28.766 | 1.00 | 30.93 | 1DIK3388 |
| ATOM | 3297 | N   | SER | 435 | 15.123 | 16.367 | 32.157 | 1.00 | 26.13 | 1DIK3389 |
| ATOM | 3298 | CA  | SER | 435 | 15.394 | 15.696 | 33.427 | 1.00 | 28.09 | 1DIK3390 |
| ATOM | 3299 | C   | SER | 435 | 14.126 | 15.122 | 34.088 | 1.00 | 26.80 | 1DIK3391 |
| ATOM | 3300 | O   | SER | 435 | 14.208 | 14.433 | 35.103 | 1.00 | 27.78 | 1DIK3392 |
| ATOM | 3301 | CB  | SER | 435 | 16.112 | 16.659 | 34.392 | 1.00 | 29.48 | 1DIK3393 |
| ATOM | 3302 | OG  | SER | 435 | 15.322 | 17.811 | 34.687 | 1.00 | 36.42 | 1DIK3394 |
| ATOM | 3303 | N   | GLY | 436 | 12.960 | 15.407 | 33.515 | 1.00 | 26.30 | 1DIK3395 |
| ATOM | 3304 | CA  | GLY | 436 | 11.719 | 14.894 | 34.068 | 1.00 | 24.08 | 1DIK3396 |
| ATOM | 3305 | C   | GLY | 436 | 11.003 | 15.827 | 35.025 | 1.00 | 25.00 | 1DIK3397 |
| ATOM | 3306 | O   | GLY | 436 | 10.114 | 15.383 | 35.763 | 1.00 | 25.04 | 1DIK3398 |
| ATOM | 3307 | N   | GLY | 437 | 11.376 | 17.107 | 35.015 | 1.00 | 24.66 | 1DIK3399 |
| ATOM | 3308 | CA  | GLY | 437 | 10.755 | 18.076 | 35.901 | 1.00 | 26.30 | 1DIK3400 |
| ATOM | 3309 | C   | GLY | 437 | 10.743 | 17.560 | 37.330 | 1.00 | 28.82 | 1DIK3401 |
| ATOM | 3310 | O   | GLY | 437 | 11.697 | 16.913 | 37.767 | 1.00 | 30.32 | 1DIK3402 |
| ATOM | 3311 | N   | ASP | 438 | 9.666  | 17.839 | 38.058 | 1.00 | 29.95 | 1DIK3403 |
| ATOM | 3312 | CA  | ASP | 438 | 9.516  | 17.374 | 39.438 | 1.00 | 31.82 | 1DIK3404 |
| ATOM | 3313 | C   | ASP | 438 | 8.453  | 16.273 | 39.477 | 1.00 | 32.65 | 1DIK3405 |
| ATOM | 3314 | O   | ASP | 438 | 7.674  | 16.197 | 40.434 | 1.00 | 29.97 | 1DIK3406 |
| ATOM | 3315 | CB  | ASP | 438 | 9.094  | 18.534 | 40.363 | 1.00 | 33.43 | 1DIK3407 |
| ATOM | 3316 | CG  | ASP | 438 | 10.174 | 19.610 | 40.499 | 1.00 | 37.98 | 1DIK3408 |
| ATOM | 3317 | OD1 | ASP | 438 | 11.372 | 19.271 | 40.545 | 1.00 | 43.62 | 1DIK3409 |
| ATOM | 3318 | OD2 | ASP | 438 | 9.834  | 20.806 | 40.563 | 1.00 | 40.73 | 1DIK3410 |
| ATOM | 3319 | N   | TRP | 439 | 8.423  | 15.420 | 38.446 | 1.00 | 32.12 | 1DIK3411 |
| ATOM | 3320 | CA  | TRP | 439 | 7.415  | 14.357 | 38.365 | 1.00 | 31.93 | 1DIK3412 |
| ATOM | 3321 | C   | TRP | 439 | 7.429  | 13.410 | 39.571 | 1.00 | 35.50 | 1DIK3413 |
| ATOM | 3322 | O   | TRP | 439 | 6.388  | 12.886 | 39.979 | 1.00 | 34.13 | 1DIK3414 |
| ATOM | 3323 | CB  | TRP | 439 | 7.545  | 13.573 | 37.045 | 1.00 | 23.82 | 1DIK3415 |
| ATOM | 3324 | CG  | TRP | 439 | 6.379  | 12.641 | 36.794 | 1.00 | 25.59 | 1DIK3416 |
| ATOM | 3325 | CD1 | TRP | 439 | 6.331  | 11.304 | 37.067 | 1.00 | 22.86 | 1DIK3417 |
| ATOM | 3326 | CD2 | TRP | 439 | 5.076  | 12.989 | 36.279 | 1.00 | 25.24 | 1DIK3418 |
| ATOM | 3327 | NE1 | TRP | 439 | 5.089  | 10.802 | 36.764 | 1.00 | 27.19 | 1DIK3419 |
| ATOM | 3328 | CE2 | TRP | 439 | 4.299  | 11.813 | 36.280 | 1.00 | 25.01 | 1DIK3420 |
| ATOM | 3329 | CE3 | TRP | 439 | 4.494  | 14.179 | 35.819 | 1.00 | 25.14 | 1DIK3421 |
| ATOM | 3330 | CZ2 | TRP | 439 | 2.967  | 11.790 | 35.842 | 1.00 | 26.41 | 1DIK3422 |
| ATOM | 3331 | CZ3 | TRP | 439 | 3.169  | 14.157 | 35.381 | 1.00 | 21.25 | 1DIK3423 |
| ATOM | 3332 | CH2 | TRP | 439 | 2.424  | 12.970 | 35.398 | 1.00 | 27.53 | 1DIK3424 |
| ATOM | 3333 | N   | ALA | 440 | 8.608  | 13.198 | 40.147 | 1.00 | 39.08 | 1DIK3425 |
| ATOM | 3334 | CA  | ALA | 440 | 8.740  | 12.325 | 41.304 | 1.00 | 40.38 | 1DIK3426 |
| ATOM | 3335 | C   | ALA | 440 | 7.783  | 12.771 | 42.429 | 1.00 | 42.18 | 1DIK3427 |
| ATOM | 3336 | O   | ALA | 440 | 7.072  | 11.948 | 43.026 | 1.00 | 44.41 | 1DIK3428 |
| ATOM | 3337 | CB  | ALA | 440 | 10.173 | 12.341 | 41.776 | 1.00 | 36.80 | 1DIK3429 |
| ATOM | 3338 | N   | GLU | 441 | 7.758  | 14.077 | 42.689 | 1.00 | 41.96 | 1DIK3430 |
| ATOM | 3339 | CA  | GLU | 441 | 6.903  | 14.687 | 43.713 | 1.00 | 42.69 | 1DIK3431 |
| ATOM | 3340 | C   | GLU | 441 | 5.397  | 14.402 | 43.529 | 1.00 | 42.04 | 1DIK3432 |
| ATOM | 3341 | O   | GLU | 441 | 4.575  | 14.766 | 44.373 | 1.00 | 42.51 | 1DIK3433 |
| ATOM | 3342 | CB  | GLU | 441 | 7.109  | 16.207 | 43.710 | 1.00 | 49.22 | 1DIK3434 |
| ATOM | 3343 | CG  | GLU | 441 | 8.554  | 16.671 | 43.787 | 1.00 | 56.93 | 1DIK3435 |
| ATOM | 3344 | CD  | GLU | 441 | 9.184  | 16.346 | 45.122 | 1.00 | 65.76 | 1DIK3436 |
| ATOM | 3345 | OE1 | GLU | 441 | 8.602  | 16.733 | 46.161 | 1.00 | 69.69 | 1DIK3437 |
| ATOM | 3346 | OE2 | GLU | 441 | 10.260 | 15.704 | 45.139 | 1.00 | 69.76 | 1DIK3438 |
| ATOM | 3347 | N   | CYS | 442 | 5.034  | 13.765 | 42.426 | 1.00 | 39.99 | 1DIK3439 |

FIG. 8-52

| | | | | | | | | | |
|---|---|---|---|---|---|---|---|---|---|
| ATOM | 3348 | CA | CYS | 442 | 3.638 | 13.468 | 42.160 | 1.00 40.48 | 1DIK3440 |
| ATOM | 3349 | C | CYS | 442 | 3.068 | 12.411 | 43.073 | 1.00 43.32 | 1DIK3441 |
| ATOM | 3350 | O | CYS | 442 | 1.859 | 12.405 | 43.337 | 1.00 43.60 | 1DIK3442 |
| ATOM | 3351 | CB | CYS | 442 | 3.452 | 12.982 | 40.715 | 1.00 39.39 | 1DIK3443 |
| ATOM | 3352 | SG | CYS | 442 | 3.541 | 14.265 | 39.429 | 1.00 32.94 | 1DIK3444 |
| ATOM | 3353 | N | PHE | 443 | 3.930 | 11.517 | 43.546 | 1.00 45.06 | 1DIK3445 |
| ATOM | 3354 | CA | PHE | 443 | 3.479 | 10.403 | 44.372 | 1.00 50.79 | 1DIK3446 |
| ATOM | 3355 | C | PHE | 443 | 3.941 | 10.416 | 45.813 | 1.00 55.76 | 1DIK3447 |
| ATOM | 3356 | O | PHE | 443 | 3.268 | 9.863 | 46.684 | 1.00 57.52 | 1DIK3448 |
| ATOM | 3357 | CB | PHE | 443 | 3.882 | 9.111 | 43.681 | 1.00 45.54 | 1DIK3449 |
| ATOM | 3358 | CG | PHE | 443 | 3.724 | 9.182 | 42.205 | 1.00 45.83 | 1DIK3450 |
| ATOM | 3359 | CD1 | PHE | 443 | 2.453 | 9.192 | 41.636 | 1.00 43.41 | 1DIK3451 |
| ATOM | 3360 | CD2 | PHE | 443 | 4.840 | 9.294 | 41.379 | 1.00 46.74 | 1DIK3452 |
| ATOM | 3361 | CE1 | PHE | 443 | 2.292 | 9.315 | 40.262 | 1.00 43.31 | 1DIK3453 |
| ATOM | 3362 | CE2 | PHE | 443 | 4.694 | 9.417 | 39.999 | 1.00 45.78 | 1DIK3454 |
| ATOM | 3363 | CZ | PHE | 443 | 3.416 | 9.428 | 39.441 | 1.00 45.42 | 1DIK3455 |
| ATOM | 3364 | N | ALA | 444 | 5.089 | 11.039 | 46.060 | 1.00 62.20 | 1DIK3456 |
| ATOM | 3365 | CA | ALA | 444 | 5.621 | 11.144 | 47.412 | 1.00 66.60 | 1DIK3457 |
| ATOM | 3366 | C | ALA | 444 | 4.893 | 12.333 | 48.043 | 1.00 68.05 | 1DIK3458 |
| ATOM | 3367 | O | ALA | 444 | 3.938 | 12.089 | 48.817 | 1.00 68.94 | 1DIK3459 |
| ATOM | 3368 | CB | ALA | 444 | 7.151 | 11.380 | 47.381 | 1.00 66.83 | 1DIK3460 |
| ATOM | 3369 | OXT | ALA | 444 | 5.274 | 13.489 | 47.747 | 1.00 69.24 | 1DIK3461 |
| TER | 3370 | | ALA | 444 | | | | | 1DIK3462 |
| HETATM | 3371 | O | HOH | 1 | 5.314 | 11.951 | 16.327 | 1.00 10.28 | 1DIK3463 |
| HETATM | 3372 | O | HOH | 2 | -6.660 | 26.826 | 16.721 | 1.00 14.37 | 1DIK3464 |
| HETATM | 3373 | O | HOH | 3 | 0.327 | 31.364 | 16.394 | 1.00 14.78 | 1DIK3465 |
| HETATM | 3374 | O | HOH | 4 | -11.448 | 9.894 | 26.651 | 1.00 15.14 | 1DIK3466 |
| HETATM | 3375 | O | HOH | 5 | -1.808 | 14.907 | 36.587 | 1.00 15.18 | 1DIK3467 |
| HETATM | 3376 | O | HOH | 6 | -16.607 | 13.889 | 26.028 | 1.00 15.50 | 1DIK3468 |
| HETATM | 3377 | O | HOH | 7 | 8.014 | 7.031 | 26.624 | 1.00 15.90 | 1DIK3469 |
| HETATM | 3378 | O | HOH | 8 | 2.890 | 16.506 | 29.187 | 1.00 16.33 | 1DIK3470 |
| HETATM | 3379 | O | HOH | 9 | -3.509 | 12.674 | 9.344 | 1.00 16.84 | 1DIK3471 |
| HETATM | 3380 | O | HOH | 10 | 12.661 | 12.918 | 24.069 | 1.00 17.03 | 1DIK3472 |
| HETATM | 3381 | O | HOH | 11 | 0.759 | 15.125 | 16.187 | 1.00 18.48 | 1DIK3473 |
| HETATM | 3382 | O | HOH | 12 | -4.619 | 39.381 | 32.613 | 1.00 18.74 | 1DIK3474 |
| HETATM | 3383 | O | HOH | 13 | -9.462 | 31.056 | 14.118 | 1.00 18.80 | 1DIK3475 |
| HETATM | 3384 | O | HOH | 14 | -5.677 | 35.681 | 21.397 | 1.00 19.53 | 1DIK3476 |
| HETATM | 3385 | O | HOH | 15 | -11.372 | 5.811 | 26.977 | 1.00 20.29 | 1DIK3477 |
| HETATM | 3386 | O | HOH | 16 | 1.644 | 9.234 | 20.239 | 1.00 20.38 | 1DIK3478 |
| HETATM | 3387 | O | HOH | 17 | 7.980 | 5.282 | 24.219 | 1.00 20.45 | 1DIK3479 |
| HETATM | 3388 | O | HOH | 18 | -2.840 | 6.618 | 26.553 | 1.00 21.48 | 1DIK3480 |
| HETATM | 3389 | O | HOH | 19 | 10.194 | 6.545 | 20.888 | 1.00 21.50 | 1DIK3481 |
| HETATM | 3390 | O | HOH | 20 | -10.932 | 8.587 | 24.215 | 1.00 22.02 | 1DIK3482 |
| HETATM | 3391 | O | HOH | 21 | -3.698 | 27.479 | 12.828 | 1.00 22.24 | 1DIK3483 |
| HETATM | 3392 | O | HOH | 22 | -9.209 | 6.732 | 23.045 | 1.00 22.35 | 1DIK3484 |
| HETATM | 3393 | O | HOH | 23 | -11.843 | 33.526 | 16.995 | 1.00 22.95 | 1DIK3485 |
| HETATM | 3394 | O | HOH | 24 | -10.730 | 33.322 | 13.268 | 1.00 23.32 | 1DIK3486 |
| HETATM | 3395 | O | HOH | 25 | -5.232 | 6.280 | 25.125 | 1.00 23.99 | 1DIK3487 |
| HETATM | 3396 | O | HOH | 26 | -2.692 | 31.651 | 13.662 | 1.00 24.43 | 1DIK3488 |
| HETATM | 3397 | O | HOH | 27 | 9.007 | 7.301 | 10.872 | 1.00 24.65 | 1DIK3489 |
| HETATM | 3398 | O | HOH | 28 | 4.550 | 15.458 | 32.235 | 1.00 24.79 | 1DIK3490 |
| HETATM | 3399 | O | HOH | 29 | 0.579 | 35.238 | 22.968 | 1.00 24.95 | 1DIK3491 |
| HETATM | 3400 | O | HOH | 30 | 0.056 | 10.426 | 25.818 | 1.00 25.40 | 1DIK3492 |
| HETATM | 3401 | O | HOH | 31 | 2.362 | 9.432 | 24.562 | 1.00 26.19 | 1DIK3493 |
| HETATM | 3402 | O | HOH | 32 | 8.504 | 5.960 | 17.071 | 1.00 26.33 | 1DIK3494 |
| HETATM | 3403 | O | HOH | 33 | -3.535 | 16.451 | 2.757 | 1.00 26.46 | 1DIK3495 |
| HETATM | 3404 | O | HOH | 34 | 1.506 | 9.018 | 33.598 | 1.00 26.96 | 1DIK3496 |
| HETATM | 3405 | O | HOH | 35 | -18.820 | 19.116 | 20.350 | 1.00 27.18 | 1DIK3497 |
| HETATM | 3406 | O | HOH | 36 | 8.399 | 9.350 | 9.458 | 1.00 27.24 | 1DIK3498 |
| HETATM | 3407 | O | HOH | 37 | -9.061 | 36.957 | 6.577 | 1.00 27.38 | 1DIK3599 |
| HETATM | 3408 | O | HOH | 38 | -12.921 | 16.340 | 9.063 | 1.00 27.46 | 1DIK3500 |
| HETATM | 3409 | O | HOH | 39 | -12.574 | 24.639 | 28.242 | 1.00 27.73 | 1DIK3501 |
| HETATM | 3410 | O | HOH | 40 | -12.507 | 26.784 | 33.545 | 1.00 27.75 | 1DIK3502 |
| HETATM | 3411 | O | HOH | 41 | -7.187 | 31.641 | 12.393 | 1.00 27.85 | 1DIK3503 |
| HETATM | 3412 | O | HOH | 42 | 10.571 | 32.202 | 19.033 | 1.00 28.02 | 1DIK3504 |

FIG. 8-53

| | | | | | | | | | | |
|---|---|---|---|---|---|---|---|---|---|---|
| HETATM | 3413 | O | HOH | 43 | 8.426 | 35.536 | 30.142 | 1.00 | 28.34 | 1DIK3505 |
| HETATM | 3414 | O | HOH | 44 | -6.691 | 36.766 | 30.786 | 1.00 | 28.87 | 1DIK3506 |
| HETATM | 3415 | O | HOH | 45 | 12.389 | 22.580 | 30.279 | 1.00 | 29.03 | 1DIK3507 |
| HETATM | 3416 | O | HOH | 46 | -16.222 | 15.844 | 27.511 | 1.00 | 29.03 | 1DIK3508 |
| HETATM | 3417 | O | HOH | 47 | -10.420 | 13.136 | 6.619 | 1.00 | 29.13 | 1DIK3509 |
| HETATM | 3418 | O | HOH | 48 | 6.987 | 21.974 | 38.216 | 1.00 | 29.26 | 1DIK3510 |
| HETATM | 3419 | O | HOH | 49 | -17.438 | 17.382 | 24.990 | 1.00 | 29.33 | 1DIK3511 |
| HETATM | 3420 | O | HOH | 50 | -22.489 | 30.175 | 17.758 | 1.00 | 29.51 | 1DIK3512 |
| HETATM | 3421 | O | HOH | 51 | -2.152 | 40.434 | 32.506 | 1.00 | 29.67 | 1DIK3513 |
| HETATM | 3422 | O | HOH | 52 | -10.794 | 11.992 | 11.258 | 1.00 | 29.84 | 1DIK3514 |
| HETATM | 3423 | O | HOH | 53 | -5.062 | 39.959 | 28.886 | 1.00 | 29.89 | 1DIK3515 |
| HETATM | 3424 | O | HOH | 54 | -19.008 | 30.051 | 23.934 | 1.00 | 29.97 | 1DIK3516 |
| HETATM | 3425 | O | HOH | 55 | 14.324 | 12.475 | 22.179 | 1.00 | 29.97 | 1DIK3517 |
| HETATM | 3426 | O | HOH | 56 | -15.744 | 47.285 | 28.530 | 1.00 | 29.97 | 1DIK3518 |
| HETATM | 3427 | O | HOH | 57 | -2.017 | 21.298 | 33.876 | 1.00 | 30.51 | 1DIK3519 |
| HETATM | 3428 | O | HOH | 58 | -10.164 | 23.699 | 27.468 | 1.00 | 30.66 | 1DIK3520 |
| HETATM | 3429 | O | HOH | 59 | 21.068 | 30.466 | 19.064 | 1.00 | 30.86 | 1DIK3521 |
| HETATM | 3430 | O | HOH | 60 | 15.633 | 26.247 | 25.288 | 1.00 | 31.46 | 1DIK3522 |
| HETATM | 3431 | O | HOH | 61 | 2.539 | 13.006 | 3.675 | 1.00 | 31.51 | 1DIK3523 |
| HETATM | 3432 | O | HOH | 62 | 0.718 | 11.503 | 8.049 | 1.00 | 31.69 | 1DIK3524 |
| HETATM | 3433 | O | HOH | 63 | 6.296 | 32.820 | 36.174 | 1.00 | 31.69 | 1DIK3525 |
| HETATM | 3434 | O | HOH | 64 | -6.588 | 42.450 | 32.884 | 1.00 | 31.91 | 1DIK3526 |
| HETATM | 3435 | O | HOH | 65 | 2.321 | 35.791 | 25.121 | 1.00 | 32.04 | 1DIK3527 |
| HETATM | 3436 | O | HOH | 66 | -11.516 | 36.087 | 6.335 | 1.00 | 32.59 | 1DIK3528 |
| HETATM | 3437 | O | HOH | 67 | -25.724 | 25.284 | 29.618 | 1.00 | 32.59 | 1DIK3529 |
| HETATM | 3438 | O | HOH | 68 | -18.133 | 26.391 | 31.970 | 1.00 | 32.62 | 1DIK3530 |
| HETATM | 3439 | O | HOH | 69 | -14.947 | 45.064 | 46.354 | 1.00 | 33.42 | 1DIK3531 |
| HETATM | 3440 | O | HOH | 70 | 21.082 | 26.576 | 25.533 | 1.00 | 33.44 | 1DIK3532 |
| HETATM | 3441 | O | HOH | 71 | 11.263 | 14.005 | 39.063 | 1.00 | 33.76 | 1DIK3533 |
| HETATM | 3442 | O | HOH | 72 | 6.695 | 36.561 | 26.464 | 1.00 | 33.92 | 1DIK3534 |
| HETATM | 3443 | O | HOH | 73 | -5.225 | 27.878 | -1.684 | 1.00 | 34.01 | 1DIK3535 |
| HETATM | 3444 | O | HOH | 74 | -0.802 | 9.860 | -0.093 | 1.00 | 34.16 | 1DIK3536 |
| HETATM | 3445 | O | HOH | 75 | -12.291 | 22.260 | 29.152 | 1.00 | 34.19 | 1DIK3537 |
| HETATM | 3446 | O | HOH | 76 | 9.096 | 28.265 | 3.852 | 1.00 | 35.19 | 1DIK3538 |
| HETATM | 3447 | O | HOH | 77 | 14.838 | 41.703 | 18.071 | 1.00 | 35.41 | 1DIK3539 |
| HETATM | 3448 | O | HOH | 78 | 7.786 | 14.132 | 5.764 | 1.00 | 35.54 | 1DIK3540 |
| HETATM | 3449 | O | HOH | 79 | 14.772 | 24.028 | 31.196 | 1.00 | 35.79 | 1DIK3541 |
| HETATM | 3450 | O | HOH | 80 | -6.978 | 43.656 | 22.677 | 1.00 | 35.90 | 1DIK3542 |
| HETATM | 3451 | O | HOH | 81 | -10.032 | 8.600 | 15.243 | 1.00 | 36.00 | 1DIK3543 |
| HETATM | 3452 | O | HOH | 82 | 24.248 | 25.836 | 18.908 | 1.00 | 36.04 | 1DIK3544 |
| HETATM | 3453 | O | HOH | 83 | -9.437 | 28.721 | 1.634 | 1.00 | 36.20 | 1DIK3545 |
| HETATM | 3454 | O | HOH | 84 | -2.779 | 26.774 | 21.988 | 1.00 | 36.25 | 1DIK3546 |
| HETATM | 3455 | O | HOH | 85 | -20.467 | 37.474 | 17.552 | 1.00 | 36.27 | 1DIK3547 |
| HETATM | 3456 | O | HOH | 86 | 8.166 | 29.232 | 31.117 | 1.00 | 36.46 | 1DIK3548 |
| HETATM | 3457 | O | HOH | 87 | -26.538 | 28.576 | 41.161 | 1.00 | 36.47 | 1DIK3549 |
| HETATM | 3458 | O | HOH | 88 | -2.580 | 22.992 | 47.692 | 1.00 | 36.48 | 1DIK3550 |
| HETATM | 3459 | O | HOH | 89 | 12.366 | 14.284 | 9.003 | 1.00 | 36.58 | 1DIK3551 |
| HETATM | 3460 | O | HOH | 90 | -21.790 | 30.576 | 46.190 | 1.00 | 36.67 | 1DIK3552 |
| HETATM | 3461 | O | HOH | 91 | -15.282 | 25.935 | 33.446 | 1.00 | 36.75 | 1DIK3553 |
| HETATM | 3462 | O | HOH | 92 | 14.144 | 14.560 | 25.959 | 1.00 | 36.89 | 1DIK3554 |
| HETATM | 3463 | O | HOH | 93 | -1.689 | 11.245 | 32.455 | 1.00 | 36.99 | 1DIK3555 |
| HETATM | 3464 | O | HOH | 94 | -15.117 | 10.158 | 15.158 | 1.00 | 37.08 | 1DIK3556 |
| HETATM | 3465 | O | HOH | 95 | -14.135 | 46.511 | 18.743 | 1.00 | 37.17 | 1DIK3557 |
| HETATM | 3466 | O | HOH | 96 | -4.814 | 10.202 | 6.231 | 1.00 | 37.24 | 1DIK3558 |
| HETATM | 3467 | O | HOH | 97 | 7.946 | 31.148 | 35.040 | 1.00 | 37.53 | 1DIK3559 |
| HETATM | 3468 | O | HOH | 98 | -6.586 | 41.003 | 26.383 | 1.00 | 37.57 | 1DIK3560 |
| HETATM | 3469 | O | HOH | 99 | -19.902 | 18.883 | 33.687 | 1.00 | 37.74 | 1DIK3561 |
| HETATM | 3470 | O | HOH | 100 | -18.028 | 40.102 | 50.822 | 1.00 | 37.89 | 1DIK3562 |
| HETATM | 3471 | O | HOH | 101 | -13.315 | 28.183 | 35.513 | 1.00 | 38.10 | 1DIK3563 |
| HETATM | 3472 | O | HOH | 102 | -28.008 | 45.248 | 30.179 | 1.00 | 38.86 | 1DIK3564 |
| HETATM | 3473 | O | HOH | 103 | 0.486 | 39.943 | 46.308 | 1.00 | 39.11 | 1DIK3565 |
| HETATM | 3474 | O | HOH | 104 | -2.576 | 4.959 | 28.921 | 1.00 | 39.13 | 1DIK3566 |
| HETATM | 3475 | O | HOH | 105 | -25.042 | 47.163 | 37.757 | 1.00 | 39.65 | 1DIK3567 |
| HETATM | 3476 | O | HOH | 106 | -13.645 | 35.978 | 48.302 | 1.00 | 40.20 | 1DIK3568 |
| HETATM | 3477 | O | HOH | 107 | 14.699 | 38.630 | 20.218 | 1.00 | 40.52 | 1DIK3569 |

FIG. 8-54

```
HETATM 3478 O   HOH 108   -8.278 44.086 42.473 1.00 41.00    1DIK3570
HETATM 3479 O   HOH 109   -5.494 11.036 32.617 1.00 42.26    1DIK3571
HETATM 3480 O   HOH 110    9.842 15.499 12.296 1.00 43.26    1DIK3572
HETATM 3481 O   HOH 111  -16.929 18.595 14.159 1.00 43.73    1DIK3573
HETATM 3482 O   HOH 112   -2.958 42.099 16.177 1.00 43.99    1DIK3574
HETATM 3483 O   HOH 113  -20.129 25.973 11.583 1.00 44.43    1DIK3575
HETATM 3484 O   HOH 114    8.119 26.656 -2.650 1.00 44.66    1DIK3576
HETATM 3485 O   HOH 115   17.556 35.041  8.367 1.00 45.27    1DIK3577
HETATM 3486 S   SO4 201   18.476 17.347 10.473 1.00 98.34    1DIK3578
HETATM 3487 O1  SO4 201   17.123 18.013 10.311 1.00 96.57    1DIK3579
HETATM 3488 O2  SO4 201   18.756 16.524  9.233 1.00 97.48    1DIK3580
HETATM 3489 O3  SO4 201   18.472 16.383 11.631 1.00 95.71    1DIK3581
HETATM 3490 O4  SO4 201   19.535 18.422 10.640 1.00 95.40    1DIK3582
CONECT 3486 3490 3489 3488 3487                              1DIK3583
CONECT 3487 3486                                             1DIK3584
CONECT 3488 3486                                             1DIK3585
CONECT 3489 3486                                             1DIK3586
CONECT 3490 3486                                             1DIK3587
MASTER    46    0    1    0    0    0    0 3488    1    5   34 1DIK3588
END                                                          1DIK3589
```

FIG. 8-55

PRIMER SET A

| PRIMER Q27L s  | 5' | CAT | CTA | TGG | GGC | CTG | TAC | TCG | CCA | TTC | 3' |
|---|---|---|---|---|---|---|---|---|---|---|---|
| PRIMER Q27L as | 3' | GTA | GAT | ACC | CCG | GAC | ATG | AGC | GGT | AAG | 5' |
|  |  | H | L | W | G | $L_{27}$ | Y | S | P | F |  |

PRIMER SET B

| PRIMER Q274L s  | 5' | TAC | AAC | TAC | CTT | CTG | TCC | TTG | GGC | AAG | 3' |
|---|---|---|---|---|---|---|---|---|---|---|---|
| PRIMER Q274L as | 3' | ATG | TTG | ATG | GAA | GAC | AGG | AAC | CCG | TTC | 5' |
|  |  | Y | N | Y | L | $L_{274}$ | S | L | G | K |  |

PRIMER SET C

| PRIMER G277D s  | 5' | CTT | CAG | TCC | TTG | GAC | AAG | TAC | TAC | GGC | 3' |
|---|---|---|---|---|---|---|---|---|---|---|---|
| PRIMER G277D as | 3' | GAA | GTC | AGG | AAC | CTG | TTC | ATG | ATG | CCG | 5' |
|  |  | L | Q | S | L | $D_{277}$ | K | Y | Y | G |  |

PRIMER SET D

| PRIMER G277D* s  | 5' | CTT | CTG | TCC | TTG | GAC | AAG | TAC | TAC | GGC | 3' |
|---|---|---|---|---|---|---|---|---|---|---|---|
| PRIMER G277D* as | 3' | GAA | GAC | AGG | AAC | CTG | TTC | ATG | ATG | CCG | 5' |
|  |  | L | $L_{274}$ | S | L | $D_{277}$ | K | Y | Y | G |  |

PRIMER SET E

| PRIMER N340S s  | 5' | TTT | TCA | CAC | GAC | AGC | AGC | ATG | GTT | TCC | 3' |
|---|---|---|---|---|---|---|---|---|---|---|---|
| PRIMER N340S as | 3' | AAA | AGT | GTG | CTG | TCG | TCG | TAC | CAA | AGG | 5' |
|  |  | F | S | H | D | $S_{340}$ | S | M | V | I |  |

FIG. 14a-1

PRIMER SET F

| PRIMER G277K s | 5' | C CTT CAG TCC TTG A̲A̲G̲ AAG TAC TAC GGC TAC | 3' |
|---|---|---|---|
| PRIMER G277K as | 3' | G GAA GTC AGG AAC T̲T̲C̲ TTC ATG ATG CCG ATG | 5' |

L    Q    S    L   $K_{277}$  K    Y    Y    G    Y

PRIMER SET G

| PRIMER A205E s | 5' | GGA GAT GAG GTT G̲AG GCC AAT TTC ACT G | 3' |
|---|---|---|---|
| PRIMER A205E as | 3' | CCT CTA CTC CAA C̲TC CGG TTA AAG TGA C | 5' |

G    D    E    V   $E_{205}$  A    N    F    T

PRIMER SET H

| PRIMER Y282H s | 5' | AAG TAC TAC GGC C̲AC GGC GCA GGC AAC | 3' |
|---|---|---|---|
| PRIMER Y282H as | 3' | TTC ATG ATG CCG G̲TG CCG CGT CCG TTG | 5' |

K    Y    Y    G   $H_{282}$  G    A    G    N

PRIMER SET I

| PRIMER AvrII s | 5' | GAT ACG GTA GAC̲ C̲TA̲ G̲GG TAC CAG TGC | 3' |
|---|---|---|---|
| PRIMER AvrII as | 3' | CTA TGC CAT CTG̲ G̲AT̲ C̲CC ATG GTC ACG | 5' |

D    T    V    D    L    G    Y    Q    C

PRIMER SET J

| PRIMER S66D s | 5' | CGG TAC CCA ACC G̲AT̲ TCG AAG AGC AAA AAG | 3' |
|---|---|---|---|
| PRIMER S66D as | 3' | GCC ATG GGT TGG C̲TA̲ AGC TTC TCG TTT TTC | 5' |

R    Y    P    T   $D_{66}$  S    K    S    K    K

PRIMER SET K

| PRIMER S140Y/D141G s | 5' | GC GCC TCA GGC T̲AC̲ G̲GC CGG GTT ATT GC | 3' |
|---|---|---|---|
| PRIMER S140Y/D141G as | 3' | CG CGG AGT CCG A̲TG̲ C̲CG GCC CAA TAA CG | 5' |

PRIMER SET L

PRIMER S130N s     5'    CTG GCG CGC AAT GTG GTG CCG TTT ATT C   3'

PRIMER S130N as    3'    GAC CGC GCG TTA CAC CAC GGC AAA TAA G   5'

L   A   R   $N_{130}$ V   V   P   F   I

PRIMER SET M

PRIMER R129L/S130N s     5'    GCT CTG GCG CTC AAT GTG GTG CCG TTT ATT C   3'

PRIMER R129L/S130N as    3'    CGA GAC CGC GAG TTA CAC CAC GGC AAA TAA G   5'

A   L   A   $L_{129}$ $N_{130}$V   V   P   F   I

PRIMER SET N

PRIMER K167G/R168Q s     5'    GAC CAT GGC TCC GGA CAA GCT ACG CCA G   3'

PRIMER K167G/R168Q as    3'    CTG GTA CCG AGG CCT GTT CGA TGC GGT C   5'

PRIMER SET O
FumG27-s   5' - CTA GGG TAC CAG TGC TCC CCT GCG ACT TCT CAT CTA TGG GGC GGA TAC TCG CCA TTC TTT TCG C - 3'
FumG27-as  3' -    CC ATG GTC ACG AGG GGA CGC TGA AGA GTA GAT ACC CCG CCT ATG AGC GGT AAG AAA AGC GAG CT - 5'

PRIMER SET P
FumV27-s   5' - CTA GGG TAC CAG TGC TCC CCT GCG ACT TCT CAT CTA TGG GGC GTG TAC TCG CCA TTC TTT TCG C - 3'
FumV27-as  3' -    CC ATG GTC ACG AGG GGA CGC TGA AGA GTA GAT ACC CCG CAC ATG AGC GGT AAG AAA AGC GAG CT - 5'

PRIMER SET Q
FumN27-s   5' - CTA GGG TAC CAG TGC TCC CCT GCG ACT TCT CAT CTA TGG GGC AAC TAC TCG CCA TTC TTT TCG C - 3'
FumN27-as  3' -    CC ATG GTC ACG AGG GGA CGC TGA AGA GTA GAT ACC CCG TTG ATG AGC GGT AAG AAA AGC GAG CT - 5'

PRIMER SET R
FumI27-s   5' - CTA GGG TAC CAG TGC TCC CCT GCG ACT TCT CAT CTA TGG GGC ATC TAC TCG CCA TTC TTT TCG C - 3'
FumI27-as  3' -    CC ATG GTC ACG AGG GGA CGC TGA AGA GTA GAT ACC CCG TAG ATG AGC GGT AAG AAA AGC GAG CT - 5'

PRIMER SET S
FumA27-s   5' - CTA GGG TAC CAG TGC TCC CCT GCG ACT TCT CAT CTA TGG GGC GCG TAC TCG CCA TTC TTT TCG C - 3'
FumA27-as  3' -    CC ATG GTC ACG AGG GGA CGC TGA AGA GTA GAT ACC CCG CGC ATG AGC GGT AAG AAA AGC GAG CT - 5'

PRIMER SET T
FumT27-s   5' - CTA GGG TAC CAG TGC TCC CCT GCG ACT TCT CAT CTA TGG GGC ACG TAC TCG CCA TTC TTT TCG C - 3'
FumgT27-as 3' -    CC ATG GTC ACG AGG GGA CGC TGA AGA GTA GAT ACC CCG TGC ATG AGC GGT AAG AAA AGC GAG CT - 5'

FIG. 14b

```
                                                                              80
  1 MVTLTFLLSA AYLLSGRVSA APSS-----A GSKSCDTVDL GYQCSPATSH LWGQYSPFFS LEDELSVSSK LPKDCRITLV
#13073 .......... .......... .......... .......... .......... .......... .......... ..........
#32722 .......... .......... .......... .......... .......... .......... .......... ..........
#58128 .......... .......... ----...... .......... .......... .......... .......... ..........
#26906 .......... .......... ----...... .......... .......... .......... .......... ..........
#32239 .GA....... V M....-.AG ....GCSAGS ....A....E ....G..... .......... ......D... ....V.F...

81 QVLSRHGARY PTSSKSKKYK KLVTAIQANA TDFKGKFAFL KTYNYTLGAD DLTPFGEQQL VNSGIKFYQR YKALARSVVP  160
#13073 .......... .......... .......... .......... .......... .......... .......... ..........
#32722 .......... .......... .......... .......... .......... ......A... .......... ..........
#58128 .......... ....A..... .......... .......... .......... .......... .......... ..........
#26906 .......... .......... .......... .......... ....E..... .......... .......... ..........
#32239 .......... .......... .......... .......... .......... .......... ......M... ......K...G

161 FIRASGSDRV IASGEKFIEG FQQAKLADPG ATNRAAPAIS VIIPESETFN NTLDHGVCTK FEASQLGDEV AANFTALFAP  240
#13073 .......... .......... .......... .......... .......... .......... .......... ..........
#32722 .......... .......... .......... ...NV..... .......... .......... .......... ..........
#58128 ...S...... .......... .......... .......... .......... ....Y..... .......... ..........
#26906 .......... .......... .......... .......... .......... ......S..N .......... ..........
#32239 .......... .......... .......... .......... .......... .......... .......E.. ..........

241 DIRARAEKHL PGVTLTDEDV VSLMDMCSFD TVARTSDASQ LSPFCQLFTH NEWKKYNYLQ SLGKYYGYGA GNPLGPAQGI  320
#13073 .......... .......... .......... .......... .......... .......... .......... ..........
#32722 .......... .......... .......... .......... .......... .......... .......... ..........
#58128 ......K... .......... .......... .......... .......... .......... .......... ..........
#26906 ....I..... ...Q...D.. .......... .......... .......... ....AI.... .......... ..........
#32239 A......... .......... .......... ....A....E .......... .......D.. .......... ..........
```

FIG. 23-1

```
                                                                    400
      321
#13073 GFTNELIARL TRSPVQDHTS TNSTLVSNPA TFPLNATMYV DFSHDNSMVS IFFALGLYNG TEPLSRTSVE SAKELDGYSA
#32722 .......... .......... .......... .......... .......... .......... .......G.. ..........
#58128 .......... .......... .......... .......... .......... .......... .......... ..........
#26906 .......... .......N.. .......... .....D.D.. .......I.. .......... .......... ..........
#32239 .......... .......... .......... .......... ......G.IP .....M.... .....Q..E. .T..SN....

470
      401
#13073 SWVVPFGARA YFETMQCKSE KEPLVRALIN DRVVPLHGCD VDKLGRCKLN DFVKGLSWAR SGGNWGECFS
#32722 .......... .......... .......... .......... .......... .......... ..........
#58128 .......... .......... ...S...... .......... .......... .......... ..........
#26906 .......... .......... .......... .......... .......... .......... ..........
#32239 ...A...... .......... .......... ......A... .......K.. .......... ....SEQS..
```

FIG. 23-2

SEQUENCE LISTING

```
<160> NUMBER OF SEQ ID NOS: 82

<210> SEQ ID NO 1
<211> LENGTH: 444
<212> TYPE: PRT
<213> ORGANISM: Aspergillus niger

<400> SEQUENCE: 1

Ala Ser Arg Asn Gln Ser Ser Cys Asp Thr Val Asp Gln Gly Tyr Gln
  1               5                  10                  15

Cys Phe Ser Glu Thr Ser His Leu Trp Gly Gln Tyr Ala Pro Phe Phe
             20                  25                  30

Ser Leu Ala Asn Glu Ser Val Ile Ser Pro Glu Val Pro Ala Gly Cys
         35                  40                  45

Arg Val Thr Phe Ala Gln Val Leu Ser Arg His Gly Ala Arg Tyr Pro
     50                  55                  60

Thr Asp Ser Lys Gly Lys Lys Tyr Ser Ala Leu Ile Glu Glu Ile Gln
 65                  70                  75                  80

Gln Asn Ala Thr Thr Phe Asp Gly Lys Tyr Ala Phe Leu Lys Thr Tyr
                 85                  90                  95

Asn Tyr Ser Leu Gly Ala Asp Asp Leu Thr Pro Phe Gly Glu Gln Glu
            100                 105                 110

Leu Val Asn Ser Gly Ile Lys Phe Tyr Gln Arg Tyr Glu Ser Leu Thr
        115                 120                 125

Arg Asn Ile Val Pro Phe Ile Arg Ser Ser Gly Ser Ser Arg Val Ile
    130                 135                 140

Ala Ser Gly Lys Lys Phe Ile Glu Gly Phe Gln Ser Thr Lys Leu Lys
145                 150                 155                 160

Asp Pro Arg Ala Gln Pro Gly Gln Ser Ser Pro Lys Ile Asp Val Val
                165                 170                 175

Ile Ser Glu Ala Ser Ser Ser Asn Asn Thr Leu Asp Pro Gly Thr Cys
            180                 185                 190

Thr Val Phe Glu Asp Ser Glu Leu Ala Asp Thr Val Glu Ala Asn Phe
        195                 200                 205

Thr Ala Thr Phe Val Pro Ser Ile Arg Gln Arg Leu Glu Asn Asp Leu
    210                 215                 220

Ser Gly Val Thr Leu Thr Asp Thr Glu Val Thr Tyr Leu Met Asp Met
225                 230                 235                 240

Cys Ser Phe Asp Thr Ile Ser Thr Ser Thr Val Asp Thr Lys Leu Ser
                245                 250                 255

Pro Phe Cys Asp Leu Phe Thr His Asp Glu Trp Ile Asn Tyr Asp Tyr
            260                 265                 270

Leu Gln Ser Leu Lys Lys Tyr Tyr Gly His Gly Ala Gly Asn Pro Leu
        275                 280                 285

Gly Pro Thr Gln Gly Val Gly Tyr Ala Asn Glu Leu Ile Ala Arg Leu
    290                 295                 300
```

```
Thr His Ser Pro Val His Asp Asp Thr Ser Ser Asn His Thr Leu Asp
305                 310                 315                 320

Ser Ser Pro Ala Thr Phe Pro Leu Asn Ser Thr Leu Tyr Ala Asp Phe
            325                 330                 335

Ser His Asp Asn Gly Ile Ile Ser Ile Leu Phe Ala Leu Gly Leu Tyr
            340                 345                 350

Asn Gly Thr Lys Pro Leu Ser Thr Thr Val Glu Asn Ile Thr Gln
            355                 360                 365

Thr Asp Gly Phe Ser Ser Ala Trp Thr Val Pro Phe Ala Ser Arg Leu
370                 375                 380

Tyr Val Glu Met Met Gln Cys Gln Ala Glu Gln Pro Leu Val Arg
385                 390                 395                 400

Val Leu Val Asn Asp Arg Val Val Pro Leu His Gly Cys Pro Val Asp
                405                 410                 415

Ala Leu Gly Arg Cys Thr Arg Asp Ser Phe Val Arg Gly Leu Ser Phe
            420                 425                 430

Ala Arg Ser Gly Gly Asp Trp Ala Glu Cys Phe Ala
435                 440
```

<210> SEQ ID NO 2
<211> LENGTH: 438
<212> TYPE: PRT
<213> ORGANISM: Aspergillus terreus

<400> SEQUENCE: 2

```
Ser Asp Cys Thr Ser Val Asp Arg Gly Tyr Gln Cys Phe Pro Glu Leu
1               5                   10                  15

Ser His Lys Trp Gly Leu Tyr Ala Pro Tyr Phe Ser Leu Gln Asp Glu
                20                  25                  30

Ser Phe Pro Leu Asp Val Pro Asp Cys His Ile Thr Phe Val
            35                  40                  45

Gln Val Leu Ala Arg His Gly Ala Arg Ser Pro Thr Asp Ser Lys Thr
50                  55                  60

Lys Ala Tyr Ala Ala Thr Ile Ala Ala Ile Gln Lys Asn Ala Thr Ala
65                  70                  75                  80

Leu Pro Gly Lys Tyr Ala Phe Leu Lys Ser Tyr Asn Tyr Ser Met Gly
                85                  90                  95

Ser Glu Asn Leu Thr Pro Phe Gly Arg Asn Gln Leu Gln Asp Leu Gly
            100                 105                 110

Ala Gln Phe Tyr Arg Arg Tyr Asp Thr Leu Thr Arg His Ile Asn Pro
            115                 120                 125

Phe Val Arg Ala Ala Asp Ser Ser Arg Val His Glu Ser Ala Glu Lys
130                 135                 140

Phe Val Glu Gly Phe Gln Asn Ala Arg Gln Gly Asp Pro His Ala Asn
145                 150                 155                 160

Pro His Gln Pro Ser Pro Arg Val Asp Val Ile Pro Glu Gly Thr
            165                 170                 175

Ala Tyr Asn Asn Thr Leu Glu His Ser Ile Cys Thr Ala Phe Glu Ala
            180                 185                 190

Ser Thr Val Gly Asp Ala Ala Asp Asn Phe Thr Ala Val Phe Ala
            195                 200                 205

Pro Ala Ile Ala Lys Arg Leu Glu Ala Asp Leu Pro Gly Val Gln Leu
210                 215                 220

Ser Ala Asp Asp Val Val Asn Leu Met Ala Met Cys Pro Phe Glu Thr
225                 230                 235                 240
```

```
Val Ser Leu Thr Asp Asp Ala His Thr Leu Ser Pro Phe Cys Asp Leu
            245                 250                 255

Phe Thr Ala Ala Glu Trp Thr Gln Tyr Asn Tyr Leu Leu Ser Leu Asp
            260                 265                 270

Lys Tyr Gly Tyr Gly Gly Asn Pro Leu Gly Pro Val Gln Gly
            275                 280                 285

Val Gly Trp Ala Asn Glu Leu Ile Ala Arg Leu Thr Arg Ser Pro Val
    290                 295                 300

His Asp His Thr Cys Val Asn Asn Thr Leu Asp Ala Asn Pro Ala Thr
305                 310                 315                 320

Phe Pro Leu Asn Ala Thr Leu Tyr Ala Asp Phe Ser His Asp Ser Asn
            325                 330                 335

Leu Val Ser Ile Phe Trp Ala Leu Gly Leu Tyr Asn Gly Thr Lys Pro
            340                 345                 350

Leu Ser Gln Thr Thr Val Glu Asp Ile Thr Arg Thr Asp Gly Tyr Ala
            355                 360                 365

Ala Ala Trp Thr Val Pro Phe Ala Ala Arg Ala Tyr Ile Glu Met Met
    370                 375                 380

Gln Cys Arg Ala Glu Lys Gln Pro Leu Val Arg Val Leu Val Asn Asp
385                 390                 395                 400

Arg Val Met Pro Leu His Gly Cys Ala Val Asp Asn Leu Gly Arg Cys
            405                 410                 415

Lys Arg Asp Asp Phe Val Glu Gly Leu Ser Phe Ala Arg Ala Gly Gly
            420                 425                 430

Asn Trp Ala Glu Cys Phe
            435

<210> SEQ ID NO 3
<211> LENGTH: 439
<212> TYPE: PRT
<213> ORGANISM: Aspergillus fumigatus

<400> SEQUENCE: 3

Ser Lys Ser Cys Asp Thr Val Asp Leu Gly Tyr Gln Cys Ser Pro Ala
1               5                   10                  15

Thr Ser His Leu Trp Gly Gln Tyr Ser Pro Phe Phe Ser Leu Glu Asp
            20                  25                  30

Glu Leu Ser Val Ser Ser Lys Leu Pro Lys Asp Cys Arg Ile Thr Leu
        35                  40                  45

Val Gln Val Leu Ser Arg His Gly Ala Arg Tyr Pro Thr Ser Ser Lys
    50                  55                  60

Ser Lys Lys Tyr Lys Lys Leu Val Thr Ala Ile Gln Ala Asn Ala Thr
65                  70                  75                  80

Asp Phe Lys Gly Lys Phe Ala Phe Leu Lys Thr Tyr Asn Tyr Thr Leu
            85                  90                  95

Gly Ala Asp Asp Leu Thr Pro Phe Gly Glu Gln Gln Leu Val Asn Ser
            100                 105                 110

Gly Ile Lys Phe Tyr Gln Arg Tyr Lys Ala Leu Ala Arg Ser Val Val
            115                 120                 125

Pro Phe Ile Arg Ala Ser Gly Ser Asp Arg Val Ile Ala Ser Gly Glu
    130                 135                 140

Lys Phe Ile Glu Gly Phe Gln Gln Ala Lys Leu Ala Asp Pro Gly Ala
145                 150                 155                 160

Thr Asn Arg Ala Ala Pro Ala Ile Ser Val Ile Ile Pro Glu Ser Glu
```

```
                    165                 170                 175
Thr Phe Asn Asn Thr Leu Asp His Gly Val Cys Thr Lys Phe Glu Ala
            180                 185                 190

Ser Gln Leu Gly Asp Glu Val Ala Ala Asn Phe Thr Ala Leu Phe Ala
        195                 200                 205

Pro Asp Ile Arg Ala Arg Ala Glu Lys His Leu Pro Gly Val Thr Leu
    210                 215                 220

Thr Asp Glu Asp Val Val Ser Leu Met Asp Met Cys Ser Phe Asp Thr
225                 230                 235                 240

Val Ala Arg Thr Ser Asp Ala Ser Gln Leu Ser Pro Phe Cys Gln Leu
            245                 250                 255

Phe Thr His Asn Glu Trp Lys Lys Tyr Asn Tyr Leu Gln Ser Leu Gly
        260                 265                 270

Lys Tyr Tyr Gly Tyr Gly Ala Gly Asn Pro Leu Gly Pro Ala Gln Gly
    275                 280                 285

Ile Gly Phe Thr Asn Glu Leu Ile Ala Arg Leu Thr Arg Ser Pro Val
290                 295                 300

Gln Asp His Thr Ser Thr Asn Ser Thr Leu Val Ser Asn Pro Ala Thr
305                 310                 315                 320

Phe Pro Leu Asn Ala Thr Met Tyr Val Asp Phe Ser His Asp Asn Ser
            325                 330                 335

Met Val Ser Ile Phe Phe Ala Leu Gly Leu Tyr Asn Gly Thr Glu Pro
        340                 345                 350

Leu Ser Arg Thr Ser Val Glu Ser Ala Lys Glu Leu Asp Gly Tyr Ser
    355                 360                 365

Ala Ser Trp Val Val Pro Phe Gly Ala Arg Ala Tyr Phe Glu Thr Met
370                 375                 380

Gln Cys Lys Ser Glu Lys Glu Pro Leu Val Arg Ala Leu Ile Asn Asp
385                 390                 395                 400

Arg Val Val Pro Leu His Gly Cys Asp Val Asp Lys Leu Gly Arg Cys
            405                 410                 415

Lys Leu Asn Asp Phe Val Lys Gly Leu Ser Trp Ala Arg Ser Gly Gly
        420                 425                 430

Asn Trp Gly Glu Cys Phe Ser
        435

<210> SEQ ID NO 4
<211> LENGTH: 1931
<212> TYPE: DNA
<213> ORGANISM: Aspergillus nidulans
<220> FEATURE:
<221> NAME/KEY: CDS
<222> LOCATION: (158)..(205)
<220> FEATURE:
<221> NAME/KEY: CDS
<222> LOCATION: (260)..(1600)

<400> SEQUENCE: 4
tctgtaaccg atagcggacc gactaggcat cgttgatcca caatatctca gacaatgcaa      60
ctcagtcgaa tatgaagggc tacagccagc atttaaatac ggccgtctag gtcgggctcc     120
ggggatgagg aggagcaggc tcgtgttcat tccggtc atg gct ttt ttc acg gtc     175
                                        Met Ala Phe Phe Thr Val
                                          1               5 gct ctt tcg ctt tat tac ttg cta tcg agg tgagatctct acaatatctg         225
Ala Leu Ser Leu Tyr Tyr Leu Leu Ser Arg
         10                  15
```

-continued

```
tctgcttagt tgaattggta cttatctgta caga gtc tct gct cag gcc cca gtg        280
                                    Val Ser Ala Gln Ala Pro Val
                                                     20 gtc cag aat cat tca tgc aat acg gcg gac ggt gga tat caa tgc ttc          328
Val Gln Asn His Ser Cys Asn Thr Ala Asp Gly Gly Tyr Gln Cys Phe
        25                  30                  35 ccc aat gtc tct cat gtt tgg ggt cag tac tcg ccg tac ttc tcc atc          376
Pro Asn Val Ser His Val Trp Gly Gln Tyr Ser Pro Tyr Phe Ser Ile
 40                  45                  50                  55 gag cag gag tca gct atc tct gag gac gtg cct cat ggc tgt gag gtt          424
Glu Gln Glu Ser Ala Ile Ser Glu Asp Val Pro His Gly Cys Glu Val
                 60                  65                  70 acc ttt gtg cag gtg ctc tcg cgg cat ggg gct agg tat ccg aca gag          472
Thr Phe Val Gln Val Leu Ser Arg His Gly Ala Arg Tyr Pro Thr Glu
         75                  80                  85 tcg aag agt aag gcg tac tcg ggg ttg att gaa gca atc cag aag aat          520
Ser Lys Ser Lys Ala Tyr Ser Gly Leu Ile Glu Ala Ile Gln Lys Asn
     90                  95                 100 gct acc tct ttt tgg gga cag tat gct ttt ctg gag agt tat aac tat          568
Ala Thr Ser Phe Trp Gly Gln Tyr Ala Phe Leu Glu Ser Tyr Asn Tyr
105                 110                 115 acc ctc ggc gcg gat gac ttg act atc ttc ggc gag aac cag atg gtt          616
Thr Leu Gly Ala Asp Asp Leu Thr Ile Phe Gly Glu Asn Gln Met Val
120                 125                 130                 135 gat tcg ggt gcc aag ttc tac cga cgg tat aag aat ctc gcc agg aaa          664
Asp Ser Gly Ala Lys Phe Tyr Arg Arg Tyr Lys Asn Leu Ala Arg Lys
                140                 145                 150 aat act cct ttt atc cgt gca tca ggg tct gac cgt gtc gtt gcg tct          712
Asn Thr Pro Phe Ile Arg Ala Ser Gly Ser Asp Arg Val Val Ala Ser
            155                 160                 165 gcg gag aag ttc att aat gga ttt cgc aag gct cag ctc cac gac cat          760
Ala Glu Lys Phe Ile Asn Gly Phe Arg Lys Ala Gln Leu His Asp His
        170                 175                 180 ggc tcc aaa cgt gct acg cca gtt gtc aat gtg att atc cct gaa atc          808
Gly Ser Lys Arg Ala Thr Pro Val Val Asn Val Ile Ile Pro Glu Ile
    185                 190                 195 gat ggg ttt aac aac acc ctg gac cat agc acg tgc gta tct ttt gag          856
Asp Gly Phe Asn Asn Thr Leu Asp His Ser Thr Cys Val Ser Phe Glu
200                 205                 210                 215 aat gat gag cgg gcg gat gaa att gaa gcc aat ttc acg gca att atg          904
Asn Asp Glu Arg Ala Asp Glu Ile Glu Ala Asn Phe Thr Ala Ile Met
                220                 225                 230 gga cct ccg atc cgc aaa cgt ctg gaa aat gac ctc cct ggc atc aaa          952
Gly Pro Pro Ile Arg Lys Arg Leu Glu Asn Asp Leu Pro Gly Ile Lys
            235                 240                 245 ctt aca aac gag aat gta ata tat ttg atg gat atg tgc tct ttc gac         1000
Leu Thr Asn Glu Asn Val Ile Tyr Leu Met Asp Met Cys Ser Phe Asp
        250                 255                 260 acc atg gcg cgc acc gcc cac gga acc gag ctg tct cca ttt tgt gcc         1048
Thr Met Ala Arg Thr Ala His Gly Thr Glu Leu Ser Pro Phe Cys Ala
    265                 270                 275 atc ttc act gaa aag gag tgg ctg cag tac gac tac ctt caa tct cta         1096
Ile Phe Thr Glu Lys Glu Trp Leu Gln Tyr Asp Tyr Leu Gln Ser Leu
280                 285                 290                 295 tca aag tac tac ggc tac ggt gcc gga agc ccc ctt ggc cca gct cag         1144
Ser Lys Tyr Tyr Gly Tyr Gly Ala Gly Ser Pro Leu Gly Pro Ala Gln
                300                 305                 310 gga att ggc ttc acc aac gag ctg att gcc cga cta acg caa tcg ccc         1192
Gly Ile Gly Phe Thr Asn Glu Leu Ile Ala Arg Leu Thr Gln Ser Pro
            315                 320                 325
```

```
gtc cag gac aac aca agc acc aac cac act cta gac tcg aac cca gcc   1240
Val Gln Asp Asn Thr Ser Thr Asn His Thr Leu Asp Ser Asn Pro Ala
        330                 335                 340 aca ttt ccg ctc gac agg aag ctc tac gcc gac ttc tcc cac gac aat   1288
Thr Phe Pro Leu Asp Arg Lys Leu Tyr Ala Asp Phe Ser His Asp Asn
    345                 350                 355 agc atg ata tcg ata ttc ttc gcc atg ggt ctg tac aac ggc acc cag   1336
Ser Met Ile Ser Ile Phe Phe Ala Met Gly Leu Tyr Asn Gly Thr Gln
360                 365                 370                 375 ccg ctg tca atg gat tcc gtg gag tcg atc cag gag atg gac ggt tac   1384
Pro Leu Ser Met Asp Ser Val Glu Ser Ile Gln Glu Met Asp Gly Tyr
                380                 385                 390 gcg gcg tct tgg act gtt ccg ttt ggt gcg agg gct tac ttt gag ctc   1432
Ala Ala Ser Trp Thr Val Pro Phe Gly Ala Arg Ala Tyr Phe Glu Leu
        395                 400                 405 atg cag tgc gag aag aag gag ccg ctt gtg cgg gta tta gtg aat gat   1480
Met Gln Cys Glu Lys Lys Glu Pro Leu Val Arg Val Leu Val Asn Asp
            410                 415                 420 cgc gtt gtt cct ctt cat ggc tgc gca gtt gac aag ttt gga cgg tgc   1528
Arg Val Val Pro Leu His Gly Cys Ala Val Asp Lys Phe Gly Arg Cys
425                 430                 435 act ttg gac gat tgg gta gag ggc ttg aat ttt gca agg agc ggc ggg   1576
Thr Leu Asp Asp Trp Val Glu Gly Leu Asn Phe Ala Arg Ser Gly Gly
440                 445                 450                 455 aac tgg aag act tgt ttt acc cta taaagggcgt tgctcattc ataagtgttg   1630
Asn Trp Lys Thr Cys Phe Thr Leu
                460 tgcaggtata ggaaggttag ggaattagct gtttggcttt actcttatta gaccaagaat  1690 gatttgtttg ttctcaaggc cttctagcat atcgtcaagt gggataaatc acctatcctc  1750 catgtgtagg tgaacccgct cttgcatcaa cctcttgtgt ttcagagtag tttcaccaaa  1810 catatcctcg tgtcctctct tctgctcttc ggtctcatat tacactgttc tctatctata  1870 tcgtcaacaa aactaccacc caaacaccaa atgtcacact ttccagcacg aaatttcttc  1930 g                                                                 1931

<210> SEQ ID NO 5
<211> LENGTH: 16
<212> TYPE: PRT
<213> ORGANISM: Aspergillus nidulans

<400> SEQUENCE: 5

Met Ala Phe Phe Thr Val Ala Leu Ser Leu Tyr Tyr Leu Leu Ser Arg
1               5                   10                  15

<210> SEQ ID NO 6
<211> LENGTH: 447
<212> TYPE: PRT
<213> ORGANISM: Aspergillus nidulans

<400> SEQUENCE: 6

Val Ser Ala Gln Ala Pro Val Gln Asn His Ser Cys Asn Thr Ala
1               5                   10                  15

Asp Gly Gly Tyr Gln Cys Phe Pro Asn Val Ser His Val Trp Gly Gln
                20                  25                  30

Tyr Ser Pro Tyr Phe Ser Ile Glu Gln Glu Ser Ala Ile Ser Glu Asp
            35                  40                  45

Val Pro His Gly Cys Glu Val Thr Phe Val Gln Val Leu Ser Arg His
        50                  55                  60
```

-continued

Gly Ala Arg Tyr Pro Thr Glu Ser Lys Ser Lys Ala Tyr Ser Gly Leu
65                  70                  75                  80

Ile Glu Ala Ile Gln Lys Asn Ala Thr Ser Phe Trp Gly Gln Tyr Ala
                85                  90                  95

Phe Leu Glu Ser Tyr Asn Tyr Thr Leu Gly Ala Asp Asp Leu Thr Ile
            100                 105                 110

Phe Gly Glu Asn Gln Met Val Asp Ser Gly Ala Lys Phe Tyr Arg Arg
        115                 120                 125

Tyr Lys Asn Leu Ala Arg Lys Asn Thr Pro Phe Ile Arg Ala Ser Gly
    130                 135                 140

Ser Asp Arg Val Val Ala Ser Ala Glu Lys Phe Ile Asn Gly Phe Arg
145                 150                 155                 160

Lys Ala Gln Leu His Asp His Gly Ser Lys Arg Ala Thr Pro Val Val
                165                 170                 175

Asn Val Ile Ile Pro Glu Ile Asp Gly Phe Asn Asn Thr Leu Asp His
            180                 185                 190

Ser Thr Cys Val Ser Phe Glu Asn Asp Glu Arg Ala Asp Glu Ile Glu
        195                 200                 205

Ala Asn Phe Thr Ala Ile Met Gly Pro Pro Ile Arg Lys Arg Leu Glu
210                 215                 220

Asn Asp Leu Pro Gly Ile Lys Leu Thr Asn Glu Asn Val Ile Tyr Leu
225                 230                 235                 240

Met Asp Met Cys Ser Phe Asp Thr Met Ala Arg Thr Ala His Gly Thr
                245                 250                 255

Glu Leu Ser Pro Phe Cys Ala Ile Phe Thr Glu Lys Glu Trp Leu Gln
            260                 265                 270

Tyr Asp Tyr Leu Gln Ser Leu Ser Lys Tyr Gly Tyr Gly Ala Gly
        275                 280                 285

Ser Pro Leu Gly Pro Ala Gln Gly Ile Gly Phe Thr Asn Glu Leu Ile
    290                 295                 300

Ala Arg Leu Thr Gln Ser Pro Val Gln Asp Asn Thr Ser Thr Asn His
305                 310                 315                 320

Thr Leu Asp Ser Asn Pro Ala Thr Phe Pro Leu Asp Arg Lys Leu Tyr
                325                 330                 335

Ala Asp Phe Ser His Asp Asn Ser Met Ile Ser Ile Phe Phe Ala Met
            340                 345                 350

Gly Leu Tyr Asn Gly Thr Gln Pro Leu Ser Met Asp Ser Val Glu Ser
        355                 360                 365

Ile Gln Glu Met Asp Gly Tyr Ala Ala Ser Trp Thr Val Pro Phe Gly
    370                 375                 380

Ala Arg Ala Tyr Phe Glu Leu Met Gln Cys Glu Lys Lys Glu Pro Leu
385                 390                 395                 400

Val Arg Val Leu Val Asn Asp Arg Val Val Pro Leu His Gly Cys Ala
                405                 410                 415

Val Asp Lys Phe Gly Arg Cys Thr Leu Asp Asp Trp Val Glu Gly Leu
            420                 425                 430

Asn Phe Ala Arg Ser Gly Gly Asn Trp Lys Thr Cys Phe Thr Leu
        435                 440                 445

<210> SEQ ID NO 7
<211> LENGTH: 1845
<212> TYPE: DNA
<213> ORGANISM: Talaromyces thermophilus
<220> FEATURE:

```
<221> NAME/KEY: CDS
<222> LOCATION: (288)..(335)
<220> FEATURE:
<221> NAME/KEY: CDS
<222> LOCATION: (391)..(1740)

<400> SEQUENCE: 7
```

| | |
|---|---|
| ttccacgctg aaagcctgac tgcgatttcc aagctgcatg caggctgctc aactgcctgc | 60 |
| ttatcttcat cagacgcaga tacacaacct ggtctgtaga tgcacccatg acggacgaac | 120 |
| gcaccgctct cttggcctcc agggacccgg aggtcgaggg cgatgaggtc gcgccctcga | 180 |
| cggcctccca gtccctgttg cagttgagat ctcgctgcga acgtcgaccg cagatatggt | 240 |
| tgtcttcgac gttttctcgc cttcgaggaa gaattgctgc tgtgacg atg agt ctg | 296 |
|                                                                                          Met Ser Leu<br>                                                                                              1 | |

```
ttg ttg ctg gtg ctg tcc ggc ggg ttg gtc gcg tta tag tatgctcctt      345
Leu Leu Leu Val Leu Ser Gly Gly Leu Val Ala Leu
        5                  10                  15 ctctctggtc atattgtttt ctgctaacgt tctcataatt gaagt gtc tca aga aat   402
                                                Val Ser Arg Asn
                                                              20 ccg cat gtt gat agc cac tct tgc aat aca gtg gaa gga ggg tat cag    450
Pro His Val Asp Ser His Ser Cys Asn Thr Val Glu Gly Gly Tyr Gln
                25                  30                  35 tgt cgt cca gaa atc tcc cac tcc tgg ggc cag tat tct cca ttc ttc    498
Cys Arg Pro Glu Ile Ser His Ser Trp Gly Gln Tyr Ser Pro Phe Phe
            40                  45                  50 tcc ctg gca gac cag tcg gag atc tcg cca gat gtc cca cag aac tgc    546
Ser Leu Ala Asp Gln Ser Glu Ile Ser Pro Asp Val Pro Gln Asn Cys
        55                  60                  65 aag att acg ttt gtc cag ctg ctt tct cgt cac ggc gct aga tac cct    594
Lys Ile Thr Phe Val Gln Leu Leu Ser Arg His Gly Ala Arg Tyr Pro
    70                  75                  80 acg tct tcc aag acg gag ctg tat tcg cag ctg atc agt cgg att cag    642
Thr Ser Ser Lys Thr Glu Leu Tyr Ser Gln Leu Ile Ser Arg Ile Gln
85                  90                  95                 100 aag acg gcg act gcg tac aaa ggc tac tat gcc ttc ttg aaa gac tac    690
Lys Thr Ala Thr Ala Tyr Lys Gly Tyr Tyr Ala Phe Leu Lys Asp Tyr
                105                 110                 115 aga tac cag ctg gga gcg aac gac ctg acg ccc ttt ggg gaa aac cag    738
Arg Tyr Gln Leu Gly Ala Asn Asp Leu Thr Pro Phe Gly Glu Asn Gln
            120                 125                 130 atg atc cag ttg ggc atc aag ttt tat aac cat tac aag agt ctc gcc    786
Met Ile Gln Leu Gly Ile Lys Phe Tyr Asn His Tyr Lys Ser Leu Ala
        135                 140                 145 agg aat gcc gtc cca ttc gtt cgt tgc tcc ggc tct gat cgg gtc att    834
Arg Asn Ala Val Pro Phe Val Arg Cys Ser Gly Ser Asp Arg Val Ile
    150                 155                 160 gcc tcg ggg aga ctt ttc atc gaa ggt ttc cag agc gcc aaa gtg ctg    882
Ala Ser Gly Arg Leu Phe Ile Glu Gly Phe Gln Ser Ala Lys Val Leu
165                 170                 175                 180 gat cct cat tca gac aag cat gac gct cct ccc acg atc aac gtg atc    930
Asp Pro His Ser Asp Lys His Asp Ala Pro Pro Thr Ile Asn Val Ile
                185                 190                 195 atc gag gag ggt ccg tcc tac aat aac acg ctc gac acc ggc agc tgt    978
Ile Glu Glu Gly Pro Ser Tyr Asn Asn Thr Leu Asp Thr Gly Ser Cys
            200                 205                 210 cca gtc ttt gag gac agc agc ggg gga cat gac gca cag gaa aag ttc   1026
Pro Val Phe Glu Asp Ser Ser Gly Gly His Asp Ala Gln Glu Lys Phe
        215                 220                 225
```

```
gca aag caa ttc gca cca gct atc ctg gaa aag atc aag gac cat ctt   1074
Ala Lys Gln Phe Ala Pro Ala Ile Leu Glu Lys Ile Lys Asp His Leu
        230                 235                 240 ccc ggc gtg gac ctg gcc gtg tcg gat gta ccg tac ttg atg gac ttg   1122
Pro Gly Val Asp Leu Ala Val Ser Asp Val Pro Tyr Leu Met Asp Leu
245                 250                 255                 260 tgt ccg ttt gag acc ttg gct cgc aac cac aca gac acg ctg tct ccg   1170
Cys Pro Phe Glu Thr Leu Ala Arg Asn His Thr Asp Thr Leu Ser Pro
                265                 270                 275 ttc tgc gct ctt tcc acg caa gag gag tgg caa gca tat gac tac tac   1218
Phe Cys Ala Leu Ser Thr Gln Glu Glu Trp Gln Ala Tyr Asp Tyr Tyr
            280                 285                 290 caa agt ctg ggg aaa tac tat ggc aat ggc ggg ggt aac ccg ttg ggg   1266
Gln Ser Leu Gly Lys Tyr Tyr Gly Asn Gly Gly Gly Asn Pro Leu Gly
        295                 300                 305 cca gcc caa ggc gtg ggg ttt gtc aac gag ttg att gct cgc atg acc   1314
Pro Ala Gln Gly Val Gly Phe Val Asn Glu Leu Ile Ala Arg Met Thr
310                 315                 320 cat agc cct gtc cag gac tac acc acg gtc aac cac act ctt gac tcg   1362
His Ser Pro Val Gln Asp Tyr Thr Thr Val Asn His Thr Leu Asp Ser
325                 330                 335                 340 aat ccg gcg aca ttc cct ttg aac gcg acg ctg tac gca gat ttc agc   1410
Asn Pro Ala Thr Phe Pro Leu Asn Ala Thr Leu Tyr Ala Asp Phe Ser
                345                 350                 355 cac gac aac aca atg acg tca att ttc gcg gcc ttg ggc ctg tac aac   1458
His Asp Asn Thr Met Thr Ser Ile Phe Ala Ala Leu Gly Leu Tyr Asn
            360                 365                 370 ggg acc gcg aag ctg tcc acg acc gag atc aag tcc att gaa gag acg   1506
Gly Thr Ala Lys Leu Ser Thr Thr Glu Ile Lys Ser Ile Glu Glu Thr
        375                 380                 385 gac ggc tac tcg gcg gcg tgg acc gtt ccg ttc ggg ggg cga gcc tat   1554
Asp Gly Tyr Ser Ala Ala Trp Thr Val Pro Phe Gly Gly Arg Ala Tyr
390                 395                 400 atc gag atg atg cag tgt gat gat tcg gat gag cca gtc gtt cgg gtg   1602
Ile Glu Met Met Gln Cys Asp Asp Ser Asp Glu Pro Val Val Arg Val
405                 410                 415                 420 ctg gtc aac gac cgg gtg gtg cca ctg cat ggc tgc gag gtg gac tcc   1650
Leu Val Asn Asp Arg Val Val Pro Leu His Gly Cys Glu Val Asp Ser
                425                 430                 435 ctg ggg cga tgc aaa cga gac gac ttt gtc agg gga ctg agt ttt gcg   1698
Leu Gly Arg Cys Lys Arg Asp Asp Phe Val Arg Gly Leu Ser Phe Ala
            440                 445                 450 cga cag ggt ggg aac tgg gag ggg tgt tac gct gct tct gag            1740
Arg Gln Gly Gly Asn Trp Glu Gly Cys Tyr Ala Ala Ser Glu
        455                 460                 465 taggtttatt cagcgagttt cgacctttct atccttcaaa cactgcacaa agacacactg  1800
catgaaatgg taacaggcct ggagcgtttt agaaggaaaa aagtt                  1845

<210> SEQ ID NO 8
<211> LENGTH: 15
<212> TYPE: PRT
<213> ORGANISM: Talaromyces thermophilus

<400> SEQUENCE: 8

Met Ser Leu Leu Leu Leu Val Leu Ser Gly Gly Leu Val Ala Leu
 1               5                  10                  15

<210> SEQ ID NO 9
<211> LENGTH: 450
```

```
<212> TYPE: PRT
<213> ORGANISM: Talaromyces thermophilus

<400> SEQUENCE: 9

Val Ser Arg Asn Pro His Val Asp Ser His Ser Cys Asn Thr Val Glu
 1               5                  10                  15

Gly Gly Tyr Gln Cys Arg Pro Glu Ile Ser His Ser Trp Gly Gln Tyr
             20                  25                  30

Ser Pro Phe Phe Ser Leu Ala Asp Gln Ser Glu Ile Ser Pro Asp Val
         35                  40                  45

Pro Gln Asn Cys Lys Ile Thr Phe Val Gln Leu Leu Ser Arg His Gly
     50                  55                  60

Ala Arg Tyr Pro Thr Ser Ser Lys Thr Glu Leu Tyr Ser Gln Leu Ile
 65                  70                  75                  80

Ser Arg Ile Gln Lys Thr Ala Thr Ala Tyr Lys Gly Tyr Tyr Ala Phe
                 85                  90                  95

Leu Lys Asp Tyr Arg Tyr Gln Leu Gly Ala Asn Asp Leu Thr Pro Phe
            100                 105                 110

Gly Glu Asn Gln Met Ile Gln Leu Gly Ile Lys Phe Tyr Asn His Tyr
        115                 120                 125

Lys Ser Leu Ala Arg Asn Ala Val Pro Phe Val Arg Cys Ser Gly Ser
    130                 135                 140

Asp Arg Val Ile Ala Ser Gly Arg Leu Phe Ile Glu Gly Phe Gln Ser
145                 150                 155                 160

Ala Lys Val Leu Asp Pro His Ser Asp Lys His Asp Ala Pro Pro Thr
                165                 170                 175

Ile Asn Val Ile Ile Glu Glu Gly Pro Ser Tyr Asn Asn Thr Leu Asp
            180                 185                 190

Thr Gly Ser Cys Pro Val Phe Glu Asp Ser Ser Gly His Asp Ala
        195                 200                 205

Gln Glu Lys Phe Ala Lys Gln Phe Ala Pro Ala Ile Leu Glu Lys Ile
    210                 215                 220

Lys Asp His Leu Pro Gly Val Asp Leu Ala Val Ser Asp Val Pro Tyr
225                 230                 235                 240

Leu Met Asp Leu Cys Pro Phe Glu Thr Leu Ala Arg Asn His Thr Asp
                245                 250                 255

Thr Leu Ser Pro Phe Cys Ala Leu Ser Thr Gln Glu Glu Trp Gln Ala
            260                 265                 270

Tyr Asp Tyr Tyr Gln Ser Leu Gly Lys Tyr Tyr Gly Asn Gly Gly
        275                 280                 285

Asn Pro Leu Gly Pro Ala Gln Gly Val Gly Phe Val Asn Glu Leu Ile
    290                 295                 300

Ala Arg Met Thr His Ser Pro Val Gln Asp Tyr Thr Thr Val Asn His
305                 310                 315                 320

Thr Leu Asp Ser Asn Pro Ala Thr Phe Pro Leu Asn Ala Thr Leu Tyr
                325                 330                 335

Ala Asp Phe Ser His Asp Asn Thr Met Thr Ser Ile Phe Ala Ala Leu
            340                 345                 350

Gly Leu Tyr Asn Gly Thr Ala Lys Leu Ser Thr Thr Glu Ile Lys Ser
        355                 360                 365

Ile Glu Glu Thr Asp Gly Tyr Ser Ala Ala Trp Thr Val Pro Phe Gly
    370                 375                 380

Gly Arg Ala Tyr Ile Glu Met Met Gln Cys Asp Asp Ser Asp Glu Pro
385                 390                 395                 400
```

-continued

```
Val Val Arg Val Leu Val Asn Asp Arg Val Pro Leu His Gly Cys
            405                 410                 415

Glu Val Asp Ser Leu Gly Arg Cys Lys Arg Asp Asp Phe Val Arg Gly
        420                 425                 430

Leu Ser Phe Ala Arg Gln Gly Gly Asn Trp Glu Gly Cys Tyr Ala Ala
        435                 440                 445

Ser Glu
    450

<210> SEQ ID NO 10
<211> LENGTH: 1571
<212> TYPE: DNA
<213> ORGANISM: Aspergillus fumigatus
<220> FEATURE:
<221> NAME/KEY: CDS
<222> LOCATION: (43)..(90)
<220> FEATURE:
<221> NAME/KEY: CDS
<222> LOCATION: (148)..(1494)

<400> SEQUENCE: 10
agattcaacg acggaggaat cgcaacccta attgtcggta tc atg gtg act ctg       54
                                              Met Val Thr Leu
                                                1 act ttc ctg ctt tcg gcg gcg tat ctg ctt tct ggg tgagtggctt          100
Thr Phe Leu Leu Ser Ala Ala Tyr Leu Leu Ser Gly
  5                  10                  15 ggatctattg ctcggatagg gctgtggtgc tgattctgaa acggagt aga gtg tct     156
                                                    Arg Val Ser gcg gca cct agt tct gct ggc tcc aag tcc tgc gat acg gta gac ctc    204
Ala Ala Pro Ser Ser Ala Gly Ser Lys Ser Cys Asp Thr Val Asp Leu
 20                  25                  30                  35 ggg tac cag tgc tcc cct gcg act tct cat cta tgg ggc cag tac tcg    252
Gly Tyr Gln Cys Ser Pro Ala Thr Ser His Leu Trp Gly Gln Tyr Ser
                 40                  45                  50 cca ttc ttt tcg ctc gag gac gag ctg tcc gtg tcg agt aag ctt ccc    300
Pro Phe Phe Ser Leu Glu Asp Glu Leu Ser Val Ser Ser Lys Leu Pro
         55                  60                  65 aag gat tgc cgg atc acc ttg gta cag gtg cta tcg cgc cat gga gcg    348
Lys Asp Cys Arg Ile Thr Leu Val Gln Val Leu Ser Arg His Gly Ala
     70                  75                  80 cgg tac cca acc agc tcc aag agc aaa aag tat aag aag ctt gtg acg    396
Arg Tyr Pro Thr Ser Ser Lys Ser Lys Lys Tyr Lys Lys Leu Val Thr
 85                  90                  95 gcg atc cag gcc aat gcc acc gac ttc aag ggc aag ttt gcc ttt ttg    444
Ala Ile Gln Ala Asn Ala Thr Asp Phe Lys Gly Lys Phe Ala Phe Leu
100                 105                 110                 115 aag acg tac aac tat act ctg ggt gcg gat gac ctc act ccc ttt ggg    492
Lys Thr Tyr Asn Tyr Thr Leu Gly Ala Asp Asp Leu Thr Pro Phe Gly
                120                 125                 130 gag cag cag ctg gtg aac tcg ggc atc aag ttc tac cag agg tac aag    540
Glu Gln Gln Leu Val Asn Ser Gly Ile Lys Phe Tyr Gln Arg Tyr Lys
        135                 140                 145 gct ctg gcg cgc agt gtg gtg ccg ttt att cgc gcc tca ggc tcg gac    588
Ala Leu Ala Arg Ser Val Val Pro Phe Ile Arg Ala Ser Gly Ser Asp
    150                 155                 160 cgg gtt att gct tcg gga gag aag ttc atc gag ggg ttc cag cag gcg    636
Arg Val Ile Ala Ser Gly Glu Lys Phe Ile Glu Gly Phe Gln Gln Ala
165                 170                 175 aag ctg gct gat cct ggc gcg acg aac cgc gcc gct ccg gcg att agt    684
```

```
Lys Leu Ala Asp Pro Gly Ala Thr Asn Arg Ala Ala Pro Ala Ile Ser
180                 185                 190                 195 gtg att att ccg gag agc gag acg ttc aac aat acg ctg gac cac ggt         732
Val Ile Ile Pro Glu Ser Glu Thr Phe Asn Asn Thr Leu Asp His Gly
            200                 205                 210 gtg tgc acg aag ttt gag gcg agt cag ctg gga gat gag gtt gcg gcc         780
Val Cys Thr Lys Phe Glu Ala Ser Gln Leu Gly Asp Glu Val Ala Ala
            215                 220                 225 aat ttc act gcg ctc ttt gca ccc gac atc cga gct cgc gcc gag aag         828
Asn Phe Thr Ala Leu Phe Ala Pro Asp Ile Arg Ala Arg Ala Glu Lys
            230                 235                 240 cat ctt cct ggc gtg acg ctg aca gac gag gac gtt gtc agt cta atg         876
His Leu Pro Gly Val Thr Leu Thr Asp Glu Asp Val Val Ser Leu Met
245                 250                 255 gac atg tgt tcg ttt gat acg gta gcg cgc acc agc gac gca agt cag         924
Asp Met Cys Ser Phe Asp Thr Val Ala Arg Thr Ser Asp Ala Ser Gln
260                 265                 270                 275 ctg tca ccg ttc tgt caa ctc ttc act cac aat gag tgg aag aag tac         972
Leu Ser Pro Phe Cys Gln Leu Phe Thr His Asn Glu Trp Lys Lys Tyr
            280                 285                 290 aac tac ctt cag tcc ttg ggc aag tac tac ggc tac ggc gca ggc aac        1020
Asn Tyr Leu Gln Ser Leu Gly Lys Tyr Tyr Gly Tyr Gly Ala Gly Asn
            295                 300                 305 cct ctg gga ccg gct cag ggg ata ggg ttc acc aac gag ctg att gcc        1068
Pro Leu Gly Pro Ala Gln Gly Ile Gly Phe Thr Asn Glu Leu Ile Ala
            310                 315                 320 cgg ttg act cgt tcg cca gtg cag gac cac acc agc act aac tcg act        1116
Arg Leu Thr Arg Ser Pro Val Gln Asp His Thr Ser Thr Asn Ser Thr
325                 330                 335 cta gtc tcc aac ccg gcc acc ttc ccg ttg aac gct acc atg tac gtc        1164
Leu Val Ser Asn Pro Ala Thr Phe Pro Leu Asn Ala Thr Met Tyr Val
340                 345                 350                 355 gac ttt tca cac gac aac agc atg gtt tcc atc ttc ttt gca ttg ggc        1212
Asp Phe Ser His Asp Asn Ser Met Val Ser Ile Phe Phe Ala Leu Gly
            360                 365                 370 ctg tac aac ggc act gaa ccc ttg tcc cgg acc tcg gtg aaa agc gcc        1260
Leu Tyr Asn Gly Thr Glu Pro Leu Ser Arg Thr Ser Val Glu Ser Ala
            375                 380                 385 aag gaa ttg gat ggg tat tct gca tcc tgg gtg gtg cct ttc ggc gcg        1308
Lys Glu Leu Asp Gly Tyr Ser Ala Ser Trp Val Val Pro Phe Gly Ala
            390                 395                 400 cga gcc tac ttc gag acg atg caa tgc aag tcg gaa aag gag cct ctt        1356
Arg Ala Tyr Phe Glu Thr Met Gln Cys Lys Ser Glu Lys Glu Pro Leu
405                 410                 415 gtt cgc gct ttg att aat gac cgg gtt gtg cca ctg cat ggc tgc gat        1404
Val Arg Ala Leu Ile Asn Asp Arg Val Val Pro Leu His Gly Cys Asp
420                 425                 430                 435 gtg gac aag ctg ggg cga tgc aag ctg aat gac ttt gtc aag gga ttg        1452
Val Asp Lys Leu Gly Arg Cys Lys Leu Asn Asp Phe Val Lys Gly Leu
            440                 445                 450 agt tgg gcc aga tct ggg ggc aac tgg gga gag tgc ttt agt                1494
Ser Trp Ala Arg Ser Gly Gly Asn Trp Gly Glu Cys Phe Ser
            455                 460                 465 tgagatgtca ttgttatgct atactccaat agaccgttgc ttagccattc acttcacttt     1554
gctcgaaccg cctgccg                                                     1571

<210> SEQ ID NO 11
<211> LENGTH: 16
<212> TYPE: PRT
```

<213> ORGANISM: Aspergillus fumigatus

<400> SEQUENCE: 11

Met Val Thr Leu Thr Phe Leu Leu Ser Ala Ala Tyr Leu Leu Ser Gly
 1               5                  10                  15

<210> SEQ ID NO 12
<211> LENGTH: 449
<212> TYPE: PRT
<213> ORGANISM: Aspergillus fumigatus

<400> SEQUENCE: 12

Arg Val Ser Ala Ala Pro Ser Ser Ala Gly Ser Lys Ser Cys Asp Thr
 1               5                  10                  15

Val Asp Leu Gly Tyr Gln Cys Ser Pro Ala Thr Ser His Leu Trp Gly
                20                  25                  30

Gln Tyr Ser Pro Phe Phe Ser Leu Glu Asp Glu Leu Ser Val Ser Ser
            35                  40                  45

Lys Leu Pro Lys Asp Cys Arg Ile Thr Leu Val Gln Val Leu Ser Arg
    50                  55                  60

His Gly Ala Arg Tyr Pro Thr Ser Ser Lys Ser Lys Tyr Lys Lys
65                  70                  75                  80

Leu Val Thr Ala Ile Gln Ala Asn Ala Thr Asp Phe Lys Gly Lys Phe
                85                  90                  95

Ala Phe Leu Lys Thr Tyr Asn Tyr Thr Leu Gly Ala Asp Asp Leu Thr
            100                 105                 110

Pro Phe Gly Glu Gln Leu Val Asn Ser Gly Ile Lys Phe Tyr Gln
        115                 120                 125

Arg Tyr Lys Ala Leu Ala Arg Ser Val Val Pro Phe Ile Arg Ala Ser
    130                 135                 140

Gly Ser Asp Arg Val Ile Ala Ser Gly Glu Lys Phe Ile Glu Gly Phe
145                 150                 155                 160

Gln Gln Ala Lys Leu Ala Asp Pro Gly Ala Thr Asn Arg Ala Ala Pro
                165                 170                 175

Ala Ile Ser Val Ile Ile Pro Glu Ser Glu Thr Phe Asn Asn Thr Leu
            180                 185                 190

Asp His Gly Val Cys Thr Lys Phe Glu Ala Ser Gln Leu Gly Asp Glu
        195                 200                 205

Val Ala Ala Asn Phe Thr Ala Leu Phe Ala Pro Asp Ile Arg Ala Arg
    210                 215                 220

Ala Glu Lys His Leu Pro Gly Val Thr Leu Thr Asp Glu Asp Val Val
225                 230                 235                 240

Ser Leu Met Asp Met Cys Ser Phe Asp Thr Val Ala Arg Thr Ser Asp
                245                 250                 255

Ala Ser Gln Leu Ser Pro Phe Cys Gln Leu Phe Thr His Asn Glu Trp
            260                 265                 270

Lys Lys Tyr Asn Tyr Leu Gln Ser Leu Gly Lys Tyr Gly Tyr Gly
        275                 280                 285

Ala Gly Asn Pro Leu Gly Pro Ala Gln Gly Ile Gly Phe Thr Asn Glu
    290                 295                 300

Leu Ile Ala Arg Leu Thr Arg Ser Pro Val Gln Asp His Thr Ser Thr
305                 310                 315                 320

Asn Ser Thr Leu Val Ser Asn Pro Ala Thr Phe Pro Leu Asn Ala Thr
                325                 330                 335

Met Tyr Val Asp Phe Ser His Asp Asn Ser Met Val Ser Ile Phe Phe

-continued

```
                340             345             350
Ala Leu Gly Leu Tyr Asn Gly Thr Glu Pro Leu Ser Arg Thr Ser Val
            355                 360                 365

Glu Ser Ala Lys Glu Leu Asp Gly Tyr Ser Ala Ser Trp Val Val Pro
        370                 375                 380

Phe Gly Ala Arg Ala Tyr Phe Glu Thr Met Gln Cys Lys Ser Glu Lys
385                 390                 395                 400

Glu Pro Leu Val Arg Ala Leu Ile Asn Asp Arg Val Val Pro Leu His
                405                 410                 415

Gly Cys Asp Val Asp Lys Leu Gly Arg Cys Lys Leu Asn Asp Phe Val
            420                 425                 430

Lys Gly Leu Ser Trp Ala Arg Ser Gly Gly Asn Trp Gly Glu Cys Phe
        435                 440                 445

Ser
```

<210> SEQ ID NO 13
<211> LENGTH: 1567
<212> TYPE: DNA
<213> ORGANISM: Aspergillus terreus
<220> FEATURE:
<221> NAME/KEY: CDS
<222> LOCATION: (78)..(125)
<220> FEATURE:
<221> NAME/KEY: CDS
<222> LOCATION: (178)..(1527)

<400> SEQUENCE: 13

```
acgtcccagg tcggggacta catccgctat gtggtcctct acttcgtcgg aagaatatac      60
tgtctcttgt ggctacc atg ggg gtt ttc gtc gtt cta tta tct atc gcg        110
                Met Gly Val Phe Val Val Leu Leu Ser Ile Ala
                  1               5                  10 act ctg ttc ggc agg tatgtgcacc gctctaggtt caactcgcct ggtaactgac      165
Thr Leu Phe Gly Arg
            15 aaacagtaca gc aca tcg ggc act gcg ctg ggc ccc cgt gga aat cac agc    216
              Thr Ser Gly Thr Ala Leu Gly Pro Arg Gly Asn His Ser
                                20                  25 gac tgc acc tca gtc gac cgg ggg tat caa tgc ttc cct gag ctc tcc      264
Asp Cys Thr Ser Val Asp Arg Gly Tyr Gln Cys Phe Pro Glu Leu Ser
 30                  35                  40                  45 cat aaa tgg ggt ctc tac gcg ccc tat ttc tcc ctc cag gat gaa tct      312
His Lys Trp Gly Leu Tyr Ala Pro Tyr Phe Ser Leu Gln Asp Glu Ser
                50                  55                  60 ccg ttt cct ctg gac gtc ccg gat gac tgc cac atc acc ttt gtg cag      360
Pro Phe Pro Leu Asp Val Pro Asp Asp Cys His Ile Thr Phe Val Gln
             65                  70                  75 gtg ctg gcc cga cat gga gcg cgg tct cca acc gat agc aag aca aag      408
Val Leu Ala Arg His Gly Ala Arg Ser Pro Thr Asp Ser Lys Thr Lys
         80                  85                  90 gcg tat gcc gcg act att gca gcc atc cag aag aat gcc acc gcg ttg      456
Ala Tyr Ala Ala Thr Ile Ala Ala Ile Gln Lys Asn Ala Thr Ala Leu
     95                 100                 105 ccg ggc aaa tac gcc ttc ctg aag tcg tac aat tac tcc atg ggc tcc      504
Pro Gly Lys Tyr Ala Phe Leu Lys Ser Tyr Asn Tyr Ser Met Gly Ser
110                 115                 120                 125 gag aac ctg aac ccc ttc ggg cgg aac caa ctg caa gat ctg ggc gcc      552
Glu Asn Leu Asn Pro Phe Gly Arg Asn Gln Leu Gln Asp Leu Gly Ala
                130                 135                 140 cag ttc tac cgt cgc tac gac acc ctc acc cgg cac atc aac cct ttc      600
```

```
Gln Phe Tyr Arg Arg Tyr Asp Thr Leu Thr Arg His Ile Asn Pro Phe
            145                 150                 155 gtc cgg gcc gcg gat tcc tcc cgc gtc cac gaa tca gcc gag aag ttc       648
Val Arg Ala Ala Asp Ser Ser Arg Val His Glu Ser Ala Glu Lys Phe
        160                 165                 170 gtc gag ggc ttc caa aac gcc cgc caa ggc gat cct cac gcc aac cct       696
Val Glu Gly Phe Gln Asn Ala Arg Gln Gly Asp Pro His Ala Asn Pro
    175                 180                 185 cac cag ccg tcg ccg cgc gtg gat gta gtc atc ccc gaa ggc acc gcc       744
His Gln Pro Ser Pro Arg Val Asp Val Val Ile Pro Glu Gly Thr Ala
190                 195                 200                 205 tac aac aac acg ctc gag cac agc atc tgc acc gcc ttc gag gcc agc       792
Tyr Asn Asn Thr Leu Glu His Ser Ile Cys Thr Ala Phe Glu Ala Ser
                210                 215                 220 acc gtc ggc gac gcc gcg gca gac aac ttc act gcc gtg ttc gcg ccg       840
Thr Val Gly Asp Ala Ala Ala Asp Asn Phe Thr Ala Val Phe Ala Pro
            225                 230                 235 gcg atc gcc aag cgt ctg gag gcc gat ctc ccc ggc gtg cag ctg tcc       888
Ala Ile Ala Lys Arg Leu Glu Ala Asp Leu Pro Gly Val Gln Leu Ser
        240                 245                 250 gcc gac gac gtg gtc aat ctg atg gcc atg tgt ccg ttc gag acg gtc       936
Ala Asp Asp Val Val Asn Leu Met Ala Met Cys Pro Phe Glu Thr Val
    255                 260                 265 agc ctg acc gac gac gcg cac acg ctg tcg ccg ttc tgc gac ctc ttc       984
Ser Leu Thr Asp Asp Ala His Thr Leu Ser Pro Phe Cys Asp Leu Phe
270                 275                 280                 285 acc gcc gcc gag tgg acg cag tac aac tac ctg ctc tcg ctg gac aag      1032
Thr Ala Ala Glu Trp Thr Gln Tyr Asn Tyr Leu Leu Ser Leu Asp Lys
                290                 295                 300 tac tac ggc tac ggc ggc ggc aat ccg ctg ggc ccc gtg cag ggc gtg      1080
Tyr Tyr Gly Tyr Gly Gly Gly Asn Pro Leu Gly Pro Val Gln Gly Val
            305                 310                 315 ggc tgg gcg aac gag ctg atc gcg cgg ctg acg cgc tcc ccc gtc cac      1128
Gly Trp Ala Asn Glu Leu Ile Ala Arg Leu Thr Arg Ser Pro Val His
        320                 325                 330 gac cac acc tgc gtc aac aac acc ctc gac gcc aac ccg gcc acc ttc      1176
Asp His Thr Cys Val Asn Asn Thr Leu Asp Ala Asn Pro Ala Thr Phe
    335                 340                 345 ccg ctg aac gcc acc ctc tac gcg gac ttt tcg cac gac agt aac ctg      1224
Pro Leu Asn Ala Thr Leu Tyr Ala Asp Phe Ser His Asp Ser Asn Leu
350                 355                 360                 365 gtg tcg atc ttc tgg gcg ctg ggt ctg tac aac ggc acc aag ccc ctg      1272
Val Ser Ile Phe Trp Ala Leu Gly Leu Tyr Asn Gly Thr Lys Pro Leu
                370                 375                 380 tcg cag acc acc gtg gag gat atc acc cgg acg gac ggg tac gcg gcc      1320
Ser Gln Thr Thr Val Glu Asp Ile Thr Arg Thr Asp Gly Tyr Ala Ala
            385                 390                 395 gcc tgg acg gtg ccg ttt gcc gcc cgc gcc tac atc gag atg atg cag      1368
Ala Trp Thr Val Pro Phe Ala Ala Arg Ala Tyr Ile Glu Met Met Gln
        400                 405                 410 tgt cgc gcg gag aag cag ccg ctg gtg cgc gtg ctg gtc aac gac cgt      1416
Cys Arg Ala Glu Lys Gln Pro Leu Val Arg Val Leu Val Asn Asp Arg
    415                 420                 425 gtc atg ccg ctg cac ggc tgc gcg gtg gat aat ctg ggc agg tgt aaa      1464
Val Met Pro Leu His Gly Cys Ala Val Asp Asn Leu Gly Arg Cys Lys
430                 435                 440                 445 cgg gac gac ttt gtg gag gga ctg agc ttt gcg cgg gca gga ggg aac      1512
Arg Asp Asp Phe Val Glu Gly Leu Ser Phe Ala Arg Ala Gly Gly Asn
                450                 455                 460
```

```
                                                                        1567
tgg gcc gag tgt ttc tgatgtacat gctgtagtta gctttgagtc ctgaggtacc
Trp Ala Glu Cys Phe
        465
```

<210> SEQ ID NO 14
<211> LENGTH: 16
<212> TYPE: PRT
<213> ORGANISM: Aspergillus terreus

<400> SEQUENCE: 14

Met Gly Val Phe Val Leu Leu Ser Ile Ala Thr Leu Phe Gly Arg
 1               5                  10                  15

<210> SEQ ID NO 15
<211> LENGTH: 450
<212> TYPE: PRT
<213> ORGANISM: Aspergillus terreus

<400> SEQUENCE: 15

Thr Ser Gly Thr Ala Leu Gly Pro Arg Gly Asn His Ser Asp Cys Thr
 1               5                  10                  15

Ser Val Asp Arg Gly Tyr Gln Cys Phe Pro Glu Leu Ser His Lys Trp
            20                  25                  30

Gly Leu Tyr Ala Pro Tyr Phe Ser Leu Gln Asp Glu Ser Pro Phe Pro
        35                  40                  45

Leu Asp Val Pro Asp Asp Cys His Ile Thr Phe Val Gln Val Leu Ala
    50                  55                  60

Arg His Gly Ala Arg Ser Pro Thr Asp Ser Lys Thr Lys Ala Tyr Ala
65                  70                  75                  80

Ala Thr Ile Ala Ala Ile Gln Lys Asn Ala Thr Ala Leu Pro Gly Lys
                85                  90                  95

Tyr Ala Phe Leu Lys Ser Tyr Asn Tyr Ser Met Gly Ser Glu Asn Leu
            100                 105                 110

Asn Pro Phe Gly Arg Asn Gln Leu Gln Asp Leu Gly Ala Gln Phe Tyr
        115                 120                 125

Arg Arg Tyr Asp Thr Leu Thr Arg His Ile Asn Pro Phe Val Arg Ala
    130                 135                 140

Ala Asp Ser Ser Arg Val His Glu Ser Ala Glu Lys Phe Val Glu Gly
145                 150                 155                 160

Phe Gln Asn Ala Arg Gln Gly Asp Pro His Ala Asn Pro His Gln Pro
                165                 170                 175

Ser Pro Arg Val Asp Val Val Ile Pro Glu Gly Thr Ala Tyr Asn Asn
            180                 185                 190

Thr Leu Glu His Ser Ile Cys Thr Ala Phe Glu Ala Ser Thr Val Gly
        195                 200                 205

Asp Ala Ala Ala Asp Asn Phe Thr Ala Val Phe Ala Pro Ala Ile Ala
    210                 215                 220

Lys Arg Leu Glu Ala Asp Leu Pro Gly Val Gln Leu Ser Ala Asp Asp
225                 230                 235                 240

Val Val Asn Leu Met Ala Met Cys Pro Phe Glu Thr Val Ser Leu Thr
                245                 250                 255

Asp Asp Ala His Thr Leu Ser Pro Phe Cys Asp Leu Phe Thr Ala Ala
            260                 265                 270

Glu Trp Thr Gln Tyr Asn Tyr Leu Leu Ser Leu Asp Lys Tyr Tyr Gly
        275                 280                 285

Tyr Gly Gly Gly Asn Pro Leu Gly Pro Val Gln Gly Val Gly Trp Ala
    290                 295                 300

```
Asn Glu Leu Ile Ala Arg Leu Thr Arg Ser Pro Val His Asp His Thr
305                 310                 315                 320

Cys Val Asn Asn Thr Leu Asp Ala Asn Pro Ala Thr Phe Pro Leu Asn
            325                 330                 335

Ala Thr Leu Tyr Ala Asp Phe Ser His Asp Ser Asn Leu Val Ser Ile
        340                 345                 350

Phe Trp Ala Leu Gly Leu Tyr Asn Gly Thr Lys Pro Leu Ser Gln Thr
    355                 360                 365

Thr Val Glu Asp Ile Thr Arg Thr Asp Gly Tyr Ala Ala Ala Trp Thr
370                 375                 380

Val Pro Phe Ala Ala Arg Ala Tyr Ile Glu Met Met Gln Cys Arg Ala
385                 390                 395                 400

Glu Lys Gln Pro Leu Val Arg Val Leu Val Asn Asp Arg Val Met Pro
                405                 410                 415

Leu His Gly Cys Ala Val Asp Asn Leu Gly Arg Cys Lys Arg Asp Asp
            420                 425                 430

Phe Val Glu Gly Leu Ser Phe Ala Arg Ala Gly Gly Asn Trp Ala Glu
        435                 440                 445

Cys Phe
    450

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:  Nucleotide
                        Sequence of Primer #39 designed based on
                        Aspergillus fumigatus ATCC 13073

<400> SEQUENCE: 16
tatatcatga ttactctgac tttcctgctt tcg                              33

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:  Amino Acid
                        Sequence Corresponding to Primer #39

<400> SEQUENCE: 17

Met Ile Thr Leu Thr Phe Leu Leu Ser
  1               5

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:  Nucleotide
                        Sequence of Primer #40 designed based on
                        Aspergillus fumigatus ATCC 13073

<400> SEQUENCE: 18
tatatagata tctcaactaa agcactctcc                                  30

<210> SEQ ID NO 19
<211> LENGTH: 5
<212> TYPE: PRT
<213> ORGANISM: Artificial Sequence
<220> FEATURE:
```

```
<223> OTHER INFORMATION: Description of Artificial Sequence:  Amino Acid
                        Sequence Corresponding to Primer #40

<400> SEQUENCE: 19

Gly Glu Cys Phe Ser
  1               5

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:  Fum28 PCR
                        Primer

<400> SEQUENCE: 20
atatatcggc cgagtgtctg cggcacctag t                               31

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:  Fum11 PCR
                        Primer

<400> SEQUENCE: 21
tgaggtcatc cgcacccaga g                                          21

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence:  Fum26 PCR
                        Primer

<400> SEQUENCE: 22
ctagaattca tggtgactct gactttcctg ctttcggcgg cgtatctgct ttcc       54

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence:  Fum27 PCR
                        Primer

<400> SEQUENCE: 23
ggccggaaag cagatacgcc gccgaaagca ggaaagtcag agtcaccatg aatt       54

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:Primer
                        Q27L s

<400> SEQUENCE: 24
catctatggg gcctgtactc gccattc                                    27

<210> SEQ ID NO 25
<211> LENGTH: 27
<212> TYPE: DNA
<213> ORGANISM: Artificial Sequence
<220> FEATURE:
```

<223> OTHER INFORMATION: Description of Artificial Sequence:Primer Q27L
         as

<400> SEQUENCE: 25
gaatggcgag tacaggcccc atagatg                                        27

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:Amino Acid
         Sequence Encoded by Primer Set A

<400> SEQUENCE: 26

His Leu Trp Gly Leu Tyr Ser Pro Phe
 1               5

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:Primer
         Q274L s

<400> SEQUENCE: 27
tacaactacc ttctgtcctt gggcaag                                        27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:Primer
         Q274L as

<400> SEQUENCE: 28
cttgcccaag gacagaaggt agttgta                                        27

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:Amino Acid
         Sequence Encoded by Primer Set B

<400> SEQUENCE: 29

Tyr Asn Tyr Leu Leu Ser Leu Gly Lys
 1               5

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:Primer
         G277D s

<400> SEQUENCE: 30
cttcagtcct tggacaagta ctacggc                                        27

<210> SEQ ID NO 31
<211> LENGTH: 27
<212> TYPE: DNA
<213> ORGANISM: Artificial Sequence

```
<220> FEATURE:
<223> OTHER INFORMATION: Description of Artificial Sequence:Primer G
               277D as

<400> SEQUENCE: 31
gccgtagtac ttgtccaagg actgaag                                             27

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:Amino Acid
               Sequence encoded by Primer set C

<400> SEQUENCE: 32

Leu Gln Ser Leu Asp Lys Tyr Tyr Gly
 1               5

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:Primer
               G277D* s

<400> SEQUENCE: 33
cttctgtcct tggacaagta ctacggc                                             27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence:Primer
               G277D* as

<400> SEQUENCE: 34
gccgtagtac ttgtccaagg acagaag                                             27

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:Amino Acid
               Sequence Encoded by Primer Set D

<400> SEQUENCE: 35

Leu Leu Ser Leu Asp Lys Tyr Tyr Gly
 1               5

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:Primer
               N340S s

<400> SEQUENCE: 36
ttttcacacg acagcagcat ggtttcc                                             27

<210> SEQ ID NO 37
<211> LENGTH: 27
<212> TYPE: DNA
```

```
<213> ORGANISM: Artificial Sequence
<220> FEATURE:
<223> OTHER INFORMATION: Description of Artificial Sequence:Primer N
      340S as

<400> SEQUENCE: 37
ggaaaccatg ctgctgtcgt gtgaaaa                                          27

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set E

<400> SEQUENCE: 38

Phe Ser His Asp Ser Ser Met Val Ile
  1               5

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence:Primer
      G277K s

<400> SEQUENCE: 39
ccttcagtcc ttgaagaagt actacggcta c                                    31

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence:Primer
      G277K as

<400> SEQUENCE: 40
gtagccgtag tacttcttca aggactgaag g                                    31

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set F

<400> SEQUENCE: 41

Leu Gln Ser Leu Lys Lys Tyr Tyr Gly Tyr
  1               5                  10

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence:Primer
      A205E s

<400> SEQUENCE: 42
ggagatgagg ttgaggccaa tttcactg                                        28

<210> SEQ ID NO 43
<211> LENGTH: 28
```

```
<212> TYPE: DNA
<213> ORGANISM: Artificial Sequence
<220> FEATURE:
<223> OTHER INFORMATION: Description of Artificial Sequence:Primer
                A205E as

<400> SEQUENCE: 43
cagtgaaatt ggcctcaacc tcatctcc                                          28

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence:Amino Acid
                Sequence Encoded by Primer Set G

<400> SEQUENCE: 44

Gly Asp Glu Val Glu Ala Asn Phe Thr
  1               5

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:Primer
                Y282H s

<400> SEQUENCE: 45
aagtactacg gccacggcgc aggcaac                                           27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:Primer Y
                282H as

<400> SEQUENCE: 46
gttgcctgcg ccgtggccgt agtactt                                           27

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:Amino Acid
                Sequence Encoded by Primer Set H

<400> SEQUENCE: 47

Lys Tyr Tyr Gly His Gly Ala Gly Asn
  1               5

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:Primer
                AvrII s

<400> SEQUENCE: 48
gatacggtag acctagggta ccagtgc                                           27

<210> SEQ ID NO 49
```

```
<211> LENGTH: 27
<212> TYPE: DNA
<213> ORGANISM: Artificial Sequence
<220> FEATURE:
<223> OTHER INFORMATION: Description of Artificial Sequence:Primer A
                        vrII as

<400> SEQUENCE: 49
gcactggtac cctaggtcta ccgtatc                                              27

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence:Amino Acid
                        Sequence Encoded by Primer Set I

<400> SEQUENCE: 50

Asp Thr Val Asp Leu Gly Tyr Gln Cys
 1               5

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:Primer
                        S66D s

<400> SEQUENCE: 51
cggtacccaa ccgattcgaa gagcaaaaag                                           30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence:Primer
                        S66D as

<400> SEQUENCE: 52 cttttttgctc ttcgaatcgg ttgggtaccg                                          30

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence:Amino Acid
                        Sequence Encoded by Primer Set J

<400> SEQUENCE: 53

Arg Tyr Pro Thr Asp Ser Lys Ser Lys Lys
 1               5                  10

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence:Primer
                        S140Y/D141G s

<400> SEQUENCE: 54
gcgcctcagg ctacggccgg gttattgc                                             28
```

```
<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence:Primer
                        S140Y/D141G as

<400> SEQUENCE: 55
gcaataaccc ggccgtagcc tgaggcgc                                              28

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence:Amino Acid
                        Sequence Encoded by Primer Set K

<400> SEQUENCE: 56

Ala Ser Gly Tyr Gly Arg Val Ile Ala
 1               5

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:Primer
                        S130N s

<400> SEQUENCE: 57
ctggcgcgca atgtggtgcc gtttattc                                              28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence:Primer
                        S130N as

<400> SEQUENCE: 58
gaataaacgg caccacattg cgcgccag                                              28

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:Amino Acid
                        Sequence Encoded by Primer Set L

<400> SEQUENCE: 59

Leu Ala Arg Asn Val Val Pro Phe Ile
 1               5

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence:Primer
                        R129L/S130N s

<400> SEQUENCE: 60
gctctggcgc tcaatgtggt gccgtttatt c                                          31
```

```
<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence:Primer
      R129L/S130N as

<400> SEQUENCE: 61
gaataaacgg caccacattg agcgccagag c                                    31

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set M

<400> SEQUENCE: 62

Ala Leu Ala Leu Asn Val Val Pro Phe Ile
 1               5                  10

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence:Primer
      K167G/R168Q s

<400> SEQUENCE: 63
gaccatggct ccggacaagc tacgccag                                        28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence:Primer
      K167G/R168Q as

<400> SEQUENCE: 64
ctggcgtagc ttgtccggag ccatggtc                                        28

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set N

<400> SEQUENCE: 65

Asp His Gly Ser Gly Gln Ala Thr Pro
 1               5

<210> SEQ ID NO 66
<211> LENGTH: 64
<212> TYPE: DNA
<213> ORGANISM: Artificial Sequence
<220> FEATURE:
<223> OTHER INFORMATION: Description of Artificial Sequence:FumG27-s
      from Primer Set O

<400> SEQUENCE: 66
ctagggtacc agtgctcccc tgcgacttct catctatggg gcggatactc gccattcttt    60
```

```
tcgc                                                                64
```

<210> SEQ ID NO 67
<211> LENGTH: 64
<212> TYPE: DNA
<213> ORGANISM: Artificial Sequence
<220> FEATURE:
<223> OTHER INFORMATION: Description of Artificial Sequence:FumG27-as
      from Primer Set O

<400> SEQUENCE: 67

```
tcgagcgaaa agaatggcga gtatccgccc catagatgag aagtcgcagg ggagcactgg    60
tacc                                                                64
```

<210> SEQ ID NO 68
<211> LENGTH: 64
<212> TYPE: DNA
<213> ORGANISM: Artificial Sequence
<220> FEATURE:
<223> OTHER INFORMATION: Description of Artificial Sequence:FumV27-s
      from Primer Set P

<400> SEQUENCE: 68

```
ctagggtacc agtgctcccc tgcgacttct catctatggg gcgtgtactc gccattcttt    60
tcgc                                                                64
```

<210> SEQ ID NO 69
<211> LENGTH: 64
<212> TYPE: DNA
<213> ORGANISM: Artificial Sequence
<220> FEATURE:
<223> OTHER INFORMATION: Description of Artificial Sequence:FumV27-as
      from Primer Set P

<400> SEQUENCE: 69

```
tcgagcgaaa agaatggcga gtacacgccc catagatgag aagtcgcagg ggagcactgg    60
tacc                                                                64
```

<210> SEQ ID NO 70
<211> LENGTH: 64
<212> TYPE: DNA
<213> ORGANISM: Artificial Sequence
<220> FEATURE:
<223> OTHER INFORMATION: Description of Artificial Sequence:FumN27-s
      from Primer Set Q

<400> SEQUENCE: 70

```
ctagggtacc agtgctcccc tgcgacttct catctatggg gcaactactc gccattcttt    60
tcgc                                                                64
```

<210> SEQ ID NO 71
<211> LENGTH: 64
<212> TYPE: DNA
<213> ORGANISM: Artificial Sequence
<220> FEATURE:
<223> OTHER INFORMATION: Description of Artificial Sequence:FumN27-as
      from Primer Set Q

<400> SEQUENCE: 71

```
tcgagcgaaa agaatggcga gtagttgccc catagatgag aagtcgcagg ggagcactgg    60
tacc                                                                64
```

<210> SEQ ID NO 72
<211> LENGTH: 64
<212> TYPE: DNA
<213> ORGANISM: Artificial Sequence
<220> FEATURE:
<223> OTHER INFORMATION: Description of Artificial Sequence:FumI27-s
       from Primer Set R

<400> SEQUENCE: 72
ctagggtacc agtgctcccc tgcgacttct catctatggg gcatctactc gccattcttt    60
tcgc                                                                 64

<210> SEQ ID NO 73
<211> LENGTH: 64
<212> TYPE: DNA
<213> ORGANISM: Artificial Sequence
<220> FEATURE:
<223> OTHER INFORMATION: Description of Artificial Sequence:FumI27-as
       from Primer Set R

<400> SEQUENCE: 73
tcgagcgaaa agaatggcga gtagatgccc catagatgag aagtcgcagg ggagcactgg    60
tacc                                                                 64

<210> SEQ ID NO 74
<211> LENGTH: 64
<212> TYPE: DNA
<213> ORGANISM: Artificial Sequence
<220> FEATURE:
<223> OTHER INFORMATION: Description of Artificial Sequence:FumA27-s
       from Primer Set S

<400> SEQUENCE: 74
ctagggtacc agtgctcccc tgcgacttct catctatggg gcgcgtactc gccattcttt    60
tcgc                                                                 64

<210> SEQ ID NO 75
<211> LENGTH: 64
<212> TYPE: DNA
<213> ORGANISM: Artificial Sequence
<220> FEATURE:
<223> OTHER INFORMATION: Description of Artificial Sequence:FumA27-as
       from Primer Set S

<400> SEQUENCE: 75
tcgagcgaaa agaatggcga gtacgcgccc catagatgag aagtcgcagg ggagcactgg    60
tacc                                                                 64

<210> SEQ ID NO 76
<211> LENGTH: 64
<212> TYPE: DNA
<213> ORGANISM: Artificial Sequence
<220> FEATURE:
<223> OTHER INFORMATION: Description of Artificial Sequence:FumT27-s
       from Primer Set T

<400> SEQUENCE: 76
ctagggtacc agtgctcccc tgcgacttct catctatggg gcacgtactc gccattcttt    60
tcgc                                                                 64

<210> SEQ ID NO 77
<211> LENGTH: 64
<212> TYPE: DNA
<213> ORGANISM: Artificial Sequence -continued

```
<220> FEATURE:
<223> OTHER INFORMATION: Description of Artificial Sequence:FumT27-as
      from Primer Set T

<400> SEQUENCE: 77
tcgagcgaaa agaatggcga gtacgtgccc catagatgag aagtcgcagg ggagcactgg    60
tacc                                                                 64

<210> SEQ ID NO 78
<211> LENGTH: 465
<212> TYPE: PRT
<213> ORGANISM: Aspergillus fumigatus

<400> SEQUENCE: 78
```

Met Val Thr Leu Thr Phe Leu Leu Ser Ala Ala Tyr Leu Leu Ser Gly
 1               5                  10                  15

Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr

-continued

```
                325                 330                 335
Asn Ser Thr Leu Val Ser Asn Pro Ala Thr Phe Pro Leu Asn Ala Thr
            340                 345                 350
Met Tyr Val Asp Phe Ser His Asp Asn Ser Met Val Ser Ile Phe Phe
            355                 360                 365
Ala Leu Gly Leu Tyr Asn Gly Thr Glu Pro Leu Ser Arg Thr Ser Val
            370                 375                 380
Glu Ser Ala Lys Glu Leu Asp Gly Tyr Ser Ala Ser Trp Val Val Pro
385                 390                 395                 400
Phe Gly Ala Arg Ala Tyr Phe Glu Thr Met Gln Cys Lys Ser Glu Lys
                405                 410                 415
Glu Pro Leu Val Arg Ala Leu Ile Asn Asp Arg Val Val Pro Leu His
                420                 425                 430
Gly Cys Asp Val Asp Lys Leu Gly Arg Cys Lys Leu Asn Asp Phe Val
            435                 440                 445
Lys Gly Leu Ser Trp Ala Arg Ser Gly Gly Asn Trp Gly Glu Cys Phe
    450                 455                 460
Ser
465

<210> SEQ ID NO 79
<211> LENGTH: 465
<212> TYPE: PRT
<213> ORGANISM: Aspergillus fumigatus

<400> SEQUENCE: 79

Met Val Thr Leu Thr Phe Leu Leu Ser Ala Ala Tyr Leu Leu Ser Gly
1               5                   10                  15
Arg Val Ser Ala Ala Pro Ser Ser Ala Gly Ser Lys Ser Cys Asp Thr
                20                  25                  30
Val Asp Leu Gly Tyr Gln Cys Ser Pro Ala Thr Ser His Leu Trp Gly
            35                  40                  45
Gln Tyr Ser Pro Phe Phe Ser Leu Glu Asp Glu Leu Ser Val Ser Ser
        50                  55                  60
Lys Leu Pro Lys Asp Cys Arg Ile Thr Leu Val Gln Val Leu Ser Arg
65                  70                  75                  80
His Gly Ala Arg Tyr Pro Thr Ser Ser Lys Ser Lys Tyr Lys Lys
                85                  90                  95
Leu Val Thr Ala Ile Gln Ala Asn Ala Thr Asp Phe Lys Gly Lys Phe
                100                 105                 110
Ala Phe Leu Lys Thr Tyr Asn Tyr Thr Leu Gly Ala Asp Asp Leu Thr
            115                 120                 125
Pro Phe Gly Glu Gln Gln Leu Val Asn Ser Gly Ile Lys Phe Tyr Gln
        130                 135                 140
Arg Tyr Lys Ala Leu Ala Arg Ser Val Val Pro Phe Ile Arg Ala Ser
145                 150                 155                 160
Gly Ser Asp Arg Val Ile Ala Ser Gly Glu Lys Phe Ile Glu Gly Phe
                165                 170                 175
Gln Gln Ala Lys Leu Ala Asp Pro Gly Ala Thr Asn Arg Ala Ala Pro
                180                 185                 190
Ala Ile Ser Val Ile Ile Pro Glu Ser Glu Thr Phe Asn Asn Thr Leu
            195                 200                 205
Asp His Gly Val Cys Thr Lys Phe Glu Ala Ser Gln Leu Gly Asp Glu
        210                 215                 220
```

-continued

```
Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
            245                 250                 255

Ser Leu Met Asp Met Cys Ser Phe Asp Thr Val Ala Arg Thr Ser Asp
        260                 265                 270

Ala Ser Gln Leu Ser Pro Phe Cys Gln Leu Phe Thr His Asn Glu Trp
    275                 280                 285

Lys Lys Tyr Asn Tyr Leu Gln Ser Leu Gly Lys Tyr Gly Tyr Gly
290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
        355                 360                 365

Ala Leu Gly Leu Tyr Asn Gly Thr Glu Gly Leu Ser Arg Thr Ser Val
370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
        435                 440                 445

Lys Gly Leu Ser Trp Ala Arg Ser Gly Gly Asn Trp Gly Glu Cys Phe
    450                 455                 460

Ser
465

<210> SEQ ID NO 80
<211> LENGTH: 465
<212> TYPE: PRT
<213> ORGANISM: Aspergillus fumigatus

<400> SEQUENCE: 80

Met Val Thr Leu Thr Phe Leu Leu Ser Ala Ala Tyr Leu Leu Ser Gly
1               5                   10                  15

Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125
```

```
Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
        355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Ser Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
        435                 440                 445

Lys Gly Leu Ser Trp Ala Arg Ser Gly Gly Asn Trp Gly Glu Cys Phe
    450                 455                 460

Ser
465

<210> SEQ ID NO 81
<211> LENGTH: 465
<212> TYPE: PRT
<213> ORGANISM: Aspergillus fumigatus

<400> SEQUENCE: 81

Met Val Thr Leu Thr Phe Leu Leu Ser Ala Ala Tyr Leu Leu Ser Gly
  1               5                  10                  15

Arg Val Ser Ala Ala Pro Ser Ser Ala Gly Ser Lys Ser Cys Asp Thr
```

-continued

```
            20                  25                  30
Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
            115                 120                 125

Ala Phe Gly Glu Gln Gln Leu Val Asn Ser Gly Ile Lys Phe Tyr Gln
        130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Lys Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
        355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
        435                 440                 445
```

```
Lys Gly Leu Ser Trp Ala Arg Ser Gly Gly Asn Trp Gly Glu Cys Phe
    450                 455                 460

Ser
465

<210> SEQ ID NO 82
<211> LENGTH: 469
<212> TYPE: PRT
<213> ORGANISM: Aspergillus fumigatus

<400> SEQUENCE: 82

Met Gly Ala Leu Thr Phe Leu Leu Ser Val Met Tyr Leu Leu Ser Gly
  1               5                  10                  15

Val Ala Gly Ala Pro Ser Ser Gly Cys Ser Ala Gly Ser Gly Ser Lys
             20                  25                  30

Ala Cys Asp Thr Val Glu Leu Gly Tyr Gln Cys Ser Pro Gly Thr Ser
         35                  40                  45

His Leu Trp Gly Gln Tyr Ser Pro Phe Phe Ser Leu Glu Asp Glu Leu
     50                  55                  60

Ser Val Ser Ser Asp Leu Pro Lys Asp Cys Arg Val Thr Phe Val Gln
 65                  70                  75                  80

Val Leu Ser Arg His Gly Ala Arg Tyr Pro Thr Ala Ser Lys Ser Lys
                 85                  90                  95

Lys Tyr Lys Lys Leu Val Thr Ala Ile Gln Lys Asn Ala Thr Glu Phe
            100                 105                 110

Lys Gly Lys Phe Ala Phe Leu Glu Thr Tyr Asn Tyr Thr Leu Gly Ala
        115                 120                 125

Asp Asp Leu Thr Pro Phe Gly Glu Gln Gln Met Val Asn Ser Gly Ile
130                 135                 140

Lys Phe Tyr Gln Lys Tyr Lys Ala Leu Ala Gly Ser Val Val Pro Phe
145                 150                 155                 160

Ile Arg Ser Ser Gly Ser Asp Arg Val Ile Ala Ser Gly Glu Lys Phe
                165                 170                 175

Ile Glu Gly Phe Gln Gln Ala Asn Val Ala Asp Pro Gly Ala Thr Asn
            180                 185                 190

Arg Ala Ala Pro Val Ile Ser Val Ile Pro Glu Ser Glu Thr Tyr
        195                 200                 205

Asn Asn Thr Leu Asp His Ser Val Cys Thr Asn Phe Glu Ala Ser Glu
    210                 215                 220

Leu Gly Asp Glu Val Glu Ala Asn Phe Thr Ala Leu Phe Ala Pro Ala
225                 230                 235                 240

Ile Arg Ala Arg Ile Glu Lys His Leu Pro Gly Val Gln Leu Thr Asp
                245                 250                 255

Asp Asp Val Val Ser Leu Met Asp Met Cys Ser Phe Asp Thr Val Ala
            260                 265                 270

Arg Thr Ala Asp Ala Ser Glu Leu Ser Pro Phe Cys Ala Ile Phe Thr
        275                 280                 285

His Asn Glu Trp Lys Lys Tyr Asp Tyr Leu Gln Ser Leu Gly Lys Tyr
    290                 295                 300

Tyr Gly Tyr Gly Ala Gly Asn Pro Leu Gly Pro Ala Gln Gly Ile Gly
305                 310                 315                 320

Phe Thr Asn Glu Leu Ile Ala Arg Leu Thr Asn Ser Pro Val Gln Asp
                325                 330                 335

His Thr Ser Thr Asn Ser Thr Leu Asp Ser Asp Pro Ala Thr Phe Pro
```

-continued

```
                    340                 345                 350
Leu Asn Ala Thr Ile Tyr Val Asp Phe Ser His Asp Asn Gly Met Ile
        355                 360                 365

Pro Ile Phe Phe Ala Met Gly Leu Tyr Asn Gly Thr Glu Pro Leu Ser
        370                 375                 380

Gln Thr Ser Glu Glu Ser Thr Lys Glu Ser Asn Gly Tyr Ser Ala Ser
385                 390                 395                 400

Trp Ala Val Pro Phe Gly Ala Arg Ala Tyr Phe Glu Thr Met Gln Cys
                405                 410                 415

Lys Ser Glu Lys Glu Pro Leu Val Arg Ala Leu Ile Asn Asp Arg Val
                420                 425                 430

Val Pro Leu His Gly Cys Ala Val Asp Lys Leu Gly Arg Cys Lys Leu
        435                 440                 445

Lys Asp Phe Val Lys Gly Leu Ser Trp Ala Arg Ser Gly Gly Asn Ser
        450                 455                 460

Glu Gln Ser Phe Ser
465
```

MODIFIED PHYTASES

This application is a divisional of U.S. application Ser. No. 10/062,848, filed Feb. 1, 2002, now U.S. Pat. No. 6,734,004, which is a divisional of U.S. application Ser. No. 09/044,718, filed Mar. 19, 1998, now U.S. Pat. No. 6,391,605.

BACKGROUND OF THE INVENTION

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A phytase was first described in rice bran in 1907 [Suzuki et al., Bull. Coll. Agr. Tokio Imp. Univ. 7, 495 (1907)] and phytases from *Aspergillus* species in 1911 [Dox and Golden, J. Biol. Chem. 10, 183–186 (1911)]. Phytases have also been found in wheat bran, plant seeds, animal intestines and in microorganisms [Howsen and Davis, Enzyme Microb. Technol. 5, 377–382 (1983), Lambrechts et al., Biotech. Lett. 14, 61–66 (1992), Shieh and Ware, Appl. Microbiol. 16, 1348–1351 (1968)].

The cloning and expression of the phytase from *Aspergillus niger (ficuum)* has been described by Van Hartingsveldt et al., in Gene, 127, 87–94 (1993) and in European Patent Application, Publication No. (EP) 420 358 and from *Aspergillus niger* var. *awamori* by Piddington et al., in Gene 133, 55–62 (1993).

Cloning, expression and purification of phytases with improved properties have been disclosed in EP 684 313. However, since there is a still ongoing need for further improved phytases, especially with respect to the activity properties, it is an object of the present invention to provide such improvements.

SUMMARY OF THE INVENTION

Accordingly, this invention is directed to a process for the production of a modified phytase with a desired property improved over the property of the corresponding unmodified phytase which comprises:
  (a) determining the three dimensional structure of the unmodified phytase and of a second phytase which has the desired property by aligning the amino acid sequences of said phytases with the amino acid sequence of a third phytase which is the phytase of *Aspergillus niger* and using the three dimensional structure of the phytase of *Aspergillus niger* as a template based on the alignment to determine said three dimensional structures;
  (b) determining from the structures of step (a) the amino acids of the active sites of the unmodified phytase and of the second phytase having the desired property which active site provides the desired property and comparing the amino acids which form the active sites to identify which amino acids are different in the active site of the second phytase from the amino acids in the active site of the unmodified phytase;
  (c) constructing a DNA sequence coding for the modified phytase by obtaining the DNA sequence of the unmodified phytase and changing the nucleotides coding for the active site which provides the desired property for said unmodified phytase so that at least one of the amino acids in the active site which provides the desired property is substituted by one of the amino acids which was identified as being different in step (b);
  (d) integrating such a DNA sequence into a vector capable of expression in a suitable host cell; and
  (e) transforming the suitable host cell by the DNA sequence of step (c) or the vector of step (d), growing said host cell under suitable growth conditions and isolating the modified phytase from the host cell or the culture medium.

Either or both of the unmodified phytase and the phytase with the desired property may be of eukaryotic origin, especially of fungal origin. Such phytases are preferably of *Aspergillus* origin, for example phytase from *Aspergillus fumigatus*. In a preferred process, the phytase with the desired property is a phytase from *Aspergillus terreus*. In another preferred process, the unmodified phytase is a phytase of *Aspergillus fumigatus* and the phytase with the desired property is the *Aspergillus niger* phytase. In yet another preferred process, the unmodified phytase is a phytase of *Aspergillus fumigatus* and the phytase with the desired property is the *Aspergillus terreus* phytase.

Also part of this invention is a modified phytase with a specific activity improved over the specific activity of the corresponding unmodified phytase (for example *Aspergillus fumigatus*) wherein the amino acid sequence of the corresponding unmodified phytase has been changed by one or more of deletion, substitution and addition by one or more amino acids to obtain the amino acid sequence of the modified phytase. A preferred phytase has an amino acid sequence homologous to that of the phytase of *Aspergillus niger* (SEQ ID NO:1) and has an amino acid sequence that has been changed in at least one amino acid position selected from the following amino acid positions which correspond to positions of the amino acid sequence of the phytase of *Aspergillus niger:* 27, 66, 71, 103, 140, 141, 188, 205, 234, 238, 274, 277, 282, 340 and 424, in particular wherein the amino acid position is selected from 27, 66, 140, 205, 274, 277, 282, and 340.

A preferred modified phytase has an amino acid sequence which has been changed at position 27 alone or in addition to other of the above positions, in particular at least at position 66 and/or position 140. Thus preferred phytases are modified at position 27 and 66 or 27 and 140.

For any such phytase, the amino acid at position 27 may be replaced by a specific amino acid selected from one of the following groups:
  a) Ala, Val, Leu, Ile; or b) Thr; or c) Asn.

Particular modified phytases of this invention are characterized by at least one of the following changes in amino acids at positions: Q27L, Q27N, Q27T, Q27I, Q27V, Q27A, Q27G, S66D, S140Y, D141G, A205E, Q274L, Q277D, G277K, Y282H and/or N340S.

Also part of this invention are polynucleotides comprising a DNA sequence coding for the modified phytases produced by the above method. Polynucleotides comprising DNA sequences coding for the phytases described above which are modified at particular amino acid positions are included.

Also included are vectors, especially expression vectors, which contain the polynucleotides of this invention, and host cells which contain these polynucleotides directly or within a vector.

Another aspect of this invention is a food or feed composition which contains modified phytases described above.

BRIEF DESCRIPTION OF THE FIGURES

FIG. 1: Primary sequence alignment of *A. niger (ficuum)*, (SEQ ID NO:1) *A. terreus* cbs116.46 (SEQ ID NO:2) and *A. fumigatus* [ATCC 13073] (SEQ ID NO:3) phytase. Stars show identical residues within the active site and rectangles, non-identical residues within the active site.

FIG. 4: Complete coding sequence and encoded amino acid sequence of the *Aspergillus nidulans* phytase (SEQ ID NOs:4–6).

FIG. 5: Complete coding sequence (SEQ ID NO: 7) and encoded amino acid sequence (SEQ ID NOs:8–9) of *Talaromyces thermophilus* phytase.

FIG. 6: Complete coding sequence (SEQ ID NO:10) and encoded amino acid sequence (SEQ ID NOs.11–12) of *Aspergillus fumigatus* [ATCC 13073] phytase.

FIG. 7: Complete coding sequence (SEQ ID NO:13) and encoded amino acid sequence (SEQ ID NOs:14–15) of *Aspergillus terreus* CBS 116.46 phytase.

FIG. 8: Crystallographic data of the structure of the *Aspergillus niger* phytase.

FIG. 14a: Primer sets A–N (SEQ ID NOs:24–65) used for site directed mutagenesis.

FIG. 14b: Primer sets O–T (SEQ ID NOs:66–77) used for site directed mutagenesis.

FIG. 23: Natural variation of phytases in different isolates of *A. fumigatus* [ATCC 13073]. The predicted protein sequences (SEQ ID NOs:78–82) are shown and compared to that of the phytase from *A. fumigatus* strain ATCC 13073. Only the amino acids which differ from those in #13073 are shown.

DETAILED DESCRIPTION OF THE INVENTION

Figure 2:
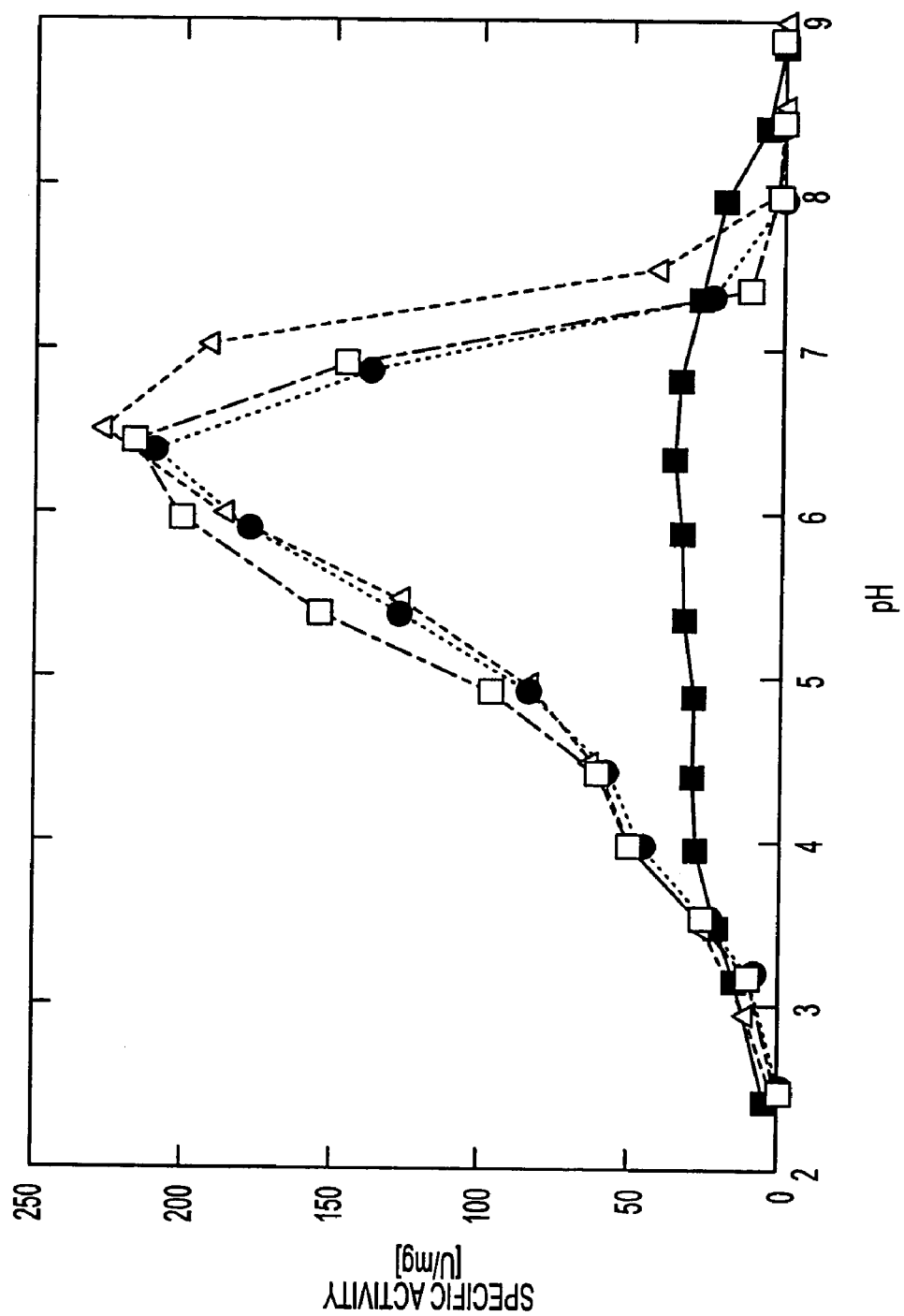
FIG. 2: pH optima curves. Specific activity of wild-type and mutant *A. fumigatus* phytases is plotted against pH of incubation. Filled squares represent *A. fumigatus* wild-type phytase; Open triangles represent *A. fumigatus* Q27L mutant; Filled circles represent *A. fumigatus* Q27L, Q274L mutant; Open squares represent *A. fumigatus* Q27L, Q274L, G277D mutant.

The process of this invention allows the production of a modified phytase with improved activity by using structural information about phytases to design the improvement. First, the three dimensional structure of the phytase to be modified and, optionally of another phytase with activity properties which are more favorable than the ones of the phytase to be modified is/are computer modelled on the basis of the three dimensional structure of the phytase of *Aspergillus niger (ficuum)*. Then, the structure of the active sites of the phytase to be modified and of the phytase with the more favorable activity properties are compared and those amino acid residues in both active sites which are different are identified, after which a DNA sequence coding for a modified phytase is constructed by changing the nucleotides coding for at least one of the amino acids by which both active sites differ. The modified phytase is then obtained by integrating such a DNA sequence into a vector capable of expression in a suitable host cell, transforming a suitable host cell by the DNA sequence or the vector, growing the host cell under suitable growth conditions and isolating the modified phytase from the host cell or the culture medium by methods known in the state of the art.

As stated above, this process is particularly useful where the phytase to be modified is of eukaryotic, preferably fungal, more preferably *Aspergillus*, e.g. *Aspergillus fumigatus* origin and the phytase with more favorable activity properties is of eukaryotic, preferably fungal, more preferably *Aspergillus*, e.g. *Aspergillus niger* or *Aspergillus terreus* (*Aspergillus terreus* cbs 116.46 or 9A1) origin, or the phytase to be modified is a phytase of *Aspergillus fumigatus* and the phytase with the more favorable activity properties is the *Aspergillus terreus* phytase or the phytase of *Aspergillus niger*.

Thus, the unmodified phytase (for example a wild-type phytase) which has a property to be improved, and the phytase which has that property in an improved version (i.e. the desired property which the modified phytase will be designed to possess) may be derived from any known source of phytases. Various plants and microorganisms are known to produce phytases [e.g. reviewed in Wodzinski, R. J. and Ullah, H. J., Advances in Applied Microbiology 42, 263 (1996)]. Thus any enzyme which may be isolated by conventional methods and determined to be a phytase by standard assays (see e.g. EP 420 358) is a suitable phytase for this invention. Sequence and structure information for such phytases may be obtained by conventional techniques or from publicly available databases.

Preferred phytases are those isolated from fungi such as *Aspergillus* species [Shieh, T. R. and Ware, J. H. Appl. Microbiology 16, 1348 (1968); Yamada et al., Agr. Biol. Chem. 32, 1275 (1968); Van Hartingsveldt et al., in Gene, 127, 87–94 (1993), European Patent Application, Publication No. (EP) 420 358, Piddington et al., in Gene 133, 55–62 (1993); Wodzinski, R. J. and Ullah, H. J. (s.a.) and Mitchell et al., Microbiology 143, 245 (1997)]. *Aspergillus* are well known fungi commonly isolated from natural sources by conventional methods. In addition, *Aspergillus* species may be obtained from depositories.

Once such a fungus is obtained, DNA expressing its phytase can be isolated by conventional methods [see Mitchell et al., Microbiology 143:245 (1997) Van Hartingsveldt et al. (s.a.); Dox and Golden (s.a.); EP 420 358; Piddington et al (s.a.) and WO 94/03612] (for example cloned, expressed, and assayed by phytase activity assays to obtain a clone expressing the phytase) for use in this invention. Specifically, the phytase DNA can be used to isolat the phytase, whose amino acid sequence and three-dimensional structures can also be obtained by known methods, such as crystallography or computer modelling. Alternatively, the phytase may be isolated by conventional methods for isolating proteins such as enzymes, and analyzed as described. Also, DNA and amino acid sequences may be obtained from publicly available databases.

Although other three-dimensional phytase structures may be obtained and used, it is preferred to use the three-dimensional of the *Aspergillus niger* phytase in the process of this invention (see Kostrewa et al., *Nature Structural Biology* 4:185 (1997)) or of *Aspergillus fumigatus*. A useful strain of *Aspergillus niger* may be obtained from the American Type Culture Collection [address] under accession number ATCC 9142. Like any three-dimensional phytase structure useful in this invention, the three-dimensional structure of the *A. niger* phytase is obtained by techniques known to a skilled practitioner. Based on an amino acid sequence such as the *A. niger* amino acid sequence provided herein, (SEQ ID NO:1) computer programs can provide theoretical structures. Crystal structures can also be obtained, as in Example 1 below. From these three-dimensional structures, active sites can be defined, such as the part of the phytase which interacts with substrate. This active site can then be localized to the segment or segments of the amino acid sequence which together form the active site, which segment or segments can then be modified, the whole sequence expressed as a modified phytase which is then tested to see if the activity has been improved. By this means a desired property can be designed into an unmodified phytase, using the three dimensional structure of the *A. niger* phytase as a template based on the alignment.

Specifically, the structure of *A. niger* is analyzed to find out which amino acid residues form the active site which determines specific activity. Then, the amino acid sequence of an unmodified phytase with a given specific activity and that of a phytase which has a desired property, e.g. a higher specific activity, are aligned homologous (as defined below) to that of *A. niger* to provide a best fit, and the amino acid residues which correspond to the *A. niger* active site in the other phytases are determined and compared, to identify which amino acids are different in the active site of the phytase with the desired property. The active site amino acid residues of the unmodified phytase may then be changed by known methods to duplicate some or all of the active site amino acid residues of the phytase with the desired property. The modified phytase is then obtained by known methods (for example determining the DNA sequence, mutating the sequence to provide the desired amino acid sequence, and expressing the resulting protein), and is tested by assays for the desired property, e.g. specific activity, to confirm that the desired property is present.

In this context it should be mentioned that another possibility for producing phytases with improved properties is by isolating phytases from the same organism, like for example the *Aspergillus ficuum*, but different strains which can be found in nature and have been deposited by any of the known depository authorities. Their amino acid sequences can be determined by cloning their corresponding DNA sequences by methods as described, e.g. in European Patent Application No. (EP) 684 313. Once such sequences have been defined they can be modeled on the basis of the three-dimensional structure of the *A. niger* phytase and the active sites of both sequences can be compared to find out whether such phytase should have improved activity properties (see Example 8) or both active site sequences can be compared directly and than tested for increased and/or improved activity by the assays described in the present application.

It is furthermore an object of the present invention to provide a modified phytase which is obtainable by a process as described above.

Figure 1:
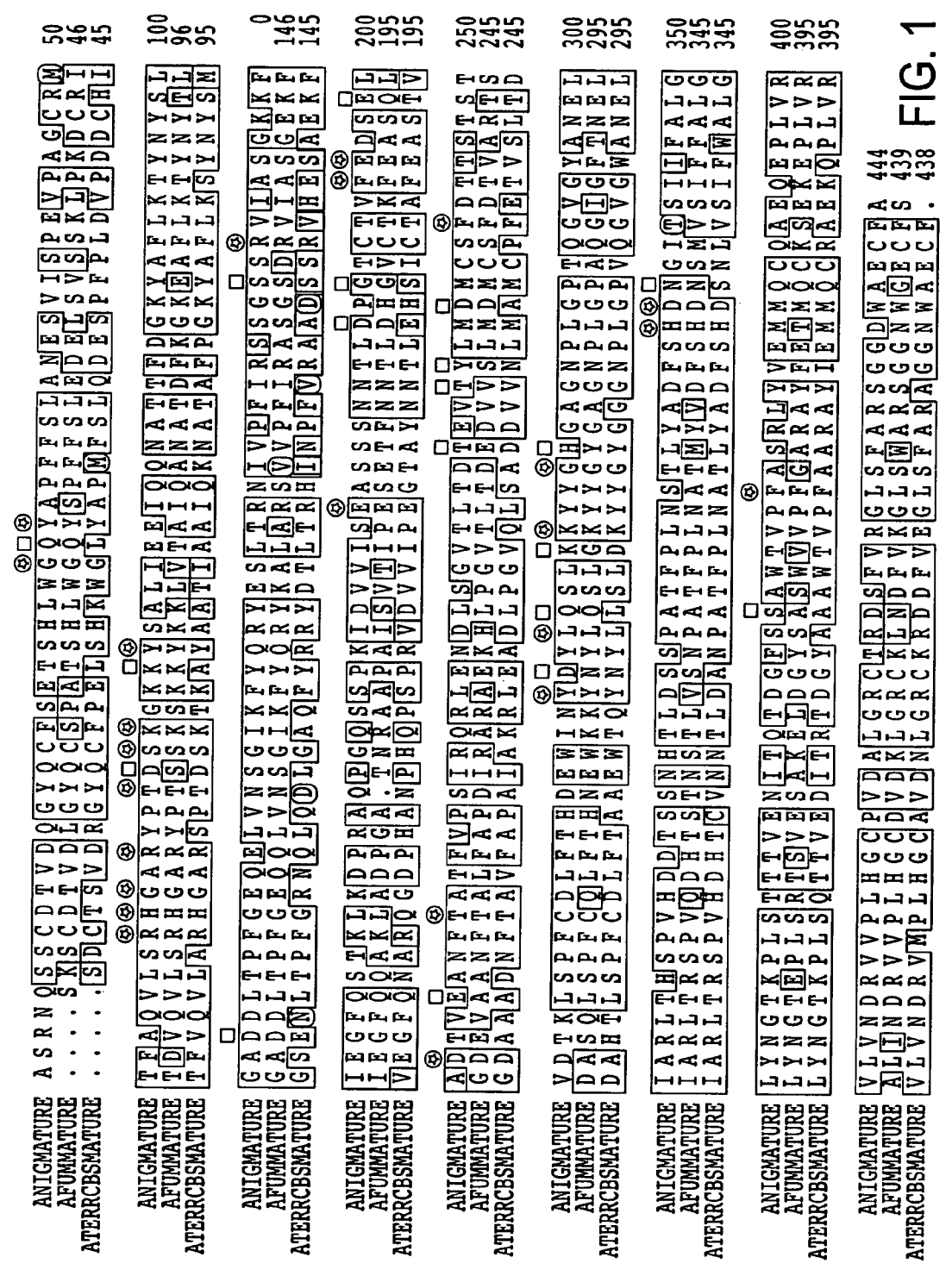

It is in general an object of the present invention to provide a phytase which has been modified in a way that its activity property is more favorable than the one of the non-modified phytase, specifically such a phytase characterized therein that the amino acid sequence of the non-modified phytase has been changed by deletion, substitution and/or addition of one or more amino acids, more specifically such a phytase wherein changes have been made at at least one position which is homologous to one of the following positions of the amino acid sequence of the phytase of *Aspergillus* (*A.*) *niger* (see FIG. 1): 27, 66, 71, 103, 140, 141, 188, 205, 234, 235, 238, 274, 277, 282, 340 and/or 424, preferably 27, 66, 140, 205, 274, 277, 282 and/or 340, and even more specifically such a phytase which is the phytase of eukaryotic, preferably fungal, more preferably *Aspergillus* and most preferably *Aspergillus fumigatus*, origin.

It is furthermore an object of the present invention to provide such a phytase wherein at position 27 or at least at position 27 a change occurs, preferably a phytase wherein the amino acid at position 27 is replaced by one selected from one of the following groups:

a) Ala, Val, Leu, Ile; or b) Thr or c) Asn; and furthermore such a phytase wherein in addition to position 27 a change occurs also at position 66 or wherein in addition to position 27 a change occurs also at position 140 and/or at positions 274 and/or 277.

It is also an object of the present invention to provide a phytase as specified above which is characterized by at least one of the following mutations: Q27L, Q27N, Q27T, Q27I, Q27V, Q27A, Q27G, S66D, S140Y, D141G, A205E, Q274L, G277D, G277K, Y282H and/or N340S.

It is furthermore an object of the present invention to provide phytase muteins which are resistant against degradation by proteases of fungal, preferably *Aspergillus* and most preferably *Aspergillus niger* (*ficuum*) origin. Such muteins are characterized therein that at least one of the following positions (which refers to the homologous position in the amino acid sequence of *A. niger*), namely position 130 or 129 and 130, preferably of the *Aspergillus fumigatus* or 167, 168 preferably of the *A. nidulans* phytase amino acid sequence, the amino acid which is present in the wild type sequence has been replaced against another amino acid which is known to change the protease sensitivity, e.g. in the case of *A. fumigatus* at position 130 from "S" to "N" and at position 129 from "R" to "L" and in case of *A. nidulans* at position 167 from "K" to "G" and at position 168 from R to Q. Such positions can be also combined with those providing for improved activity properties.

A desired property to be integrated into an unmodified phytase by sequence modification as described herein, may be a new property not present in the unmodified phytase, or may preferably be an existing property of the unmodified phytase which is to be improved, for example a specific activity over a broader pH range than in the unmodified phytase. The active site of the phytases is the part of the phytase which is the physical structure which provides all or part of the property. For example the binding site of the phytase provides the property of substrate specificity. Other parts of the phytase may have an influence on a given property, however the active site is the part which changes the property upon modification as described.

In this context a desired property which is to be improved, or an improved activity property means any type of improvement of the activity of the modified phytase as compared to the unmodified. This could mean for example a higher specific activity, preferably at least two fold or more preferably at least 3 to 4 fold higher in an assay known in the state of the art to measure phytase activity, see e.g. in EP 684 313 or described in the examples of the present application. Furthermore this could mean a different substrate specificity determined in an assay known in the state of the art or as described e.g. in the specific examples of the present invention. This could also mean a maximum of the specific activity at a different more favorable pH or a broad pH optimum ("improved pH profile") determined by an assay as known in the state of the art or as described e.g. in the examples. This also could mean improved resistance to protease degradation, as described above. Finally this could also mean any combination of such properties.

"Homologous" in the context of the present invention means the best fit of the primary, preferably also secondary and most preferably also tertiary structure of the phytase to be modified and the phytase of *Aspergillus niger*. How such best fit can be obtained is described in detail in Example 1 of the present invention. FIG. 1 gives an example of such best fit for the phytase amino acid sequences of *Aspergillus fumigatus* and *Aspergillus terreus* aligned on the basis of the *Aspergillus niger* amino acid sequence which latter sequence is also used as the reference to which the positions of the other sequences, e.g. the ones named before, are referred to. Furthermore the modified *Aspergillus fumigatus* phytase with the Q27L mutation, means nothing else than the phytase of *Aspergillus fumigatus* wherein at position 27 according to the assignment as defined above (which is in fact position 23 of the *Aspergillus fumigatus* amino acid sequence) the naturally occurring glutamine ("Q" refers to the standard UPAC one letter amino acid code) has been replaced by leucine ("L"). All muteins of the present invention are designated in this way independent from whether they are protease resistant muteins or muteins with improved activity properties.

Constructing a polynucleotide comprising a DNA sequence coding for the modified phytase whose amino acid sequence was obtained as described above is performed by known methods such as those described below. The nucleotides coding for the active site which provides the desired property are changed so that at least one of the amino acids now encoded corresponds to an amino acid which is different in the active site of the unmodified phytase and the active site of the phytase which has the desired property. Integrating such a polynucleotide into vectors and host cells so as to express the modified phytase is also part of this invention and may be accomplished by known methods and as described below.

Thus it is furthermore an object of the present invention to provide a polynucleotide comprising a DNA sequence coding for a phytase as described above, a vector, preferably an expression vector, comprising such a polynucleotide, a host cell which has been transformed by such a polynucleotide or vector, a process for the preparation of a phytase of the present invention wherein the host cell as described before is cultured under suitable culture conditions and the phytase is isolated from such host cell or the culture medium by methods known in the art, and a food or feed composition comprising a phytase of the present invention.

In this context it should be noted that it is also an object of the present invention to provide a DNA sequence which codes for a phytase carrying at least one of the specific mutations of the present invention and which hybridizes under standard conditions with the DNA sequences of the specific modified phytases of the present invention or a DNA sequence which, because of the degeneracy of the genetic code does not hybridize but which codes for a polypeptide with exactly the same amino acid sequence as the one encoded by the DNA sequence to which it does not hybridize or a DNA sequence which is a fragment of such DNA sequences which maintains the activity properties of the polypeptide of which it is a fragment.

"Standard conditions" for hybridization mean in the context the conditions which are generally used by a person skilled in the art to detect specific hybridization signals and which are described, e.g. by Sambrook et al., "Molecular Cloning", second edition, Cold Spring Harbor Laboratory Press 1989, New York, or preferably so called stringent hybridization and non-stringent washing conditions or more preferably so called stringent hybridization and stringent washing conditions a person skilled in the art is familiar with and which are described, e.g. in Sambrook et al. (s.a.).

It is furthermore an object of the present invention to provide a DNA sequence which can be obtained by the so called polymerase chain reaction method ("PCR") by PCR primers designed on the basis of the specifically described DNA sequences of the present invention. It is understood that the so obtained DNA sequences code for phytases with at least the same mutation as the ones from which they are designed and show comparable activity properties.

The principles of the polymerase chain reaction (PCR) method are outlined e.g. by White et al., Trends in Genetics, 5, 185–189 (1989), whereas improved methods are described e.g. in Innis et al. [PCR Protocols: A guide to Methods and Applications, Academic Press, Inc. (1990)].

DNA sequences of the present invention can be constructed starting from genomic or cDNA sequences coding for phytases known in the state of the art [for sequence information see references mentioned above, e.g.

EP 684 313 or sequence data bases, for example like Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA) or disclosed in the figures by methods of in vitro mutagenesis [see e.g. Sambrook et al., Molecular Cloning, Cold Spring Harbor Laboratory Press, New York]. A widely used strategy for such "site directed mutagenesis", as originally outlined by Hurchinson and Edgell [J. Virol. 8, 181 (1971)], involves the annealing of a synthetic oligonucleotide carrying the desired nucleotide substitution to a target region of a single-stranded DNA sequence wherein the mutation should be introduced [for review see Smith, Annu. Rev. Genet. 19, 423 (1985) and for improved methods see references 2–6 in Stanssen et al., Nucl. Acid Res., 17, 4441–4454 (1989)]. Another possibility of mutating a given DNA sequence which is also preferred for the practice of the present invention is the mutagenesis by using the polymerase chain reaction (PCR). DNA as starting material can be isolated by methods known in the art and described e.g. in Sambrook et al. (Molecular Cloning) from the respective strains. For strain information see, e.g. EP 684 313 or any depository authority indicated below. *Aspergillus niger* [ATCC 9142*], Myceliophthora thermophila* [ATCC 48102*], Talaromyces thermophilus* [ATCC 20186] and *Aspergillus fumigatus* [ATCC 34625] have been redeposited on Mar. 14, 1997 according to the conditions of the Budapest Treaty at the American Type Culture Cell Collection under the following accession numbers: ATCC 74337, ATCC 74340, ATCC 74338 and ATCC 74339, respectively. It is however, understood that DNA encoding a phytase to be mutated in accordance with the present invention can also be prepared on the basis of a known DNA sequence, e.g. as shown in FIG. 6 in a synthetic manner and described e.g. in EP 747 483 by methods known in the art.

Once complete DNA sequences of the present invention have been obtained they can be integrated into vectors by methods known in the art and described e.g. in Sambrook et al. (s.a.) to overexpress the encoded polypeptide in appropriate host systems. However, a man skilled in the art knows that also the DNA sequences themselves can be used to transform the suitable host systems of the invention to get overexpression of the encoded polypeptide. Appropriate host systems are for example fungi, like *Aspergilli*, e.g. *Aspergillus niger* [ATCC 9142] or *Aspergillus ficuum* [NRRL 3135] or like *Trichoderma*, e.g. *Trichoderma reesei* or yeasts, like *Saccharomyces*, e.g. *Saccharomyces cerevisiae* or *Pichia*, like *Pichia pastoris*, or *Hansenula polymorpha*, e.g. *H. polymorpha* (DSM5215). A man skilled in the art knows that such microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSM) or any other depository authority as listed in the Journal "Industrial Property" [(1991) 1, pages 29–40]. Bacteria which can be used are e.g. *E. coli*, Bacilli as, e.g. *Bacillus subtilis* or *Streptomyces*, e.g. *Streptomyces lividans* (see e.g. Anné and Mallaert in FEMS Microbiol. Letters 114, 121 (1993). *E. coli*, which could be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Vectors which can be used for expression in fungi are known in the art and described e.g. in EP 420 358, or by Cullen et al. [Bio/Technology 5, 369–376 (1987)] or Ward in Molecular Industrial Mycology, Systems and Applications for Filamentous Fungi, Marcel Dekker, New York (1991), Upshall et al. [Bio/Technology 5, 1301–1304 (1987)] Gwynne et al. [Bio/Technology 5, 71–79 (1987)], Punt et al. [J. Biotechnol. 17, 19–34 (1991)] and for yeast by Sreekrishna et al. [J. Basic Microbiol. 28, 265–278 (1988), Biochemistry 28, 4117–4125 (1989)], Hitzemann et al. [Nature 293, 717–722 (1981)] or in EP 183 070, EP 183 071, EP 248 227, EP 263 311. Suitable vectors which can be used for expression in *E. coli* are mentioned, e.g. by Sambrook et al. [s.a.] or by Fiers et al. in Procd. 8th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, e.g. in EP 405 370, Procd. Natl. Acad. Sci. USA 81, 439 (1984) by Yansura and Henner, Meth. Enzymol. 185, 199–228 (1990) or EP 207 459. Vectors which can be used for the expression in *H. Polymorpha* are known in the art and described, e.g. in Gellissen et al., Biotechnology 9, 291–295 (1991).

Either such vectors already carry regulatory elements, e.g. promoters, or the DNA sequences of the present invention can be engineered to contain such elements. Suitable promotor elements which can be used are known in the art and are, e.g. for *Trichoderma reesei* the cbh1-[Haarki et al., Biotechnology 7, 596–600 (1989)] or the pki1-promotor [Schindler et al., Gene 130, 271–275 (1993)], for *Aspergillus oryzae* the amy-promotor [Christensen et al., Abstr. 19th Lunteren Lectures on Molecular Genetics F23 (1987), Christensen et al., Biotechnology 6, 1419–1422 (1988), Tada et al., Mol. Gen. Genet. 229, 301 (1991)], for *Aspergillus niger* the glaA-[Cullen et al., Bio/Technology 5, 369–376 (1987), Gwynne et al., Bio/Technology 5, 713–719 (1987), Ward in Molecular Industrial Mycology, Systems and Applications for Filamentous Fungi, Marcel Dekker, New York, 83–106 (1991)], alcA-[Gwynne et al., Bio/Technology 5, 718–719 (1987)], suc1-[Boddy et al., Curr. Genet. 24, 60–66 (1993)], aphA-[MacRae et al., Gene 71, 339–348 (1988), MacRae et al., Gene 132, 193–198 (1993)], tpiA-[McKnight et al., Cell 46, 143–147 (1986), Upshall et al., Bio/Technology 5, 1301–1304 (1987)], gpdA-[Punt et al., Gene 69, 49–57 (1988), Punt et al., J. Biotechnol. 17, 19–37 (1991)] and the pkiA-promotor [de Graaff et al., Curr. Genet. 22, 21–27 (1992)]. Suitable promotor elements which could be used for expression in yeast are known in the art and are, e.g. the pho5-promotor [Vogel et al., Mol. Cell. Biol., 2050–2057 (1989); Rudolf and Hinnen, Proc. Natl. Acad. Sci. 84, 1340–1344 (1987)] or the gap-promotor for expression in *Saccharomyces cerevisiae* and for *Pichia pastoris*, e.g. the aox1-promotor [Koutz et al., Yeast 5, 167–177 (1989); Sreekrishna et al., J. Basic Microbiol. 28, 265–278 (1988)], or the FMD promoter [Hollenberg et al., EPA No. 0299108] or MOX-promotor [Ledeboer et al., Nucleic Acids Res. 13, 3063–3082 (1985)] for *H. polymorpha*.

Accordingly vectors comprising DNA sequences of the present invention, preferably for the expression of said DNA sequences in bacteria or a fungal or a yeast host and such transformed bacteria or fungal or yeast hosts are also an object of the present invention.

Once such DNA sequences have been expressed in an appropriate host cell in a suitable medium the encoded phytase can be isolated either from the medium in the case the phytase is secreted into the medium or from the host organism in case such phytase is present intracellularly by methods known in the art of protein purification or described, e.g. in EP 420 358 Known methods of protein purification may be used to isolate the phytases of this invention. For example various types of chromatography may be used individually or in combination. Gel purification may also be used. Accordingly a process for the preparation of a polypeptide of the present invention characterized in that transformed bacteria or a host cell as described above is cultured under suitable culture conditions and the polypeptide is recovered therefrom and a polypeptide when produced by such a process or a polypeptide encoded by a DNA sequence of the present invention are also an object of the present invention.

Phytases of the present invention can be also expressed in plants according to methods as described, e.g. by Pen et al. in Bio/Technology 11, 811–814 (1994) or in EP 449 375, preferably in seeds as described, e.g. in EP 449 376.

For example, a DNA sequence encoding a phytase of the present invention can be placed under the control of regulatory sequences from the gene encoding the 12S storage protein cruciferin from *Brassica napus*. The construct is thereafter subcloned into a binary vector such as pMOG23 (in *E. coli* K-12 strain DH5α, deposited at the Centraal Bureau voor Schimmelcultures, Baarn, The Netherlands under accession number CBS 102.90). This vector is introduced into *Agrobacterium tumefaciens* which contains a disarmed Ti plasmid. Bacterial cells containing this contruct are co-cultivated with tissues from tobacco or Brassica plants, and transformed plant cells are selected by nutrient media containing antibiotics and induced to regenerate into differentiated plants on such media. The resulting plants will produce seeds that contain and express the DNA contruct. Or the phytase-encoding DNA sequence can be placed under the control of regulatory sequences from the 35S promoter of Cauliflower Mosaic Virus (CaMV). The contruct is thereafter subcloned into a binary vector. This vector is then introduced into *Agrobacterium tumefaciens* which contains a disarmed Ti plasmid. Bacterial cells containing this construct are cocultivated with tissues from tobacco or Brassica plants, and transformed plant cells are selected by nutrient media containing antibiotics and induced to regenerate into differentiated plants on such media. The resulting plants contain and express the DNA construct constitutively.

The plant or plant part containing phytase can be used directly for the preparation of a feed composition or can be extracted from plants or plant organs by methods known in the art. Accordingly it is also an object of the present invention to provide a process for the production of the phytases of the present invention in plants or plant organs, like seeds, the phytases when produced by such methods, the transformed plants and plant organs, like seeds itself.

Once obtained the polypeptides of the present invention (which include modified phytases as described and active fragments thereof, and fusion proteins which include the phytases or fragments, or proteins which have stabilized by other moieties such as conjugation with polyalkylene glycols and such) can be characterized regarding their properties which make them useful in agriculture any assay known in the art and described e.g. by Simons et al. [Br. J. Nutr. 64, 525–540 (1990)], Schöner et al. [J. Anim. Physiol. a. Anim. Nutr. 66, 248–255 (1991)], Vogt [Arch. Geflügelk. 56, 93–98 (1992)], Jongbloed et al. [J. Anim. Sci., 70, 1159–1168 (1992)], Perney et al. [Poultry Sci. 72, 2106–2114 (1993)], Farrell et al., [J. Anim. Physiol. a. Anim. Nutr. 69, 278–283 (1993), Broz et al., [Br. Poultry Sci. 35, 273–280 (1994)] and Düngelhoef et al. [Animal Feed Sci. Technol. 49, 1–10 (1994)] can be used.

In general the polypeptides of the present invention can be used without being limited to a specific field of application for the conversion of inositol polyphosphates, like phytate to inositol and inorganic phosphate. For example phytases can be used to increase the nutrient value of plant material in animal feed by liberating from it inorganic phosphate which otherwise would otherwise not be accessible to non-ruminants. This reduces the amount of phosphorous which must be added to feed as a supplement and also reduces the amount of phosphorous which is excreted. Thus, phytases of this invention which have improved properties will enhance this process, or impart new benefits.

Furthermore the polypeptides of the present invention can be used in a process for the preparation of compound food or feeds wherein the components of such a composition are mixed with one or more polypeptides of the present invention. Accordingly compound food or feeds comprising one or more polypeptides of the present invention are also an object of the present invention. A person skilled in the art is familiar with their process of preparation. A phytase of this invention may be added to the complete feed preparation or to any component or premix or pelleted component. The effect of the added phytase may be an improvement in food utilization by virtue of the improved property or properties of the phytase. For example a phytase may have improved heat resistance to resist degradation caused by the food preparation process, and/or may have improved specific activity to liberate more phosphorous, and/or to liberate phosphorous in a wider range of conditions. Other properties of the modified phytase which increase the value or stability or other properties of the feed are also contemplated. Such compound foods or feeds can further comprise additives or components generally used for such purpose and known in the state of the art.

It is furthermore an object of the present invention to provide a process for the reduction of levels of phytate in animal manure characterized in that an animal is fed such a feed composition in an amount effective in converting phytate contained in the feedstuff to inositol and inorganic phosphate.

EXAMPLES

Example 1

Homology Modeling of *A. fumigatus* and *A. terreus* cbs116.46 Phytase

The amino acid sequences of *A. fumigatus* [ATCC 13073] (see FIG. 1) and *A. terreus* cbs116.46 phytase (see FIG. 1) were compared with the sequence of *A. niger* (*ficuum*) phytase (see FIG. 1) for which the three-dimensional structure had been determined by X-ray crystallography. Crystallographic data are given in FIG. 8.

A multiple amino acid sequence alignment of *A. niger* (*ficuum*) phytase, *A. fumigatus* phytase and *A. terreus* cbs116.46 phytase was calculated with the program "PILEUP" (Prog. Menu for the Wisconsin Package, version 8, September 1994, Genetics Computer Group, 575 Science Drive, Madison Wis., USA 53711). The three-dimensional models of *A. fumigatus* phytase and *A. terreus* cbs116.46 phytase were built by using the structure of *A. niger* (*ficuum*) phytase as template and exchanging the amino acids of *A. niger* (*ficuum*) phytase according to the sequence alignment to amino acids of *A. fumigatus* and *A. terreus* cbs116.46 phytases, respectively. Model construction and energy optimization were performed by using the program Moloc (Gerber and Müller, 1995). C-alpha positions were kept fixed except for new insertions/deletions and in loop regions distant from the active site.

Only small differences of the modelled structures to the original crystal structure could be observed in external loops. Furthermore the different substrate molecules that mainly occur on the degradation pathway of phytic acid (myo-inositol-hexakisphosphate) by *Pseudomonas* sp. bacterium phytase and, as far as determined, by *A. niger* (*ficuum*) phytase (Cosgrove, 1980; FIG. 1) were constructed and forged into the active site cavity of each phytase structure. Each of these substrates was oriented in a hypothetical binding mode proposed for histidine acid phosphatases (Van Etten, 1982). The scissile phosphate group was oriented towards the catalytically essential His 59 to form the covalent phosphoenzyme intermediate. The oxygen of the substrate phosphoester bond which will be protonated by Asp 339 after cleavage was orientated towards the proton donor. Conformational relaxation of the remaining structural part of the substrates as well as the surrounding active site residues was performed by energy optimization with the program Moloc.

Based on the structure models the residues pointing into the active site cavity were identified. More than half (60%) of these positions were identical between these three phytases, whereas only few positions were not conserved (see FIG. 1). This observation could be extended to four additional phytase sequences (*A. nidulans, A. terreus* 9A1, *Talaromyces thermophilus, Myceliophthora thermophila*).

The results coming from sequence alignment and structural information including favourable enzyme-substrate interactions were combined to define the positions for mutational analysis which are shown in Table 1.

REFERENCES

Gerber, P. and Müller, K. (1995) Moloc molecular modeling software. J. Comput. Aided Mol. Des. 9, 251–268
Van Etten, R. L. (1982) Human prostatic acid phosphatase: a histidine phosphatase. Ann. NY Acad. Sci. 390,27–50
Cosgrove, D. J. (1980) Inositol phosphates—their chemistry, biochemistry and physiology: studies in organic chemistry, chapter 4. Elsevier Scientific Publishing Company, Amsterdam, Oxford, N.Y.

Example 2

Construction of Plasmids pUC18-AfumgDNA and pUC18-AfumcDNA

Plasmids pUC18-AfumgDNA and pUC18-AfumcDNA, the basic constructs for all the *A. fumigatus* muteins described below were constructed as follows.

pUC18-AfumgDNA: The genomic DNA sequence of the phytase gene of *Aspergillus fumigatus* was obtained by PCR using the "Expand™ High Fidelity PCR Kit" (Boehringer Mannheim, Mannheim, Germany) with primers #39 and #40 (designed on the basis of the genomic sequence shown in FIG. 6) and genomic DNA of *Aspergillus fumigatus* [ATCC 13073] from the *A. fumigatus* (NIH stock 5233) genomic library in a Lambda FixII vector [Stratagene, Lugolla, Calif. 92037, USA; catalog No. 946055].

```
Primer #39:
        BspHI
5' TAT ATC ATG ATT ACT CTG ACT TTC CTG CTT TCG 3'    (SEQ ID NO:16)
    M   I   T   L   T   F   L   L   S              (SEQ ID NO:17)

Primer #40:
                        EcoRV
3' CCT CTC ACG AAA TCA ACT CTA TAG ATA TAT 5'        (SEQ ID NO:18)
    G   E   C   F   S   *                            (SEQ ID NO:19)
```

The reaction mix included 10 pmol of each primer and 200 ng of template DNA. 35 rounds of amplification were done with the following cycling values: 95° C. 1 min/56° C., 1 min/72° C., 90 sec. The PCR-amplified *Aspergillus fumigatus* mutein genes had a new BspHI site at the ATG start codon, introduced with primer #39, which resulted in the change of the second amino acid from a valine to an isoleucine. Furthermore, an EcoRV site was created with primer #40 downstream of the TGA termination codon of the gene.

The PCR fragment (approx. 1450 bp) was subsequently cloned into the SmaI site of pUC18 using the "sure clone Kit" (Boehringer Mannheim s.a.) according to the supplier's recommendations. The resulting plasmid was named pUC18-AfumgDNA.

pUC18-AfumcDNA: This plasmid lacks the intron (small gap letters in FIG. 6) of the *A. fumigatus* phytase gene and was constructed as outlined in FIG. 13. Briefly, using primers Fum28 and Fum11 the 5' end of exon 2 was amplified by PCR (see below), digested with NcoI and EagI (new restriction site introduced with primer Fum28) and ligated together with the linker coding for exon 1 made of primers Fum26 and Fum27 into the XbaI and NcoI sites of pUC18-AfumgDNA, thereby resulting in plasmid pUC18-AfumcDNA.

```
Fum28:
5' ATATATCGGCCGAGTGTCTGCGGCACCTAGT 3'          (SEQ ID NO:20)
         EagI

Fum11:
5' TGAGGTCATCCGCACCCAGAG 3'                    (SEQ ID NO:21)

Fum26:
5' CTAGAATTCATGGTGACTCTGACTTTCCTGCTTTCGGCGGCGTATCT   (SEQ ID NO:22)

GCTTTCC 3'

Fum27:
5' GGCCGGAAAGCAGATACGCCGCCGAAAGCAGGAAAGTCAGAGTC      (SEQ ID NO:23)

ACCATGAATT 3'
```

PCR reaction to get 5' end of exon 2 of the *A. fumigatus* phytase:

| | |
|---|---|
| 2 µl | template: pUC18-AfumgDNA (20 ng) |
| 1 µl | dNTP's-mix (Boehringer Mannheim s.a.) |
| 5 µl | 10x Buffer |
| 1 µl | Taq polymerase (Boehringer Mannheim s.a.) |
| 1.9 µl | Fum11 (=10 pmol) |
| 2 µl | Fum28 (=10 pmol) |
| 37,1 µl | H₂O |

In total 35 cycles with the temperature profile: 95° C. for 30 sec/56° C. for 30 sec/72° C. for 45 sec were made. The amplified fragment (approx. 330 bp) was extracted once with an equal volume of phenol/chloroform (1:1). To the recovered aqueous phase 0.1 volume of 3 M sodium acetate, pH 4.8 and 2.5 volumes of ethanol were added. The mixture was centrifuged for 10 min at 12000 g and the pellet resuspended in 20 µl of H₂O. Subsequently, the purified fragment was digested with NcoI and EagI and processed as outlined above.

Example 3

Construction of Muteins of the Phytase of *Aspergillus fumigatus* for Expression in *A. niger*

Figure 15:
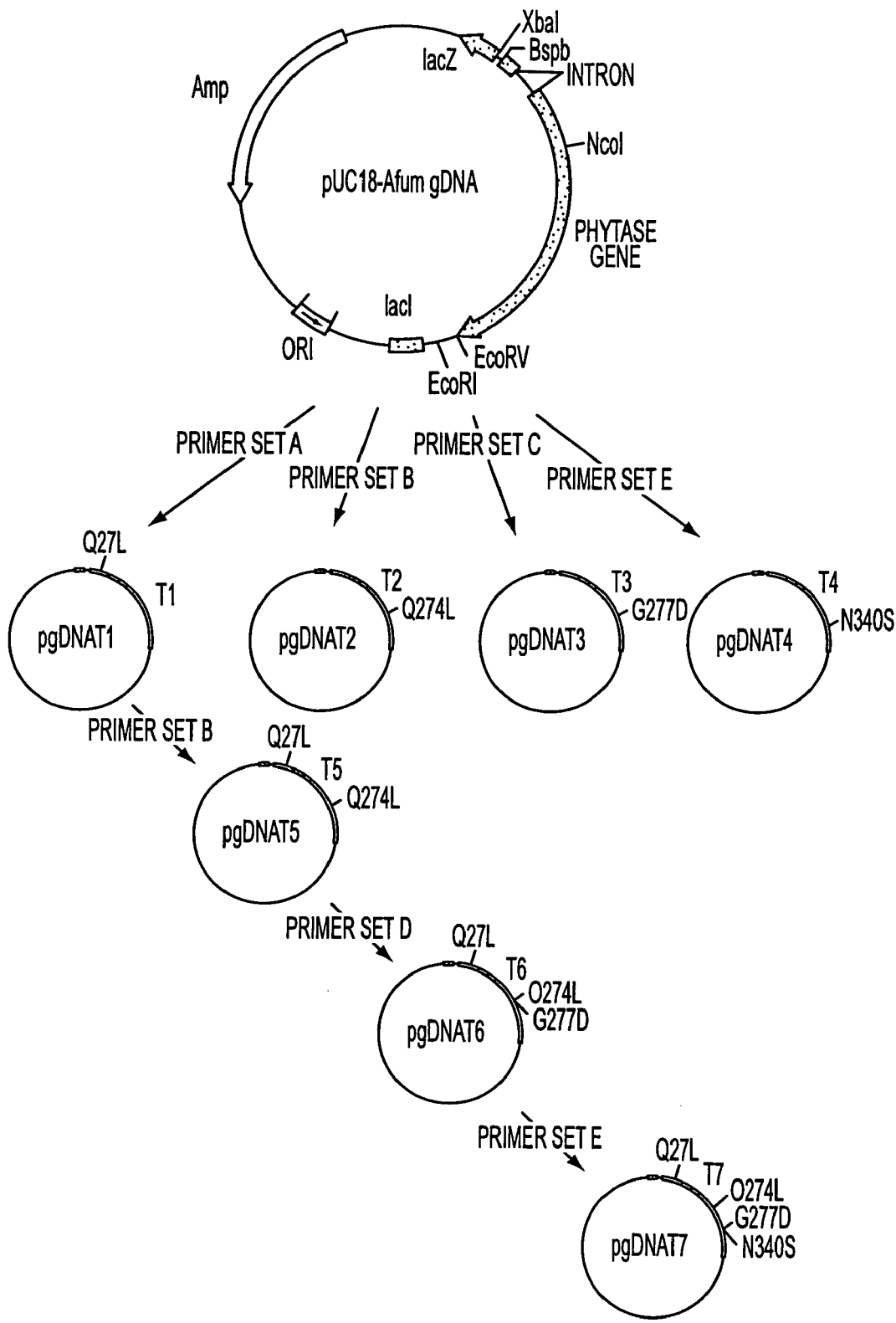
FIG. 15: Construction of plasmids pgDNAT1–pgDNAT7.
Figure 16:
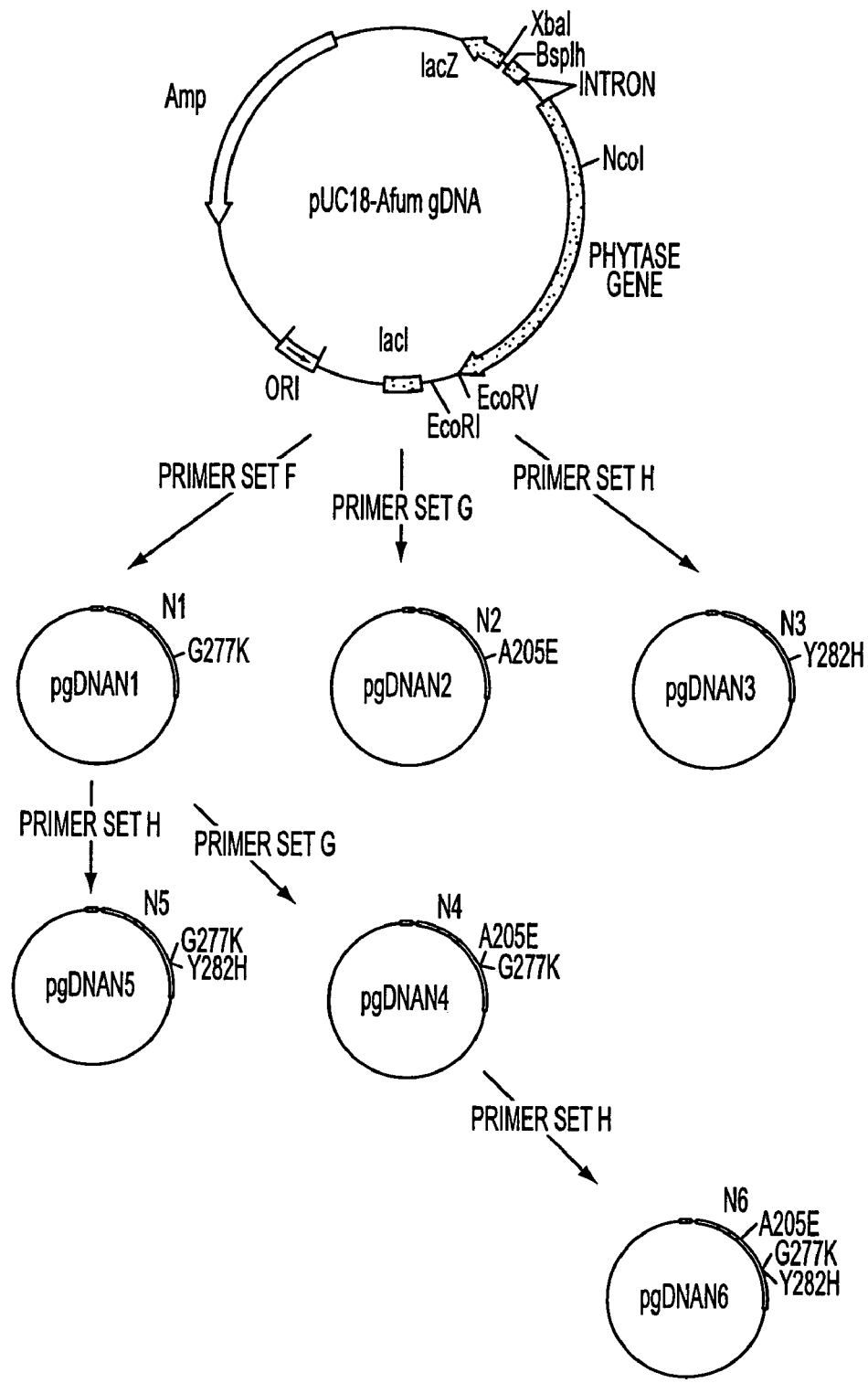
FIG. 16: Construction of plasmids pgDNAN1–pgDNAN6.

To construct all muteins for the expression in *A. niger*, plasmid pUC18-AfumgDNA was used as template for site-directed mutagenesis. Mutations were introduced using the "quick exchange site-directed mutagenesis kit" from Stratagene (La Jolla, Calif., USA) following the manufacturer's protocol and using the corresponding primers (FIG. 14). All mutations made are summarized in Table 1A and B wherein T1 to T7 and N1 to N6, respectively, refer to the muteins and "Mutation" to the amino acids replaced at such position. For example T5 refers to a mutein with a double mutation: L at position 27 for Q and L at position 274 for Q. The primer sets (A–H) used to introduce the corresponding mutations are shown in FIG. 14a. The newly introduced amino acid is shown in bold and the subscript indicates the position in the mature *Aspergillus fumigatus* enzyme concerning to the numbering of the *A. niger* amino acid sequence. FIGS. 15 and 16 outline the scheme for the construction of different plasmids pgT1–pgT7 and pgN1–pgN6 encoding the muteins carrying only one mutation (T1–T4; N1–N3) or more mutations (T5–T7; N4–N6). Clones harboring the desired mutations were identified by DNA sequence analysis as known in the art. The mutated phytases were verified by complete sequencing of the genes.

Example 4

Construction of Muteins of the Phytase of *Aspergillus fumigatus* for Expression in *Saccharomyces cerevisiae*

Figure 13:
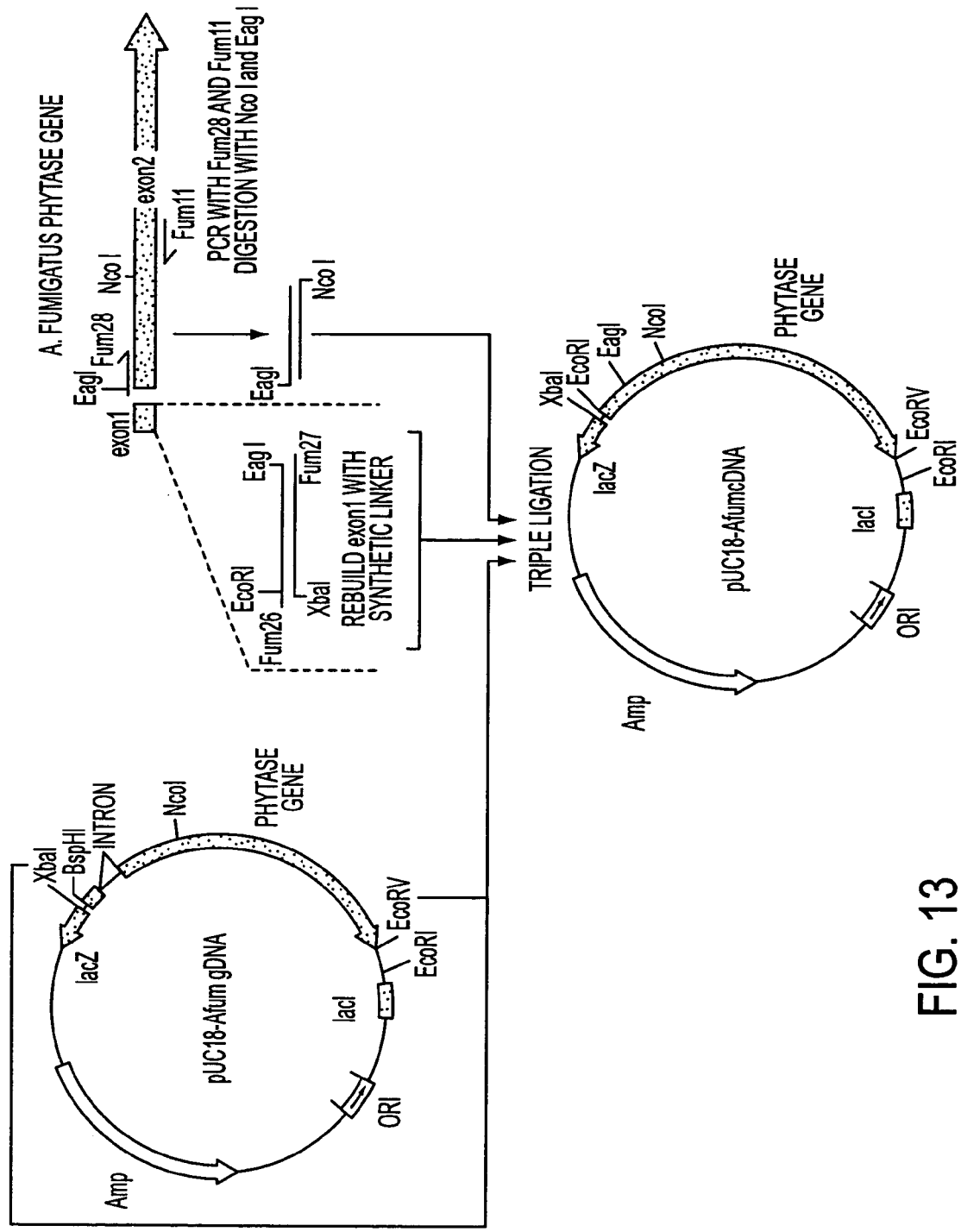
FIG. 13: Construction of the basic plasmids pUC18-AfumgDNA and pUC18-AfumcDNA for site directed mutagenesis.
Figure 17A:
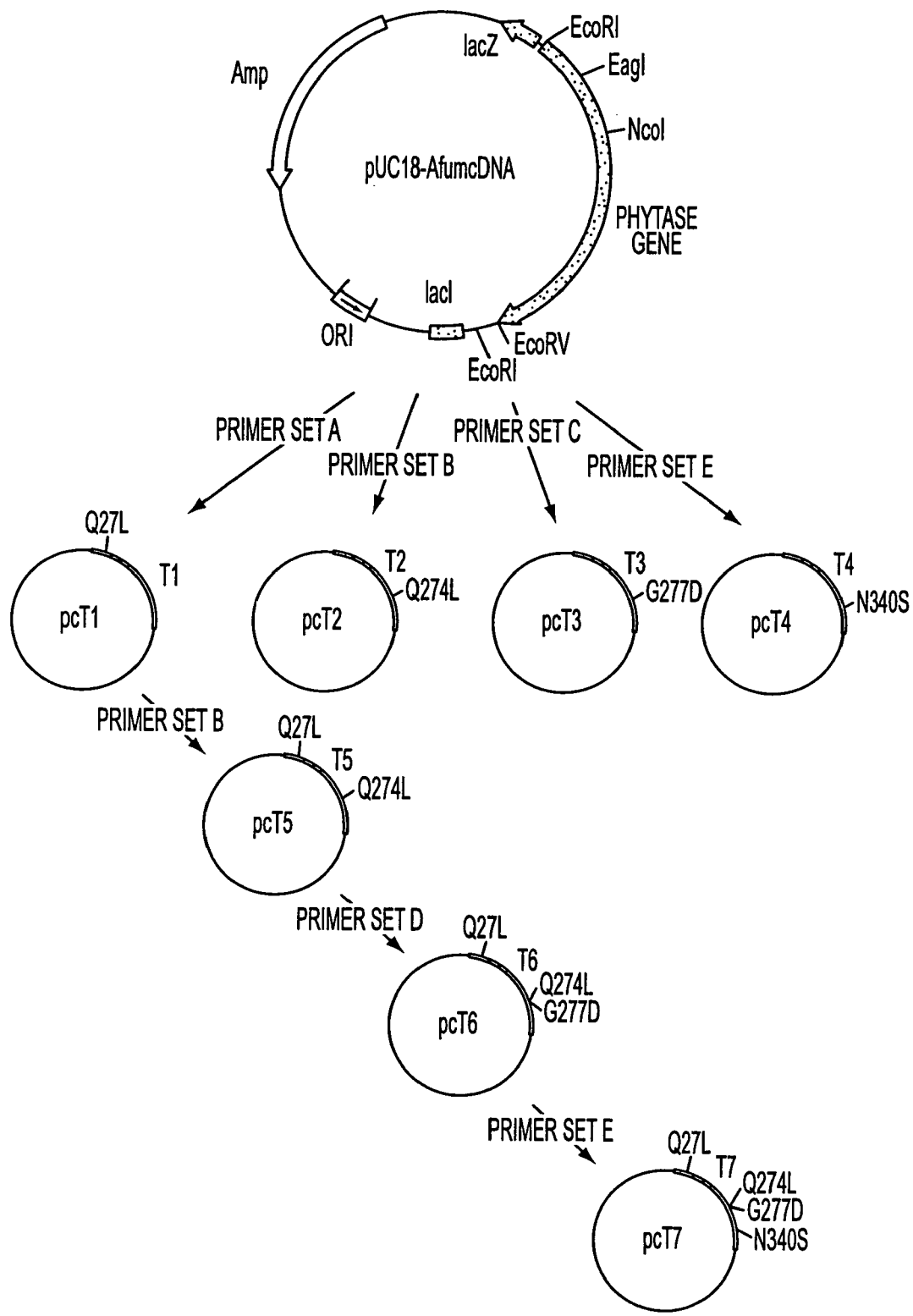
FIG. 17a: Construction of plasmids pcT1–pcT7.
Figure 18:
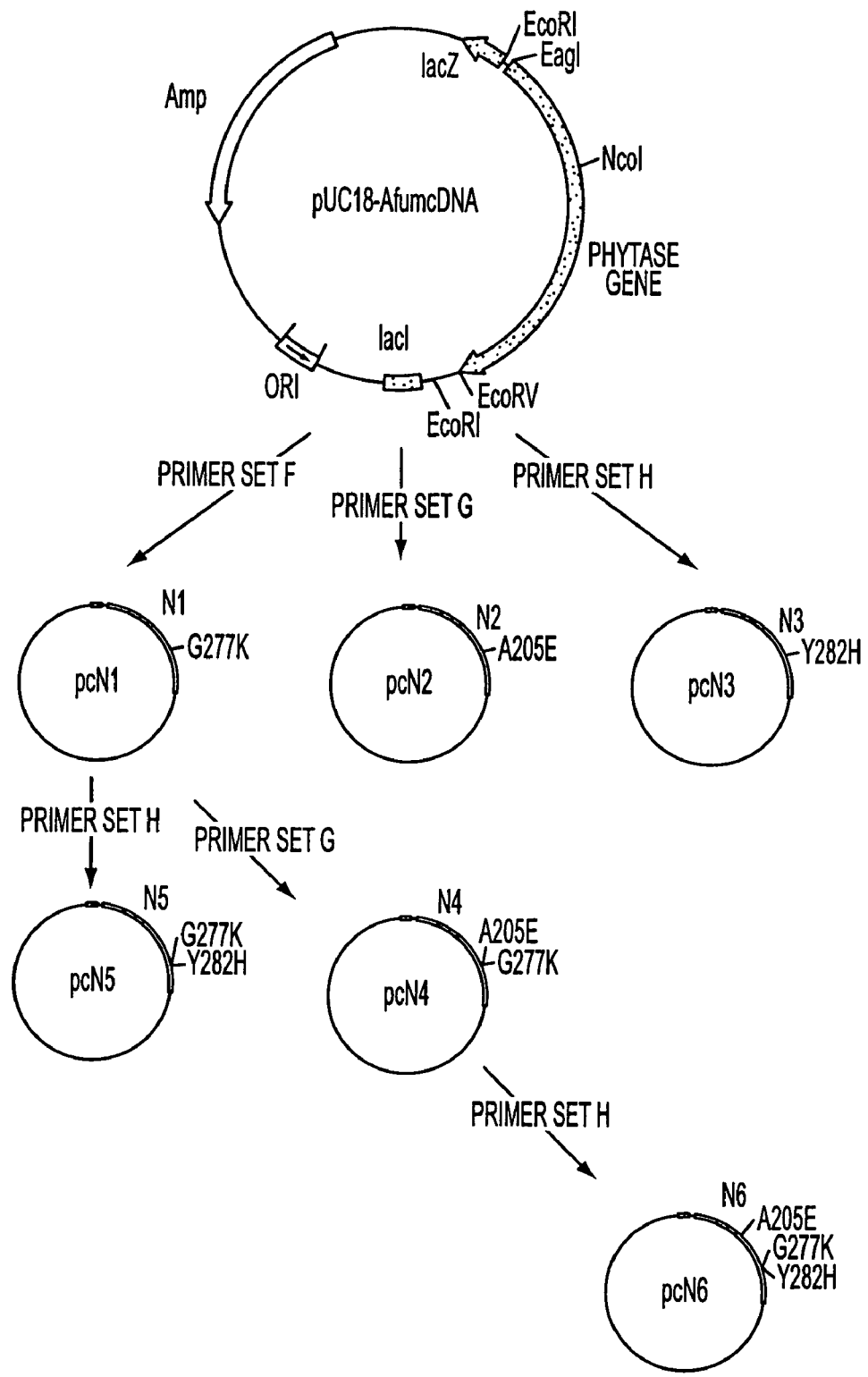
FIG. 18: Construction of plasmids pcN1–pcN6.

Construction of plasmids pcT1–pcT7 (FIG. 17a) and pcN1–pcN6 (FIG. 18), respectively, encoding the muteins T1–T7 and N1–N6 for the expression in *S. cerevisiae* was basically done as outlined in Example 3. Instead of using pUC18-AfumgDNA as the basic construct to introduce the mutations, plasmid pUC18-AfumcDNA was used (FIG. 13).

Figure 17B:
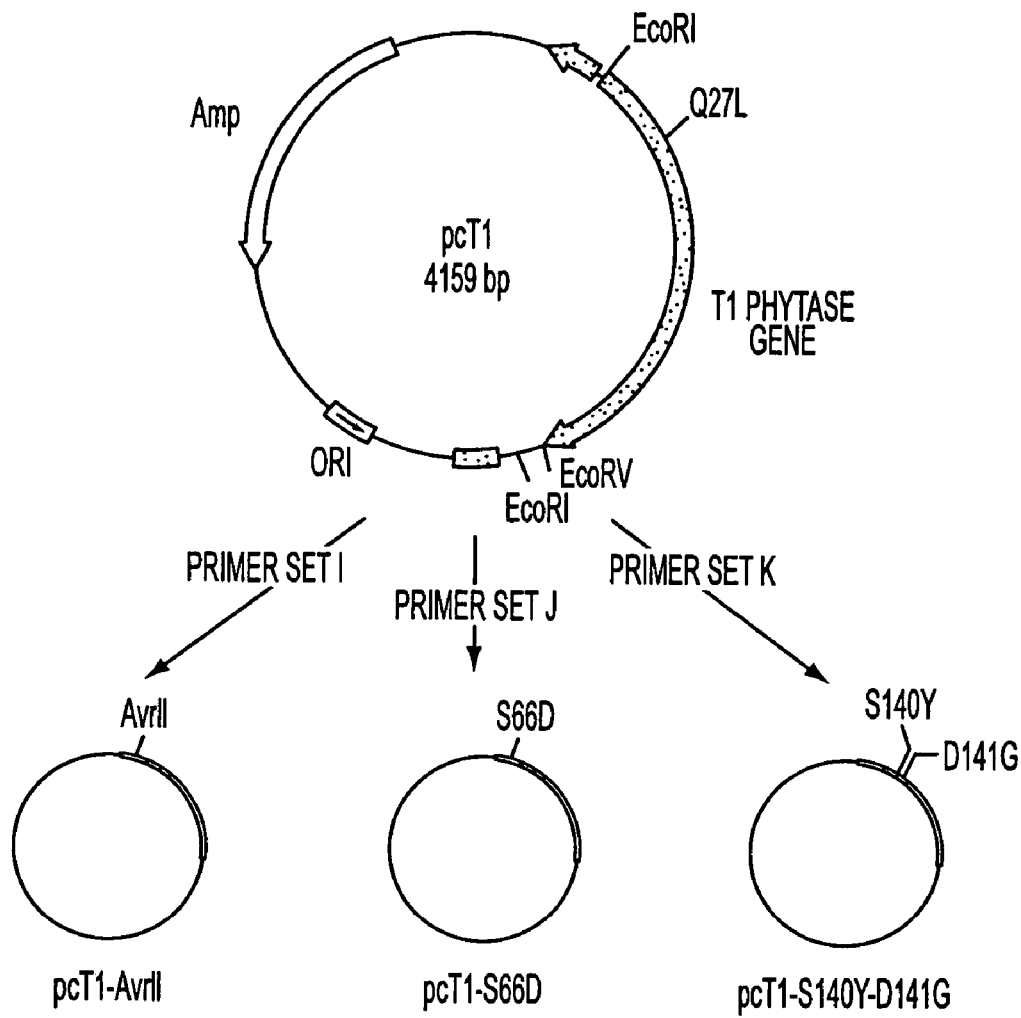
FIG. 17b: Construction of plasmids pcT1-AvrII, pcT1-S66D and pcT1-S140Y-D141G.
Figure 17C:
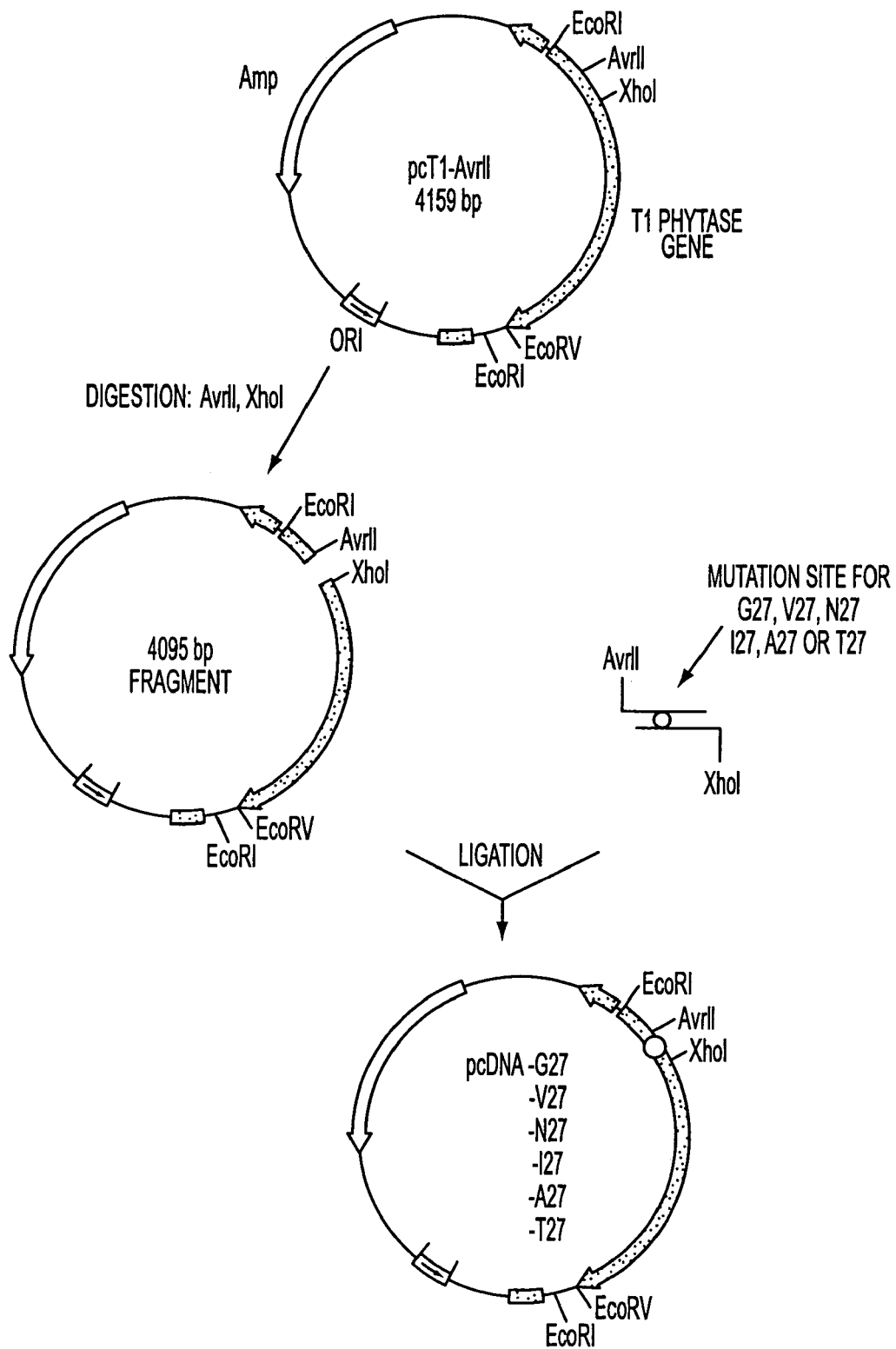
FIG. 17c: Construction of plasmids pcDNA-N27, -T27, -I127, -V27, -A27, -G27.

The plasmids pcDNA-N27, -G27, -V27, -A27, -I27 and -T27 encoding the muteins N27, G27, V27, A27, I27 and T27 were constructed as follows:

A silent restriction site for AvrII was introduced into plasmid pcT1 by site directed mutagenesis as described in Example 3 using primer set I (FIG. 14a; FIG. 17b). The *A. fumigatus* phytase gene fragment AvrII/XhoI was then replaced by the linker fragment harbouring the desired mutations (FIG. 17c). Each linker fragment was generated by annealing of the respective pairs of synthesized polynucleotides (FIG. 14b; sense and antisense strand; 90 ng each) for 3 min at 70 γC in 9 µl distilled water.

Construction of plasmids pcT1-S66D and pcT1-S140Y-D141G encoding the *A. fumigatus* Q27L-S66D double mutant and the *A. fumigatus* Q27L-S140Y-D141G triple mutant was basically carried out as described in Example 3. Plasmid pcT1, harbouring the mutation coding for Q27L, was used as template for site directed mutagenesis together with the corresponding primer sets J and K (FIG. 14a; FIG. 17b)

All mutations were verified by DNA sequence analysis of the entire gene.

Example 5

Expression in *Aspergillus niger*

Figure 19:
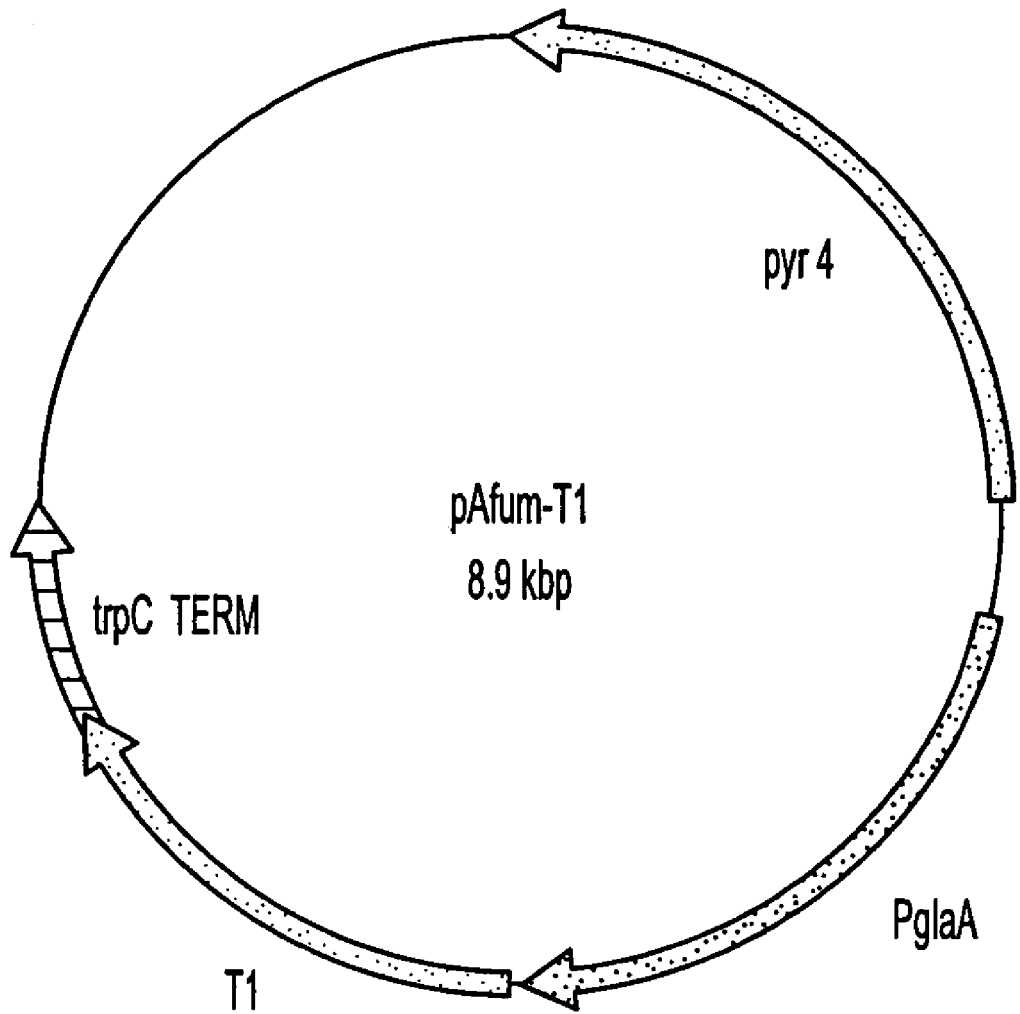
FIG. 19: Plasmid pAfum-T1 for the expression of mutein T1 in *Aspergillus niger*.

The genes encoding the aforementioned *A. fumigatus* wild-type phytase and muteins (FIG. 16) were isolated with BspHI and EcoRV from plasmids pgDNAT1–pgDNAT7 and pgDNAN1–pgDNAN6 and ligated into the NcoI site downstream of the glucoamylase promoter of *Aspergillus niger* (glaA) and the EcoRV site upstream of the *Aspergillus nidulans* tryptophan C terminator (trpC) (Mullaney et al., 1985). The resulting expression plasmids had in addition the orotidine-5'-phosphate decarboxylase gene (pyr4) of *Neurospora crassa* as selection marker. FIG. 19 shows an example for such an expression plasmid carrying the gene encoding mutein T1 (van den Hondel et al., 1991). The basic expression plasmid described above corresponds basically to the pGLAC vector described in example 9 of EP 684 313. Transformation of *Aspergillus niger* and expression of the muteins was done as described in EP 684 313.

The supernatant was concentrated by way of ultrafiltration in Amicon 8400 cells (PM30 membranes) and ultrafree-15 centrifugal filter devices (Biomax-30K, Millipore).

The concentrate (typically 1.5–5 ml) was desalted in aliquots of 1.5 ml on a Fast Desalting HR 10/10 column (Pharmacia Biotech), with 10 mM sodium acetate, pH 5.0, serving as elution buffer. The desalted *A. fumigatus* samples were directly loaded onto a 1.7 ml Poros HS/M cation exchange chromatography column (PerSeptive Biosystems, Framingham, Mass., USA). *A. terreus* cbs116.46 [CBS 220.95] phytase was directly loaded onto a 1.7 ml Poros HQ/M anion exchange chromatography column. In both cases, phytase was eluted in pure form by way of a sodium chloride gradient.

REFERENCES

Mullaney, E. J., J. E. Hamer, K. A. Roberti, M. M. Yelton, and W. E. Timberlake. 1985. Primary structure of the trpC gene from *Aspergillus nidulans*. Mol. Gen. Genet. 199: 37–45.

Van den Hondel, C. A. M. J. J., P. J. Punt, and R. F. M. van Gorcom. 1991. Heterologous gene expression in filamentous fungi. In: More gene manipulations in fungi. pp. 396–428. Bennett, J. W. and Lasure, L. L. (eds.). Academic Press Inc., San Diego, Calif.

Example 6

Expression in *Saccharomyces cerevisiae*

The intron less genes encoding the *A. fumigatus* wild-type phytase and the different muteins (FIGS. 17/18) mentioned above were isolated from the respective plasmids pUC18-AfumcDNA, pcDNAT1–pcDNAT7 and pcDNAN1–pcDNAN6 with EcoRI and EcoRV and subcloned either between the blunt ended XhoI and the EcoRI sites of plasmid pYES2 (Invitrogen, San Diego, Calif., USA) or the shortened GAPFL (glyceraldehyde-3-phosphate dehydrogenase) promoter and the PHO5 terminator as described by Janes et al. (1990). Transformation of *Saccharomyces cerevisiae* strains, e.g. INVSc1 (Invitrogen, San Diego, Calif., USA) was done according to Hinnen et al. (1978). Single colonies harbouring the phytase gene under the control of the GAPFL promoter were picked and cultivated in 5 ml selection medium (SD-uracil) (Sherman et al., 1986) at 30 γC under vigorous shaking (250 rpm) for 1 day. The preculture was then added to 500 ml YPD medium (Sherman et al., 1986) and cultivated under the same conditions. After four days cell broth was centrifuged (7000 rpm, GS3 rotor, 15 min. 5 γC) and the supernatant was collected. Induction of the GAL1 promotor (plasmid pYES2 from Invitrogen, San Diego, Calif., USA) was done according to the manufacturers instructions. Purification of the muteins was as described in example 5 (s.a.).

REFERENCES

Janes, M., B. Meyhack, W. Zimmermann and A. Hinnen. 1990. The influence of GAP promoter variants on hirudine production, avarage plasmid copy number and cell growth in *Saccharomyces cerevisiae*. Curr. Genet. 18: 97–103

Hinnen, A., J. B. Hicks and G. R. Fink. 1978. Proc. Natl. Acad. Sci. USA 75: 1929–1933

Sheman, J. P., Finck, G. R. and Hicks, J. B. (1986). Laboratory Course Manual for Methods in Yeast Genetics. Cold Spring Harbor University Press.

Example 7

Determination of Phytase Activity and Substrate Specificity

Phytase activity was measured in an assay mixture containing 0.5% phytic acid (~5 mM), 200 mM sodium acetate, pH 5.0. After 15 min incubation at 37° C., the reaction was stopped by addition of an equal volume of 15% trichloroacetic acid. The liberated phosphate ions were quantified by mixing 100 μl of the assay mixture with 900 μl $H_2O$ and 1 ml of 0.6 M $H_2SO_4$, 2% ascorbic acid and 0.5% ammonium molybdate. Standard solutions of potassium phosphate were used as reference.

In case of pH optimum curves, purified enzymes were diluted in 10 mM sodium acetate, pH 5.0. Incubations were started by mixing aliquots of the diluted protein with an equal volume of 1% phytic acid (~10 mM) in a series of different buffers: 0.4 M glycine/HCl, pH 2.5; 0.4 M acetate/NaOH, pH 3.0, 3.5, 4.0, 4.5, 5.0, 5.5; 0.4 M imidazole/HCl, pH 6.0, 6.5; 0.4 M Tris/HCl, pH 7.0, 7.5, 8.0, 8.5, 9.0. Control experiments showed that pH was only slightly affected by the mixing step. Incubations were performed for 15 min at 37° C. as described above.

For determination of the substrate specificities of wild-type and mutant *A. fumigatus* phytases, phytic acid in the assay mixture was replaced by 5 mM-concentrations of the respective phosphate compounds. The activity tests were performed as described above.

Protein concentrations were calculated from the OD at 280 nm, using theoretical absorption values calculated from the known protein sequences with the DNA* software (DNASTAR, Inc., Madison, Wis., USA). An absorption of 1.0 OD at 280 nm corresponds to 0.94 mg/ml *A. fumigatus* phytase and 0.85 mg/ml of *A. terreus* cbs116.46 phytase.

pH profiles of *Aspergillus fumigatus* mutants T1 (Q27L), T5 (Q27L, Q274L) and T6 (Q27L, Q274L, G277D) have drastically changed compared to the wild-type *A. fumigatus* phytase (see FIG. 2). All mutants showed equal pH profiles. Increase in specific activity at pH 5.0 of the muteins as compared to the wild-type phytase of *Aspergillus fumigatus* is shown in Table 2. Enzyme activities were measured under standard assay conditions at pH 5.0. Several individual measurements (n: number of assays) were averaged.

Figure 20:
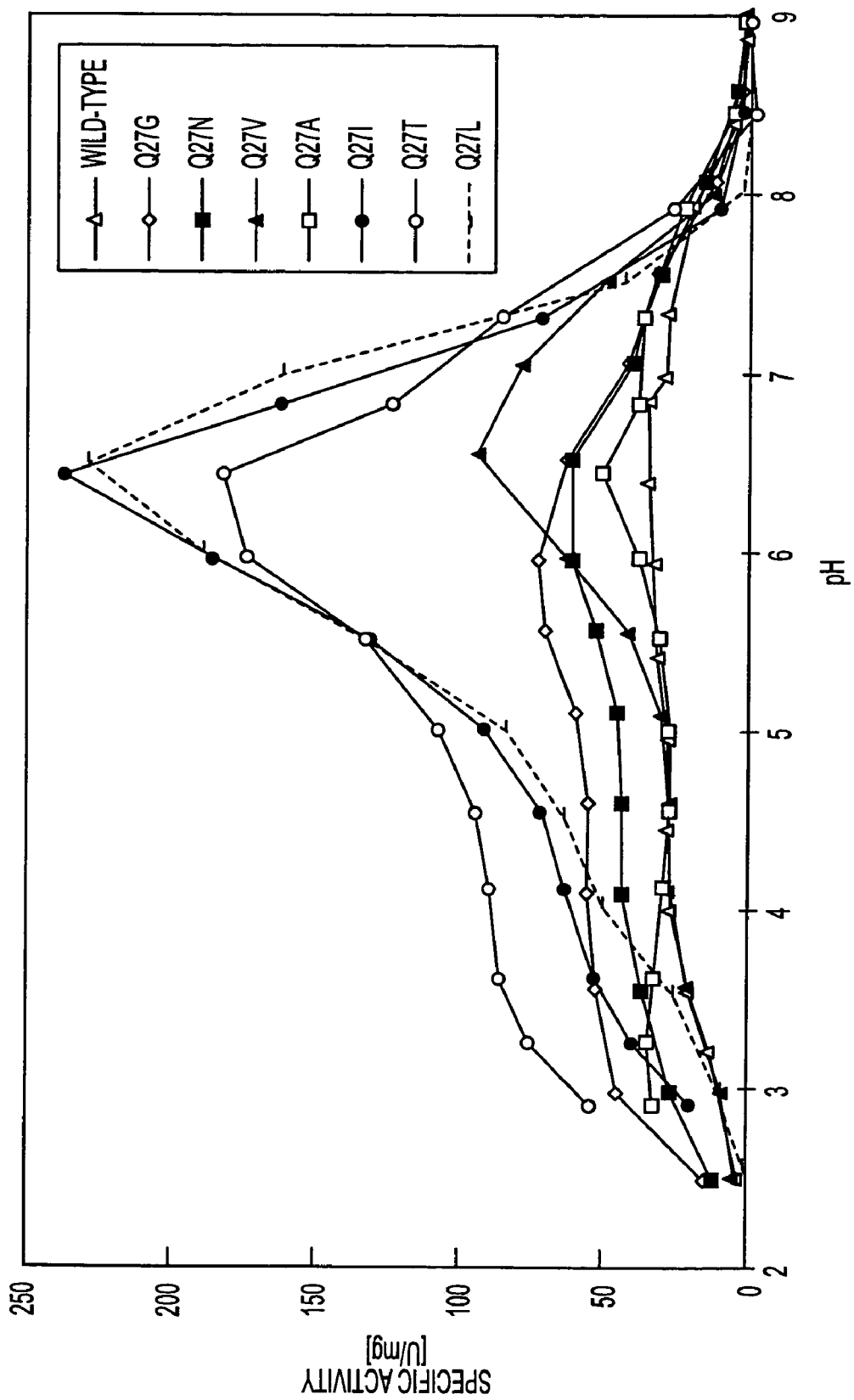
FIG. 20: pH optima curves. Specific activity of wild-type and mutant *A. fumigatus* phytases is plotted against pH of incubation. Open triangles: *A. fumigatus* [ATCC 13073] wild-type phytase; Open rhombs: *A. fumigatus* Q27G phytase; Filled squares: *A. fumigatus* Q27N phytase; Filled triangles: *A. fumigatus* Q27V phytase; Open squares: *A. fumigatus* Q27A phytase; Filled circles: *A. fumigatus* Q27I phytase; Open circles: *A. fumigatus* Q27T phytase; Dashed line: *A. fumigatus* Q27L phytase.

The pH profile of *A. fumigatus* phytase mutant Q27A resembles the pH profile of *A. fumigatus* wild-type phytase over nearly the whole pH range (FIG. 20). Whereas the specific activity of wild-type phytase is decreasing at pH values below pH 4.0, the specific activity of the phytase mutant Q27A remains nearly constant down to pH 2.9.

The single amino acid exchanges Q27L, Q27I, Q27V or Q27T have remarkably increased the specific activity over the whole pH range, especially between pH 5.0 and 7.5 (FIG. 20). Maximum values are reached at pH 6.5. In addition, mutation Q27T caused the highest specific activity values for phytic acid at low pH (pH 3.0–5.0).

Higher specific activities are also gained by the single mutations Q27G or Q27N, between pH 2.5 and 7.0, with maximum values at pH 6.0 (FIG. 20). The specific activity decreases at pH values below 3.5.

Figure 21:
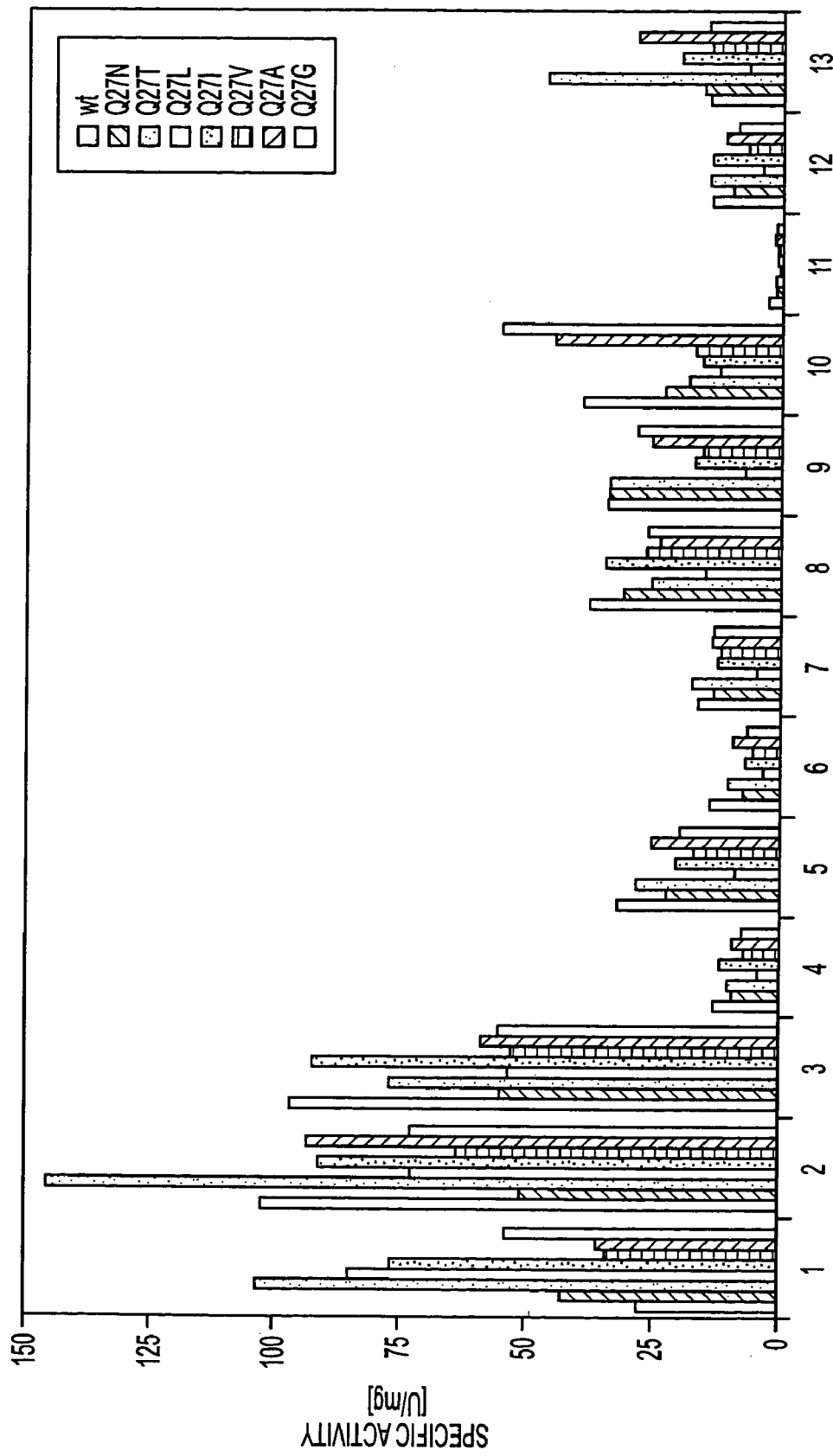
FIG. 21: Substrate specificities of wild-type and mutant *A. fumigatus* [ATCC 13073] phytases. The used substrates 1–13 are the same as mentioned in FIG. 3. The specific activities of the different phytases with any one of the 13 substrates tested are given in the following order (from left to right): *A. fumigatus* wild-type phytase, *A. fumigatus* Q27N phytase, *A. fumigatus* Q27T phytase, *A. fumigatus* Q27L phytase, *A. fumigatus* Q27I phytase, *A. fumigatus* Q27V phytase, *A. fumigatus* Q27A phytase, *A. fumigatus* Q27G phytase.

All single mutants still show a broad substrate specificity which is comparable to that of A. fumigatus wild-type phytase (FIG. 21). Some of the mutants show significantly higher specific activities than other mutants for selected substrates, e.g., the Q27T mutant for p-nitrophenyl phosphate and ATP, or the Q27G mutant for phosphoenolpyruvate.

Figure 22:
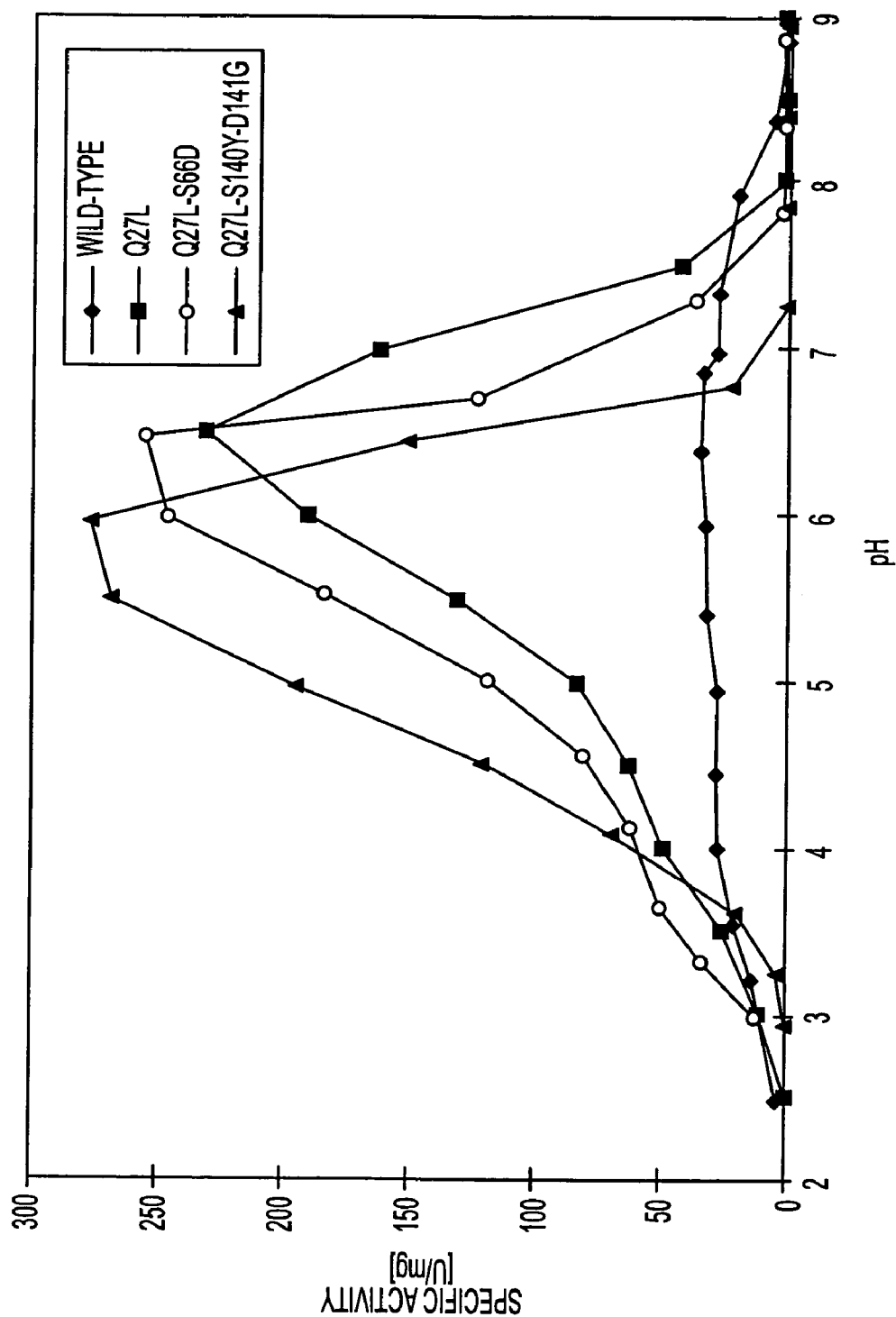
FIG. 22: pH optima curves. Specific activity of wild-type and mutant *A. fumigatus* [ATCC 13073] phytases is plotted against pH of incubation. Filled rhombs: *A. fumigatus* wild-type phytase; Filled squares: *A. fumigatus* Q27L single mutant; Open circles: *A. fumigatus* Q27L-S66D double mutant; Filled triangles: *A. fumigatus* Q27L-S140Y-D141G triple mutant.

As shown in FIG. 22 the combination of mutation Q27L with S66D or S140Y and D141G led to a shift of the pH profile towards lower pH. The maximum specific activity gained by the single mutation Q27L is further increased by the additional amino acid exchanges.

Figure 3A:
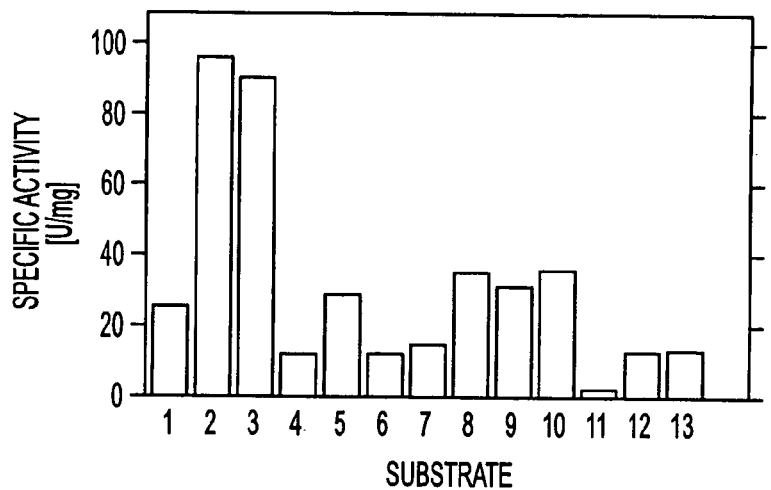
FIG. 3: Substrate specificities of wild-type and mutant *A. fumigatus* phytases. (A) wild-type; (B) Q27L single mutant; (C) Q27L, Q274L, G277D triple mutant. The following substrates were used: (1) phytic acid; (2) p-nitrophenyl phosphate; (3) fructose-1,6-bisphosphate; (4) fructose-6-phosphate; (5) glucose-6-phosphate; (6) ribose-5-phosphate; (7) α-glycerophosphate; (8) β-glycerophosphate; (9) 3-phosphoglycerate; (10) phosphoenolpyruvate; (11) AMP; (12) ADP; (13) ATP.
Figure 3B:
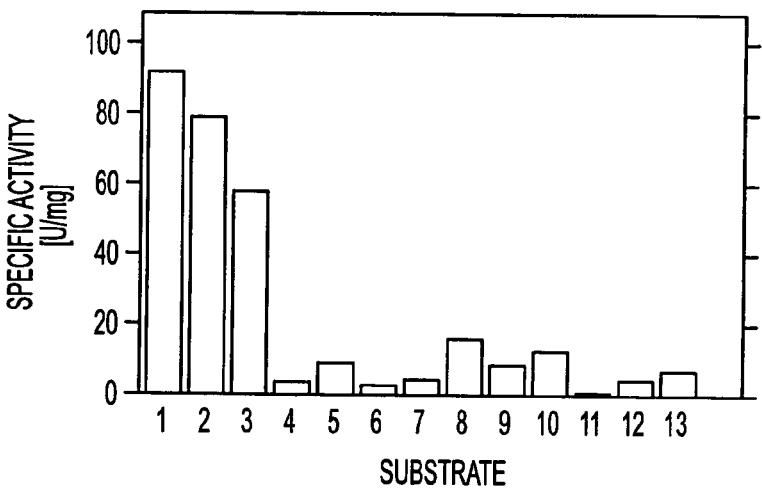
Figure 3C:
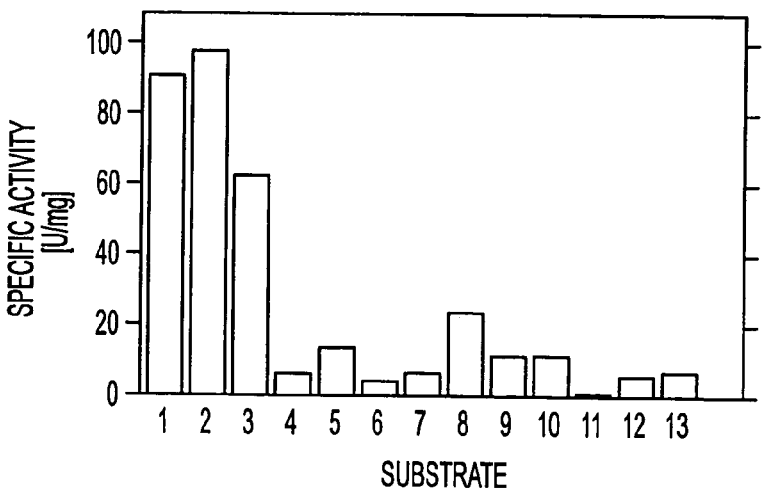

As shown in FIG. 3, Aspergillus fumigatus phytase mutant T1 (Q27L) showed no difference in substrate specificity compared to the triple mutant T6 (Q27L, Q274L, G277D).

Figure 10:
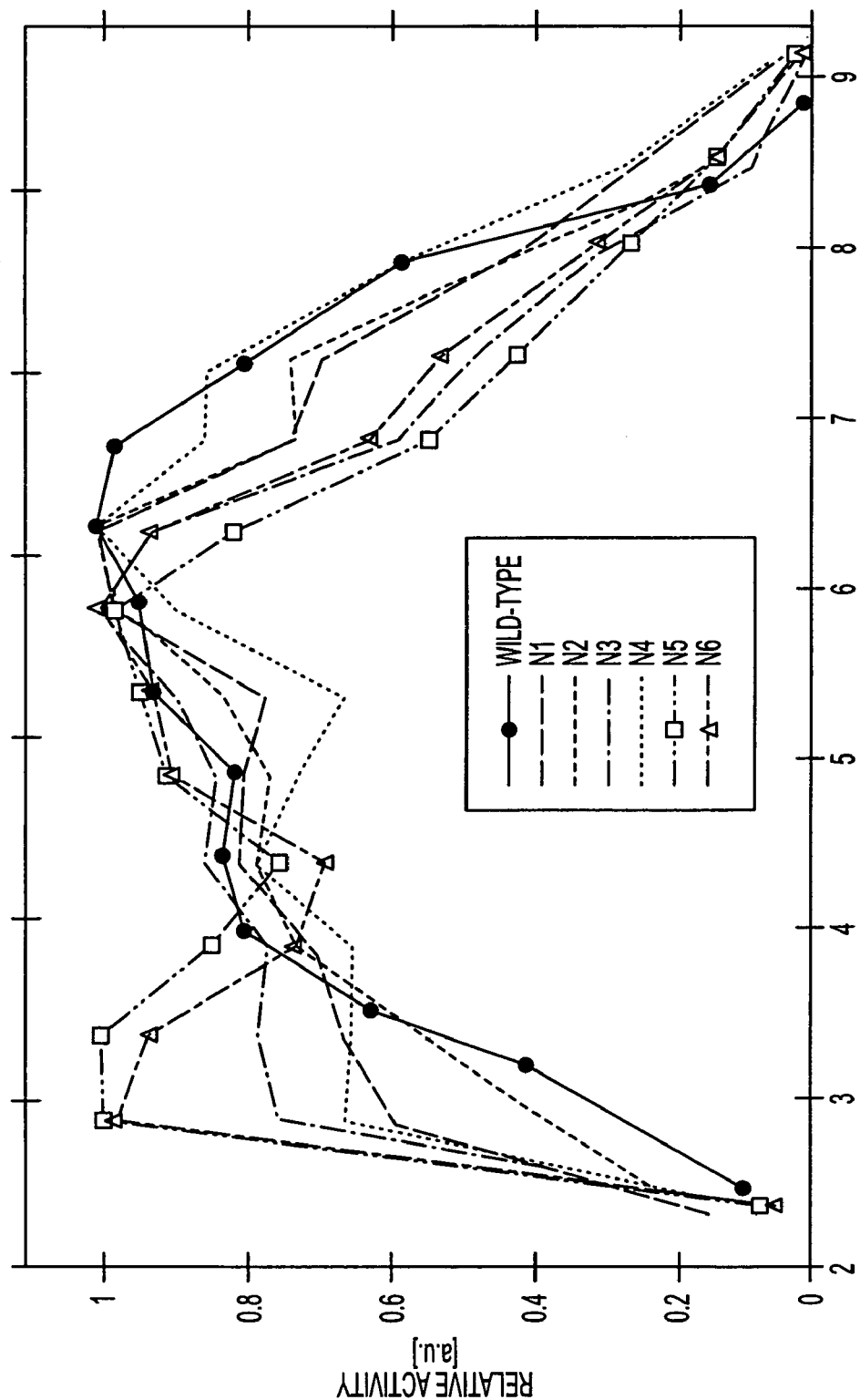
FIG. 10: pH optima curves of further mutant *A. fumigatus* phytases (N-1–N6). All activity values were standardized (maximum activity=1.0).
Figure 11A:
FIG. 11a: Stereo picture of the three-dimensional fold of *A. niger* (*A. ficuum*; NRRL 3135) phytase. The active site is indicated with a circle and the catalytically essential amino acid residues Arg 58 and His 59 are shown in ball-and-stick representation. This figure was prepared with the programs "MOLSCRIPT" [Kraulis, P. J., J. Appl. Cryst. 24, 946–950 (1991)] and "RASTER3D" [Merritt, E. A. & Murphy, M. E. P., Acta Cryst., 869–873 (1994)].
Figure 11B:
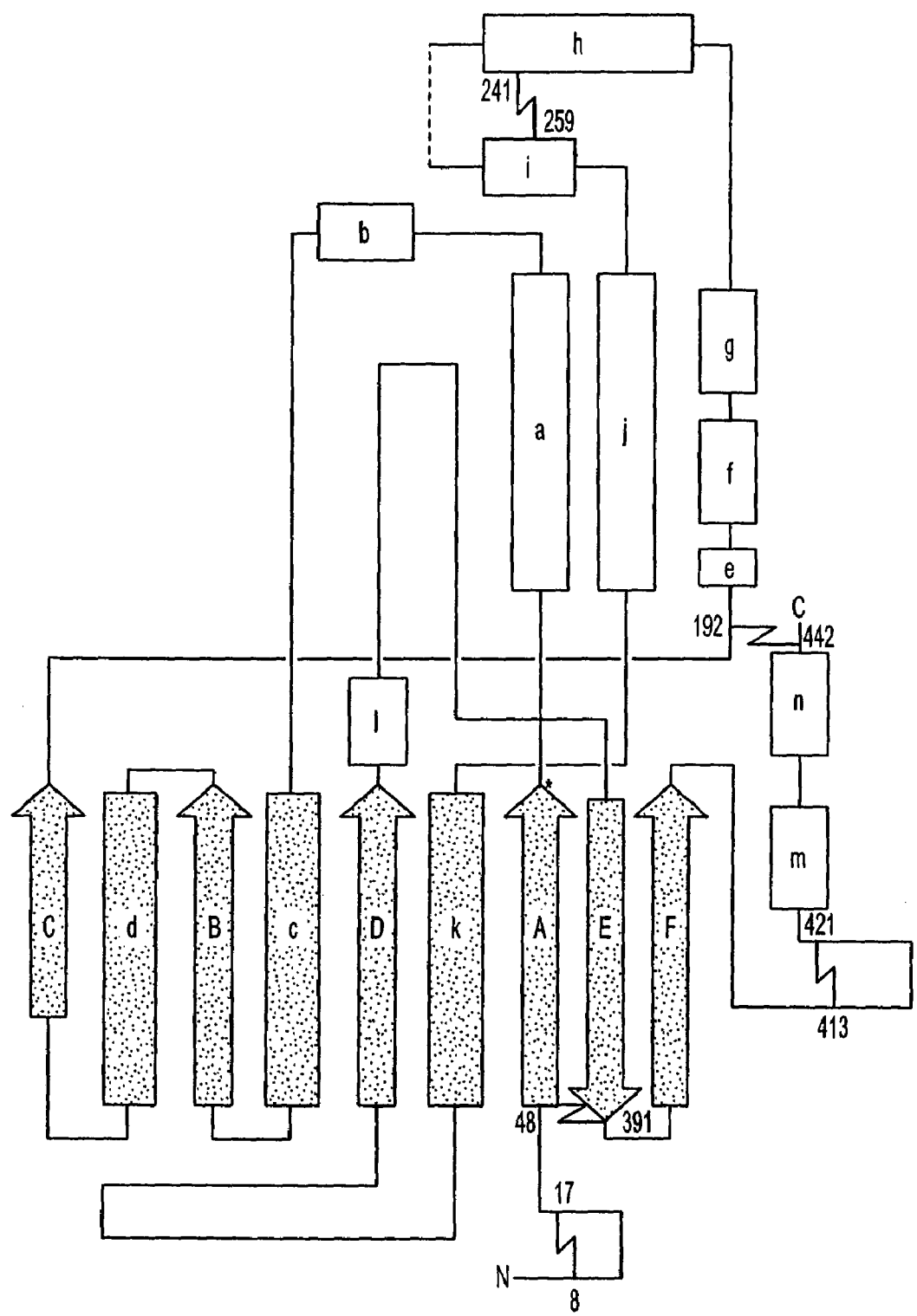
FIG. 11b: Topological sketch, using the same scheme as in (a). The five disulphide bridges are shown as black zigzag lines together with the sequence numbers of the cysteine residues involved. The β-strands are defined with the sequence numbers A: 48–58, B: 134–138, C: 173–177, D: 332–337, E: 383–391, and F: 398–403. The α-helices are defined with the sequence numbers a: 66–82, b: 88–95, c: 107–123, d: 141–159, e: 193–197, f: 200–210, g: 213–223, h: 231–246, i: 257–261, j: 264–281, k: 290–305, l: 339–348, m: 423–429, and n: 439–443. The asterisk at the C-terminal end of β-strand A marks the location of the catalytically essential amino acid residues Arg 58 and His 59.
Figure 12:
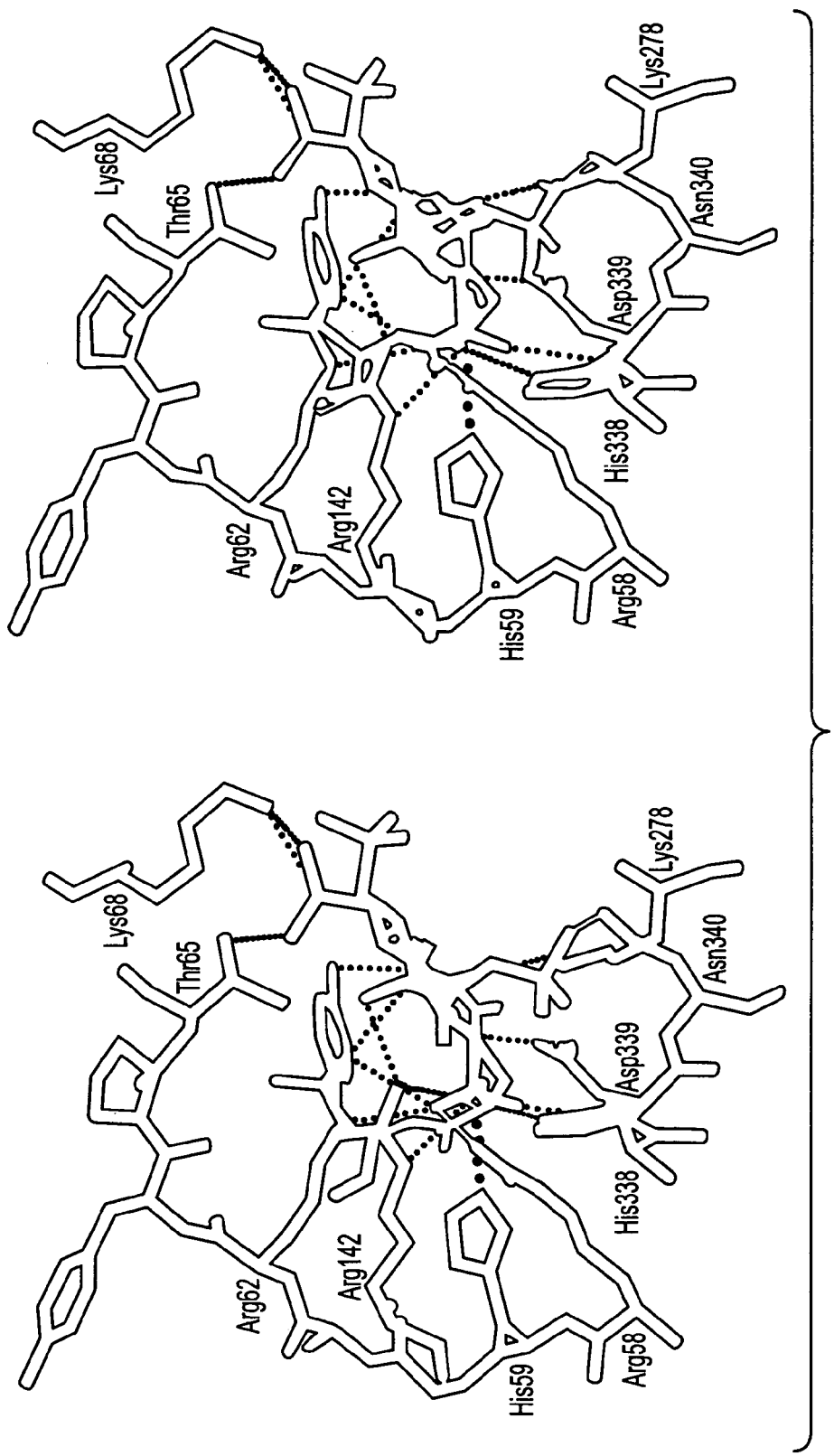
FIG. 12: Stereo picture of the active site of *A. ficuum* (ATCC 13073) phytase with a hypothetical binding mode of the substrate phytate. In this model, the bound crystal water molecules were removed and the protein atom positions were held fixed, except for small adaptations of the side chain torsion angles of Lys 68 in order to interact with the substrate. All the conserved amino acid residues Arg 58, His 59, Arg 62, Arg 142, His 338 and Asp 339 form hydrogen bonds to the scissile 3-phosphate group of phytate, as indicated with lines of small dots. His 59 is in a favorable position to make a nucleophilic attack at the scissile phosphorous, indicated with a line of larger dots, and Asp 339 is in a position to protonate the leaving group.

The pH profiles of the muteins N1–6, except N2 show significant differences compared to the wild-type phytase (FIG. 10). Whereas the pH profile of mutein N4 is expanded towards lower pH, the profiles of muteins N3 to N6 are shifted towards lower pH. The muteins N5, N6 reach maximum activity already at pH 3.0.

Figure 9:
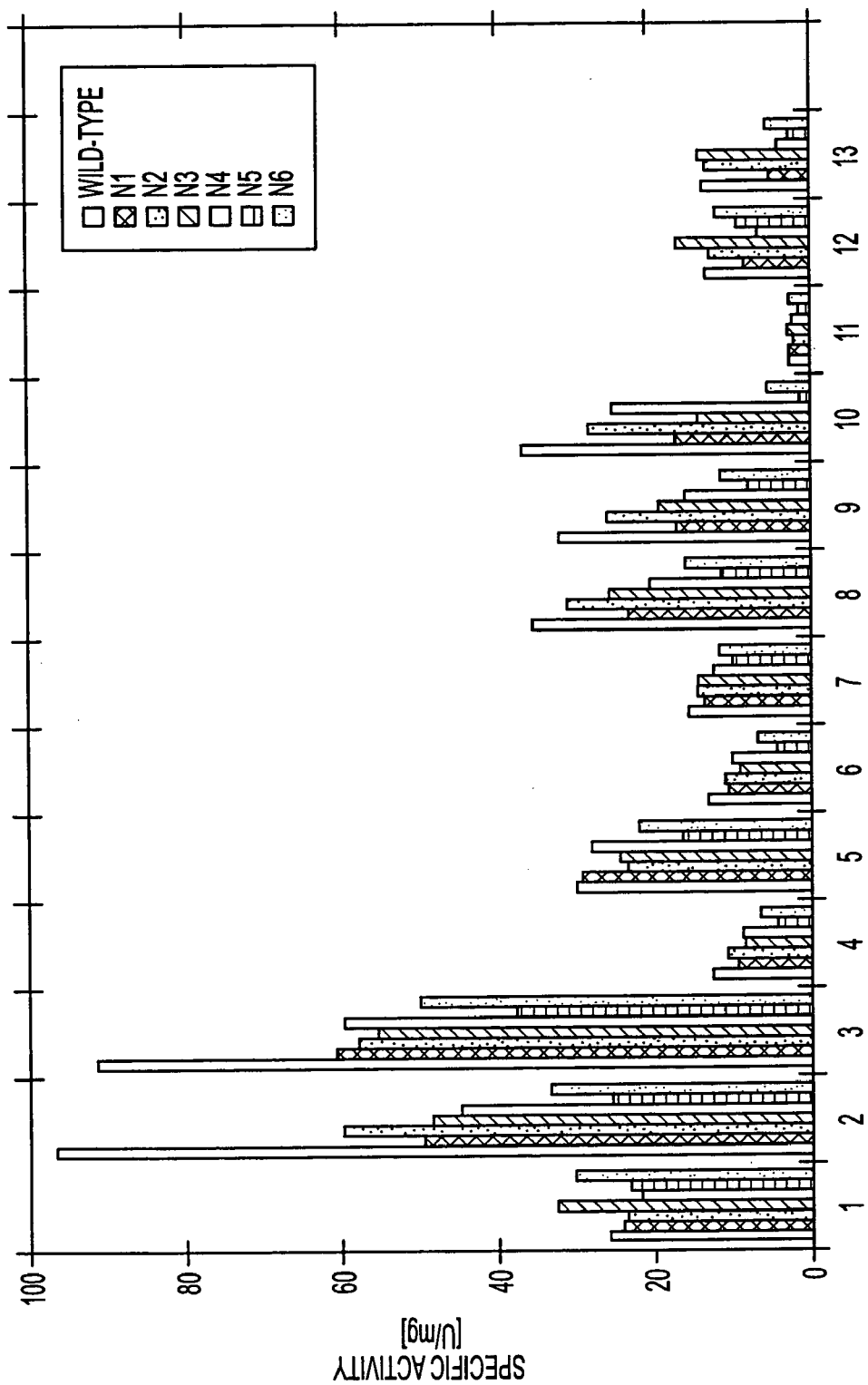
FIG. 9: Substrate specificities of wild-type and mutant *A. fumigatus* phytase (N-1–N6). Substrates 1 to 13 are as indicated for FIG. 3.

The muteins N1 to N6 show in almost all cases a drastic reduction in specific activity for all tested substrates, except for phytic acid (FIG. 9). Specific activity for phytic acid remained unchanged compared to the wild-type phytase, whereas mutant N3 and N6 show a tendential higher activity (FIG. 19).

TABLE 1

A) Mutations towards A. terreus cbs116.46 phytase

| Mutation | T1 | T2 | T3 | T4 | T5 | T6 | T7 |
|---|---|---|---|---|---|---|---|
| Q27L | X |  |  |  | X | X | X |
| Q274L |  | X |  |  | X | X | X |
| G277D |  |  | X |  |  | X | X |
| N340S |  |  |  | X |  |  | X |

B) Mutations towards A. niger (ficuum) phytase

| Mutation | N1 | N2 | N3 | N4 | N5 | N6 |
|---|---|---|---|---|---|---|
| G277K | X |  |  | X | X | X |
| A205E |  | X |  | X |  | X |
| Y282H |  |  | X |  | X | X |

TABLE 2

|  | U/mg |  |
|---|---|---|
| A. fumigatus wild-type phytase | 26.5 ± 5.2 | 22 |
| A. fumigatus Q27L | 83.4 | 4 |
| A. fumigatus Q27L, Q274L | 88.7 ± 13.5 | 8 |
| A. fumigatus Q27L, Q274L, G277D | 92.3 ± 12.0 | 9 |
| A. terreus cbs116.46 phytase | 195.8 ± 17.8 | 7 |

TABLE 3

Specific activity under standard assay conditions at pH 5.0. Average standard deviation is 10%.

|  | Specific activity [U/mg] | Number of independent assays |
|---|---|---|
| A. fumigatus wild-type phytase | 26.5 | 22 |
| A. fumigatus Q27N | 45.5 | 3 |
| A. fumigatus Q27T | 106.9 | 3 |
| A. fumigatus Q27L | 83.4 | 4 |
| A. fumigatus Q27I | 91.2 | 3 |
| A. fumigatus Q27V | 35.0 | 3 |
| A. fumigatus Q27A | 27.3 | 3 |
| A. fumigatus Q27G | 59.6 | 3 |
| A. fumigatus Q27L-S66D | 118.5 | 3 |
| A. fumigatus Q27L-S140Y-D141G | 193.0 | 3 |

Example 8

Figure 24:
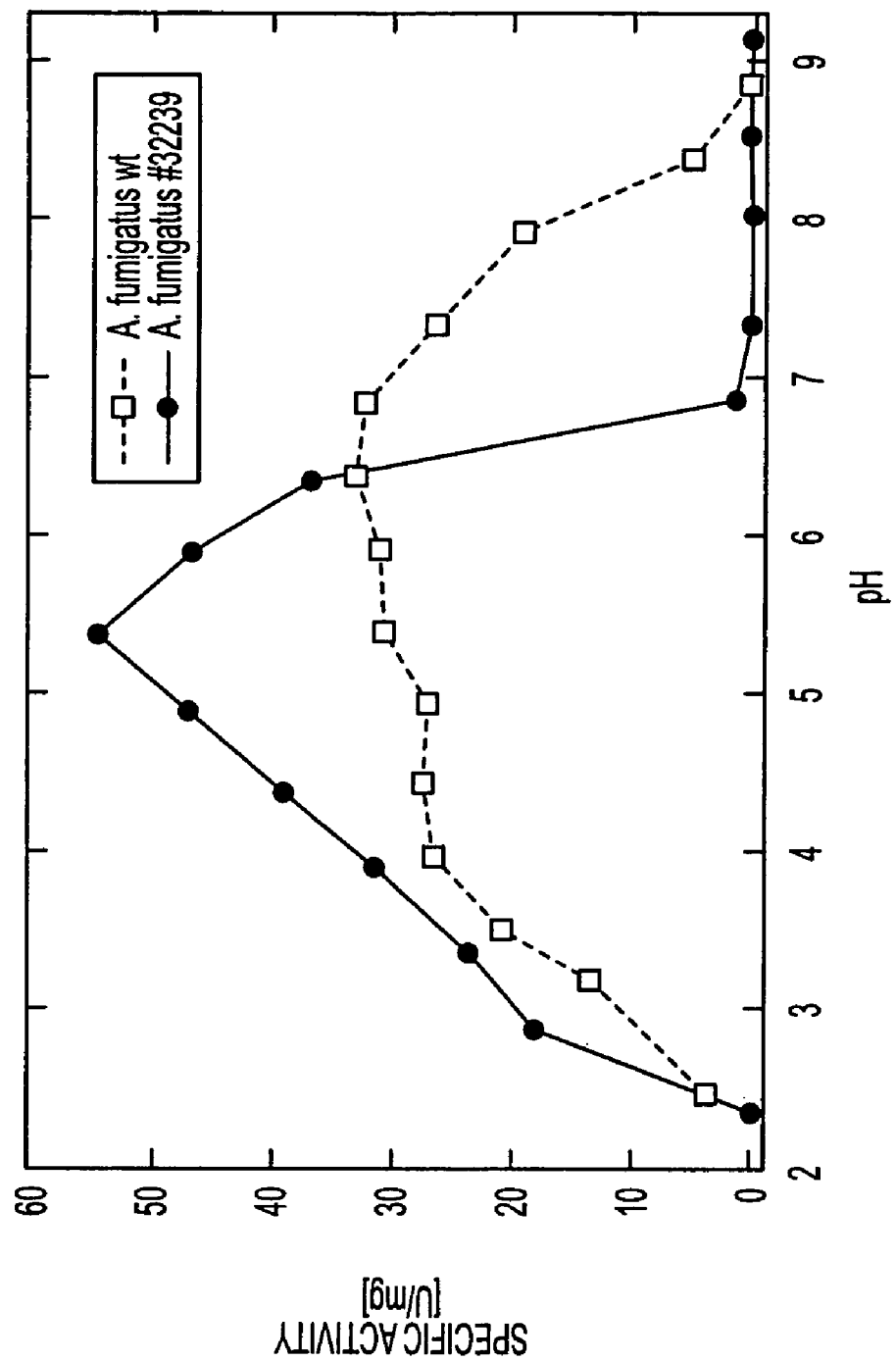
FIG. 24: pH dependent specific activity of phytases isolated from two different *A. fumigatus* wildtype strains. Open squares: wild-type strain ATCC 13073; Filled circles: strain ATCC 32239.
Figure 25:
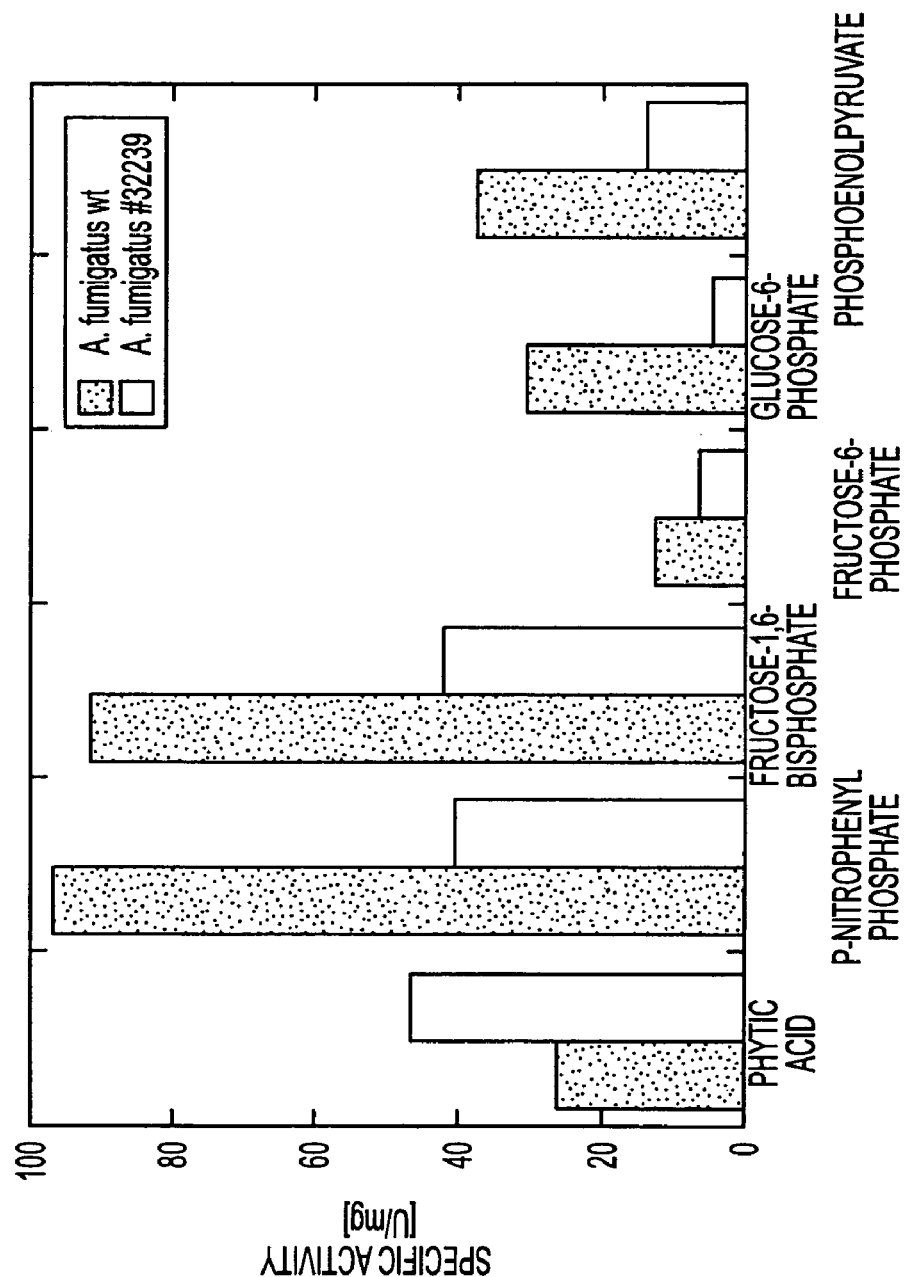
FIG. 25: Substrate specificities of phytases isolated from two different *A. fumigatus* wildtype strains. Black bars: wild-type strain ATCC 13073; White bars: strain ATCC 32239.

As an alternative approach to obtain phytases with modified characteristics and to get a better idea about the natural variation found in phytase characteristics within a certain species, naturally occurring variants of A. fumigatus phytase were analysed. Phytase genes were obtained from six different isolates of A. fumigatus. The amino acid sequence of phytase from two of the A. fumigatus isolates (ATCC 26934 and ATCC 34625) showed no difference to the original amino acid sequence of wild-type A. fumigatus phytase ATCC 13073. Phytase from three other isolates had one or two amino acid substitutions, none of which directly affected the active site. Enzymatic characteristics remained unaffected by these substitutions (not shown). The phytase from isolate of A. fumigatus (ATCC 32239) differed in 13 positions in the signal sequence and 51 positions in the mature part of the protein compared to the original wild-type A. fumigatus phytase (ATCC 13073). Several of these substitutions affect variable amino acids of the active site cavity. This resulted in an increase in specific activity with phytic acid as substrate (47 U/mg, standard enzyme assay) and in loss of enzymatic activity above pH 7 (FIG. 24). Also in this case, the specific activity against phytic acid was increased relative to the specific activities with other substrates (FIG. 25).

Example 9

Figure 26:
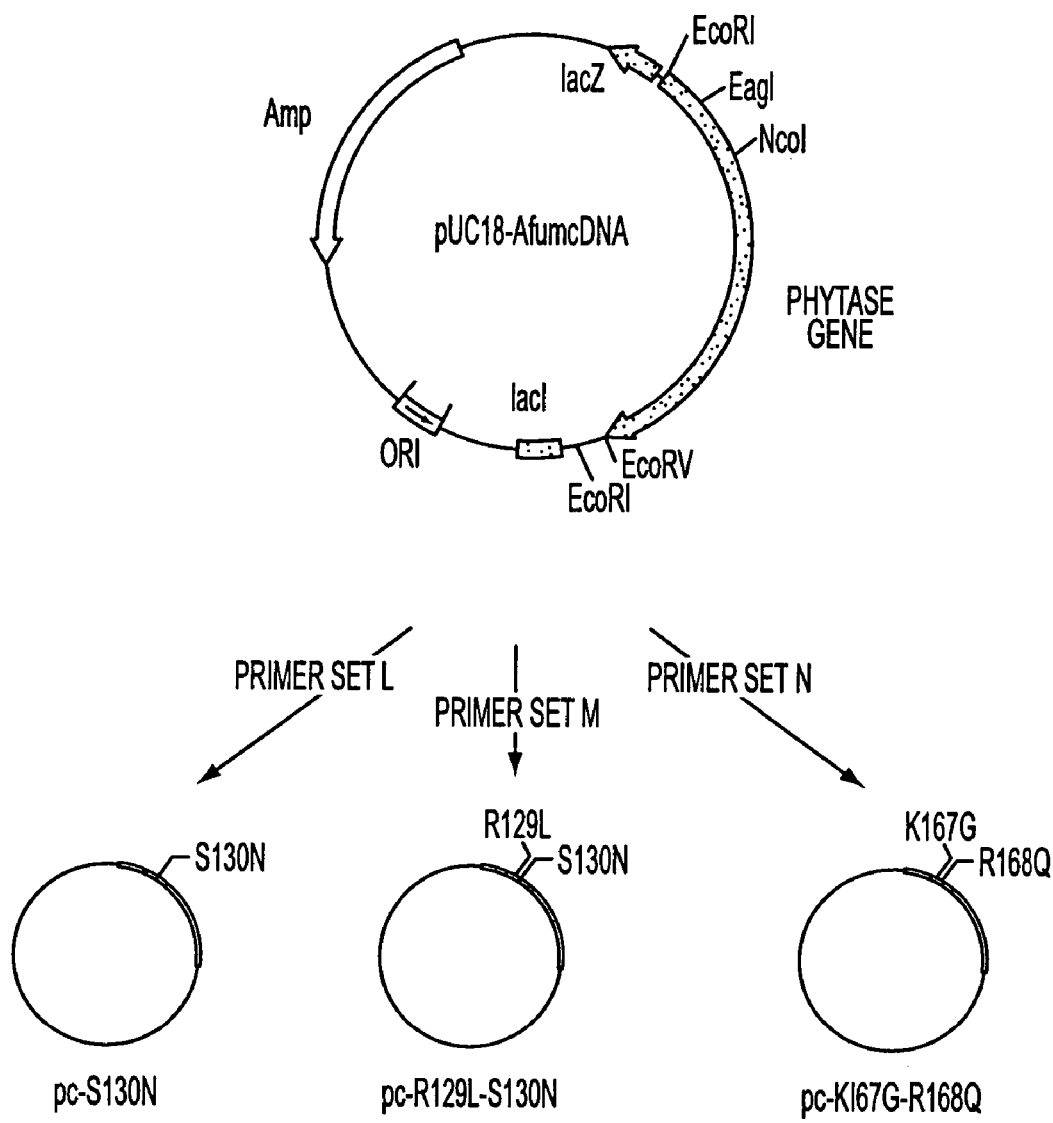
FIG. 26: Construction of plasmids pc-S130N, pc-R129L-S130N, pc-K167G-R168Q.

Construction of plasmids pc-S130N, pc-R129L-S130N, pc-K167G-R168Q encoding A. fumigatus [ATCC 13073] phytase S130N single mutant and R129L-S130N double mutant and A. nidulans phytase K167G-R168Q double mutant was basically carried out as described in Example 3. Plasmid pUC18-AfumcDNA was used as template for site directed mutagenesis together with the corresponding primer sets L, M and N (FIG. 14a; FIG. 26).

All mutations were verified by DNA sequence analysis of the entire gene.

Example 10

When expressed in A. niger and stored as concentrated culture supernatants at 4° C., the phytases from A. fumigatus, A. nidulans displayed tendency to undergo proteolytic degradation. N-terminal sequencing of fragments suggested that cleavage occured between amino acids S130-V131 and K167-R168 or R168-A169, respectively. Compared with 3D structure of *A. niger* phytase revealed that all cleavage sites are found within surface-exposed loop structures and are therefore accessible to proteases.

Site-directed mutagenesis at protease-sensitive sites of *A. fumigatus* phytase (S130N, R129L-S130N) and *A. nidulans* phytase (K167G-R168Q) yielded mutant proteins with considerably reduced susceptibility to proteolysis.

In contrast to expression in *A. niger*, proteolytic degradation was not observed when the phytases were expressed in *Hansenula polymorpha*.

The invention claimed is:

1. A process for preparing a modified *Aspergillus* phytase with a specific activity improved over the specific activity of an unmodified *Aspergillus* phytase which comprises:
   (a) determining the three dimensional structure of the unmodified *Aspergillus* phytase and of a second phytase which has the improved specific activity by aligning the amino acid sequences of said phytases with the amino acid sequence of a third phytase which is the phytase of *Aspergillus niger* and using the three dimensional structure of the phytase of *Aspergillus niger* as a template based on the alignment to determine said three dimensional structures;
   (b) determining from the structures of step (a) the amino acids of the active sites of the unmodified *Aspergillus* phytase and of the second phytase having the improved specific activity which active site provides the improved specific activity and comparing the amino acids which form the active sites to identify which amino acids are different in the active site of the second phytase from the amino acids in the active site of the unmodified *Aspergillus* phytase;
   (c) constructing a DNA sequence coding for the modified phytase by obtaining the DNA sequence of the unmodified *Aspergillus* phytase and changing the nucleotides coding for the active site which provides the improved specific activity for said unmodified *Aspergillus* phytase so that at least one of the amino acids in the active site which provides the improved specific activity is substituted by one of the amino acids which was identified as being different in step (b);
   (d) integrating such a DNA sequence into a vector capable of expression in a suitable host cell; and
   (e) transforming the suitable host cell by the DNA sequence of step (c) or the vector of step (d), growing said host cell under suitable growth conditions and isolating the modified phytase from the host cell or the culture medium.

2. The process of claim 1 wherein the unmodified phytase is a phytase from *Aspergillus fumigatus*.

3. The process of claim 1 wherein the phytase with the improved specific activity is of eukaryotic origin.

4. The process of claim 3 wherein the phytase with the improved specific activity is of fungal origin.

5. The process of claim 4 wherein the phytase with the improved specific activity is of *Aspergillus* origin.

6. The process of claim 5 wherein the phytase with the improved specific activity is a phytase from *Aspergillus terreus*.

7. The process of claim 1 wherein the unmodified phytase is a phytase of *Aspergillus fumigatus* and the second phytase with the improved specific activity is an the *Aspergillus niger* phytase.

8. The process of claim 1 wherein the unmodified phytase is a phytase of *Aspergillus fumigatus* and the second phytase with the improved specific activity is an the *Aspergillus terreus* phytase.

9. The process according to claim 1, wherein the DNA sequence encoding the modified *Aspergillus* phytase has been changed at a position corresponding to position 27 of the phytase of *Aspergillus niger* (SEQ ID NO:1) to an amino acid selected from the group consisting of Ala, Val, Leu, Ile, Thr, Gly, and Asn.

\* \* \* \* \*